US011969476B2

(12) United States Patent
Viswanathan et al.

(10) Patent No.: US 11,969,476 B2
(45) Date of Patent: Apr. 30, 2024

(54) ANTIBODY MOLECULE-DRUG CONJUGATES AND USES THEREOF

(71) Applicant: VISTERRA, INC., Waltham, MA (US)

(72) Inventors: Karthik Viswanathan, Acton, MA (US); Kenneth Douglas Johnson, Marshfield, MA (US); Obadiah Joseph Plante, Danvers, MA (US); James C. Delaney, Cambridge, MA (US); Tyree J. Koch, Seattle, WA (US); Hamid Tissire, Millis, MA (US); Andrew M. Wollacott, Milton, MA (US); Boopathy Ramakrishnan, Braintree, MA (US)

(73) Assignee: VISTERRA, INC., Waltham, MA (US)

( * ) Notice: Subject to any disclaimer, the term of this patent is extended or adjusted under 35 U.S.C. 154(b) by 0 days.

(21) Appl. No.: 17/221,421

(22) Filed: Apr. 2, 2021

(65) Prior Publication Data

US 2021/0316004 A1 Oct. 14, 2021

Related U.S. Application Data

(60) Provisional application No. 63/004,946, filed on Apr. 3, 2020.

(51) Int. Cl.
| | | |
|---|---|---|
| A61K 47/68 | (2017.01) | |
| A61K 45/06 | (2006.01) | |
| A61P 31/04 | (2006.01) | |
| C07K 16/12 | (2006.01) | |

(52) U.S. Cl.
CPC .......... *A61K 47/6811* (2017.08); *A61K 45/06* (2013.01); *A61P 31/04* (2018.01); *C07K 16/1214* (2013.01); *C07K 2317/24* (2013.01)

(58) Field of Classification Search
CPC .... A61K 47/6811; A61K 45/06; A61K 47/00; A61K 47/50; A61K 47/51; A61K 47/68; A61K 47/6801; A61P 31/04; C07K 16/1214; C07K 2317/24
See application file for complete search history.

(56) References Cited

U.S. PATENT DOCUMENTS

| | | | |
|---|---|---|---|
| 7,597,893 B2 | 10/2009 | Lang et al. | |
| 7,972,845 B2 | 7/2011 | Schreiber et al. | |
| 8,197,816 B2 | 6/2012 | Lang et al. | |
| 8,729,232 B2 | 5/2014 | Rush et al. | |
| 8,986,990 B2 | 3/2015 | Schreiber et al. | |
| 9,089,557 B2 | 7/2015 | Schreiber et al. | |
| 9,238,878 B2 | 1/2016 | Rabuka et al. | |
| 9,540,438 B2 | 1/2017 | Barfield et al. | |
| 9,879,249 B2 | 1/2018 | Rabuka et al. | |
| 10,183,998 B2 | 1/2019 | Barfield et al. | |
| 11,168,131 B2 * | 11/2021 | Plante .................... | A61P 31/04 |
| 2004/0052814 A1 | 3/2004 | Shi et al. | |
| 2011/0117621 A1 | 5/2011 | Rush et al. | |

| | | | |
|---|---|---|---|
| 2014/0065064 A1 * | 3/2014 | Alper ............... | G01N 33/57415 |
| | | | 424/1.49 |
| 2015/0056253 A1 * | 2/2015 | Bancel ............... | A61K 38/1729 |
| | | | 424/278.1 |
| 2015/0344524 A1 | 12/2015 | Hoffmann et al. | |
| 2017/0129942 A1 | 5/2017 | Plante et al. | |
| 2018/0127501 A1 * | 5/2018 | Bernett ............. | C07K 16/2818 |
| 2021/0283220 A1 | 9/2021 | Shriver et al. | |
| 2021/0316004 A1 | 10/2021 | Viswanathan et al. | |
| 2022/0267418 A1 * | 8/2022 | Plante ..................... | C07K 7/08 |

FOREIGN PATENT DOCUMENTS

| | | |
|---|---|---|
| CN | 103415621 A | 11/2013 |
| EP | 0441395 A2 | 8/1991 |
| GB | 2186592 A | 8/1987 |
| JP | 2004-514423 A | 5/2004 |
| JP | 4-211393 B2 | 1/2009 |
| JP | 7041628 B2 | 3/2022 |
| WO | 1986003754 A1 | 7/1986 |
| WO | 88/08135 A1 | 10/1988 |
| WO | 90/03186 A1 | 4/1990 |
| WO | 92/16624 A1 | 10/1992 |
| WO | 00/64487 A2 | 11/2000 |
| WO | 2002020619 A2 | 3/2002 |
| WO | 03/007989 A1 | 1/2003 |
| WO | 2004101622 A1 | 11/2004 |
| WO | 2005056601 A2 | 6/2005 |
| WO | 2006084758 A1 | 8/2006 |
| WO | 2009120611 A2 | 10/2009 |
| WO | 2010096394 A2 | 8/2010 |
| WO | 2010115606 A1 | 10/2010 |
| WO | 2011102551 A1 | 8/2011 |
| WO | 2011102552 A1 | 8/2011 |
| WO | 2011102553 A1 | 8/2011 |
| WO | 2011102554 A1 | 8/2011 |

(Continued)

OTHER PUBLICATIONS

McCombs and Owen, Antibody Drug Conjugates: Design and Selection of Linker, Payload, and Conjugation Chemistry, 2015, The AAPS Journal, vol. 17, No. 2, pp. 339-351 (Year: 2015).*
Pechmann & Frydman, Interplay between Chaperones and Protein Disorder Promotes the Evolution of Protein Networks, 2014, PLOS Computational Biology, vol. 10, Issue 6, pp. 1-15 (Year: 2014).*
International Search Report and Written Opinion in corresponding International Patent Application No. PCT/US2021/025615 dated Jun. 23, 2021.
International Search Report and Written Opinion in International Patent Application No. PCT/US2016/061330 dated May 15, 2017.
International Search Report and Written Opinion in International Patent Application No. PCT/US2018/014224 dated Apr. 12, 2018.

(Continued)

*Primary Examiner* — Adam Weidner
*Assistant Examiner* — Brittney E Donoghue
(74) *Attorney, Agent, or Firm* — K&L Gates LLP

(57) ABSTRACT

Antibody molecule-drug conjugates (ADCs) that specifically bind to lipopolysaccharides (LPS) are disclosed. The antibody molecule-drug conjugates can be used to treat, prevent, and/or diagnose bacterial infections and related disorders.

27 Claims, 40 Drawing Sheets

Specification includes a Sequence Listing.

(56) References Cited

FOREIGN PATENT DOCUMENTS

| WO | 2011102555 | A1 | 8/2011 | |
|---|---|---|---|---|
| WO | 2011102556 | A1 | 8/2011 | |
| WO | 2012/097333 | A2 | 7/2012 | |
| WO | 2013/012924 | A2 | 1/2013 | |
| WO | 2013024905 | A1 | 2/2013 | |
| WO | WO-2014106235 | A1 * | 7/2014 | ............ C07K 16/18 |
| WO | 2015046505 | A1 | 4/2015 | |
| WO | 2017/083515 | A2 | 5/2017 | |
| WO | 2018/136626 | A1 | 7/2018 | |
| WO | 2021/203024 | A1 | 10/2021 | |

OTHER PUBLICATIONS

Burrows, L. L. "The Therapeutic Pipeline for Pseudomonas aeruginosa Infections." ACS Infectious Diseases, vol. 4, No. 7 (2018) pp. 1041-1047.
Caldas, C. et al. "Humanization of the anti-CD18 antibody 6.7: an unexpected effect of a framework residue in binding to antigen, " Molecular Immunology, vol. 39, No. 15 (2003) pp. 941-952.
Casadevall, A. & Janda, A. "Immunoglobulin isotype influences affinity and specificity," Proceedings of the National Academy of Sciences of the United States of America, vol. 109, No. 31 (2012) pp. 12272-12273.
Chien, N. C. et al. "Significant structural and functional change of an antigen-binding site by a distant amino acid substitution: proposal of a structural mechanism," Proceedings of the National Academy of Sciences of the United States of America, vol. 86, No. 14 (1989) pp. 5532-5536.
Fletcher, M. A. et al. "A Novel Peptide-IgG Conjugate, CAP18106-138-IgG, that Binds and Neutralizes Endotoxin and Kills Gram-Negative Bacteria," The Journal of Infectious Diseases, vol. 175, No. 3 (1997) pp. 621-632.
Giusti, A. M. et al. "Somatic diversification of S107 from an antiphosphocholine to an anti-DNA autoantibody is due to a single base change in its heavy chain variable region," Proceedings of the National Academy of Sciences of the United States of America, vol. 84, No. 9 (1987) pp. 2926-2930.
Greenspan, N. S. & Di Cera, E. "Defining epitopes: It's not as easy as it seems," Nature Biotechnology, vol. 17, No. 10 (1999) pp. 936-937.
Mutharia, L. M. et al. "Monoclonal Antibodies Specific for *Escherichia coli* J5 Lipopolysaccharide: Cross-Reaction with Other Gram-Negative Bacterial Species," (1984) pp. 631-636.
Skolnick, J. and Fetrow, J. S. "From genes to protein structure and function: novel applications of computational approaches in the genomic era," Trends in Biotechnology, vol. 18, No. 1 (2000) pp. 34-39.
Warren, H. S. et al. "Protective Efficacy of CAP18 106-138-Immunoglobulin G in Sepsis, "The Journal of Infectious Diseases, vol. 188, No. 9 (2003) pp. 1382-1393.
Winkler, K. et al. "Changing the antigen binding specificity by single point mutations of an anti-p24 (HIV-1) antibody," Journal of Immunology, vol. 165, No. 8 (2000) pp. 4505-4514.
Bowie, J. U. et al. "Deciphering the message in protein sequences: tolerance to amino acid substitutions." Science (New York, N.Y.) vol. 247,4948 (1990): 1306-10.
Burgess, W. H. et al. "Possible dissociation of the heparin-binding and mitogenic activities of heparin-binding (acidic fibroblast) growth factor-1 from its receptor-binding activities by site-directed mutagenesis of a single lysine residue." The Journal of Cell Biology vol. 111 (1990): 2129-38.
Lazar, E. et al. "Transforming growth factor alpha: mutation of aspartic acid 47 and leucine 48 results in different biological activities." Molecular and Cellular Biology vol. 8,3 (1988): 1247-52.
Sela-Culang, I. et al. "The structural basis of antibody-antigen recognition." Frontiers in Immunology vol. 4, 302 (2013): 1-13.

Bahar et al., "Antimicrobial Peptides," Pharmaceutials (2013) vol. 6, pp. 1543-1575.
Chen et al., "A general strategy for the evolution of bond-forming enzymes using yeast display," PNAS (2011) vol. 108, No. 28, pp. 11399-11404.
Chen et al., "Antibody Preparation of P. æruginosa and Research on Antibacterial Effect," Progress in Veterinary Medicine (2010), vol. 31, No. 8, pp. 38-40.
Chen et al., "Comparison of Biophysical and Biologic Properties of a-Helical Enantiomeric Antimicrobial Peptides," Chem Biol Drug Des (2006) vol. 67, No. 2, pp. 162-173.
De Kievit et al., "Monoclonal Antibodies That Distinguish Inner Core, Outer Core, and Lipid A Regions of Pseudomonas aeruginosa Lipopolysaccharide," Journal o Bacteriology (1994) vol. 176, No. 23, pp. 7129-7139.
Delucia, A.M. et al. "Lipopolysaccharide (LPS) inner-core phosphates are required for complete LPS synthesis and transport to the outer membrane in Pseudomonas aeruginosa PAO1." mBio vol. 2,4 (2011) e00142-11.
Di Padova et al., "A Broadly Cross-Protective Monoclonal Antibody Binding to *Escherichia coli* and *Salmonella* Lipopolysaccharides," Infect and Immun (1993) vol. 61, No. 9, pp. 3863-3872.
Digianodomenico et al., "Identification of broadly protective human antibodies to Pseudomonas aeruginosa exopolysaccharide Ps1 by phenotype screening," Journal Exp Med (2012) vol. 209, No. 7, pp. 1273-1287.
Drabick et al., "Covalent Polymyxin B Conjugate with Human Immunoglobulin G as an Antiendotoxin Reagent," Antimicrob Agents Chemother (1998), vol. 42, No. 3, pp. 583-588.
Drake, P.M. et al. "Aldehyde tag coupled with HIPS chemistry enables the production of ADCs conjugated site-specifically to different antibody regions with distinct in vivo efficacy and PK outcomes." Bioconjugate Chemistry vol. 25,7 (2014): 1331-41.
Hamamoto et al., "Antimicrobial Activity and Stability to Proteolysis of Small Linear Cationic Peptides with D-Amino Acid Substitutions," Microbiol Immunol (2002) vol. 46, No. 11, pp. 741-749.
Hershberger et al., "Chemistry and Metabolism of 3-Deoxy-D-mannooctulosonic Acid," J Biol Chem (1968) vol. 243, No. 7, pp. 1578-1584.
Hurdle et al., "Targeting bacterial membrane function: an underexploited mechanism for treating persistent infections," Nat Rev Microbiol (2011), vol. 9, No. 1, pp. 62-75.
Johnson, K. et al. "Development of an antibody fused with an antimicrobial peptide targeting Pseudomonas aeruginosa: a new approach to prevent and treat bacterial infections," bioRxiv (Dec. 29, 2022): 51 pages.
Kosciuczuk et al., "Cathelicidins: family of antimicrobial peptides. A review," Mol Biol Rep (2012) vol. 29, pp. 10957-10970.
Pier, "Pseudomonas aeruginosa lipoploysaccharide: a major virulence factor, initiator of inflammation and target for effective immunity," Int J Med Microbiol (2007) vol. 297, No. 5, pp. 277-295.
Raetz et al., "Lipopolysaccharide Endotoxins," Annu Rev Biochem (2002), vol. 71, pp. 635-700.
Spokoyny et al., "A Perfluoroaryl-Cysteine SNAr Chemistry Approach to Unprotected Peptide Stapling," J Am Chem Soc (2013), vol. 135, No. 16, pp. 5946-5949.
Szijártó et al., "Bactericidal Monoclonal Antibodies Specific to the Lipopolysaccharide O Antigen from Multidrug-Resistant *Escherichia coli* Clone ST131-Ob25b:H4 Elicit Protection in Mice," Antimicrobial Agents and Chemotherapy (2015) vol. 59, No. 6, pp. 3109-3116.
Touti et al., "Antibody-Bactericidal Macrocyclic Peptide Conjugates to Target Gram-Negative Bacteria," ChemBioChem (2018) vol. 19, pp. 2039-2044.
Trautmann et al., "Bacterial lipopolysaccharide (LPS)-specific antibodies in commercial human immunoglobulin preparations: superior antibody content of an IgM-enriched product," Clin Exp Immunol (1998) vol. 111, pp. 81-90.
Yamasaki et al., "Structural and Immunochemical Characterization of a Neisseria gonorrhoeae Epitope Defined by a Monoclonal Antibody 2C7; the Antibody Recognizes a Conserved Epitope on a

(56) References Cited

OTHER PUBLICATIONS

Specific Lipo-oligosaccharides in Spite of the Presence of Human Carbohydrate Epitopes," J Biol Chem (1999) vol. 274, No. 51, pp. 36550-36558.

* cited by examiner

CDR and FW Description

| Region | Definition | Sequence Fragment | Residues | Length |
|---|---|---|---|---|
| HFR1 | Chothia | EVKLVESGGGLVQPGGSLRLSCAAS----- | 1 - 25 | 25 |
| | Kabat | EVKLVESGGGLVQPGGSLRLSCAASEFTFS | 1 - 30 | 30 |
| CDR-H1 | Chothia | EFTFSDY------ | 26 - 32 | 7 |
| | Kabat | -----DYAMS | 31 - 35 | 5 |
| HFR2 | Chothia | AMSWVRQAPGKRLEWVAYI | 33 - 51 | 19 |
| | Kabat | ---WVRQAPGKRLEWVA-- | 36 - 49 | 14 |
| CDR-H2 | Chothia | -----SSDGDS------ | 52 - 57 | 6 |
| | Kabat | ---YISSDGDSTYPDSVKG | 50 - 66 | 17 |
| HFR3 | Chothia | TYYPDSVKGRFTISRDNAKNSLYLQMNSLRAEDTAMYFCAR | 58 - 98 | 41 |
| | Kabat | ---------RFTISRDNAKNSLYLQMNSLRAEDTAMYFCAR | 67 - 98 | 32 |
| CDR-H3 | Chothia | --EIRLRGYFDV | 99 - 108 | 10 |
| | Kabat | --EIRLRGYFDV | 99 - 108 | 10 |
| HFR4 | Chothia | -WGQGTTVTVSS | 109 - 119 | 11 |
| | Kabat | -WGQGTTVTVSS | 109 - 119 | 11 |

FROM FIG. 1A-1

CDR and FW Description

| Region | Definition | Sequence Fragment | Residues | Length |
|---|---|---|---|---|
| LFR1 | Chothia | DIQMTQSPSTLSASVGDRVTITC ---- | 1-23 | 23 |
| | Kabat | DIQMTQSPSTLSASVGDRVTITC ---- | 1-23 | 23 |
| CDR-L1 | Chothia | RASESVFGHGISPLH -- | 24-38 | 15 |
| | Kabat | RASESVFGHGISPLH -- | 24-38 | 15 |
| LFR2 | Chothia | WYQQKPGKAPKLLIY | 39-53 | 15 |
| | Kabat | WYQQKPGKAPKLLIY | 39-53 | 15 |
| CDR-L2 | Chothia | ---- RASNLKS | 54-60 | 7 |
| | Kabat | ---- RASNLKS | 54-60 | 7 |
| LFR3 | Chothia | --GVPSRFSGSGSGRTEFTLTISSLQPDDFATYYC | 61-92 | 32 |
| | Kabat | --GVPSRFSGSGSGRTEFTLTISSLQPDDFATYYC | 61-92 | 32 |
| CDR-L3 | Chothia | QQSNEYPRT | 93-101 | 9 |
| | Kabat | QQSNEYPRT | 93-101 | 9 |
| LFR4 | Chothia | --FGGGTKVEIK | 102-111 | 10 |
| | Kabat | --FGGGTKVEIK | 102-111 | 10 |

FIG. 1A-2

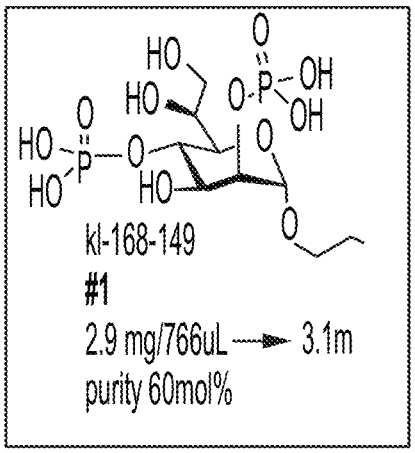
kl-168-149
1
2.9 mg/766uL ⟶ 3.1m
purity 60mol%
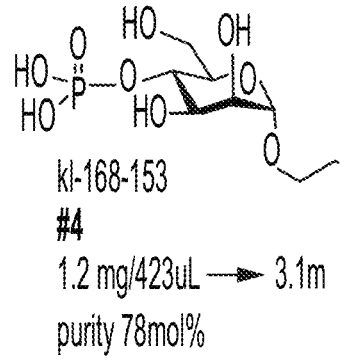
kl-168-153
4
1.2 mg/423uL ⟶ 3.1m
purity 78mol%
FROM FIG. 2A-1
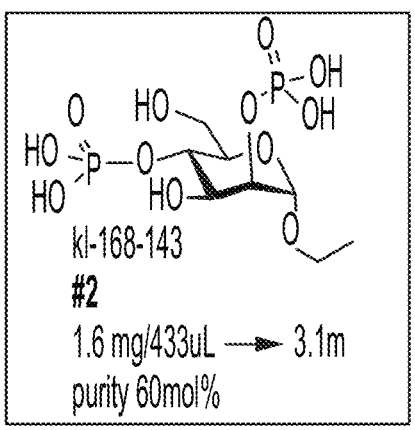
kl-168-143
2
1.6 mg/433uL ⟶ 3.1m
purity 60mol%
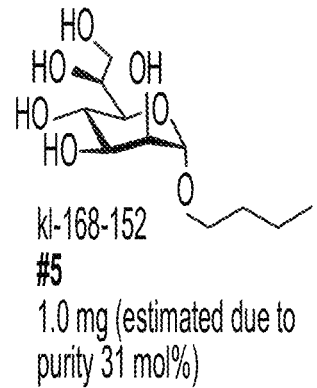
kl-168-152
5
1.0 mg (estimated due to purity 31 mol%)
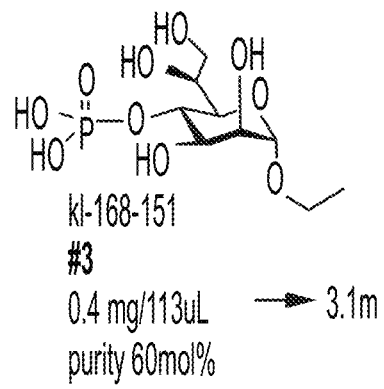
kl-168-151
3
0.4 mg/113uL ⟶ 3.1m
purity 60mol%
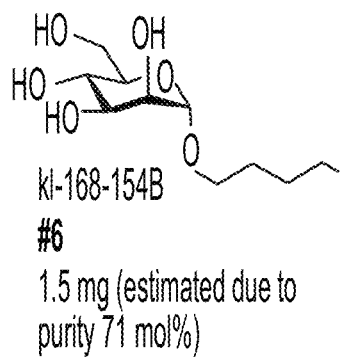
kl-168-154B
6
1.5 mg (estimated due to purity 71 mol%)
FIG. 2A-2

VSX Mutations to Confirm Binding Site

| Location | Mutation | Binding to 2,4-p-Hep* |
|---|---|---|
| VSX wt | NA | +++ |
| VH | A33T | + |
| VH | R101A/Q | -/- |
| VH | R103A/Q | -/- |
| VL | R100Q | - |
| VL | H32E | - |

+++, binding similar to wild type; +, weak binding; -, no binding detected

FIG. 6A

| | | |
|---|---|---|
| Heavy Chain % Ligation | 0.887 | 0.949 |
| Light Chain % Ligation | 0.913 | not applicable |
| % Population containing 4 D-P297 peptides | 66 | not applicable |
| % Population containing 3 D-P297 peptides | 29 | not applicable |
| % Population containing 2 D-P297 peptides | 5 | 84 |
| % Population containing 1 D-P297 peptides | 0 | 15 |
| % Population containing 0 D-P297 peptides | 0 | 1 |
| Average DAR | 3.6 | 1.8 |

FROM FIG. 9B-1

FIG. 9B-2

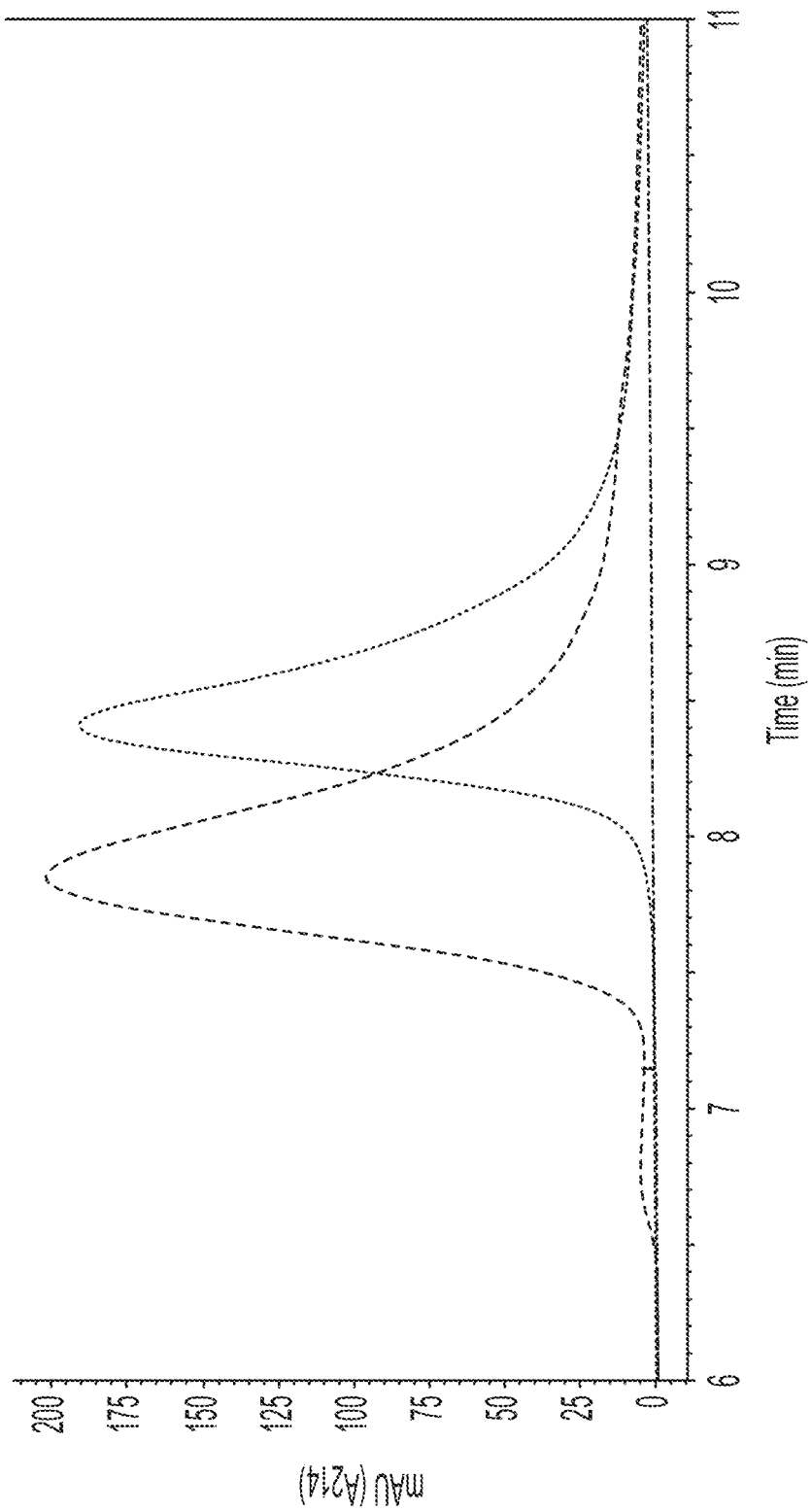

| mAb | Payload | Killing Activity (µg/ml) | |
|---|---|---|---|
| | | Pae 27853 | Pae 39324 |
| VSX | P271 | 25 | 6.3 |
| VSX | P293 | 25 | 12.5 |
| VSX | P294 | 6.3 | 3.1 |
| VSX | P295 | 6.3 | 0.8 |
| VSX | P297 | 1.6 | 0.4 |

FIG. 10

| VSX-1 Activity Profile | |
|---|---|
| Bactericidal activity | 1-4 µg/ml |
| Hemolytic activity | >340 µg/ml |
| Cytotoxicity | 310 µg/ml |
| Opsonic activity | 20 µg/ml |

FIG. 12

| DAR | VSX-1 | VSX-2 |
|---|---|---|
| | 4 | 2 |
| Killing (µg/mL) | 1.6-6.3 | 3.1-25 |
| MLC (µg/mL) | >800 | >800 |
| CC50 (µg/mL) | ~400 | >800 |

FIG. 14B

ANTIBODY MOLECULE-DRUG CONJUGATES AND USES THEREOF

CROSS-REFERENCE TO RELATED APPLICATION

This application claims the benefit of U.S. Provisional Application No. 63/004,946, filed Apr. 3, 2020. The contents of the aforementioned application is hereby incorporated by reference in its entirety.

SEQUENCE LISTING

The instant application contains a Sequence Listing which has been submitted electronically in ASCII format and is hereby incorporated by reference in its entirety. Said ASCII copy, created on Mar. 31, 2021, is named P2029-703610_SL.txt and is 116,138 bytes in size.

BACKGROUND

A wide range of bacteria can cause infections that lead to mild to serious illnesses. Bacterial infections are often treated by antibiotics. However, the emergence of antibiotic-resistant bacterial strains has complicated the treatment of infections. Antibiotic-resistant infections often result in greater disability and death compared with infections that are easily treatable with antibiotics. According to the Centers for Disease Control and Prevention (CDC), each year in the United States, at least 2 million people acquire serious infections with bacteria that are resistant to one or more of the antibiotics designed to treat those infections. At least 23,000 people die each year as a direct result of these antibiotic-resistant infections. These estimates were based on conservative assumptions and are likely minimum estimates. More patients may die from other conditions that were complicated by a bacterial infection. When first-line and then second-line antibiotic treatment options are limited by resistance or are unavailable, healthcare providers are forced to use antibiotics that may be more toxic to the patient and frequently more expensive and less effective. In many cases, antibiotic-resistant infections require prolonged or costlier treatments, extend hospital stays, and necessitate additional doctor visits and healthcare use.

The use of antibiotics is one of the most important factors leading to antibiotic resistance around the world. Antibiotics are among the most commonly prescribed drugs used in human medicine. However, according to CDC, up to 50% of all the antibiotics prescribed for people are not needed or are not optimally effective as prescribed. Antibiotics are also commonly used in food animals to prevent, control, and treat disease, and to promote the growth of food-producing animals. The resistant strains of bacteria may spread from person to person, or from the non-human sources in the environment, including food.

There is a need for developing new approaches for treating, preventing and diagnosing bacterial infections.

SUMMARY

This disclosure provides, at least in part, antibody molecules or antibody molecule-drug conjugates (ADC) that bind to bacteria, e.g., Gram-negative bacteria, e.g., lipopolysaccharides (LPS) on the outer membrane of Gram-negative bacteria, and that comprise functional and structural properties disclosed herein. In an embodiment, the ADC comprises an antimicrobial peptide site-specifically coupled (e.g., conjugated) to an anti-LPS antibody molecule. In an embodiment, the ADC comprises a plurality of antimicrobial peptides, each site-specifically coupled (e.g., conjugated) to an anti-LPS antibody molecule. In an embodiment, the antibody molecule or ADC binds to a core region of the LPS. In an embodiment, the antibody molecule or ADC binds to a monosaccharide component (e.g., heptose) of *Pseudomonas aeruginosa* LPS. In an embodiment, the antibody molecule or ADC binds to the phosphorylated (e.g., hyper-phosphorylated or biphosphorylated) HepI residue of core LPS (e.g., in *Pseudomonas aeruginosa*). In an embodiment, the antibody molecule or ADC does not bind to heptose. In an embodiment, the antibody molecule or ADC does not bind to mono-phosphorylated heptose analogs (e.g., 2-P-Hep and/or 4-P-Hep). In an embodiment, the antibody molecule or ADC binds more strongly to a 4-P phosphate group than to a 2-P phosphate group. In an embodiment, the antibody molecule or ADC binds to di-phosphorylated 2,4-P-Hep monosaccharide. In an embodiment, the antibody molecule or ADC comprises one or more mutations in an amino acid residue that contacts a monosaccharide component (e.g., heptose) of *Pseudomonas aeruginosa* LPS. In an embodiment, the antibody molecule or ADC comprises one or more (e.g., 1 or 2) conservative substitutions at VH residues A33 or E99. In an embodiment, the antibody molecule or ADC comprises a conservative substitution at VL residue H32. In an embodiment, the antibody molecule or ADC comprises a mutation of VH residue D54 and/or D56.

In an embodiment, the antibody molecule or ADC binds to, inhibits, and/or reduces the viability of, one or more bacteria, e.g., Gram-negative bacteria, of different genera, species, and/or subspecies. In an embodiment, the antibody molecule is selected from Table 1 or 3. In an embodiment, the ADC comprises an antibody molecule that is selected from Table 1 or 3. In an embodiment, the antibody molecule or ADC comprises one or more heavy chain variable regions and/or one or more light chain variable regions described in Table 1 or 3. In an embodiment, the antibody molecule or ADC comprises one or more heavy chain CDRs and/or one or more light chain CDRs described in Table 1 or 3. In an embodiment, the ADC comprises an antimicrobial peptide, e.g., an antimicrobial peptide described herein, e.g., in Table 4. While not wishing to be bound by theory, it is believed that in an embodiment, the conjugation of an antibody molecule with an antimicrobial peptide may improve one or more properties of the antibody molecule and/or antimicrobial peptide, e.g., improve the ability of an antimicrobial peptide to inhibit, or reduce the viability, of one or more bacteria, e.g., one or more Gram-negative bacteria, of different genera, species, and/or subspecies. Nucleic acid molecules encoding the antibody molecules, ADCs, or antimicrobial peptides, expression vectors, host cells, compositions (e.g., pharmaceutical compositions), kits, and methods for making the antibody molecules, ADCs, or antimicrobial peptides are also provided. The antibody molecules, ADCs, and antimicrobial peptides disclosed herein can be used (alone or in combination with other agents or therapeutic modalities) to treat, prevent and/or diagnose bacterial infections or related disorders, e.g., caused by or associated with Gram-negative bacteria (e.g., *Pseudomonas*, e.g., *Pseudomonas aeruginosa*).

Accordingly, in an aspect, the disclosure provides an antibody molecule-drug conjugate (ADC) comprising an antibody molecule and a covalently coupled peptide (e.g., an antimicrobial peptide), wherein the antibody molecule comprises a heavy chain variable region (VH), wherein the VH comprises three heavy chain complementarity determining regions (HCDR1, HCDR2, and HCDR3), and wherein the VH comprises:

(a) an HCDR1 comprising the amino acid sequence of SEQ ID NO: 105; an HCDR2 comprising the amino acid sequence of SEQ ID NO: 106; and an HCDR3 comprising the amino acid sequence of SEQ ID NO: 107, or (b) an HCDR1 comprising the amino acid sequence of SEQ ID NO: 108; an HCDR2 comprising the amino acid sequence of SEQ ID NO: 146; and an HCDR3 comprising the amino acid sequence of SEQ ID NO: 107; and wherein the antibody molecule comprises a light chain variable region (VL), wherein the VL comprises three light chain complementarity determining regions (LCDR1, LCDR2, and LCDR3), and wherein the VL comprises:

(a) an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112, or (b) an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112. In an embodiment, the peptide comprises the amino acid sequence of SEQ ID NO: 257 or an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO: 257. In an embodiment, the ADC has a peptide-to-antibody ratio of about two. In an embodiment, the peptide comprises the amino acid sequence of SEQ ID NO: 156 or an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO: 156. In an embodiment, the ADC has a peptide-to-antibody ratio of about four. In an embodiment, the peptide comprises or consists of D-amino acids.

In an embodiment, the VH comprises an HCDR1 comprising the amino acid sequence of SEQ ID NO: 105; an HCDR2 comprising the amino acid sequence of SEQ ID NO: 106; and an HCDR3 comprising the amino acid sequence of SEQ ID NO: 107; and the VL comprises an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112. In an embodiment, the VH comprises an HCDR1 comprising the amino acid sequence of SEQ ID NO: 108; an HCDR2 comprising the amino acid sequence of SEQ ID NO: 146; and an HCDR3 comprising the amino acid sequence of SEQ ID NO: 107; and the VL comprises an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112. In an embodiment, the peptide comprises the amino acid sequence of SEQ ID NO: 257 or an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO: 257. In an embodiment, the ADC has a peptide-to-antibody ratio of about two. In an embodiment, the peptide comprises the amino acid sequence of SEQ ID NO: 156 or an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO: 156. In an embodiment, the ADC has a peptide-to-antibody ratio of about four. In an embodiment, the peptide comprises or consists of D-amino acids.

In some embodiments, the VH comprises the amino acid sequence of SEQ ID NO 117, or an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO 117.

In an embodiment, the VH comprises the amino acid sequence of SEQ ID NO 117.

In an embodiment, the VL comprises the amino acid sequence of SEQ ID NO 135, or an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO 135.

In an embodiment, the VL comprises the amino acid sequence of SEQ ID NO: 135.

In an embodiment, the peptide comprises the amino acid sequence of SEQ ID NO: 257 or an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO: 257. In an embodiment, the ADC has a peptide-to-antibody ratio of about two. In an embodiment, the peptide comprises the amino acid sequence of SEQ ID NO: 156 or an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO: 156. In an embodiment, the ADC has a peptide-to-antibody ratio of about four. In an embodiment, the peptide comprises or consists of D-amino acids.

In an embodiment, the antibody molecule or ADC comprises the HCDR2 sequon Xaa-Xaa-Gly-Gly-(Ser/Thr/Gly).

In an embodiment, the antibody molecule is capable of binding to *Pseudomonas*. In an embodiment, the antibody molecule is capable of binding to *Pseudomonas aeruginosa*. In an embodiment, the antibody molecule is capable of binding to lipopolysaccharide (LPS) on *Pseudomonas*. In an embodiment, the antibody molecule is capable of binding to an inner core (e.g., an inner core glycan moiety) on LPS on *Pseudomonas*. In an embodiment, the antibody molecule does not bind, or does not substantially bind, to *E coli* LPS, e.g., as determined by Western blot. In an embodiment, the antibody molecule does not bind, or does not substantially bind, to heptose or a mono-phosphorylated heptose analog (e.g., 2-P-Hep or 4-P-Hep), e.g., as determined by a Biolayer Interferometry analysis.

In an embodiment, the antibody molecule binds to di-phosphorylated 2,4-P-Hep monosaccharide, e.g., as determined by a Biolayer Interferometry analysis. In an embodiment, the antibody molecule binds to di-phosphorylated mannose (2,4-P-Man), e.g., with reduced binding compared to di-phosphorylated 2,4-P-Hep monosaccharide, e.g., as determined by a Biolayer Interferometry analysis. In an embodiment, the antibody molecule binds to di-phosphorylated heptose, e.g., di-phosphorylated 2,4,-P-Hep monosaccharide, e.g., as determined by $^1$H-Saturation Transfer Difference (STD) NMR spectra. In an embodiment, the antibody molecule binds only to di-phosphorylated heptose, e.g., di-phosphorylated 2,4,-P-Hep monosaccharide, e.g., as determined by $^1$H-Saturation Transfer Difference (STD)

NMR spectra. In an embodiment, the antibody molecule binds to one or more *P. aeruginosa* strains described herein, e.g., one or more strains resistant to carbapenems, anti-*pseudomonas* third generation cephalosporins or fluoroquinolones, e.g., with an apparent avidity of about 20 to about 150 pM (e.g., about 50 to about 120 pM), e.g., as determined by a whole bacterial cell ELISA. In an embodiment, the antibody molecule kills one or more *P. aeruginosa* strains described herein, e.g., one or more strains resistant to carbapenems. In an embodiment, the antibody molecule kills a *P. aeruginosa* strain resistant to cephalosporin and/or a fluoroquinolone, e.g., at a concentration of 1 to 10 µg/mL (e.g., 1-2 µg/mL, 2-5 µg/mL, or 5-10 µg/mL) or 5-50 nM (e.g., 5-10 nM, 10-20 nM, 20-30 nM, 30-40 nM, 40-45 nM, or 45-50 nM).

In an embodiment, the antibody molecule does not bind to a gram-negative bacteria (e.g., a pathogenic gram-negative bacteria). In an embodiment, the antibody molecule does not bind, or does not substantially bind, to one or more of *Escherichia coli, Klebsiella pneumoniae, Salmonella typhimurium*, a gram-positive bacteria, or a mammalian cell, e.g., as determined by a whole cell ELISA. In an embodiment, the antibody molecule or ADC binds to over 100 *P. aeruginosa* strains. In an embodiment, the antibody molecule binds to a *Pseudomonas* species other than *Pseudomonas aeruginosa*, e.g., one or more of *Pseudomonas fluorescens, Pseudomonas putida*, or *Pseudomonas stutzeri*, e.g., as determined by a whole bacterial cell ELISA, flow cytometry, and/or electron microscopy.

In an embodiment, the antibody molecule is a monoclonal antibody molecule, a humanized antibody molecule, an isolated antibody molecule, or a synthetic antibody molecule. In an embodiment, the antibody molecule comprises two VHs and two VLs. In an embodiment, the antibody molecule further comprises a heavy chain constant region of an IgG1, IgG2, IgG3, or IgG4.

In an embodiment, the antibody molecule further comprises a light chain constant region of a kappa or lambda chain. In an embodiment, the ADC (e.g., as described herein) or the antibody molecule (e.g., as described herein) comprises a Fab, a F(ab')2, an Fv, or a single chain Fv fragment (scFv).

In an embodiment, the peptide comprises the amino acid sequence of SEQ ID NO 257. In an embodiment, the peptide comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33, D-amino acids, or at least 10%, 20%, 30%, 40%, 50%, 60%, 70%, 80%, 90%, 95%, or 100%, of the amino acid residues in the peptide are D-amino acids. In an embodiment, all of the amino acid residues in the peptide are D-amino acids. In an embodiment, the peptide is coupled to the VH, e.g., the C-terminus of the VH, e.g., indirectly (e.g., via a constant region, a linker, or both). In an embodiment, the peptide is coupled to the antibody molecule by an enzymatic ligation, e.g., using Sortase A (SrtA), e.g., via a sortase recognition sequence (e.g., LPETGGG (SEQ ID NO: 244)).

In an embodiment, the peptide comprises a sortase donor sequence, e.g., N-terminal GGG. In an embodiment, the peptide is attached to the C-terminus, the N-terminus, or both the C-terminus and N-terminus of a light chain of the antibody molecule. In an embodiment, the peptide is attached to the C-terminus, the N-terminus, or both the C-terminus and N-terminus of a heavy chain of the antibody molecule. In an embodiment, the peptide is attached to the C-terminus, the N-terminus, or both the C-terminus and N-terminus of both the light and heavy chains of the antibody molecule. In an embodiment, the ADC comprises a linker, e.g., a (Gly-Ser)n linker sequence, where n=2 to 20 (SEQ ID NO: 262), between the antibody molecule and the peptide. In an embodiment, the ADC has a peptide-to-antibody molecule ratio between about 2 and about 8, e.g., between about 2 and about 4, e.g., as determined by mass spectrometry. In an embodiment, the ADC has a peptide-to-antibody molecule ratio of about 2, e.g., as determined by mass spectrometry.

In an embodiment, the ADC has an in vitro bactericidal activity against *P. aeruginosa* at a concentration of about 2 µg/mL to about 50 µg/mL, e.g., about 3.1 µg/mL to about 25 µg/mL. In an embodiment, the ADC has an in vitro bactericidal activity against *P. aeruginosa* at a concentration of about 0.01 µg/mL to about 2 µg/mL (e.g., about 0.1 µg/mL to about 2 µg/mL, about 0.1 µg/mL to about 1.5 µg/mL, about 0.01 µg/mL to about 1.5 µg/mL, about 0.5 µg/mL to about 1.5 µg/mL). In an embodiment, the ADC has an in vitro bactericidal activity against *P. aeruginosa* at a concentration of about 1 µg/mL (e.g., about 0.5, 0.6, 0.7, 0.8, 0.9, 1.0, 1.1, 1.2, 1.3, 1.4, or 1.5 µg/mL). In an embodiment, the ADC induces killing of about 5-50% of *P. aeruginosa* cells (e.g., about 5-40%, 5-30%, 5-20%, 10-40%, 15-40%, 10-30%, 15-25% of *P. aeruginosa* cells). In an embodiment, the ADC induces killing of about 20% of *P. aeruginosa* cells (e.g., about 10, 15, 16, 17, 18, 19, 20, 21, 22, 23, 24, 25, or 30% of *P. aeruginosa* cells). In an embodiment, the ADC induces killing of about 20% at about 1 µg/mL. In an embodiment, the ADC has an in vitro bactericidal activity against *P. aeruginosa* at a concentration that differs by 50% or less, e.g., 45%, 40%, 35%, 30%, 25%, 20%, 15%, 10%, or less, compared to a reference ADC, e.g., VSX-1. In an embodiment, the ADC has a mean lytic concentration (MLC) of about 50014/mL or more, e.g., 800 µg/mL or more, for *P. aeruginosa*. In an embodiment, the ADC has an MLC that differs by 50% or less, e.g., 45%, 40%, 35%, 30%, 25%, 20%, 15%, 10%, or less, compared to a reference ADC, e.g., VSX-1, for *P. aeruginosa*. In an embodiment, the ADC has a CC50 (the concentration at which 50% cytotoxicity of mammalian cells is observed) of about 500 µg/mL or more, e.g., 800 µg/mL or more, for *P. aeruginosa*. In an embodiment, the ADC has a CC50 that is higher, e.g., at least 0.5, 1, 2, 3, 4, or 5-fold higher than a reference ADC, e.g., VSX-1, for *P. aeruginosa*. In an embodiment, the ADC inhibits LPS-mediated Toll-Like Receptor 4 (TLR4) activation, e.g., according to a HEK-blue reporter assay, e.g., as described in Example 4. In an embodiment, the ADC has an improved biodistribution compared to a reference ADC, e.g., VSX-1, e.g., as determined by pharmacokinetics measurements, whole body imaging, in vivo imaging, assessment of organ distribution (e.g., the ADC does not substantially or primarily distribute to the liver), ELISA, and/or mass spectrometry of blood samples.

In an aspect, the disclosure provides an ADC comprising an antibody molecule comprising two VHs and two VLs, wherein the VH is covalently coupled with a peptide comprises the amino acid sequence of SEQ ID NO: 257; and wherein the VH comprises an HCDR1 comprising the amino acid sequence of SEQ ID NO: 105; an HCDR2 comprising the amino acid sequence of SEQ ID NO: 106; and an HCDR3 comprising the amino acid sequence of SEQ ID NO: 107; and wherein the VL comprises an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112.

In an aspect, the disclosure provides an ADC comprising an antibody molecule comprising two VHs and two VLs, wherein the VH is covalently coupled with a peptide comprises the amino acid sequence of SEQ ID NO: 257; and wherein the VH comprises an HCDR1 comprising the amino acid sequence of SEQ ID NO: 108; an HCDR2 comprising the amino acid sequence of SEQ ID NO: 146; and an HCDR3 comprising the amino acid sequence of SEQ ID NO: 107; and wherein the VL comprises an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112. In an embodiment, the VH comprises the amino acid sequence of SEQ ID NO: 117, and the VL comprises the amino acid sequence of SEQ ID NO: 135. In an embodiment, the peptide is coupled to the C-terminus of the VH via a (Gly-Ser)n linker.

In an aspect, the disclosure provides a pharmaceutical composition comprising an ADC as described herein and a pharmaceutically acceptable carrier.

In an aspect, the disclosure provides an ADC or a pharmaceutical composition as described herein, for use in a method of treating or preventing a bacterial infection, e.g., associated with *Pseudomonas*, in a subject. In an embodiment, the bacterial infection is associated with *Pseudomonas aeruginosa*. In an embodiment, the bacterial infection is in the lung of the subject. In an embodiment, the ADC or pharmaceutical composition reduces bacterial load in the lung. In an embodiment, the ADC is administered at a dose of 1-10 mg/kg. In an embodiment, the ADC or composition is administered intravenously, subcutaneously, or intranasally or by inhalation. In an embodiment, the ADC or composition is administered prior to or after onset of a symptom associated with the bacterial infection. In an embodiment, the subject has one or more of: pneumonia, a urinary tract infection (UTI), septicemia, meningitis, diarrhea, a soft tissue infection, a skin infection, bacteremia, a respiratory system infection, endocarditis, an intra-abdominal infection, septic arthritis, osteomyelitis, a CNS infection, an ophthalmic infection, cholecystitis, cholangitis, meningitis, typhoid fever, food poisoning, gastroenteritis, enteric fever, shigellosis, a blood stream infection, intra-abdominal sepsis, a brain abscess, meningitis, sepsis, a joint infection, a bone infection, a gastrointestinal infection, or a wound infection. In an embodiment, the bacterial infection is a nosocomial infection or a hospital-acquired infection. In an embodiment, the subject is a human or an animal. In an embodiment, the subject is an immunocompromised patient or a health professional. In an embodiment, the subject has, or is at risk of having, an HIV infection or AIDS, a cancer, a solid organ transplantation, a stem cell transplantation, a sickle cell disease or asplenia, a congenital immune deficiency, a chronic inflammatory condition, a cochlear implant, malnutrition, or a cerebrospinal fluid leak. In an embodiment, the subject is 18 years old or younger, 15 years old or younger, 12 years old or younger, 9 years old or younger, or 6 years old or younger, or is at least 60 years old, at least 65 years old, at least 70 years old, at least 75 years old, or at least 80 years old. In an embodiment, the method further comprises administering to the subject a second antimicrobial agent or therapy.

In an embodiment, the second antimicrobial agent or therapy comprises an antibiotic or a phage therapy. In an embodiment, the antibiotic is a polymyxin (e.g., colistin) or β-lactam (e.g., carbapenem, e.g., meropenem). In an embodiment, the antibiotic is chosen from an aminoglycoside, an ansamycin, a carbacephem, a carbapenem, a cephalosporin, a glycopeptide, a lincosamide, a lipopeptide, a macrolide, a monobactam, a nitrofuran, an oxazolidinone, a penicillin, a penicillin combination, a polypeptide, a quinolone or fluoroquinolone, a sulfonamide, a tetracycline, or a drug against mycobacteria.

In an embodiment, wherein the antibiotic is chosen from amikacin, gentamicin, kanamycin, neomycin, netilmicin, tobramycin, paromomycin, streptomycin, spectinomycin, geldanamycin, herbimycin, or rifaximin, loracarbef, ertapenem, doripenem, imipenem/cilastatin, meropenem, cefadroxil, cefazolin, cefalotin, cefalothin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, penicillin g, temocillin, ticarcillin, amoxicillin/clavulanate, ampicillin/sulbactam, piperacillin/tazobactam, ticarcillin/clavulanate, bacitracin, colistin, polymyxin b, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (co-trimoxazole), sulfonamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, or trimethoprim. In an embodiment, the antibiotic is chosen from levofloxacin, ciprofloxacin, gentamicin, ceftriaxone, ofloxacin, amikacin, tobramycin, aztreonam, or imipenem/cilastatin. In an embodiment, the second antimicrobial agent or therapy is administered before the ADC is administered, concurrently with the administration of the ADC, or after the ADC is administered.

In an aspect, the disclosure provides a method of inhibiting or reducing a bacterial infection, the method comprising contacting a cell an ADC as described herein, or a pharmaceutical composition as described herein, in an amount effective to inhibit or reduce the bacterial infection. In an embodiment, the ADC or pharmaceutical composition is contacted with the cell in vitro, ex vivo, or in vivo.

In an aspect, the disclosure provides a kit comprising: an ADC as described herein or a pharmaceutical composition as described herein; and instructions for use of the ADC or pharmaceutical composition.

In an aspect, the disclosure provides a container comprising an ADC as described herein or a pharmaceutical composition as described herein.

In an aspect, the disclosure provides a nucleic acid molecule encoding:
(a) a VH, a VL, or both, of the antibody molecule of an ADC as described herein;
(b) the antimicrobial peptide of an ADC as described herein;
(c) both (a) and (b); or
(d) an ADC as described herein.

In an embodiment, a vector comprising the nucleic acid molecule as described herein. In an embodiment, a cell comprising the nucleic acid molecule or the vector as described herein. In an embodiment, a method of producing an ADC, the method comprising culturing the cell as described hereinunder conditions that allow production of an ADC, thereby producing the ADC. In an embodiment, a method of producing an ADC, the method comprising contacting an antibody molecule that binds to LPS with a peptide comprising an antimicrobial peptide, and optionally, a sortase donor sequence, in the presence of a sortase, under conditions that allow a sortase-mediated reaction to occur, thereby producing the ADC. In an embodiment, the antibody molecule comprises a sortase acceptor sequence comprising a sortase recognition sequence, a linker sequence, or both. In an embodiment, a method of treating or preventing a bacterial infection, comprising administering to a subject in need thereof an ADC as described herein, or a pharmaceutical composition as described herein, in an amount effective to treat or prevent the bacterial infection. In an embodiment, use of an ADC as described herein in the manufacture of a medicament for treating or preventing a bacterial infection.

Accordingly, in an aspect, the disclosure provides an antibody molecule-drug conjugate (ADC) comprising an anti-LPS antibody molecule (e.g., an anti-LPS antibody molecule described herein) and a covalently coupled antimicrobial peptide (e.g., an antimicrobial peptide described herein), wherein the antibody molecule comprises a modified sulfatase motif.

In an embodiment, the modified sulfatase motif has the formula:

$X_1(FGly')X_2Z_2X_3Z_3$ where FGly' has the formula:

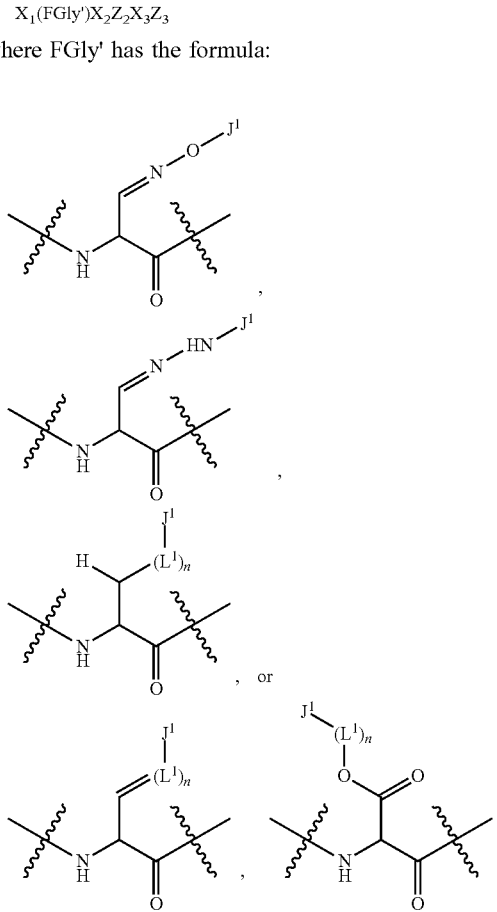

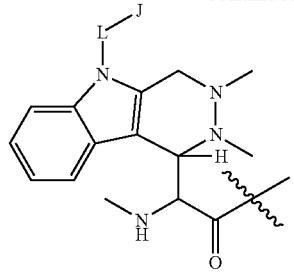

HIPS chemistry, wherein $J_1$ is the covalently coupled antimicrobial peptide;

each $L_1$ is a divalent moiety independently selected from alkylene, substituted alkylene, alkenylene, substituted alkenylene, alkynylene, alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;

n is a number selected from zero to 40;

$Z_2$ is a proline or alanine residue;

$X_1$ is present or absent and, when present, is any amino acid, with the proviso that when the sulfatase motif is at an N-terminus of the polypeptide, $X_1$ is present;

$X_2$ and $X_3$ are each independently any amino acid; and $Z_3$ is a basic amino acid.

In an embodiment, the antibody molecule presents the covalently coupled antimicrobial peptide on a solvent-accessible surface when in a folded state.

In an embodiment, the modified sulfatase motif is a heterologous modified sulfatase motif. In an embodiment, the modified sulfatase motif comprises or consists of 12 or less (e.g., 11 or less, 10 or less, 9 or less, 8 or less, 7 or less, or 6 or less) amino acid residues.

In an embodiment, the modified sulfatase motif is located in the ADC at an N-terminus of an antibody molecule chain, a C-terminus of an antibody molecule chain, or a solvent-accessible loop of the antibody molecule. In an embodiment, the modified sulfatase motif is located in a heavy chain (or a fragment thereof) of the antibody molecule. In an embodiment, the modified sulfatase motif is located in a constant region of the heavy chain (e.g., CH1, CH2, or CH3). In an embodiment, the modified sulfatase motif is located at a terminus (e.g., C-terminus) of the heavy chain constant region. In an embodiment, the sulfatase motif is located in a region in the heavy chain constant region other than a terminus (e.g., C-terminus) of the heavy chain constant region. In an embodiment, the modified sulfatase motif is located in a light chain (or a fragment thereof) of the antibody molecule. In an embodiment, the modified sulfatase motif is located in a constant region of a light chain. In an embodiment, the modified sulfatase motif is located at a terminus (e.g., C-terminus) of the light chain constant region. In an embodiment, the sulfatase motif is located in a region in the light chain constant region other than a terminus (e.g., C-terminus) of the light chain constant region.

In an embodiment, the ADC comprises a plurality of modified sulfatase motifs. In an embodiment, the ADC comprises two or more (e.g., 3, 4, 5, 6, 7, 8, or more) modified sulfatase motifs. In an embodiment, the ADC comprises three or more (e.g., 4, 5, 6, 7, 8, or more) modified sulfatase motifs. In an embodiment, the ADC comprises four or more (e.g., 5, 6, 7, 8, or more) modified sulfatase motifs. In an embodiment, the ADC comprises four modified sulfatase motif.

In an embodiment, the modified sulfatase motifs are located in the ADC at an N-terminus of an antibody molecule chain, a C-terminus of an antibody molecule chain, or a solvent-accessible loop of the antibody molecule. In an embodiment, the modified sulfatase motifs are located in a heavy chain (or a fragment thereof), a light chain (or a fragment thereof), or both, of the antibody molecule. In an embodiment, the modified sulfatase motifs are located in a constant region of the heavy chain (e.g., one or more of CH1, CH2, or CH3), a constant region of the light chain, or both. In an embodiment, the antibody molecule or ADC comprises two or more heavy chains, each comprising a modified sulfatase motif. In an embodiment, the antibody molecule or ADC comprises two or more light chains, each comprising a modified sulfatase motif. In an embodiment, the antibody molecule or ADC comprises two heavy chains and two light chains, each heavy chain comprising two modified sulfatase motifs (e.g., one in CH1 and one in CH3, one in CH1 and one in CH2, or one in CH2 and one in CH3).

In an embodiment, the modified sulfatase motifs are provided as a concatamer comprising modified sulfatase motifs separated by a flexible linker.

In an embodiment, $Z_3$ is arginine (R). In an embodiment, $X_1$, when present, $X_2$, and $X_3$ are each independently an aliphatic amino acid, a sulfur-containing amino acid, or a polar, uncharged amino acid. In an embodiment, $X_1$, when present, is L, M, V, S or T. In an embodiment, $X_2$ and $X_3$ are each independently S, T, A, V, G, or C. In an embodiment, the modified sulfatase motif has the formula: L(FGly')TPSR (SEQ ID NO: 168).

In another aspect, the disclosure features an aldehyde-tagged anti-LPS antibody molecule (e.g., an anti-LPS antibody molecule described herein) comprising a sulfatase motif having an amino acid sequence of:

$X_1Z_1X_2Z_2X_3Z_3$ where
$Z_1$ is a cysteine, a serine, or a 2-formylglycine residue;
$Z_2$ is a proline or alanine residue;
$X_1$ is present or absent and, when present, is any amino acid, with the proviso that when the heterologous sulfatase motif is at an N-terminus of the aldehyde tagged polypeptide, $X_1$ is present; and
$X_2$ and $X_3$ are each independently any amino acid; and
$Z_3$ is a basic amino acid.

In an embodiment, the antibody molecule is capable of presenting a covalently coupled antimicrobial peptide on a solvent-accessible surface when in a folded state.

In an embodiment, the sulfatase motif is a heterologous sulfatase motif. In an embodiment the sulfates motif is an unmodified sulfatase motif. In another embodiment, the sulfatase motif is a modified sulfatase motif. In an embodiment, the sulfatase motif comprises or consists of 12 or less (e.g., 11 or less, 10 or less, 9 or less, 8 or less, 7 or less, or 6 or less) amino acid residues.

In an embodiment, the sulfatase motif is located at an N-terminus of an antibody molecule chain, a C-terminus of an antibody molecule chain, or a solvent-accessible loop of the antibody molecule. In an embodiment, the sulfatase motif is located in a heavy chain (or a fragment thereof) of the antibody molecule. In an embodiment, the sulfatase motif is located in a constant region of the heavy chain (e.g., CH1, CH2, or CH3). In an embodiment, the sulfatase motif is located at a terminus (e.g., C-terminus) of the heavy chain constant region. In an embodiment, the sulfatase motif is located in a region in the heavy chain constant region other than a terminus (e.g., C-terminus) of the heavy chain constant region. In an embodiment, the sulfatase motif is located in a light chain (or a fragment thereof) of the antibody molecule. In an embodiment, the sulfatase motif is located in a constant region of a light chain. In an embodiment, the sulfatase motif is located at a terminus (e.g., C-terminus) of the light chain constant region. In an embodiment, the sulfatase motif is located in a region in the light chain constant region other than a terminus (e.g., C-terminus) of the light chain constant region.

In an embodiment, the antibody molecule comprises a plurality of sulfatase motifs. In an embodiment, the antibody molecule comprises two or more (e.g., 3, 4, 5, 6, 7, 8, or more) sulfatase motifs. In an embodiment, the antibody molecule comprises three or more (e.g., 4, 5, 6, 7, 8, or more) modified sulfatase motifs. In an embodiment, the antibody molecule comprises four or more (e.g., 5, 6, 7, 8, or more) modified sulfatase motifs. In an embodiment, the antibody molecule comprises four modified sulfatase motif.

In an embodiment, the sulfatase motifs are located at an N-terminus of an antibody molecule chain, a C-terminus of an antibody molecule chain, or a solvent-accessible loop of the antibody molecule. In an embodiment, the sulfatase motifs are located in a heavy chain (or a fragment thereof), a light chain (or a fragment thereof), or both, of the antibody molecule. In an embodiment, the sulfatase motifs are located in a constant region of the heavy chain (e.g., one or more of CH1, CH2, or CH3), a constant region of the light chain, or both. In an embodiment, the antibody molecule comprises two or more heavy chains, each comprising a sulfatase motif. In an embodiment, the antibody molecule comprises two or more light chains, each comprising a modified sulfatase motif. In an embodiment, the antibody molecule comprises two heavy chains and two light chains, each heavy chain comprising two modified sulfatase motifs (e.g., one in CH1 and one in CH3, one in CH1 and one in CH2, or one in CH2 and one in CH3).

In an embodiment, the sulfatase motifs are provided as a concatamer comprising modified sulfatase motifs separated by a flexible linker.

In an embodiment, $Z_3$ is arginine (R). In an embodiment, $X_1$, when present, $X_2$, and $X_3$ are each independently an aliphatic amino acid, a sulfur-containing amino acid, or a polar, uncharged amino acid. In an embodiment, $X_1$, when present, is L, M, V, S or T. In an embodiment, $X_2$ and $X_3$ are each independently S, T, A, V, G, or C. In an embodiment, the modified sulfatase motif has the formula: LCTPSR (SEQ ID NO: 169).

In an aspect, the disclosure provides a method of producing an ADC comprising contacting an aldehyde-tagged anti-LPS antibody molecule (e.g., an aldehyde-tagged anti-LPS antibody molecule described herein) and an antimicrobial peptide (e.g., an antimicrobial peptide described herein) under conditions that allows a reaction between an aldehyde of the antibody molecule and a reactive group of the antimicrobial peptide to occur, thereby producing the ADC.

In an embodiment, the aldehyde-tagged antibody molecule comprises a 2-formyl-glycine residue (e.g., FGly' at $Z_1$). In an embodiment, the antimicrobial peptide comprises an aminooxy or hydrazide reactive group.

In an embodiment, the method comprises combining in a reaction mixture the aldehyde-tagged antibody molecule and the antimicrobial peptide.

In an embodiment, the antimicrobial peptide is contacted with the antibody molecule, or is provided in the reaction mixture, in an amount sufficient to provide for a desired ratio of antimicrobial peptide to antibody molecule. In an embodiment, the ratio of antimicrobial peptide to antibody molecule is about 1:1, 2:1, 3:1, 4:1, 5:1, 6:1, 7:1, 8:1, or more. In an embodiment, the ratio of antimicrobial peptide to antibody molecule is about 4:1.

In an embodiment, the aldehyde-tagged antibody molecule and antimicrobial peptide is coupled by the Hydrazino-iso-Pictet-Spengler (HIPS) ligation. In another embodiment, the aldehyde-tagged antibody molecule and antimicrobial peptide is coupled by conjugation with oximes and hydrazides following by reduction.

In an embodiment, the method further comprises isolating (e.g., purifying) the ADC, e.g., from the reaction mixture. In an embodiment, the aldehyde-tagged antibody molecule is folded before the aldehyde-tagged antibody molecule is contacted with the antimicrobial peptide (e.g., before the aldehyde-tagged antibody molecule is combined with the antimicrobial peptide in the reaction mixture).

In an aspect, the disclosure provides an ADC produced by a method described herein.

In an aspect, the disclosure provides a composition (e.g., a pharmaceutical composition) comprising an ADC comprising an anti-LPS antibody molecule (e.g., an anti-LPS antibody molecule described herein) and a covalently coupled antimicrobial peptide (e.g., an antimicrobial peptide described herein) and a pharmaceutically acceptable carrier, wherein the antibody molecule comprises a modified sulfatase motif described herein.

In an aspect, the disclosure provides a reaction mixture comprising an ADC comprising an anti-LPS antibody molecule (e.g., an anti-LPS antibody molecule described herein) and an antimicrobial peptide (e.g., an antimicrobial peptide described herein), wherein the antibody molecule comprises a sulfatase motif (e.g., a modified sulfatase motif) described herein.

In an aspect, the disclosure features a method of treating or preventing a bacterial infection or a related disorder, comprising administering to a subject in need thereof an ADC, or a pharmaceutical composition comprising an ADC, in an amount effective to treat or prevent the bacterial infection or related disorder, wherein the ADC comprises an anti-LPS antibody molecule (e.g., an anti-LPS antibody molecule described herein) and a covalently coupled antimicrobial peptide (e.g., an antimicrobial peptide described herein), and wherein the antibody molecule comprises a modified sulfatase motif described herein.

In an embodiment, the bacterial infection is associated with a Gram-negative bacterium. In an embodiment, the bacterial infection is a *Pseudomonas* infection. In an embodiment, the bacterial infection is associated with *Pseudomonas aeruginosa*.

In an aspect, the disclosure features a nucleic acid comprising a nucleotide sequence encoding an aldehyde-tagged anti-LPS antibody molecule described herein.

In an aspect, the disclosure provides an antibody molecule or ADC binds to an epitope described herein. In an embodiment, the antibody molecule or ADC comprises a modified sulfatase motif (e.g., a modified sulfatase motif described herein).

In an aspect, the disclosure provides an ADC comprising an anti-LPS antibody molecule (e.g., an anti-LPS antibody molecule described herein) and a covalently coupled antimicrobial peptide (e.g., an antimicrobial peptide described herein), wherein the antimicrobial peptide is coupled to the antibody molecule via (a) lysine conjugation (e.g., using a surface exposed lysine as an antibody reactive group); (b) interchain disulfides (e.g., using disulfides linking HC-HC or HC-LC); (c) a non-native amino acid (e.g., an amino acid substituted with aldehyde, azide, or alkyne); or (d) a biodegradable polymer (e.g., lysine or thiol).

In an embodiment, the antimicrobial peptide is coupled to the antibody molecule via (a). In an embodiment, the antibody molecule is directly conjugated to an activated amino acid on the antimicrobial peptide. In an embodiment, a lysine on the antibody molecule is converted to a thiol reactive group and antibody molecule with the thiol reactive group is ligated to a thiolated antimicrobial peptide. In an embodiment, a lysine on the antibody molecule is converted to a free thiol and the antibody molecule with the free thiol is ligated to a thiol reactive antimicrobial peptide.

In an embodiment, the antimicrobial peptide is coupled to the antibody molecule via (b). In an embodiment, interchain disulfides of the antibody molecule are reduced and the antibody molecule with the reduced interchain disulfides is ligated to a thiol reactive antimicrobial peptide.

In an embodiment, the antimicrobial peptide is coupled to the antibody molecule via (c). In an embodiment, the antibody molecule is ligated to the antimicrobial peptide using click chemistry (Kolb et al. *Angew Chem Int Ed Engl.* 2001; 40(11):2004-2021; Evans *Australian Journal of Chemistry.* 2007; 60 (6): 384-395).

In an embodiment, the antimicrobial peptide is coupled to the antibody molecule via (d). In an embodiment, the antimicrobial peptide is ligated to a biodegradable polymer and the polymer is ligated to the antibody molecule.

In an embodiment, the ADC is provided in a composition (e.g., a pharmaceutical composition).

In an embodiment, the ADC or pharmaceutical composition is used for treating or preventing a bacterial infection (e.g., an infection is associated with a Gram-negative bacterium, e.g., *Pseudomonas aeruginosa*) or a related disorder in a subject.

Accordingly, in certain aspects, this disclosure provides an antibody molecule-drug conjugate (ADC), e.g., an ADC comprising an antibody molecule described herein and an antimicrobial peptide (e.g., an antimicrobial peptide described herein), having one or more (e.g., 1, 2, 3, 4, 5, 6, 7, 8, 9, 10, 11, 12, 13, 14, 15, 16, 17, 18, 19, 20, 21, 22, 23, 24, 25, 26, 27, or all) of the following properties:

a) Binds to one or more (e.g., 2, 3, 4, 5, 6, 7, 8, 9, 10, or more) Gram-negative bacteria of different genera, species, and/or subspecies (e.g., one or more bacteria from Enterobacteriaceae (e.g., *Klebsiella, Enterobacter, Shigella, Escherichia, Salmonella*, or *Citrobacter*, e.g., pan-resistant Enterobacteriaceae), one or more bacteria from *Pseudomonas*, one or more bacteria from *Acinetobacter*, or any combination thereof) with high affinity, e.g., with a dissociation constant ($K_D$) of less than about 100 nM, typically about 10 nM, and more typically, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, or 0.01 nM, b) Binds to lipopolysaccharide (LPS) with high affinity, e.g., with a dissociation constant ($K_D$) of less than about 100 nM, typically about 10 nM, and more typically, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, or 0.01 nM, c) Inhibits one or more (e.g., 2, 3, 4, 5, 6, 7, 8, 9, 10, or more) Gram-negative bacteria of different genera, species, and/or subspecies (e.g., one or more Gram-negative bacteria described herein), e.g., as determined by measuring the minimum inhibitory concentration (MIC) of the ADC, e.g., by a method described herein, d) Inhibits one or more (e.g., 2, 3, 4, 5, 6, 7, 8, 9, 10, or more) Gram-negative bacteria of different genera, species, and/or subspecies (e.g., one or more Gram-negative bacteria described herein) with a lower MIC compared to the antimicrobial peptide alone, e.g., at least 2, 3, 4, 5, 6, 7, 8, 9, 10, 20, 30, 40, 50, 60, 70, 80, 90, 100, 200, 500, 1,000-fold lowered MIC, e.g., on a molar basis, e.g., as measured by a method described herein, e) Reduces the viability of one or more (e.g., 2, 3, 4, 5, 6, 7, 8, 9, 10, or more) Gram-negative bacteria of different genera, species, and/or subspecies (e.g., one or more Gram-negative bacteria described herein), e.g., as determined by measuring the minimum bactericidal concentration (MBC), e.g., by a method described herein, f) Reduces the viability of one or more (e.g., 2, 3, 4, 5, 6, 7, 8, 9, 10, or more) Gram-negative bacteria of different genera, species, and/or subspecies (e.g., one or more Gram-negative bacteria described herein) with a lower MBC compared to the antimicrobial peptide alone, e.g., at least 2, 3, 4, 5, 6, 7, 8, 9, 10, 20, 30, 40, 50, 60, 70, 80, 90, 100, 200, 500, 1,000-fold lowered MBC, e.g., on a molar basis, e.g., as measured by a method described herein, g) Displays an opsonophagocytic activity (OPA), e.g., determined by an OPA assay, e.g., as described herein, h) Binds specifically to an epitope on LPS, e.g., the same or similar epitope as the epitope recognized by an antibody molecule described in Table 1 or 3, e.g., mAb001 (e.g., a humanized mAb001), A001-25, hWN01, hWNv1, 3E7, 3G1, 2C7, or 3D6, i) Shows the same or similar binding affinity or specificity, or both, as an antibody molecule described in Table 1 or 3, e.g., mAb001 (e.g., a humanized mAb001), A001-25, hWN01, hWNv1, 3E7, 3G1, 2C7, or 3D6, j) Shows the same or similar binding affinity or specificity, or both, as an ADC comprising an antibody molecule described in Table 1 or 3, e.g., mAb001 (e.g., a humanized mAb001), A001-25, hWN01, hWNv1, 3E7, 3G1, 2C7, or 3D6, k) Shows the same or similar binding affinity or specificity, or both, as an antibody molecule comprising a heavy chain variable region and/or light chain variable region described in Table 1 or 3, e.g., a heavy chain variable region and/or light chain variable region of mAb001 (e.g., a humanized mAb001), A001-25, hWN01, hWNv1, 3E7, 3G1, 2C7, or 3D6, l) Shows the same or similar binding affinity or specificity, or both, as an ADC comprising a heavy chain variable region and/or light chain variable region described in Table 1 or 3, e.g., a heavy chain variable region and/or light chain variable region of mAb001 (e.g., a humanized mAb001), A001-25, hWN01, hWNv1, 3E7, 3G1, 2C7, or 3D6, m) Shows the same or similar binding affinity or specificity, or both, as an antibody molecule comprising one or more (e.g., two or three) heavy chain CDRs and/or one or more (e.g., two or three) light chain CDRs described in Table 1 or 3, e.g., one or more (e.g., two or three) heavy chain CDRs and/or one or more (two or three) light chain CDRs of mAb001 (e.g., a humanized mAb001), A001-25, hWN01, hWNv1, 3E7, 3G1, 2C7, or 3D6, n) Shows the same or similar binding affinity or specificity, or both, as an ADC comprising one or more (e.g., two or three) heavy chain CDRs and/or one or more (e.g., two or three) light chain CDRs described in Table 1 or 3, e.g., one or more (e.g., two or three) heavy chain CDRs and/or one or more (two or three) light chain CDRs of mAb001 (e.g., a humanized mAb001), A001-25, hWN01, hWNv1, 3E7, 3G1, 2C7, or 3D6, o) Shows the same or similar binding affinity or specificity, or both, as an antibody molecule comprising an amino acid sequence shown in Table 1 or 3, p) Shows the same or similar binding affinity or specificity, or both, as an ADC comprising an amino acid sequence shown in Table 1 or 3, q) Inhibits, e.g., competitively inhibits, the binding of a second antibody molecule to a Gram-negative bacterium, LPS, or both, wherein the second antibody molecule is an antibody molecule chosen from Table 1 or 3, e.g., mAb001 (e.g., a humanized mAb001), A001-25, hWN01, hWNv1, 3E7, 3G1, 2C7, or 3D6, r) Inhibits, e.g., competitively inhibits, the binding of a second ADC comprising a second antibody molecule to a Gram-negative bacterium, LPS, or both, wherein the second antibody molecule is an antibody molecule chosen from Table 1 or 3, e.g., mAb001 (e.g., a humanized mAb001), A001-25, hWN01, hWNv1, 3E7, 3G1, 2C7, or 3D6, s) Binds the same or an overlapping epitope as a second antibody molecule, wherein the second antibody molecule is an antibody molecule chosen from Table 1 or 3, e.g., mAb001 (e.g., a humanized mAb001), A001-25, hWN01, hWNv1, 3E7, 3G1, 2C7, or 3D6, t) Binds the same or an overlapping epitope with a second ADC comprising a second antibody molecule, wherein the second antibody molecule is an antibody molecule chosen from Table 1 or 3, e.g., mAb001 (e.g., a humanized mAb001), A001-25, hWN01, hWNv1, 3E7, 3G1, 2C7, or 3D6, u) Competes for binding with a second antibody molecule to a Gram-negative bacterium, LPS, or both, wherein the second antibody molecule is an antibody molecule chosen from Table 1 or 3, e.g., mAb001 (e.g., a humanized mAb001), A001-25, hWN01, hWNv1, 3E7, 3G1, 2C7, or 3D6, v) Competes for binding with a second ADC comprising a second ADC to a Gram-negative bacterium, LPS, or both, wherein the second antibody molecule is an antibody molecule chosen from Table 1 or 3, e.g., mAb001 (e.g., a humanized mAb001), A001-25, hWN01, hWNv1, 3E7, 3G1, 2C7, or 3D6, w) Has one or more biological properties of an antibody molecule chosen from Table 1 or 3, e.g., mAb001 (e.g., a humanized mAb001), A001-25, hWN01, hWNv1, 3E7, 3G1, 2C7, or 3D6, x) Has one or more biological properties of an ADC comprising an antibody molecule chosen from Table 1 or 3, e.g., mAb001 (e.g., a humanized mAb001), A001-25, hWN01, hWNv1, 3E7, 3G1, 2C7, or 3D6, y) Has one or more pharmacokinetic properties of ADC comprising an antibody molecule chosen from Table 1 or 3, e.g., mAb001 (e.g., a humanized mAb001), A001-25, hWN01, hWNv1, 3E7, 3G1, 2C7, or 3D6, z) Reduces the viability of Gram-negative bacteria from a first genus, species, or subspecies (e.g., *Pseudomonas*)

with high selectivity, compared to the reduction of viability of Gram-negative bacteria from a second genus, species, or subspecies (e.g., *E. coli, Klebsiella* spp., or both), e.g., at least at least 2, 5, 10, 20, 50, 100, 200, 500, or 1000 fold more in % killing, e.g., as determined by a mixed microbial killing assay described herein, aa) Binds to one or more *P. aeruginosa* strains with high affinity, e.g., with an avidity EC 50 of about 200 pM or less, e.g., less than about 150 pM or less, about 120 pM or less, about 100 pM or less, about 80 pM or less, about 60 pM or less, or about 40 pM or less, e.g., between about 40 pM and about 120 pM, between about 50 pM and 110 pM, between about 60 pM and 100 pM, between about 40 pM and 80 pM, or between 80 pM and 120 pM, or bb) Inhibits one or more (e.g., 2, 3, 4, 5, 6, 7, 8, 9, 10, or more) Gram-negative bacteria of different genera, species, and/or subspecies (e.g., one or more Gram-negative bacteria described herein, e.g., *P. aeruginosa*) in vivo, e.g., at least 2, 5, 10, 20, 50, 100, 200, 500, 1000, or more fold reduction in bacterial burden, e.g., as determined using an animal model, e.g., a murine acute pneumonia model described herein.

Accordingly, in certain aspects, this disclosure provides an antibody molecule, e.g., an antibody molecule described herein, having one or more (e.g., 1, 2, 3, 4, 5, 6, 7, 8, 9, 10, 11, 12, 13, 14, 15, or all) of the following properties:

a) Binds to one or more (e.g., 2, 3, 4, 5, 6, 7, 8, 9, 10, or more) Gram-negative bacteria of different genera, species, and/or subspecies (e.g., one or more bacteria from Enterobacteriaceae (e.g., *Klebsiella, Enterobacter, Shigella, Escherichia, Salmonella,* or *Citrobacter,* e.g., pan-resistant Enterobacteriaceae), one or more bacteria from *Pseudomonas,* one or more bacteria from *Acinetobacter,* or any combination thereof) with high affinity, e.g., with a dissociation constant ($K_D$) of less than about 100 nM, typically about 10 nM, and more typically, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, or 0.01 nM, b) Binds to lipopolysaccharide (LPS) with high affinity, e.g., with a dissociation constant ($K_D$) of less than about 100 nM, typically about 10 nM, and more typically, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, or 0.01 nM, c) Displays an opsonophagocytosis activity (OPA), e.g., determined by an OPA assay, e.g., as described herein, d) Binds specifically to an epitope on LPS, e.g., the same or similar epitope as the epitope recognized by an antibody molecule described in Table 1 or 3, e.g., mAb001 (e.g., a humanized mAb001), A001-25, hWN01, hWNv1, 3E7, 3G1, 2C7, or 3D6, e) Shows the same or similar binding affinity or specificity, or both, as an antibody molecule described in Table 1 or 3, e.g., mAb001 (e.g., a humanized mAb001), A001-25, hWN01, hWNv1, 3E7, 3G1, 2C7, or 3D6, f) Shows the same or similar binding affinity or specificity, or both, as an ADC comprising an antibody molecule described in Table 1 or 3, e.g., mAb001 (e.g., a humanized mAb001), A001-25, hWN01, hWNv1, 3E7, 3G1, 2C7, or 3D6, g) Shows the same or similar binding affinity or specificity, or both, as an antibody molecule comprising a heavy chain variable region and/or light chain variable region described in Table 1 or 3, e.g., a heavy chain variable region and/or light chain variable region of mAb001 (e.g., a humanized mAb001), A001-25, hWN01, hWNv1, 3E7, 3G1, 2C7, or 3D6, h) Shows the same or similar binding affinity or specificity, or both, as an antibody molecule comprising one or more (e.g., two or three) heavy chain CDRs and/or one or more (e.g., two or three) light chain CDRs described in Table 1 or 3, e.g., one or more (e.g., two or three) heavy chain CDRs and/or one or more (two or three) light chain CDRs of mAb001 (e.g., a humanized mAb001), A001-25, hWN01, hWNv1, 3E7, 3G1, 2C7, or 3D6, i) Shows the same or similar binding affinity or specificity, or both, as an antibody molecule comprising an amino acid sequence shown in Table 1 or 3, j) Inhibits, e.g., competitively inhibits, the binding of a second antibody molecule to a Gram-negative bacterium, LPS, or both, wherein the second antibody molecule is an antibody molecule chosen from Table 1 or 3, e.g., mAb001 (e.g., a humanized mAb001), A001-25, hWN01, hWNv1, 3E7, 3G1, 2C7, or 3D6, k) Binds the same or an overlapping epitope as a second antibody molecule, wherein the second antibody molecule is an antibody molecule chosen from Table 1 or 3, e.g., mAb001 (e.g., a humanized mAb001), A001-25, hWN01, hWNv1, 3E7, 3G1, 2C7, or 3D6, l) Competes for binding with a second antibody molecule to a Gram-negative bacterium, LPS, or both, wherein the second antibody molecule is an antibody molecule chosen from Table 1 or 3, e.g., mAb001 (e.g., a humanized mAb001), A001-25, hWN01, hWNv1, 3E7, 3G1, 2C7, or 3D6, m) Has one or more biological properties of an antibody molecule chosen from Table 1 or 3, e.g., mAb001 (e.g., a humanized mAb001), A001-25, hWN01, hWNv1, 3E7, 3G1, 2C7, or 3D6, n) Has one or more biological properties of an antibody molecule chosen from Table 1 or 3, e.g., mAb001 (e.g., a humanized mAb001), A001-25, hWN01, hWNv1, 3E7, 3G1, 2C7, or 3D6, o) Has one or more pharmacokinetic properties of an antibody molecule chosen from Table 1 or 3, e.g., mAb001 (e.g., a humanized mAb001), A001-25, hWN01, hWNv1, 3E7, 3G1, 2C7, or 3D6, or p) Binds to one or more *P. aeruginosa* strains with high affinity, e.g., with an avidity $EC_{50}$ of about 200 pM or less, e.g., less than about 150 pM or less, about 120 pM or less, about 100 pM or less, about 80 pM or less, about 60 pM or less, or about 40 pM or less, e.g., between about 40 pM and about 120 pM, between about 50 pM and 110 pM, between about 60 pM and 100 pM, between about 40 pM and 80 pM, or between 80 pM and 120 pM.

In an aspect, the disclosure features an antibody molecule-drug conjugate (ADC) comprising a) an antibody molecule that binds to lipopolysaccharide (LPS) and b) an antimicrobial peptide.

In an embodiment, the ADC or antibody molecule binds to a core pentasaccharide region of the LPS. In an embodiment, the core pentasaccharide region comprises one or more (e.g., two) Kdo residues and one or more (e.g., two or three) Hep residues. In an embodiment, the ADC or antibody molecule binds to one or more (e.g., two) Kdo residues, or one or more (e.g., two or three) Hep residues, or any combination thereof.

In an embodiment, the ADC or antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody mAb001 or humanized mAb001 (e.g., SEQ ID NO: 108); an HCDR2 comprising an amino acid sequence that differs by no more than 1, 2, or 3 amino acid residues from, or has at least 85, 90, 95, 99 or 100% homology with, the amino acid sequence of the HCDR2 of antibody mAb001 or humanized mAb001 (e.g., any of SEQ ID NOS: 109, 145, or 146); or an HCDR3 comprising an amino acid sequence that differs by no more than 1, 2, or 3 amino acid residues from, or has at least 85, 90, 95, 99 or 100% homology with, the amino acid sequence of the HCDR3 of antibody mAb001 or humanized mAb001 (e.g., SEQ ID NO: 107).

In an embodiment, the heavy chain variable region comprises one, two, or all of the following: an HCDR1 comprising the amino acid sequence of the HCDR1 of antibody mAb001 or humanized mAb001 (e.g., SEQ ID NO: 108); an HCDR2 comprising the amino acid sequence of the HCDR2 of antibody mAb001 or humanized mAb001 (e.g., any of SEQ ID NOS: 109, 145, or 146); or an HCDR3 comprising the amino acid sequence of the HCDR3 of antibody mAb001 or humanized mAb001 (e.g., SEQ ID NO: 107).

In an embodiment, the heavy chain variable region comprises an HCDR1 comprising the amino acid sequence of the HCDR1 of antibody mAb001 or humanized mAb001 (e.g., SEQ ID NO: 108); an HCDR2 comprising the amino acid sequence of the HCDR2 of antibody mAb001 or humanized mAb001 (e.g., any of SEQ ID NOS: 109, 145, or 146); and an HCDR3 comprising the amino acid sequence of the HCDR3 of antibody mAb001 or humanized mAb001 (e.g., SEQ ID NO: 107).

In an embodiment, the ADC or antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody mAb001 or humanized mAb001 (e.g., any of SEQ ID NOS: 110, 138, 140, or 144); an LCDR2 comprising an amino acid sequence that differs by no more than 1, 2, or 3 amino acid residues from, or has at least 85, 90, 95, 99 or 100% homology with, the amino acid sequence of the LCDR2 of antibody mAb001 or humanized mAb001 (e.g., any of SEQ ID NOS: 111, 139, 141, 142, or 143); or an LCDR3 comprising an amino acid sequence that differs by no more than 1, 2, or 3 amino acid residues from, or has at least 85, 90, 95, 99 or 100% homology with, the amino acid sequence of the LCDR3 of antibody mAb001 or humanized mAb001 (e.g., SEQ ID NO: 112).

In an embodiment, the light chain variable region comprises one, two, or all of the following: an LCDR1 comprising the amino acid sequence of the LCDR1 of antibody mAb001 or humanized mAb001 (e.g., any of SEQ ID NOS: 110, 138, 140, or 144); an LCDR2 comprising the amino acid sequence of the LCDR2 of antibody mAb001 or humanized mAb001 (e.g., any of SEQ ID NOS: 111, 139, 141, 142, or 143); or an LCDR3 comprising the amino acid sequence of the LCDR3 of antibody mAb001 or humanized mAb001 (e.g., SEQ ID NO: 112).

In an embodiment, the light chain variable region comprises an LCDR1 comprising the amino acid sequence of the LCDR1 of antibody mAb001 or humanized mAb001 (e.g., any of SEQ ID NOS: 110, 138, 140, or 144); an LCDR2 comprising the amino acid sequence of the LCDR2 of antibody mAb001 or humanized mAb001 (e.g., any of SEQ ID NOS: 111, 139, 141, 142, or 143); and an LCDR3 comprising the amino acid sequence of the LCDR3 of antibody mAb001 or humanized mAb001 (e.g., SEQ ID NO: 112).

In an embodiment, the ADC or antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody mAb001 or humanized mAb001 (e.g., SEQ ID NO: 108); an HCDR2 comprising an amino acid sequence that differs by no more than 1, 2, or 3 amino acid residues from, or has at least 85, 90, 95, 99 or 100% homology with, the amino acid sequence of the HCDR2 of antibody mAb001 or humanized mAb001 (e.g., any of SEQ ID NOS: 109, 145, or 146); or an HCDR3 comprising an amino acid sequence that differs by no more than 1, 2, or 3 amino acid residues from, or has at least 85, 90, 95, 99 or 100% homology with, the amino acid sequence of the HCDR3 of antibody mAb001 or humanized mAb001 (e.g., SEQ ID NO: 107), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody mAb001 or humanized mAb001 (e.g., any of SEQ ID NOS: 110, 138, 140, or 144); an LCDR2 comprising an amino acid sequence that differs by no more than 1, 2, or 3 amino acid residues from, or has at least 85, 90, 95, 99 or 100% homology with, the amino acid sequence of the LCDR2 of antibody mAb001 or humanized mAb001 (e.g., SEQ ID NO: 111, 139, 141, 142, or 143); or an LCDR3 comprising an amino acid sequence that differs by no more than 1, 2, or 3 amino acid residues from, or has at least 85, 90, 95, 99 or 100% homology with, the amino acid sequence of the LCDR3 of antibody mAb001 or humanized mAb001 (e.g., SEQ ID NO: 112).

In an embodiment, the heavy chain variable region comprises one, two, or all of the following: an HCDR1 comprising the amino acid sequence of the HCDR1 of antibody mAb001 or humanized mAb001 (e.g., SEQ ID NO: 108); an HCDR2 comprising the amino acid sequence of the HCDR2 of antibody mAb001 or humanized mAb001 (e.g., any of SEQ ID NOS: 109, 145, or 146); or an HCDR3 comprising the amino acid sequence of the HCDR3 of antibody mAb001 or humanized mAb001 (e.g., SEQ ID NO: 107), and the light chain variable region comprises one, two, or all of the following: an LCDR1 comprising the amino acid sequence of the LCDR1 of antibody mAb001 or humanized mAb001 (e.g., any of SEQ ID NOS: 110, 138, 140, or 144); an LCDR2 comprising the amino acid sequence of the LCDR2 of antibody mAb001 or humanized mAb001 (e.g., any of SEQ ID NOS: 111, 139, 141, 142, or 143); or an LCDR3 comprising the amino acid sequence of the LCDR3 of antibody mAb001 or humanized mAb001 (e.g., SEQ ID NO: 112).

In an embodiment, the heavy chain variable region comprises an HCDR1 comprising the amino acid sequence of the HCDR1 of antibody mAb001 or humanized mAb001 (e.g., SEQ ID NO: 108); an HCDR2 comprising the amino acid sequence of the HCDR2 of antibody mAb001 or humanized mAb001 (e.g., any of SEQ ID NOS: 109, 145, or 146); and an HCDR3 comprising the amino acid sequence of the HCDR3 of antibody mAb001 or humanized mAb001 (e.g., SEQ ID NO: 107), and the light chain variable region comprises an LCDR1 comprising the amino acid sequence of the LCDR1 of antibody mAb001 or humanized mAb001 (e.g., any of SEQ ID NOS: 110, 138, 140, or 144); an LCDR2 comprising the amino acid sequence of the LCDR2 of antibody mAb001 or humanized mAb001 (e.g., any of SEQ ID NOS: 111, 139, 141, 142, or 143); and an LCDR3 comprising the amino acid sequence of the LCDR3 of antibody mAb001 or humanized mAb001 (e.g., SEQ ID NO: 112).

In an embodiment, the ADC or antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody mAb001 or humanized mAb001 (e.g., SEQ ID NO: 105); an HCDR2 comprising an amino acid sequence that differs by no more than 1, 2, or 3 amino acid residues from, or has at least 85, 90, 95, 99 or 100% homology with, the amino acid sequence of the HCDR2 of antibody mAb001 or humanized mAb001 (e.g., SEQ ID NO: 106); or an HCDR3 comprising an amino acid sequence that differs by no more than 1, 2, or 3 amino acid residues from, or has at least 85, 90, 95, 99 or 100% homology with, the amino acid sequence of the HCDR3 of antibody mAb001 or humanized mAb001 (e.g., SEQ ID NO: 107).

In an embodiment, the heavy chain variable region comprises one, two, or all of the following: an HCDR1 comprising the amino acid sequence of the HCDR1 of antibody mAb001 or humanized mAb001 (e.g., SEQ ID NO: 105); an HCDR2 comprising the amino acid sequence of the HCDR2 of antibody mAb001 or humanized mAb001 (e.g., SEQ ID NO: 106); or an HCDR3 comprising the amino acid sequence of the HCDR3 of antibody mAb001 or humanized mAb001 (e.g., SEQ ID NO: 107).

In an embodiment, the heavy chain variable region comprises an HCDR1 comprising the amino acid sequence of the HCDR1 of antibody mAb001 or humanized mAb001 (e.g., SEQ ID NO: 105); an HCDR2 comprising the amino acid sequence of the HCDR2 of antibody mAb001 or humanized mAb001 (e.g., SEQ ID NO: 106); and an HCDR3 comprising the amino acid sequence of the HCDR3 of antibody mAb001 or humanized mAb001 (e.g., SEQ ID NO: 107).

In an embodiment, the ADC or antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody mAb001 or humanized mAb001 (e.g., any of SEQ ID NOS: 110, 138, 140, or 144); an LCDR2 comprising an amino acid sequence that differs by no more than 1, 2, or 3 amino acid residues from, or has at least 85, 90, 95, 99 or 100% homology with, the amino acid sequence of the LCDR2 of antibody mAb001 or humanized mAb001 (e.g., any of SEQ ID NOS: 111, 139, 141, 142, or 143); or an LCDR3 comprising an amino acid sequence that differs by no more than 1, 2, or 3 amino acid residues from, or has at least 85, 90, 95, 99 or 100% homology with, the amino acid sequence of the LCDR3 of antibody mAb001 or humanized mAb001 (e.g., SEQ ID NO: 112).

In an embodiment, the light chain variable region comprises one, two, or all of the following: an LCDR1 comprising the amino acid sequence of the LCDR1 of antibody mAb001 or humanized mAb001 (e.g., any of SEQ ID NOS: 110, 138, 140, or 144); an LCDR2 comprising the amino acid sequence of the LCDR2 of antibody mAb001 or humanized mAb001 (e.g., any of SEQ ID NOS: 111, 139, 141, 142, or 143); or an LCDR3 comprising the amino acid sequence of the LCDR3 of antibody mAb001 or humanized mAb001 (e.g., SEQ ID NO: 112).

In an embodiment, the light chain variable region comprises an LCDR1 comprising the amino acid sequence of the LCDR1 of antibody mAb001 or humanized mAb001 (e.g., any of SEQ ID NOS: 110, 138, 140, or 144); an LCDR2 comprising the amino acid sequence of the LCDR1 of antibody mAb001 or humanized mAb001 (e.g., any of SEQ ID NOS: 111, 139, 141, 142, or 143); and an LCDR3 comprising the amino acid sequence of the LCDR1 of antibody mAb001 or humanized mAb001 (e.g., SEQ ID NO: 112).

In an embodiment, the ADC or antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody mAb001 or humanized mAb001 (e.g., SEQ ID NO: 105); an HCDR2 comprising an amino acid sequence that differs by no more than 1, 2, or 3 amino acid residues from, or has at least 85, 90, 95, 99 or 100% homology with, the amino acid sequence of the HCDR2 of antibody mAb001 or humanized mAb001 (e.g., SEQ ID NO: 106); or an HCDR3 comprising an amino acid sequence that differs by no more than 1, 2, or 3 amino acid residues from, or has at least 85, 90, 95, 99 or 100% homology with, the amino acid sequence of the HCDR3 of antibody mAb001 or humanized mAb001 (e.g., SEQ ID NO: 107), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody mAb001 or humanized mAb001 (e.g., any of SEQ ID NOS: 110, 138, 140, or 144); an LCDR2 comprising an amino acid sequence that differs by no more than 1, 2, or 3 amino acid residues from, or has at least 85, 90, 95, 99 or 100% homology with, the amino acid sequence of the LCDR2 of antibody mAb001 or humanized mAb001 (e.g., any of SEQ ID NOS: 111, 139, 141, 142, or 143); or an LCDR3 comprising an amino acid sequence that differs by no more than 1, 2, or 3 amino acid residues from, or has at least 85, 90, 95, 99 or 100% homology with, the amino acid sequence of the LCDR3 of antibody mAb001 or humanized mAb001 (e.g., SEQ ID NO: 112).

In an embodiment, the heavy chain variable region comprises one, two, or all of the following: an HCDR1 comprising the amino acid sequence of the HCDR1 of antibody mAb001 or humanized mAb001 (e.g., SEQ ID NO: 105); an HCDR2 comprising the amino acid sequence of the HCDR2 of antibody mAb001 or humanized mAb001 (e.g., SEQ ID NO: 106); or an HCDR3 comprising the amino acid sequence of the HCDR3 of antibody mAb001 or humanized mAb001 (e.g., SEQ ID NO: 107), and the light chain variable region comprises one, two, or all of the following: an LCDR1 comprising the amino acid sequence of the LCDR1 of antibody mAb001 or humanized mAb001 (e.g., any of SEQ ID NOS: 110, 138, 140, or 144); an LCDR2 comprising the amino acid sequence of the LCDR2 of antibody mAb001 or humanized mAb001 (e.g., any of SEQ ID NOS: 111, 139, 141, 142, or 143); or an LCDR3 comprising the amino acid sequence of the LCDR3 of antibody mAb001 or humanized mAb001 (e.g., SEQ ID NO: 112).

In an embodiment, the heavy chain variable region comprises an HCDR1 comprising the amino acid sequence of the HCDR1 of antibody mAb001 or humanized mAb001 (e.g., SEQ ID NO: 105); an HCDR2 comprising the amino acid sequence of the HCDR2 of antibody mAb001 or humanized mAb001 (e.g., SEQ ID NO: 106); and an HCDR3 comprising the amino acid sequence of the HCDR3 of antibody mAb001 or humanized mAb001 (e.g., SEQ ID NO: 107), and the light chain variable region comprises an LCDR1 comprising the amino acid sequence of the LCDR1 of antibody mAb001 or humanized mAb001 (e.g., any of SEQ ID NOS: 110, 138, 140, or 144); an LCDR2 comprising the amino acid sequence of the LCDR2 of antibody mAb001 or humanized mAb001 (e.g., any of SEQ ID NOS: 111, 139, 141, 142, or 143); and an LCDR3 comprising the amino acid sequence of the LCDR3 of antibody mAb001 or humanized mAb001 (e.g., SEQ ID NO: 112).

In an embodiment, the ADC or antibody molecule further comprises one or more human or human derived heavy or light chain variable region frameworks.

In an embodiment, the ADC or antibody molecule comprises a heavy chain variable region (VH), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of antibody mAb001 or humanized mAb001 (e.g., any of SEQ ID NOS: 103 or 115-118). In an embodiment, the heavy chain variable region comprises the amino acid sequence of the VH of antibody mAb001 or humanized mAb001 (e.g., any of SEQ ID NOs: 103 or 115-118).

In an embodiment, the ADC or antibody molecule comprises a light chain variable region (VL), wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of antibody mAb001 or humanized mAb001 (e.g., any of SEQ ID NOS: 104 or 119-137). In an embodiment, the light chain variable region comprises the amino acid sequence of the VL of antibody mAb001 or humanized mAb001 (e.g., any of SEQ ID NOS: 104 or 119-137).

In an embodiment, the ADC or antibody molecule comprises a heavy chain variable region (VH) and a light chain variable region (VL), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of antibody mAb001 or humanized mAb001 (e.g., any of SEQ ID NOS: 103 or 115-118), and wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of antibody mAb001 or humanized mAb001 (e.g., any of SEQ ID NOS: 104 or 119-137).

In an embodiment, the heavy chain variable region comprises the amino acid sequence of the VH of antibody mAb001 or humanized mAb001 (e.g., any of SEQ ID NOS: 103 or 115-118) and the light chain variable region comprises the amino acid sequence of the VL of antibody mAb001 or humanized mAb001 (e.g., any of SEQ ID NOS: 104 or 119-137).

In an embodiment, the ADC or antibody molecule comprises or consists of two heavy chain variable regions and two light chain variable regions. In an embodiment, the ADC or antibody molecule comprises a Fab, a F(ab')2, an Fv, or a single chain Fv fragment (scFv).

In an embodiment, the ADC or antibody molecule further comprises a heavy chain constant region, a light chain constant region, or both. In an embodiment, the ADC or antibody molecule is an IgG antibody molecule, e.g., IgG1, IgG2, IgG3, or IgG4 antibody molecule. In an embodiment, the antibody molecule is not an IgM antibody molecule. In an embodiment, the ADC or antibody molecule comprises a light chain constant region from a kappa or lambda light chain.

In an embodiment, the antibody molecule is a monoclonal antibody molecule. In an embodiment, the antibody molecule is a humanized antibody molecule. In an embodiment, the antibody molecule is an isolated antibody molecule. In an embodiment, the antibody molecule is a synthetic antibody molecule.

In an embodiment, the ADC or antibody molecule binds to one or more bacteria, e.g., one or more Gram-negative bacteria, e.g., of different genera, species, subspecies, and/or strains.

In an embodiment, the one or more Gram-negative bacteria are selected from a species of Enterobacteriaceae (e.g., a species in *Klebsiella, Enterobacter, Shigella, Escherichia, Salmonella, Yersinia*, or *Citrobacter*, e.g., pan-resistant Enterobacteriaceae), a species of *Pseudomonas*, a species of *Acinetobacter*, or any combination thereof.

In an embodiment, the ADC or antibody molecule binds to one or more of: *Klebsiella pneumonia* (e.g., *Klebsiella pneumoniae* subsp. *ozaenae, Klebsiella pneumoniae* subsp. *pneumoniae*, or *Klebsiella pneumoniae* subsp. *rhinoscleromatis*), *Enterobacter cancerogenous, Enterobacter cloacae, Enterobacter hormaechei, Enterobacter asburiae, Shigella boydii, Shigella dysenteriae, Shigella flexneri, Shigella sonnei, Escherichia coli* (e.g., *Escherichia coli* ATCC 11775, *Escherichia coli* ATCC 25922, *Escherichia coli* ATCC 35401, or *Escherichia coli* ATCC 43895), *Escherichia fergusonii, Salmonella choleraesuis, Salmonella choleraesuis* subsp. *indica, Salmonella enteritidis, Salmonella virchow, Salmonella paratyphi* B, *Salmonella typhimurium, Salmonella paratyphi* A, *Salmonella typhi, Salmonella choleraesuis* subsp. *arizonae, Salmonella choleraesuis* subsp. *diarizonae, Salmonella choleraesuis* subsp. *houtenae, Salmonella bongori, Citrobacter sedlakii, Citrobacter braakii, Citrobacter werkmanii, Citrobacter freundii, Citrobacter youngae, Citrobacter amalonaticus, Yersinia enterocolitica, Yersinia frederiksenii, Yersinia pestis, Yersinia pseudotuberculosis, Pseudomonas aeruginosa, Acinetobacter baumannii*, or any combination thereof. In an embodiment, the ADC or antibody molecule binds to *Pseudomonas aeruginosa*.

In an embodiment, the ADC or antibody molecule binds to a resistant *Pseudomonas aeruginosa* strain (e.g., resistant to one or more antibiotics described herein). In an embodiment, the ADC or antibody molecule binds to a mutant *Pseudomonas aeruginosa* strain. In an embodiment, the *Pseudomonas aeruginosa* strain has a mutation in a wapQ gene. In an embodiment, the *Pseudomonas aeruginosa* strain has a mutation in a galU gene.

In an embodiment, the one or more bacteria are one or more antibiotic-resistant bacteria, e.g., one or more multidrug-resistant Gram-negative bacteria.

In an embodiment, the one or more antibiotic-resistant bacteria are selected from *Pseudomonas* (e.g., *P. aeruginosa*), Enterobacteriaceae (e.g., *Klebsiella pneumonia* or *E. coli*), or *Acinetobacter* (e.g., *A. baumannii*).

In an embodiment, the ADC or antibody molecule binds to one or more of: *Enterococcus faecium* (e.g., vancomycin-resistant (VRE) *Enterococcus faecium*), *Staphylococcus aureus* (e.g., methicillin-resistant (MRSA) *Staphylococcus aureus*), *Clostridium difficile, Acinetobacter baumannii* (e.g., multidrug resistant (MDR) *Acinetobacter*), *Pseudomonas aeruginosa* (e.g., multidrug resistant (MDR) *P. aeruginosa*, e.g., carbapenem-resistant *P. aeruginosa*), Enterobacteriaceae (e.g., *E. coli, K. pneumoniae*, or *Enterobacter* spp., e.g., carbapenem-resistant Enterobacteriaceae (CRE)), *N. gonorrhoaeae* (e.g., drug-resistant *N. gonorrhoaeae*), *Salmonella* (e.g., drug resistant *Salmonella*), *Shigella* (e.g., drug-resistant *Shigella*), a bacterium producing an extended spectrum β-lactamase (ESBL), or *Mycobacterium tuberculosis* (e.g., drug-resistant *M. tuberculosis*).

In an embodiment, the ADC or antibody molecule binds to one or more (e.g., 2, 3, 4, 5, 6, 7, 8, 9, 10, or more) *P. aeruginosa* strains. In an embodiment, the ADC or antibody molecule binds to at least 23 *P. aeruginosa* strains. In another embodiment, the ADC or antibody molecule binds to one or more (e.g., 2, 3, 4, 5, 6, or more) multidrug-resistant *P. aeruginosa* strains.

In an embodiment, the ADC or antibody molecule binds to LPS with high affinity, e.g., with a $K_D$ that is less than about 10 nM, e.g., measured by an ELISA method.

In an embodiment, the ADC or antibody molecule binds to LPS with a $K_{off}$ slower than $1\times10^{-4}$, $5\times10^{-5}$, or $1\times10^{-5}$ $s^{-1}$. In an embodiment, the ADC or antibody molecule binds to LPS with a $K_{on}$ faster than $1\times10^4$, $5\times10^4$, $1\times10^5$, or $5\times10^5$ $M^{-1}s^{-1}$.

In an embodiment, the ADC or antibody molecule has opsonophagocytic activity, e.g., as determined by an OPA assay, e.g., as described herein.

In an embodiment, the ADC or antibody molecule (e.g., VSX-1) kills bacteria resulting in about a 1 log reduction (e.g., a 0.5, 0.6, 0.7, 0.8, 0.9, 1.0, 1.1, 1.2, 1.3, 1.4, or 1.5 log reduction) in the presence of heat-inactivated complement, e.g., about 10 μg/ml (e.g., 5, 5.5, 6, 6.5, 7, 7.5, 8, 8.5, 9, 9.5, 10, 10.5, 11, 11.5, 12, 12.5, 13, 13.5, 14, 14.5, or 15 μg/ml). In an embodiment, the ADC or antibody molecule kills bacteria resulting in more than about a 3 log (e.g., a 2, 2.5, 3, 3.5, 4 log) killing activity with non-heat inactivated complement, in the presence of polymorphonuclear neutrophils.

In an embodiment, the ADC or antibody molecule does not have detectable hemolytic activity. In an embodiment, the ADC or antibody molecule has minimal hemolytic activity. In an embodiment, the antibody molecule, (e.g., VSX-1), does not have detectable cytotoxic activity against mammalian cells (e.g., 293T cells). In an embodiment, the antibody molecule, (e.g., VSX-1), has negligible cytotoxic activity against mammalian cells (e.g., 293T cells).

In an embodiment, the ADC or antibody molecule (e.g., VSX-1) exhibits synergistic activity with an antibiotic, e.g., an anti-*Pseudomonas* antibiotic. In an embodiment, the activity of a combination of the ADC or antibody molecule and the antibiotic is greater than the activity of either the ADC or antibody molecule, or the antibiotic, alone.

In an embodiment, the ADC or antibody molecule binds to an epitope comprising one or more (e.g., two) Kdo residues and/or one or more (e.g., two or three) Hep residues in LPS.

In an embodiment, a) the antibody molecule that binds to lipopolysaccharide (LPS) is coupled (e.g., fused) to b) the antimicrobial peptide.

In an embodiment, the antibody molecule comprises a heavy chain variable region (VH), wherein the heavy chain variable region is coupled (e.g., fused) to the antimicrobial peptide. In an embodiment, the heavy chain variable region is N-terminal to the antimicrobial peptide. In another embodiment, the heavy chain variable region is C-terminal to the antimicrobial peptide. In an embodiment, the VH is fused to the antimicrobial peptide to form a fusion polypeptide, e.g., encoded by an open reading frame.

In an embodiment, the heavy chain variable region is coupled (e.g., fused) to the antimicrobial peptide indirectly, e.g., wherein the C-terminus of the heavy chain variable region is coupled (e.g., fused) to the N-terminus of the antimicrobial peptide via a constant region, a linker, or both.

In an embodiment, the antibody molecule comprises a light chain variable region (VL), wherein the light chain variable region is coupled (e.g., fused) to the antimicrobial peptide. In an embodiment, the light chain variable region is N-terminal to the antimicrobial peptide. In another embodiment, the heavy chain variable region is C-terminal to the antimicrobial peptide. In an embodiment, the VL is fused to the antimicrobial peptide to form a fusion polypeptide, e.g., encoded by an open reading frame.

In an embodiment, the light chain variable region is coupled (e.g., fused) to the antimicrobial peptide indirectly, e.g., wherein the C-terminus of the light chain variable region is coupled (e.g., fused) to the N-terminus of the antimicrobial peptide via a constant region, a linker, or both.

In an embodiment, the antibody molecule comprises a sortase acceptor sequence comprising a sortase recognition sequence. For example, the sortase recognition sequence can have the amino acid sequence of LPXTG (e.g., for *Staphylococcus aureus* sortase A) (SEQ ID NO: 160) or LPXTA (e.g., for *Streptococcus pyogenes* sortase A) (SEQ ID NO: 161), wherein X can be any amino acid residue. In an embodiment, the sortase recognition sequence is LPETG (SEQ ID NO: 162). The sortase acceptor sequence may contain additional sequence(s) other than the sortase recognition sequence. In an embodiment, the sortase acceptor sequence further comprises a linker sequence, e.g., a tandem repeat of glycine-serine peptide linker sequences (e.g., (GS) 15 (SEQ ID NO: 157)). In an embodiment, a heavy chain of the antibody molecule comprises a sortase acceptor sequence, e.g., at the C-terminus. In an embodiment, a light chain of the antibody molecule comprises a sortase acceptor sequence, e.g., at the C-terminus.

In an embodiment, a heavy chain of the antibody molecule comprises a first sortase acceptor sequence and a light chain of the antibody molecule comprises a second sortase acceptor sequence. In an embodiment, the sortase acceptor sequence, e.g., the first sortase recognition sequence, comprises the amino acid sequence of (GS)$_6$LPETGGG (SEQ ID NO: 24). In another embodiment, the sortase acceptor sequence, e.g., the second sortase acceptor sequence, comprises the amino acid sequence of P(G$_4$S)$_2$LPETGGSG (SEQ ID NO: 26).

In an embodiment, the ADC comprises a linker sequence, a sortase recognition sequence, or both, as described in FIG. 37. In an embodiment, the ADC comprises two heavy chains and two light chains. In an embodiment, each of the heavy chains of the ADC comprises a linker sequence, a sortase recognition sequence, or both, as described in FIG. 37. In an embodiment, each of the light chains of the ADC comprises a linker sequence, a sortase recognition sequence, or both, as described in FIG. 37.

In an embodiment, the ADC comprises two or more (e.g., three, four, five, six, seven, eight, or more) antimicrobial peptides. In an embodiment, the ADC comprises four antimicrobial peptides. In an embodiment, at least two of the antimicrobial peptides are identical or substantially identical. In an embodiment, at least two of the antimicrobial peptides are different. For example, a plurality of antimicrobial peptides can be coupled (e.g., fused) to the antibody molecule (e.g., a heavy chain (or a portion thereof), a light chain (or a portion thereof), or both).

In an embodiment, the ADC comprises two or more (e.g., three or four) identical, or substantially identical, antimicrobial peptides, each is coupled (e.g., fused) to a heavy chain variable region, e.g., indirectly, e.g., via a constant region, linker, or both. In an embodiment, the ADC comprises two or more (e.g., three or four) identical, or substantially identical, antimicrobial peptides, each is coupled (e.g., fused) to a light chain variable region, e.g., indirectly, e.g., via a constant region, linker, or both. In an embodiment, the ADC comprises two identical, or substantially identical, antimicrobial peptides, each is coupled (e.g., fused) to a heavy chain variable region, e.g., indirectly, e.g., via a constant region, linker, or both. In an embodiment, the ADC comprises two identical, or substantially identical, antimicrobial peptides, each is coupled (e.g., fused) to a light chain variable region, e.g., indirectly, e.g., via a constant region, linker, or both. In an embodiment, the ADC comprises at least four identical, or substantially identical, antimicrobial peptides. In an embodiment, the ADC or antibody molecule comprises two heavy chain variable regions and two light chain variable regions, and each of the heavy and light chain variable regions is coupled (e.g., fused) with at least one antimicrobial peptide, e.g., indirectly, e.g., via a constant region, linker, or both.

In an embodiment, the antimicrobial peptide is coupled to the antibody molecule by enzymatic conjugation (e.g., a sortase reaction). In an embodiment the antimicrobial peptide is coupled to the antibody molecule by chemical conjugation.

In an embodiment, the ADC is more effective in inhibiting, e.g., inhibiting the growth, virulence, or infectivity of, a Gram-negative bacterium (e.g., a Gram-negative bacterium described herein) than the antimicrobial peptide or antibody molecule alone, e.g., having a minimum inhibitory concentration (MIC) that is lower, e.g., at least 2, 3, 4, 5, 6, 7, 8, 9, 10, 20, 30, 40, 50, 60, 70, 80, 90, or 100 fold lower, than the MIC of the antimicrobial peptide alone.

In an embodiment, the ADC is more effective in reducing the viability of, e.g., killing, a Gram-negative bacterium (e.g., a Gram-negative bacterium described herein) than the antimicrobial peptide or antibody molecule alone, e.g., having a minimum bactericidal concentration (MBC) that is lower, e.g., at least 2, 3, 4, 5, 6, 7, 8, 9, 10, 20, 30, 40, 50, 60, 70, 80, 90, or 100 fold lower, than the MIC of the antimicrobial peptide alone.

In an embodiment, the ADC has opsonophagocytosis activity (e.g., is phagocytized when bound to the Fc receptor (FcR) of a neutrophil), e.g., as determined by an OPA assay, e.g., as described herein.

In an embodiment, the ADC does not inhibit, e.g., does not inhibit the growth, virulence, or infectivity of, a Gram-positive bacterium (e.g., a Gram-positive bacterium described herein), e.g., having a minimum inhibitory concentration (MIC) for a Gram-negative bacterium (e.g., a Gram-negative bacterium) that is lower, e.g., at least 2, 5, 10, 20, 50, 100, 200, 500, or 1000 fold lower, than a MIC for a Gram-positive bacterium (e.g., a Gram-positive bacterium).

In an embodiment, the ADC does not reduce the viability of, e.g., does not kill, a Gram-positive bacterium (e.g., a Gram-positive bacterium described herein), e.g., having a minimum bactericidal concentration (MBC) for a Gram-negative bacterium (e.g., a Gram-negative bacterium) that is lower, e.g., at least 2, 5, 10, 20, 50, 100, 200, 500, or 1000 fold lower fold lower, than a MBC for a Gram-positive bacterium (e.g., a Gram-positive bacterium). In an embodiment, the Gram-positive bacterium is *Staphylococcus aureus*.

In an embodiment, the ADC does not alter, or does not significantly alter microbiome (e.g., is microbiome sparing).

In an embodiment, the antimicrobial peptide comprises or consists of an alpha-helical antimicrobial peptide, e.g., a peptide comprising turns where residues i and i+4 are on the same face.

In an embodiment, the antimicrobial peptide comprises or consists of an amino acid sequence that differs by no more than 1, 2, 3, 4, or 5 amino acid residues from, or has at least 80%, 85%, 90%, 95%, 96%, 97%, 98%, 99%, or 100% homology with, an amino acid sequence described herein, e.g., any of SEQ ID NOS: 67-80, 94-102, 147-156, 158-159, 163-164, or 246-258. In an embodiment, the antimicrobial peptide comprises or consists of an amino acid sequence described herein e.g., any of SEQ ID NOS: 67-80, 94-102, 147-156, 158-159, 163-164, or 246-258. In an embodiment, the antimicrobial peptide comprises a carboxamide group (e.g., a C-terminal carboxamide functional group).

In an embodiment, the antimicrobial peptide comprises 1, 2, 3, 4, 5, 6, 7, 8, 9, 10, or more D-amino acids. In another embodiment, at least 10%, 20%, 30%, 40%, 50%, 60%, 70%, 80%, 90%, or 100% of the amino acid residues of the antimicrobial peptide are D-amino acids.

In an embodiment, the antimicrobial peptide comprises a first cysteine residue and a second cysteine residue, and wherein the first cysteine residue is cross-linked to the second cysteine residue. In an embodiment, the antimicrobial peptide is a broad spectrum antimicrobial peptide, e.g., having antimicrobial activity against 2, 3, or all of the following: at least one species of Enterobacteriaceae (e.g., one or more species of *Klebsiella, Enterobacter, Shigella*,

*Escherichia, Salmonella, Yersinia,* or *Citrobacter*, e.g., pan-resistant Enterobacteriaceae), at least one species of *Pseudomonas*, or at least one species of *Acinetobacter.*

In an embodiment, the antimicrobial peptide is a broad spectrum antimicrobial peptide, e.g., having antimicrobial activity against 2, 3, 4, 5, 6, or all of the following: at least one species of *Klebsiella*, at least one species of *Enterobacter*, at least one species of *Shigella*, at least one species of *Escherichia*, at least one species of *Salmonella*, at least one species of *Yersinia*, or at least one species of *Citrobacter.*

In an embodiment, the antimicrobial peptide has a minimum inhibitory concentration (MIC) of less than 100 mg/ml, e.g., less than 90, 80, 70, 60, 50, 40, 30, 20, 10, or 5 µg/ml, for a bacterial strain described herein, e.g., *Escherichia coli* (e.g., *Escherichia coli* ATCC 25922), *Pseudomonas aeruginosa* (e.g., *Pseudomonas aeruginosa* ATCC27853), or both.

In an embodiment, the antimicrobial peptide has a minimum bactericidal concentration (MBC) of less than 100 µg/ml, e.g., less than 90, 80, 70, 60, 50, 40, 30, 20, 10, or 5 µg/ml, for a bacterial strain described herein, e.g., *Escherichia coli* (e.g., *Escherichia coli* ATCC 25922), *Pseudomonas aeruginosa* (*Pseudomonas aeruginosa* ATCC27853), or both.

In an embodiment, the antimicrobial peptide has low hemolytic activity, e.g., has a partial lytic concentration (PLC) to MIC ratio for a Gram-negative bacterium (e.g., a Gram-negative bacterium described herein) which is greater than 4:1 (e.g., greater than 8:1, 16:1, 24:1, or 32:1), e.g., as determined by a red blood cell hemolysis assay and an MIC assay, respectively. In an embodiment, the PLC is the concentration (e.g., minimum concentration) that results in lysis of 50% of the red blood cells.

In an embodiment, the antimicrobial peptide has low hemolytic activity, e.g., has a partial lytic concentration (MLC) to MIC ratio for a Gram-negative bacterium (e.g., a Gram-negative bacterium described herein) which is greater than 4:1 (e.g., greater than 8:1, 16:1, 24:1, or 32:1), e.g., as determined by a red blood cell hemolysis assay and an MIC assay, respectively. In an embodiment, the MLC is the concentration (e.g., minimum concentration) that results in lysis of 100% of the red blood cells.

In an aspect, the disclosure features a composition, e.g., a pharmaceutical composition, comprising an ADC described herein and a pharmaceutically acceptable carrier.

In an aspect, the disclosure features a method of treating or preventing a bacterial infection or a related disorder, comprising administering to a subject in need thereof an ADC described herein, or a pharmaceutical composition described herein, in an amount effective to treat or prevent the bacterial infection or related disorder.

In an embodiment, the bacterial infection is a Gram-negative bacterial infection. In an embodiment, the disorder is caused by, or associated with, a Gram-negative bacterial infection.

In an embodiment, the ADC is administered at a dose of 0.1-100 mg/kg, e.g., 0.1-50 mg/kg or 1-10 mg/kg, e.g., 1-5 or 5-10 mg/kg. In an embodiment, the ADC is administered intravenously, subcutaneously, or intranasally or by inhalation.

In an embodiment, the ADC is administered prior to onset of a symptom associated with the bacterial infection or related disorder. In an embodiment, the ADC is administered at or after onset of a symptom associated with the bacterial infection or related disorder.

In an embodiment, the subject has one or more of pneumonia (e.g., community-acquired pneumonia, ventilator-associated bacterial pneumonia (VABP), and hospital-acquired bacterial pneumonia (HABP)), a urinary tract infection (UTI), septicemia, meningitis, diarrhea (e.g., traveler's diarrhea), a soft tissue infection, a skin infection, bacteremia, a respiratory system infection (e.g., a lower respiratory tract infection), endocarditis, an intra-abdominal infection, septic arthritis, osteomyelitis, a CNS infection, an ophthalmic infection, cholecystitis, cholangitis, meningitis (e.g., neonatal meningitis), typhoid fever, food poisoning, gastroenteritis, enteric fever, shigellosis, a blood stream infection, intra-abdominal sepsis, a brain abscess, meningitis, sepsis (e.g., neonatal sepsis), a joint infection, a bone infection, a gastrointestinal infection, or a wound infection. In an embodiment, the subject has a weakened immune system. In an embodiment, the subject has cystic fibrosis. In an embodiment, the subject suffers burns.

In an embodiment, the bacterial infection is a nosocomial infection or a hospital-acquired infection. In an embodiment, the disorder related to bacterial infection is associated with a nosocomial infection or a hospital-acquired infection.

In an embodiment, the subject is a human or an animal. In an embodiment, the subject is an immunocompromised patient, e.g., a subject having an HIV infection or AIDS, cancer, solid organ transplantation, stem cell transplantation, sickle cell disease or asplenia, a congenital immune deficiency, a chronic inflammatory condition, a cochlear implant, malnutrition, or a cerebrospinal fluid leak. In an embodiment, the subject is a health professional.

In an embodiment, the subject is 18 years old or younger, e.g., 15 years old or younger, 12 years old or younger, 9 years old or younger, 6 years old or younger, or 3 years old or younger. In an embodiment, the subject is at least 60 years old, e.g., at least 65 years old, at least 70 years old, at least 75 years old, or at least 80 years old.

In an embodiment, the method further comprises administering to the subject a second antimicrobial agent or therapy, e.g., an antibiotic or phage therapy.

In an embodiment, the antibiotic is selected from the group consisting of an aminoglycoside (e.g., amikacin, gentamicin, kanamycin, neomycin, netilmicin, tobramycin, paromomycin, streptomycin, or spectinomycin), an ansamycin (e.g., geldanamycin, herbimycin, or rifaximin), a carbacephem (e.g., loracarbef), a carbapenem (e.g., ertapenem, doripenem, imipenem/cilastatin, or meropenem), a cephalosporin (cefadroxil, cefazolin, cefalotin, cefalothin, cephalexin, cefaclor, cefamandole, cefoxitin, cefprozil, cefuroxime, cefixime, cefdinir, cefditoren, cefoperazone (e.g., in combination with sulbactam), cefotaxime, cefpodoxime, ceftazidime, ceftibuten, ceftizoxime, ceftriaxone, cefepime, ceftaroline fosamil, or ceftobiprole), a glycopeptide (e.g., teicoplanin, vancomycin, telavancin, dalbavancin, or oritavancin), a lincosamide (e.g., clindamycin or lincomycin), lipopeptide (e.g., daptomycin), a macrolide (e.g., azithromycin, clarithromycin, dirithromycin, erythromycin, roxithromycin, troleandomycin, telithromycin, or spiramycin), a monobactam (e.g., aztreonam), a nitrofuran (e.g., furazolidone or nitrofurantoin), an oxazolidinone (e.g., linezolid, posizolid, radezolid, torezolid), a penicillin (e.g., amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, penicillin g, temocillin, or ticarcillin), a penicillin combination (e.g., amoxicillin/clavulanate, ampicillin/sulbactam, piperacillin/tazobactam, or ticarcillin/clavulanate), a polypeptide (e.g., bacitracin, colistin, or polymyxin b), a quinolone/fluoroquinolone (e.g., ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, or temafloxacin), a sulfonamide (e.g., mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (co-trimoxazole), or sulfonamidochrysoidine), a tetracycline (e.g., demeclocycline, doxycycline, minocycline, oxytetracycline, or tetracycline), a drug against mycobacteria (e.g., clofazimine, dapsone, capreomycin, cycloserine, ethambutol, ethionamide, isoniazid, pyrazinamide, rifampin, rifabutin, rifapentine, or streptomycin), or others (e.g., arsphenamine, chloramphenicol, fosfomycin, fusidic acid, metronidazole, mupirocin, platensimycin, quinupristin/dalfopristin, thiamphenicol, tigecycline, tinidazole, or trimethoprim).

In an embodiment, the antibiotic is selected from levofloxacin, ciprofloxacin, gentamicin, ceftriaxone, ofloxacin, amikacin, tobramycin, aztreonam, or imipenem/cilastatin. In another embodiment, the antibiotic is colistin or meropenem.

In an embodiment, the second antimicrobial agent or therapy is administered before the ADC is administered, concurrently with the administration of the ADC, or after the ADC is administered.

When administered in combination, the ADC, the additional agent (e.g., a second or third agent), or all, can be administered in an amount or dose that is higher, lower or the same than the amount or dosage of each agent used individually, e.g., as a monotherapy. In an embodiment, the administered amount or dosage of the ADC, the additional agent (e.g., a second or third agent), or all, is lower (e.g., at least 20%, at least 30%, at least 40%, or at least 50%) than the amount or dosage of each agent used individually, e.g., as a monotherapy. In another embodiment, the amount or dosage of the ADC, the additional agent (e.g., a second or third agent), or all, that results in a desired effect (e.g., inhibition of bacterial growth or treatment of a bacterial infection) is lower (e.g., at least 20%, at least 30%, at least 40%, or at least 50% lower).

In an embodiment, the administration of the ADC and the second antimicrobial agent or therapy results in a synergistic effect, e.g., in inhibiting (e.g., killing) of a bacterium described herein, e.g., P. aeruginosa. For example, when the ADC is used at about 50% of its minimum inhibition concentration (MIC), the MIC of the second antimicrobial agent is reduced by at least 2, 4, 8, 12, 16, 20, 24, 28, 32, 36, 40, 50, 60, 70, 80, 90, or 100 fold.

In an aspect, the disclosure features a method of inhibiting or reducing a bacterial infection (e.g., Gram-negative bacterial infection), comprising contacting a cell (e.g., in a sample) or a subject in need thereof an ADC described herein, or a pharmaceutical composition described herein, in an amount effective to inhibit or reduce the bacterial infection.

In an embodiment, the ADC is contacted with the cell or subject in vitro, ex vivo, or in vivo.

In an aspect, the disclosure features an ADC described herein for use in treating or preventing a bacterial infection (e.g., a Gram-negative bacterial infection) or related disorder described herein.

In another aspect, the disclosure features use of an ADC described herein in the manufacture of a medicament for treating or preventing a bacterial infection (e.g., a Gram-negative bacterial infection) or related disorder described herein.

In an aspect, the disclosure features a kit comprising an ADC described herein or a pharmaceutical composition described herein.

In an embodiment, the kit further comprises instructions for use of the ADC or pharmaceutical composition.

In an aspect, the disclosure features a container comprising an ADC described herein or a pharmaceutical composition described herein.

In an aspect, the disclosure features a nucleic acid molecule (e.g., an isolated nucleic acid molecule) that encodes an ADC described herein, e.g., a VH, a VL; or both, or a heavy chain, a light chain, or both, of an antibody molecule described herein, coupled (e.g., fused) to an antimicrobial peptide, as described herein.

In an embodiment, the nucleic acid molecule comprises a nucleotide sequence described in Table 2, e.g., any of SEQ ID NOS: 81-93 or 113-114.

In an aspect, the disclosure features a vector comprising a nucleic acid molecule described herein.

In an aspect, the disclosure features a cell (e.g., an isolated cell) comprising a nucleic acid molecule described herein or a vector described herein.

In an aspect, the disclosure features a method of producing an ADC described herein, the method comprising culturing a cell described herein under conditions that allow production of an ADC, thereby producing the ADC described herein.

In another aspect, the disclosure features a method of producing an ADC described herein, the method comprises contacting an antibody molecule (e.g., an antibody molecule described herein) with a peptide (e.g., a peptide comprising an antimicrobial peptide described herein, and optionally, a sortase donor sequence), in the presence of a sortase, under conditions that allow a sortase-mediated reaction to occur, thereby producing the ADC.

In an embodiment, the antibody molecule comprises a sortase acceptor sequence, e.g., a sortase acceptor sequence described herein. In an embodiment, a heavy chain of the antibody molecule comprises a sortase acceptor sequence, e.g., at the C-terminus. In an embodiment, a light chain of the antibody molecule comprises a sortase acceptor sequence, e.g., at the C-terminus. In an embodiment, the sortase acceptor sequence further comprises a linker sequence, e.g., a tandem repeat of glycine-serine peptide linker sequences.

In an embodiment, a heavy chain of the antibody molecule comprises a first sortase acceptor sequence and a light chain of the antibody molecule comprises a second sortase acceptor sequence. In an embodiment, the sortase acceptor sequence, e.g., the first sortase recognition sequence, comprises the amino acid sequence of $(GS)_6$LPETGGG (SEQ ID NO: 24). In another embodiment, the sortase acceptor sequence, e.g., the second sortase acceptor sequence, comprises the amino acid sequence of $P(G_4S)_2$LPETGGSG (SEQ ID NO: 26).

In an embodiment, the peptide comprises or consists of an amino acid sequence that differs by no more than 1, 2, 3, 4, or 5 amino acid residues from, or has at least 80%, 85%, 90%, 95%, 96%, 97%, 98%, 99%, or 100% homology with, an amino acid sequence described herein, e.g., any of SEQ ID NOS: 67-80, 94-102, 147-156, 158-159, 163-164, or 246-258. In an embodiment, the antimicrobial peptide comprises or consists of an amino acid sequence described herein e.g., any of SEQ ID NOS: 67-80, 94-102, 147-156, 158-159, 163-164, or 246-258. In an embodiment, the antimicrobial peptide comprises a carboxamide group (e.g., a C-terminal carboxamide functional group).

In an embodiment, 1.5 mg/mL antibody molecule is contacted with 20 mol equivalents of sortase donor peptide per sortase acceptor sequence, and 1 mol equivalent of sortase per 75 mol equivalents of sortase acceptor sequence. In an embodiment, the contacting is performed in the presence of 150 mM NaCl, 50 mM Tris (pH 7.5), and 10 mM $CaCl_2$. In an embodiment, the contacting is performed at 18° C. to 37° C., e.g., at 25° C., e.g., for 2 to 48 hours, e.g., 18 to 24 hours, e.g., 20 hours. In an embodiment, the sortase is a sortase A pentamutant.

In an embodiment, the further comprises detecting the sortase-mediated reaction, e.g., by Q-TOF mass spectrometry. In an embodiment, the further comprises purifying the ADC, e.g., by gel electrophoresis.

In an aspect, the disclosure features a reaction mixture comprising:
(i) a sortase, e.g., a sortase described herein, and
(ii) an antibody molecule described herein, an antimicrobial peptide described herein, or both.

In an aspect, the disclosure features an antibody molecule described herein.

In an aspect, the disclosure features a nucleic acid molecule (e.g., an isolated nucleic acid molecule) that encodes an antibody molecule described herein, e.g., a VH, a VL, or both; or a heavy chain, a light chain, or both, of the antibody molecule described herein.

In an aspect, the disclosure features a vector comprising a nucleic acid molecule encoding an antibody molecule described herein.

In an aspect, the disclosure features a cell (e.g., an isolated cell) comprising a nucleic acid molecule encoding an antibody molecule described herein or a vector described herein.

In an aspect, the disclosure features a method of producing an antibody molecule described herein, the method comprising culturing a cell described herein under conditions that allow production of an antibody molecule, thereby producing the antibody molecule described herein.

In an aspect, the disclosure features an antimicrobial peptide (e.g., an isolated or synthetic antimicrobial peptide) described herein.

In an aspect, the disclosure features a nucleic acid molecule (e.g., an isolated nucleic acid molecule) that encodes an antimicrobial peptide described herein.

In an aspect, the disclosure features a vector comprising a nucleic acid molecule encoding an antimicrobial peptide described herein.

In an aspect, the disclosure features a cell (e.g., an isolated cell) comprising a nucleic acid molecule encoding an antimicrobial peptide described herein or a vector of described herein.

In an aspect, the disclosure features a method of producing an antimicrobial peptide described herein, the method comprising culturing a cell of described herein under conditions that allow production of an antimicrobial peptide, thereby producing the antimicrobial peptide described herein.

In an aspect, the disclosure features an antibody molecule that binds to the same epitope, or substantially the same epitope, as an antibody molecule described herein.

In an aspect, the disclosure features an ADC comprising: a) an antibody molecule that binds to the same epitope, or substantially the same epitope, as an antibody molecule described herein; and b) an antimicrobial peptide, e.g., an antimicrobial peptide described herein.

In an aspect, the disclosure features an antibody molecule that competes for binding with an antibody molecule described herein.

In an aspect, the disclosure features an ADC comprising: a) an antibody molecule that competes for binding with an antibody molecule described herein; and b) an antimicrobial peptide, e.g., an antimicrobial peptide described herein.

ENUMERATED EMBODIMENTS

1. An antibody molecule-drug conjugate (ADC) comprising an antibody molecule and a covalently coupled peptide,
wherein the antibody molecule comprises a heavy chain variable region (VH), wherein the VH comprises three heavy chain complementarity determining regions (HCDR1, HCDR2, and HCDR3), and wherein the VH comprises:
(a) an HCDR1 comprising the amino acid sequence of SEQ ID NO: 105; an HCDR2 comprising the amino acid sequence of SEQ ID NO: 106; and an HCDR3 comprising the amino acid sequence of SEQ ID NO: 107, or
(b) an HCDR1 comprising the amino acid sequence of SEQ ID NO: 108; an HCDR2 comprising the amino acid sequence of SEQ ID NO: 146; and an HCDR3 comprising the amino acid sequence of SEQ ID NO: 107; and
wherein the antibody molecule comprises a light chain variable region (VL), wherein the VL comprises three light chain complementarity determining regions (LCDR1, LCDR2, and LCDR3), and wherein the VL comprises:
(a) an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112, or
(b) an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112; and
wherein the peptide comprises the amino acid sequence of SEQ ID NO: 257 or an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO 257.

2. The ADC of embodiment 1, wherein the VH comprises an HCDR1 comprising the amino acid sequence of SEQ ID NO: 105; an HCDR2 comprising the amino acid sequence of SEQ ID NO: 106; and an HCDR3 comprising the amino acid sequence of SEQ ID NO: 107; and wherein the VL comprises an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112.

3. The ADC of embodiment 1, wherein VH comprises an HCDR1 comprising the amino acid sequence of SEQ ID NO: 108; an HCDR2 comprising the amino acid sequence of SEQ ID NO: 146; and an HCDR3 comprising the amino acid sequence of SEQ ID NO: 107; and wherein the VL comprises an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112.

4. The ADC of any of embodiments 1-3, wherein the VH comprises the amino acid sequence of SEQ ID NO 117, or an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO 117.

5. The ADC of any of embodiments 1-4, wherein the VH comprises the amino acid sequence of SEQ ID NO 117.

6. The ADC of any of embodiments 1-5, wherein the VL comprises the amino acid sequence of SEQ ID NO 135, or an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO 135.

7. The ADC of any of embodiments 1-6, wherein the VL comprises the amino acid sequence of SEQ ID NO: 135.

8. The ADC of any of embodiments 1-7, wherein the antibody molecule is capable of binding to *Pseudomonas*.

9. The ADC of any of embodiments 1-8, wherein the antibody molecule is capable of binding to *Pseudomonas aeruginosa*.

10. The ADC of any of embodiments 1-9, wherein the antibody molecule is capable of binding to lipopolysaccharide (LPS) on *Pseudomonas*.

11. The ADC of any of embodiments 1-10, wherein the antibody molecule is capable of binding to an inner core glycan moiety on LPS on *Pseudomonas*.

12. The ADC of any of embodiments 1-11, wherein the antibody molecule does not bind, or does not substantially bind, to *E coli* LPS, e.g., as determined by Western blot.

13. The ADC of any of embodiments 1-12, wherein the antibody molecule does not bind, or does not substantially bind, to heptose or a mono-phosphorylated heptose analog (e.g., 2-P-Hep or 4-P-Hep), e.g., as determined by a Biolayer Interferometry analysis.

14. The ADC of any of embodiments 1-13, wherein the antibody molecule binds to di-phosphorylated 2,4-P-Hep monosaccharide, e.g., as determined by a Biolayer Interferometry analysis.

15. The ADC of any of embodiments 1-14, wherein the antibody molecule binds to di-phosphorylated mannose (2,4-P-Man), e.g., with reduced binding compared to di-phosphorylated 2,4-P-Hep monosaccharide, e.g., as determined by a Biolayer Interferometry analysis.

16. The ADC of any of embodiments 1-15, wherein the antibody molecule binds to one or more *P. aeruginosa* strains described herein, e.g., one or more strains resistant to carbapenems, anti-*pseudomonas* third generation cephalosporins or fluoroquinolones, e.g., with an apparent avidity of about 20 to about 150 pM (e.g., about 50 to about 120 pM), e.g., as determined by a whole bacterial cell ELISA.

17. The ADC of any of embodiments 1-16, wherein the antibody molecule does not bind, or does not substantially bind, to one or more of *Escherichia coli, Klebsiella pneumoniae, Salmonella typhimurium*, a gram-positive organism, or a mammalian cell, e.g., as determined by a whole cell ELISA.

18. The ADC of any of embodiments 1-17, wherein the antibody molecule binds to a *Pseudomonas* species other than *Pseudomonas aeruginosa*, e.g., one or more of *Pseudomonas fluorescens, Pseudomonas putida*, or *Pseudomonas stutzeri*, e.g., as determined by a whole bacterial cell ELISA.

19. The ADC of any of embodiments 1-18, wherein the antibody molecule is a monoclonal antibody molecule, a humanized antibody molecule, an isolated antibody molecule, or a synthetic antibody molecule.

20. The ADC of any of embodiments 1-19, wherein the antibody molecule comprises two VHs and two VLs.

21. The ADC of any of embodiments 1-20, wherein the antibody molecule further comprises a heavy chain constant region of an IgG1, IgG2, IgG3, or IgG4.

22. The ADC of any of embodiments 1-21, wherein the antibody molecule further comprises a light chain constant region of a kappa or lambda chain.

23. The ADC or any of embodiments 1-22, wherein the antibody molecule comprises a Fab, a F(ab')2, an Fv, or a single chain Fv fragment (scFv).

24. The ADC of any of embodiments 1-23, wherein the peptide comprises the amino acid sequence of SEQ ID NO 257.

25. The ADC of any of embodiments 1-24, wherein the peptide comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33, D-amino acids, or at least 10%, 20%, 30%, 40%, 50%, 60%, 70%, 80%, 90%, 95%, or 100%, of the amino acid residues in the peptide are D-amino acids.

26. The ADC of any of embodiments 1-25, wherein all of the amino acid residues in the peptide are D-amino acids.

27. The ADC of any of embodiments 1-26, wherein the peptide is coupled to the VH, e.g., the C-terminus of the VH, e.g., indirectly (e.g., via a constant region, a linker, or both).

28. The ADC of any of embodiments 1-27, wherein the peptide is coupled to the antibody molecule by an enzymatic ligation, e.g., using Sortase A (SrtA), e.g., via a sortase recognition sequence (e.g., LPETGGG).

29. The ADC of any of embodiments 1-28, wherein the peptide comprises a sortase donor sequence, e.g., N-terminal GGG.

30. The ADC of any of embodiments 1-29, wherein the ADC comprises a linker, e.g., a (Gly-Ser)n linker sequence, where n=2 to 20, between the antibody molecule and the peptide.

31. The ADC of any of embodiments 1-30, wherein the ADC has a peptide-to-antibody molecule ratio between about 2 and about 8, e.g., between about 2 and about 4, e.g., as determined by mass spectrometry.

32. The ADC of any of embodiments 1-31, wherein the ADC has a peptide-to-antibody molecule ratio of about 2, e.g., as determined by mass spectrometry.

33. The ADC of any of embodiments 1-32, wherein the ADC has an in vitro bactericidal activity against *P. aeruginosa* at a concentration of about 2 µg/mL to about 50 µg/mL, e.g., about 3.1 µg/mL to about 25 µg/mL.

34. The ADC of any of embodiments 1-33, wherein the ADC has an in vitro bactericidal activity against *P. aeruginosa* at a concentration that differs by 50% or less, e.g., 45%, 40%, 35%, 30%, 25%, 20%, 15%, 10%, or less, compared to a reference ADC, e.g., VSX-1.

35. The ADC of any of embodiments 1-34, wherein the ADC has a mean lytic concentration (MLC) of about 500 mg/mL or more, e.g., 800 µg/mL or more, for *P. aeruginosa*.

36. The ADC of any of embodiments 1-35, wherein the ADC has an MLC that differs by 50% or less, e.g., 45%, 40%, 35%, 30%, 25%, 20%, 15%, 10%, or less, compared to a reference ADC, e.g., VSX-1, for *P. aeruginosa*.

37. The ADC of any of embodiments 1-36, wherein the ADC has a CC50 (the concentration at which 50% cytotoxicity of mammalian cells is observed) of about 500 Kg/mL or more, e.g., 800 µg/mL or more, for *P. aeruginosa*.

38. The ADC of any of embodiments 1-37, wherein the ADC has a CC50 that is higher, e.g., at least 0.5, 1, 2, 3, 4, or 5-fold higher than a reference ADC, e.g., VSX-1, for *P. aeruginosa*.

39. The ADC of any of embodiments 1-38, wherein the ADC has an improved biodistribution compared to a reference ADC, e.g., VSX-1, e.g., as determined by pharmacokinetics measurements, whole body imaging, in vivo imaging, assessment of organ distribution (e.g., the ADC does not substantially or primarily distribute to the liver), ELISA, and/or mass spectrometry of blood samples.

40. An ADC comprising an antibody molecule comprising two VHs and two VLs,
wherein the VH is covalently coupled with a peptide comprises the amino acid sequence of SEQ ID NO: 257; and
wherein the VH comprises an HCDR1 comprising the amino acid sequence of SEQ ID NO: 105; an HCDR2 comprising the amino acid sequence of SEQ ID NO: 106; and an HCDR3 comprising the amino acid sequence of SEQ ID NO: 107; and
wherein the VL comprises an LCDR1 comprising the amino acid sequence of SEQ ID NO:
138; an LCDR2 comprising the amino acid sequence of SEQ ID NO: 142; and an LCDR3 comprising the amino acid sequence of SEQ ID NO: 112.

41. An ADC comprising an antibody molecule comprising two VHs and two VLs,
wherein the VH is covalently coupled with a peptide comprises the amino acid sequence of SEQ ID NO: 257; and
wherein the VH comprises an HCDR1 comprising the amino acid sequence of SEQ ID NO: 108; an HCDR2 comprising the amino acid sequence of SEQ ID NO: 146; and an HCDR3 comprising the amino acid sequence of SEQ ID NO: 107; and
wherein the VL comprises an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112.

42. The ADC of embodiment 40 or 41, wherein the VH comprises the amino acid sequence of SEQ ID NO: 117, and wherein the VL comprises the amino acid sequence of SEQ ID NO: 135.

43. The ADC of any of embodiments 40-42, wherein the peptide is coupled to the C-terminus of the VH via a (Gly-Ser)n linker.

44. A pharmaceutical composition comprising an ADC of any of embodiments 1-40 and a pharmaceutically acceptable carrier.

45. An ADC of any of embodiments 1-43, or a pharmaceutical composition of embodiment 44, for use in a method of treating or preventing a bacterial infection associated with *Pseudomonas* in a subject.

46. The ADC or composition for use of embodiment 45, wherein the bacterial infection is associated with *Pseudomonas aeruginosa*.

47. The ADC or composition for use of embodiment 45 or 46, wherein the ADC is administered at a dose of 1-10 mg/kg.

48. The ADC or composition for use of any of embodiments 45-47, wherein the ADC is administered intravenously, subcutaneously, or intranasally or by inhalation.

49. The ADC or composition for use of any of embodiments 45-48, wherein the ADC is administered prior to or after onset of a symptom associated with the bacterial infection.

50. The ADC or composition for use of any of embodiments 45-49, wherein the subject has one or more of: pneumonia, a urinary tract infection (UTI), septicemia, meningitis, diarrhea, a soft tissue infection, a skin infection, bacteremia, a respiratory system infection, endocarditis, an intra-abdominal infection, septic arthritis, osteomyelitis, a CNS infection, an ophthalmic infection, cholecystitis, cholangitis, meningitis, typhoid fever, food poisoning, gastroenteritis, enteric fever, shigellosis, a blood stream infection, intra-abdominal sepsis, a brain abscess, meningitis, sepsis, a joint infection, a bone infection, a gastrointestinal infection, or a wound infection.

51. The ADC or composition for use of any of embodiments 45-50, wherein the bacterial infection is a nosocomial infection or a hospital-acquired infection.

52. The ADC or composition for use of any of embodiments 45-51, wherein the subject is a human or an animal.

53. The ADC or composition for use of any of embodiments 45-52, wherein the subject is an immunocompromised patient or a health professional.

54. The ADC or composition for use of any of embodiments 45-53, wherein the subject has, or is at risk of having, an HIV infection or AIDS, a cancer, a solid organ transplantation, a stem cell transplantation, a sickle cell disease or asplenia, a congenital immune deficiency, a chronic inflammatory condition, a cochlear implant, malnutrition, or a cerebrospinal fluid leak.

55. The ADC or composition for use of any of embodiments 45-54, wherein the subject is 18 years old or younger, 15 years old or younger, 12 years old or younger, 9 years old or younger, or 6 years old or younger, or is at least 60 years old, at least 65 years old, at least 70 years old, at least 75 years old, or at least 80 years old.

56. The ADC or composition for use of any of embodiments 45-55, wherein the method further comprises administering to the subject a second antimicrobial agent or therapy.

57. The ADC or composition for use of embodiment 56, wherein the second antimicrobial agent or therapy comprises an antibiotic or a phage therapy.

58. The ADC or composition for use of embodiment 57, wherein the antibiotic is a polymyxin (e.g., colistin) or β-lactam (e.g., carbapenem, e.g., meropenem)

59. The ADC or composition for use of embodiment 57, wherein the antibiotic is chosen from an aminoglycoside, an ansamycin, a carbacephem, a carbapenem, a cephalosporin, a glycopeptide, a lincosamide, a lipopeptide, a macrolide, a monobactam, a nitrofuran, an oxazolidinone, a penicillin, a penicillin combination, a polypeptide, a quinolone or fluoroquinolone, a sulfonamide, a tetracycline, or a drug against mycobacteria.

60. The ADC or composition for use of embodiment 58 or 59, wherein the antibiotic is chosen from amikacin, gentamicin, kanamycin, neomycin, netilmicin, tobramycin, paromomycin, streptomycin, spectinomycin, geldanamycin, herbimycin, or rifaximin, loracarbef, ertapenem, doripenem, imipenem/cilastatin, meropenem, cefadroxil, cefazolin, cefalotin, cefalothin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, penicillin g, temocillin, ticarcillin, amoxicillin/clavulanate, ampicillin/sulbactam, piperacillin/tazobactam, ticarcillin/clavulanate, bacitracin, colistin, polymyxin b, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (co-trimoxazole), sulfonamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, or trimethoprim.

61. The ADC or composition for use of any of embodiments 58-60, wherein the antibiotic is chosen from levofloxacin, ciprofloxacin, gentamicin, ceftriaxone, ofloxacin, amikacin, tobramycin, aztreonam, or imipenem/cilastatin.

62. The ADC or composition for use of any of embodiments 56-61, wherein the second antimicrobial agent or therapy is administered before the ADC is administered, concurrently with the administration of the ADC, or after the ADC is administered.

63. A method of inhibiting or reducing a bacterial infection, the method comprising contacting a cell an ADC of any of embodiments 1-43, or a pharmaceutical composition of embodiment 44, in an amount effective to inhibit or reduce the bacterial infection.

64. The method of embodiment 62, wherein the ADC or pharmaceutical composition is contacted with the cell in vitro, ex vivo, or in vivo.

65. A kit comprising: an ADC of any of embodiments 1-43 or a pharmaceutical composition of embodiment 44; and instructions for use of the ADC or pharmaceutical composition.

66. A container comprising an ADC of any of embodiments 1-43 or a pharmaceutical composition of embodiment 44.

67. A nucleic acid molecule encoding:
    (a) a VH, a VL, or both, of the antibody molecule of an ADC of any of embodiments 1-43;
    (b) the antimicrobial peptide of an ADC of any of embodiments 1-43;
    (c) both (a) and (b); or
    (d) an ADC of any of embodiments 1-43.

68. A vector comprising the nucleic acid molecule of embodiment 67.

69. A cell comprising the nucleic acid molecule of embodiment 67 or the vector of embodiment 68.

70. A method of producing an ADC, the method comprising culturing the cell of embodiment 69 under conditions that allow production of an ADC, thereby producing the ADC.

71. A method of producing an ADC, the method comprising contacting an antibody molecule that binds to LPS with a peptide comprising an antimicrobial peptide, and optionally, a sortase donor sequence, in the presence of a sortase, under conditions that allow a sortase-mediated reaction to occur, thereby producing the ADC.

72. The method of embodiment 71, wherein the antibody molecule comprises a sortase acceptor sequence comprising a sortase recognition sequence, a linker sequence, or both.

73. A method of treating or preventing a bacterial infection, comprising administering to a subject in need thereof an ADC of any of embodiments 1-43, or a pharmaceutical composition of embodiment 44, in an amount effective to treat or prevent the bacterial infection.

74. Use of an ADC of any of embodiments 1-43 in the manufacture of a medicament for treating or preventing a bacterial infection.

The disclosure contemplates all combinations of any one or more of the foregoing aspects and/or embodiments, as well as combinations with any one or more of the embodiments set forth in the detailed description and examples.

Other features, objects, and advantages of the compositions and methods herein will be apparent from the description and drawings, and from the claims.

Figures and Tables are provided herewith.

BRIEF DESCRIPTION OF THE DRAWINGS

FIG. 1A, which comprises FIG. 1A-1 and FIG. 1A-2, depicts the VH, VL, framework, complementarity-determining region (CDR) amino acid sequences for the exemplary VSX antibody (e.g., as shown in Table 3). FIG. 1A discloses SEQ ID NOS 264-265, 266 and 266, respectively, in order of appearance.s

FIG. 2, which comprises FIG. 2A-1 and FIG. 2A-2, depicts biolayer interferometry analysis of VSX binding to synthetic monosaccharides.

FIG. 6A depicts mutations of monosaccharide VSX-contact and non-contact residues and their effect on binding of VSX to 2,4-P-Hep.

FIG. 8 shows that (D)-P297 is more stable than (L)-P297 in the presence of human serum. Left panel: Representative total ion chromatograms of P297 at t=0 (top) and after 60 minutes in 10% human serum (NHS). Intact peptide remaining was quantified by integration of extracted ion current for (L)- or (D)-P297. Right panel: Sixty minute time course of degradation of P297 variants in the presence of 10% human serum (NHS). Values were normalized to the starting time=0 min samples that had been incubated in serum. Y-axis is the ratio the measured amount of intact at ti over the intact peptide at to.

FIG. 9A discloses "_(GS)15_LPETGGSG" as SEQ ID NO: 267 and "_(GS)15_LPETGGG-AMP" as SEQ ID NO: 268.

FIG. 9B, which comprises FIG. 9B-1 and FIG. 9B-2, depicts the analysis of the conversion of VSX to DAR2 and 4. Q-tof analysis of the heavy chain of starting material and sortase-ligated D-P297 product for sortase acceptors on both the heavy and light chains (top two panels), and for sortase acceptors on only the heavy chains (bottom two panels). Assuming unbiased detection of starting material and product, 88.7% of the heavy chain for "DAR4" material was ligated to D-P297.

FIG. 9D depicts the size exclusion chromatography of VSX (red line) and VSX conjugate (blue line).

FIG. 10 depicts in vitro killing activity of VSX conjugates against each of two *P. aeruginosa* strains (Pae 27853 and Pae 39324).

FIG. 12 depicts in vitro bactericidal activity, hemolytic, cytotoxic, and opsonic activity of VSX-1.

FIG. 14B depicts the analysis of serum levels of VSX-297 (solid gray bars) at 1, 24, and 72 hours post-injection and DAR2 constructs with 297 (HC and LC chain constructs, hatched and spotted bars, respectively).

DETAILED DESCRIPTION

Figure 1B:
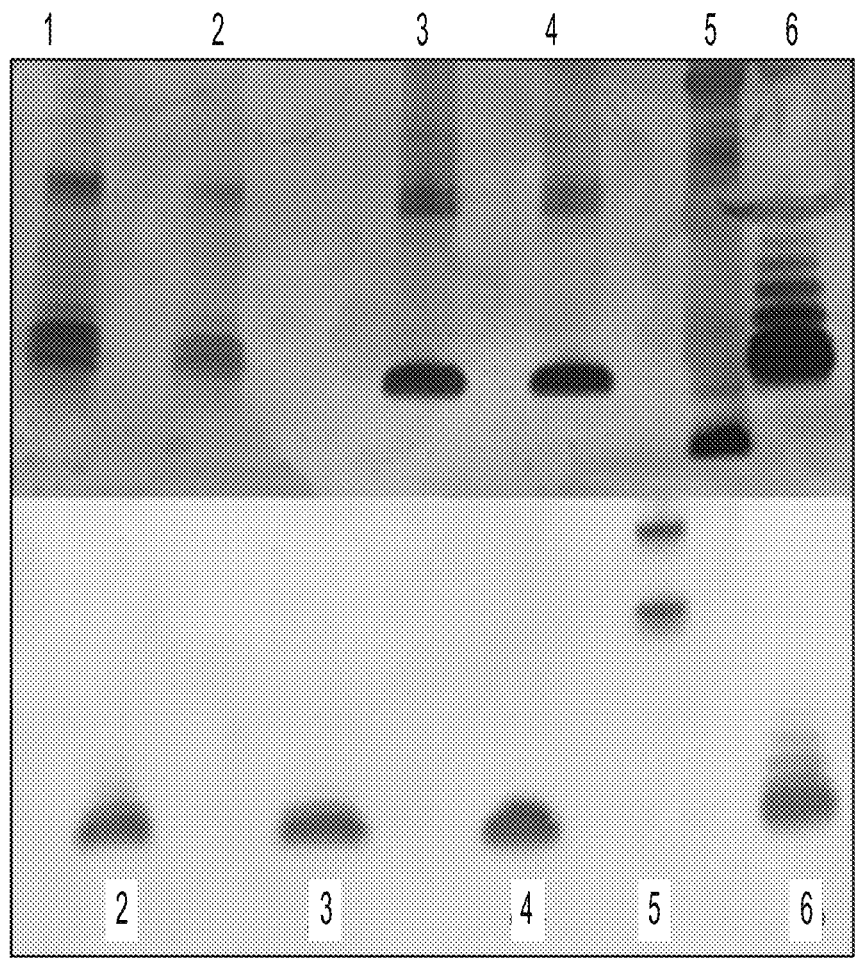
FIG. 1B depicts binding of VSX antibody to isolated LPS by Western Blot. A, Top: Silver stain SDS-Page analysis of isolated LPS from E. coli (lane 1) and Pae (lanes 2-4), lane 5—See Blue; and Pae LPS from Sigma (lane 6). Bottom: Western blot analysis of VSX binding to LPS detected no binding to E. coli but did detect binding to Pae LPS (lanes 2-4, 6); lane 5—Magic Mark.

Disclosed herein are antibody molecule-drug conjugates (ADCs), such as antibody molecule-peptide conjugates, that targets *Pseudomonas*, e.g., lipopolysaccharide (LPS) on *Pseudomonas*.

The disclosures herein include, at least in part, the development and characterization of a new strategy to treat bacterial infections, even those caused by MDR or pan-resistant strains, combining the unique specificity of a monoclonal antibody (referred hereafter to as VSX) with the direct-acting antibacterial activity of an antimicrobial peptide (AMP). This approach combines strong antimicrobial activity with the targeting capacity of an antibody. To exemplify this approach, we focused on *P. aeruginosa*.

Without wishing to be bound by theory, it is believed that in an embodiment, VSX constructs described herein function with both direct bactericidal activity and effector function through the Fc domain of the antibody. Such a construct showed potent and selective activity in vitro and in vivo, demonstrating specific killing activity with little to no non-specific cytotoxicity to mammalian cells. Additionally, VSX constructs employ a direct-acting effect at the outer membrane surface, which does not require internalization of the ADC, thereby circumventing the need for an agent that must pass through the double membrane of gram-negative pathogens. The disclosures herein demonstrate that VSX constructs provide therapeutic optionality to managing, e.g., *P. aeruginosa* infections, promoting antibiotic stewardship and sparing the microbiota.

The disclosures herein are based, at least in part, on the characterization of an antibody targeting a conserved glycan structure on the surface of *Pseudomonas aeruginosa*. The antibody was engineered in an ADC format to have direct bactericidal activity. Notably, unlike ADCs that have been constructed for oncology indications or even for gram-positive organisms, where internalization and release of the payload is required for activity, the construction of an ADC that acts exclusively at the outer membrane surface is disclosed.

Without wishing to be bound by theory, it is believed that in an embodiment, the copy number and location of LPS core glycans at the surface of the bacterial outer membrane makes it ideal for utilization in a membrane disruptive ADC approach. While the high density of LPS at the outer membrane surface is established, the conservation of a common core epitope in all *P. aeruginosa* strains is less well accepted. Through the engineering of the VSX antibody and further binding studies between VSX and synthetic heptose mimics of the LPS inner core, the studies described herein demonstrated that the core glycan of *P. aeruginosa* is accessible and, a single, bis-phosphorylated heptose monomer can be bound by an antibody.

Without wishing to be bound by theory, it is believed that in an embodiment, the functional activity associated with the core LPS glycan makes it an attractive feature as an antibody target, in addition to its high degree of its conservation across *P. aeruginosa* strains. The outer core region of *P. aeruginosa* LPS can function as a bacterial ligand for association and entry of the organism into host cells, such as corneal cells during the infection stage of keratitis. The terminal D-Glc moiety of the outer core can be critical in binding of LPS to mouse corneal epithelial cells. Furthermore, in the context of cystic fibrosis, the role of cystic fibrosis transmembrane conductance regulator protein (CFTR) as a receptor for the binding of *P. aeruginosa* to host epithelial surfaces is mediated by core glycan-CFTR interactions. Therefore, LPS mediates the uptake of *P. aeruginosa* by host epithelial cells, playing an important role in pathogenesis and being an important virulence factor.

LPS-directed antibodies with suboptimal format, e.g., IgMs, with low affinity, and targeting the hydrophobic lipid A domain, which causes significant non-specific cross-reactivity and questions of accessibility on intact bacteria, may not demonstrate a clinical benefit. VSX targets the hydrophilic inner core glycans and demonstrates no detectable non-specific binding. Further, VSX constructs have direct bactericidal activity and demonstrate endotoxin-neutralizing properties.

Without wishing to be bound by theory, it is believed that in an embodiment, by bringing together two optimized components, a broad-spectrum antibody and an optimized antimicrobial peptide, the resulting ADC disclosed herein has therapeutic properties superior to the parent components. The disclosures herein demonstrate that the engineered VSX antibody targets a conserved glycan epitope on the surface of *P. aeruginosa* and that the antimicrobial peptide (e.g., D369) is functional and safe when ligated to an antibody. The resulting ADC has shown significant in vitro activity against a variety of strains of *P. aeruginosa* and has demonstrated in vivo efficacy in an aggressive lung infection model. The data and approach presented herein offer a desired ADC strategy for the development of antimicrobials to combat Gram-negative bacteria, for example, to improve existing and ongoing efforts in small molecules and biologics.

In an embodiment, an ADC described herein is capable of binding to bacteria, e.g., Gram-negative bacteria, e.g., lipopolysaccharides on the outer membrane of Gram-negative bacteria (e.g., *Pseudomonas*, e.g., *Pseudomonas aeruginosa*), with high affinity and specificity. In an embodiment, an ADC described herein is capable of binding to the outer membrane of Gram-negative bacteria (e.g., *Pseudomonas*, e.g., *Pseudomonas aeruginosa*). The ADCs disclosed herein can include an antibody molecule and an antimicrobial peptide (AMP). Advantageously, compared to antimicrobial peptides alone, several of the ADCs describe herein have improved ability to inhibit or reduce the viability of one or more bacteria (e.g., Gram-negative bacteria) of different genera, species, and/or subspecies. Nucleic acid molecules encoding the antibody molecules, ADCs, and antimicrobial peptides, expression vectors, host cells, compositions (e.g., pharmaceutical compositions), kits, and methods for making the antibody molecules, ADCs, and antimicrobial peptides, are also provided. The antibody molecules, ADCs, antimicrobial peptides, and pharmaceutical compositions disclosed herein can be used (alone or in combination with other agents or therapeutic modalities) to treat, prevent and/or diagnose bacterial infections or related disorders and conditions, e.g., caused by Gram-negative bacteria.

In an embodiment, the ADCs described herein can have one or more of the following properties: (i) is capable of treating or preventing a bacterial disease in a patient with unmet medical need; (ii) is capable of treating a genus and species of bacteria causing a bacterial disease; acts via a new mechanism of action; (iii) has an added inhibitor that reduces or neutralizes a mechanism of resistance; or (iv) has an alteration in the structure of the molecule that reduces or neutralizes a mechanism of resistance.

In an embodiment, the ADC has an opsonophagocytosis activity (e.g., via an antibody molecule), a bactericidal activity (e.g., via a payload, e.g., an antimicrobial peptide), or both. Without wishing to be bound by theory, it is believed that in an embodiment, the use of an antimicrobial peptide in ADC can achieve one or more of the following goals: a new target with low resistance, synergistic efficacy with lower spontaneous resistance probability, improved directed treatment, or rapid bactericidal activity. In an embodiment, the ADC targets a core LPS region, e.g., to reduce the probability of resistance caused by potential target site alteration. In another embodiment, peptide stapling is used to increase activity and/or stability, e.g., to reduce or prevent potential antibiotic inactivation.

Definitions

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

The compositions and methods disclosed herein encompass polypeptides and nucleic acids having the sequences specified, or sequences substantially identical or similar thereto, e.g., sequences at least 85%, 90%, 95% identical or higher to the sequence specified.

In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

In an embodiment, "homology" is used interchangeably with "identity." Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a typical embodiment, the length of a reference sequence aligned for comparison purposes is at least 30%, e.g., at least 40%, 50%, 60%, e.g., at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In an embodiment, the percent identity between two amino acid sequences is determined using the Needleman and Wunsch ((1970) J. Mol. Biol. 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In an embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. One suitable set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215: 403-10. BLAST nucleotide searches can be performed with the NBLAST program, score=100, wordlength=12 to obtain nucleotide sequences homologous to a nucleic acid as described herein. BLAST protein searches can be performed with the XBLAST program, score=50, wordlength=3 to obtain amino acid sequences homologous to protein molecules described herein. To obtain gapped alignments for comparison purposes, Gapped BLAST can be utilized as described in Altschul et al., (1997) Nucleic Acids Res. 25:3389-3402. When utilizing BLAST and gapped BLAST programs, the default parameters of the respective programs (e.g., XBLAST and NBLAST) can be used.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions 4) are suitable conditions and the ones that should be used unless otherwise specified.

It is understood that the molecules described herein may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide," "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

As used herein, the term "treat," e.g., a bacterial infection or related disorder, means that a subject (e.g., a human) who has a bacterial infection or related disorder, and/or experiences a symptom of a bacterial infection or related disorder, will, in an embodiment, suffer less a severe symptom and/or recover faster when an antibody molecule, ADC, or antimicrobial peptide is administered than if the antibody molecule, ADC, or antimicrobial peptide were never administered. In an embodiment, when an infection or related disorder is treated, an assay to detect bacteria in the subject will detect fewer bacteria after effective treatment for the infection or disorder. For example, a diagnostic assay using an antibody molecule or ADC, such as an antibody molecule or ADC described herein, will detect fewer or no bacteria in a biological sample of a subject after administration of an antibody molecule, ADC, or antimicrobial peptide for the effective treatment of the infection or disorder. Other assays, such as PCR (e.g., qPCR) can also be used to monitor treatment in a patient, to detect the presence, e.g., decreased presence (or absence) after treatment of bacterial infection or disorder in the subject. Treatment can, e.g., partially or completely alleviate, ameliorate, relieve, inhibit, or reduce the severity of, and/or reduce incidence and optionally, delay onset of, one or more manifestations of the effects or symptoms, features, and/or causes of a particular infection, disease, disorder, and/or condition (e.g., a bacterial infection). In an embodiment, treatment is of a subject who does not exhibit certain signs of the relevant infection, disease, disorder and/or condition and/or of a subject who exhibits only early signs of the infection, disease, disorder, and/or condition. In an embodiment, treatment is of a subject who exhibits one or more established signs of the relevant infection, disease, disorder and/or condition. In an embodiment, treatment is of a subject diagnosed as suffering from a bacterial infection or related disorder.

As used herein, the term "prevent," e.g., a bacterial infection, means that a subject (e.g., a human) is less likely to have a bacterial infection if the subject receives the antibody molecule, ADC, or antimicrobial peptide prior to (e.g., 1 day, 2 days, 1 week, 2 weeks, 3 weeks, or 1 month or more) being exposed to the bacteria that cause the infection.

As used herein, the term "minimum inhibitory concentration" or "MIC" refers to the lowest concentration of an antimicrobial agent, e.g., an antibody molecule, ADC, or antimicrobial peptide, that will inhibit the growth (e.g., visible growth) of a bacterium, e.g., after incubation (e.g., overnight incubation). Methods for determining minimum inhibitory concentration or MIC are described, e.g., in Andrews, *J. Antimicrob. Chemother.* 2001; 48 Suppl 1:5-16 (Erratum in *J. Antimicrob. Chemother.* 2002; 49(6):1049). For example, MIC can be determined by using the following procedure: preparation of antibiotic stock solution, preparation of antibiotic dilution range, preparation of agar dilution plates, preparation of inoculum, inoculation, incubation, and reading and interpreting results. MICs can also be determined by agar dilution or broth microdilution, usually following the guidelines of a reference body such as the Clinical & Laboratory Standards Institute (CLSI), British Society for Antimicrobial Chemotherapy (BSAC), or European Committee on Antimicrobial Susceptibility Testing (EUCAST). In an embodiment, the MIC is the lowest concentration of an antimicrobial agent, e.g., an antibody molecule, ADC, or antimicrobial peptide, that inhibits growth of a bacterium, by at least 60%, 65%, 70%, 75%, 80%, 85%, 90%, or 95%. In an embodiment, the MIC is the lowest concentration of an antimicrobial agent, e.g., an antibody molecule, ADC, or antimicrobial peptide, that inhibits growth of a bacterium, by at least 80%. An exemplary method for determining MIC is also described in Example 5.

As used herein, the term "minimum bactericidal concentration" or "MBC" refers to the lowest concentration of an antimicrobial agent, e.g., an antibody molecule, ADC, or antimicrobial peptide, required to kill a particular bacterium. In an embodiment, minimum bactericidal concentration or MBC can be determined from broth dilution minimum inhibitory concentration (MIC) tests by subculturing to agar plates that do not contain the test agent. In an embodiment, the MBC is identified by determining the lowest concentration of antimicrobial agent that reduces the viability of the initial bacterial inoculum by ≥99.9%. In an embodiment, antimicrobial agents are usually regarded as bactericidal if the MBC is no more than four times the MIC (French, J Antimicrob Chemother. 2006; 58(6):1107-1117).

Various aspects of the compositions and methods herein are described in further detail below. Additional definitions are set out throughout the specification.

Lipopolysaccharides

Disclosed herein are antibody molecules and antibody molecule-drug conjugates (ADCs) that can bind to lipopolysaccharides (LPS), e.g., on the outer membrane of Gram-negative bacteria. In an embodiment, the antibody molecule or ADC binds to a core pentasaccharide region of the LPS. Without wishing to be bound by theory, it is believed that in an embodiment, a core LPS region is targeted, at least in part, because it has one or more of the following properties: high density, conserved within species, accessible, or essential for adhesion (Raetz and Whitfield *Annu. Rev. Biochem.* 2002; 71: 635-700; de Kievit and Lam *J Bacteriol.* 1994; 176(23):7129-39; Schmengler et al. *Eur J Cell Biol.* 2010; 89(1):25-33; Pier et al. *Am J Respir Crit Care Med.* 1996; 154(4 Pt 2):S175-82).

LPS, also known as lipoglycans or endotoxin, are large molecules including a lipid and a polysaccharide composed of O-antigen, outer core and inner core joined by a covalent bond. LPS is found, e.g., in the outer membrane of Gram-negative bacteria, which may elicit strong immune responses in animals. LPS contributes to the structural integrity of the bacteria and protects the membrane from certain kinds of chemical attack. It also increases the negative charge of the cell membrane and helps stabilize the overall membrane structure. LPS may induce a strong immune response in animals. It has also been implicated in non-pathogenic aspects of bacterial ecology, including surface adhesion, bacteriophage sensitivity, and interactions with predators such as amoebae. LPS is required for the proper conformation of omptin activity; however, smooth LPS will sterically hinder omptins. As LPS is a major component of the outer membrane of Gram-negative bacteria, mutation or removal of LPS can result in death of Gram-negative bacteria.

LPS comprises three parts: O antigen (or O polysaccharide), Core oligosaccharide, and Lipid A.

O antigen, also known as O polysaccharide or O side-chain, is a repetitive glycan polymer contained within an LPS of the bacteria. The O antigen is attached to the core oligosaccharide, and comprises the outermost domain of the LPS molecule. The composition of the O chain varies from strain to strain. For example, there are over 160 different O antigen structures produced by different *E. coli* strains (Raetz and Whitfield *Annu. Rev. Biochem.* 2002; 71: 635-700). The presence or absence of O chains determines whether the LPS is considered rough or smooth. Full-length O-chains would render the LPS smooth, whereas the absence or reduction of O-chains would make the LPS rough (Rittig et al. *J. Leukoc. Biol.* 2003; 74 (6): 1045-55). Bacteria with rough LPS usually have more penetrable cell membranes to hydrophobic antibiotics, since a rough LPS is more hydrophobic (Tsujimoto et al. *J. Infect. Chemother.* 1999, 5 (4): 196-200. O antigen is exposed on the very outer surface of the bacterial cell, and, can be targeted for recognition by host antibodies.

Figures 1, 2A:
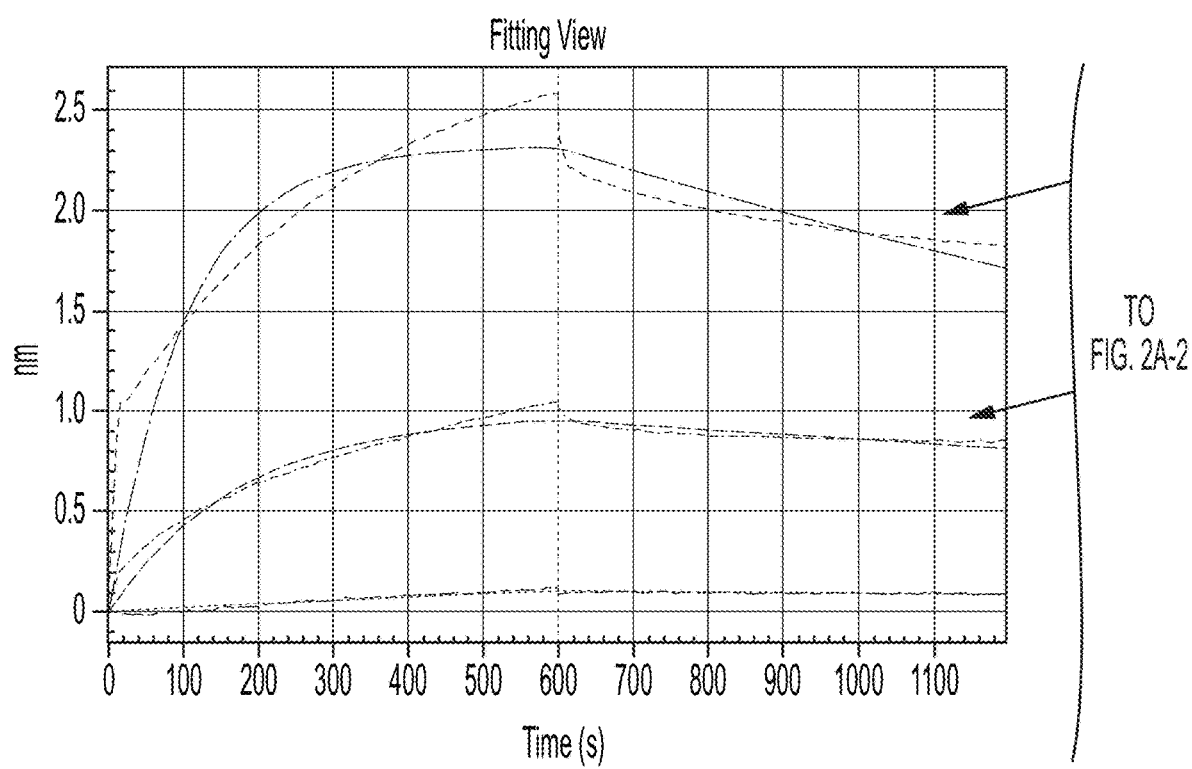

The Core oligosaccharide or core domain contains an oligosaccharide component that attaches directly to lipid A and commonly contains sugars such as heptose (Hep) and 3-deoxy-D-mannooctulosonic acid (also known as Kdo or keto-deoxyoctulosonate) (Hershberger and Binkley, *J. Biol. Chem.* 1968; 243 (7): 1578-1584). A typical core pentasaccharide or core pentasaccharide region includes, e.g., two Kdo residues and one, two or three Hep residues. The composition and structure of core pentasaccharides from exemplary bacteria are shown in FIG. 1 of PCT Publication No. WO 2018/136626 (incorporated herein by reference in its entirety). The LPS Cores of many bacteria also contain non-carbohydrate components, such as phosphate, amino acids, and ethanolamine substituents.

A LPS core can include an inner core and an outer core. The "base" of the inner core is 1-3 Kdo residues. The last Kdo is often modified with a phosphate or ethanolamine group. From the Kdo residues, there are attached 2-3 heptose residues (e.g., L-glycero-D-mannoheptulose) that are usually phosphorylated. These Kdo and heptose residues form the "inner core." The ketosidic bond between Kdo and lipid A ($\alpha 2 \rightarrow 6$) is especially susceptible to acid cleavage. The lipid and polysaccharide portions of LPS can be separated by a weak acid treatment. An LPS molecule that includes only a lipid A and an inner core (or less) is referred to as "deep-rough LPS."

The outer core is made of hexose residues that are attached to the last heptose residue in the inner core. Hexoses often found in the outer core include, e.g., D-glucose, D-mannose, or D-galactose. There is usually at least three hexoses bound $\beta 1 \rightarrow 6$, with the O antigen being ligated to the third hexose. Other hexoses are often found attached to the outer core, branching from the main oligomer. LPS that include lipid A and a complete core oligosaccharide (inner and outer) is referred to as "rough LPS."

Lipid A is, in some circumstances, a phosphorylated glucosamine disaccharide decorated with multiple fatty acids. These hydrophobic fatty acid chains anchor the LPS into the bacterial membrane, and the rest of the LPS projects from the cell surface. In an embodiment, the antibody molecule or ADC binds proximate to the cell surface. The lipid A domain is responsible for much of the toxicity of Gram-negative bacteria. When bacterial cells are lysed by the immune system, fragments of membrane containing lipid A are released into the circulation, causing fever, diarrhea, and possible fatal endotoxic shock (also called septic shock).

In an embodiment, a core glycan of *P. aeruginosa* is targeted. In an embodiment, the antibody molecule or ADC binds to an inner core glycan of *P. aeruginosa*. For example, the epitope can include HepI, and, to a lesser degree, surrounding contacts. In an embodiment, the antibody molecule or ADC binds smooth LPS, rough LPS, or both. In an embodiment, the antibody molecule or ADC binds smooth LPS. In an embodiment, the antibody molecule or ADC binds smooth LPS from *P. aeruginosa*. In an embodiment, the antibody molecule or ADC binds smooth LPS (e.g., from *P. aeruginosa*), but not to *E. coli* LPS. In an embodiment, the antibody molecule or ADC does not bind, or does not substantially bind, to O-polysaccharides. In an embodiment, the antibody molecule or ADC binds to a hyperphosphorylated heptose. In an embodiment, the antibody molecule or ADC does not bind, or does not substantially bind, to Gram-negative bacteria other than *P. aeruginosa*. In an embodiment, the antibody molecule or ADC binds to a synthetic phosphorylated heptose unit. For example, an antibody molecule or ADC described herein (e.g., mAb001) can bind to the epitope shown in FIG. 29 of PCT Publication No. WO 2018/136626 (incorporated herein by reference in its entirety). Without wishing to be bound by theory, it is believed that in an embodiment, core glycans of *P. aeruginosa* are conserved across strains, are accessible in vivo, and/or have limited phase variation/resistance elements.

In an embodiment, the antibody molecule or ADC binds to phosphorylated LPS, e.g., a phosphorylated core pentasaccharide region of the LPS. In an embodiment, the antibody molecule or ADC described herein binds to one or more (e.g., two or three) phosphate groups in the core LPS region of *P. aeruginosa*. In an embodiment, the phosphate group is bound by an Arginine residue in the antibody molecule or ADC. In an embodiment, the phosphate group is inhibited or neutralized by an Arginine residue in the antibody molecule or ADC. In an embodiment, the antibody molecule or ADC binds to at least three phosphate groups (e.g., Hep2,4,6-PO 4) in the core LPS region of *P. aeruginosa*, each of which is bound, inhibited, or neutralized by an Arginine residue (e.g., VL residue R100, or V1-1 residues R101 or R103) in the antibody molecule or ADC. For example, the H3 and L3 cavity of the antibody molecule can accommodate a monosaccharide. The interactions between the phosphorylated glycans (Hep2,4,6-PO$_4$) and three Arginine residues (VL residue R100, or VH residues R101 and R103) in an exemplary antibody molecule, mAb001, are illustrated in FIG. 30 of PCT Publication No. WO 2018/136626 (incorporated herein by reference in its entirety). In an embodiment, an antibody molecule or ADC as described herein comprises one or more (e.g., 1, 2, or 3) conservative substitutions of VL residue R100 and/or VH residues R101 and/or R103. In an embodiment, one or more of the conservative substitutions comprises a mutation to a positively charged amino acid other than arginine (e.g., lysine or histidine). In an embodiment, the antibody molecule or ADC comprises a conservative substitution of VL residue R100 (e.g., a mutation to a positively charged amino acid other than arginine, e.g., lysine or histidine). In an embodiment, the antibody molecule or ADC comprises a conservative substitution of VH residue R101 (e.g., a mutation to a positively charged amino acid other than arginine, e.g., lysine or histidine). In an embodiment, the antibody molecule or ADC comprises a conservative substitution of VH residue R103 (e.g., a mutation to a positively charged amino acid other than arginine, e.g., lysine or histidine).

Without wishing to be bound by theory, it is believed that in an embodiment, phosphates targeted by an antibody molecule or ADC described herein are essential for bacteria (e.g., *P. aeruginosa*) survival. In an embodiment, the antibody molecule or ADC binds to one or more (e.g., 2 or 3) phosphates of the inner core (e.g., HepI) of *P. aeruginosa* LPS. Proper phosphorylation of HepI is typically needed for outer membrane biosynthesis in certain Gram-negative bacteria, e.g., *P. aeruginosa*. Compromised outer membrane due to lack of proper phosphorylation of HepI can lead to non-viral bacteria.

Without wishing to be bound by theory, it is believed that in an embodiment, an operon comprising three kinases present in multiple sequenced strains of *P. aeruginosa* are involved in HepI phosphorylation. In this operon unique to *Pseudomonas*, waaP and wapP kinase genes are essential genes for *P. aeruginosa* strains and are typically required for viability (Delucia et al. *MBio*. 2011; 2(4). pii: e00142-11). The same operon also contains genes encoding additional kinases (e.g., wapQ and at least one additional putative kinase), which are specific for species of *P. aeruginosa* and encode non-essential kinases. The binding between the antibody molecules or ADCs described herein and *P. aeruginosa* is typically not affected by the deletion of these non-essential kinase genes of the operon. Accordingly, the antibody molecules and ADCs described herein have broad coverage of *P. aeruginosa* strains, have high specificity towards *Pseudomonas* infected patients, and are effective in treating or preventing infections associated with resistant or mutant *P. aeruginosa* strains.

Antibody Molecules

Disclosed herein are antibody molecules that bind to bacteria (e.g., Gram-negative bacteria) and/or lipopolysaccharides (LPS). The antibody molecule-drug conjugates (ADCs) disclosed herein can include an antibody molecule disclosed herein.

As used herein, the term "antibody molecule" refers to a protein, e.g., an immunoglobulin chain or a fragment thereof, comprising at least one immunoglobulin variable domain sequence. The term "antibody molecule" includes, for example, full-length, mature antibodies and antigen-binding fragments of an antibody. For example, an antibody molecule can include a heavy (H) chain variable domain sequence (abbreviated herein as VH), and a light (L) chain variable domain sequence (abbreviated herein as VL). In another example, an antibody molecule includes two heavy (H) chain variable domain sequences and two light (L) chain variable domain sequence, thereby forming two antigen binding sites, such as Fab, Fab', F(ab')2, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The antibody molecules can be monoclonal or polyclonal. The antibody molecule can also be a human, humanized, CDR-grafted, or in vitro generated antibody. The antibody molecule can have a heavy chain constant region chosen from, e.g., IgG1, IgG2, IgG3, or IgG4. The antibody molecule can also have a light chain chosen from, e.g., kappa or lambda. The term "immunoglobulin" (Ig) is used interchangeably with the term "antibody" herein.

Examples of antigen-binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments may be obtained using any suitable method, including several conventional techniques known to those with skill in the art, and the fragments can be screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

The antibody molecule can be a single chain antibody. A single-chain antibody (scFv) may be engineered (see, for example, Colcher, D. et al. (1999) *Ann N Y Acad Sci*

880:263-80; and Reiter, Y. (1996) *Clin Cancer Res* 2:245-52). The single chain antibody can be dimerized or multimerized to generate multivalent antibodies having specificities for different epitopes of the same target protein.

The antibody molecules disclosed herein can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to some aspects, a single domain antibody is a naturally occurring single domain antibody known as heavy chain antibody devoid of light chains. Such single domain antibodies are disclosed in International Publication No. WO 94/04678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are also contemplated.

The VH and VL regions can be subdivided into regions of hypervariability, termed "complementarity determining regions" (CDR), interspersed with regions that are more conserved, termed "framework regions" (FR or FW). The terms "complementarity determining region," and "CDR," as used herein refer to the sequences of amino acids within antibody variable regions which confer antigen specificity and binding affinity. As used herein, the terms "framework," "FW" and "FR" are used interchangeably.

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). In an embodiment, the following definitions are used: AbM definition of CDR1 of the heavy chain variable domain and Kabat definitions for the other CDRs. In an embodiment, Kabat definitions are used for all CDRs. In addition, embodiments described with respect to Kabat or AbM CDRs may also be implemented using Chothia hypervariable loops. Each VH and VL typically includes three CDRs and four FRs, arranged from amino-terminus to carboxy-terminus in the following order: FR1, CDR1, FR2, CDR2, FR3, CDR3, and FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding region" refers to the part of an antibody molecule that comprises determinants that form an interface that binds to an antigen, e.g., lipopolysaccharide (LPS), or an epitope thereof. With respect to proteins (or protein mimetics), the antigen-binding region typically includes one or more loops (of at least, e.g., four amino acids or amino acid mimics) that form an interface that binds to the antigen, e.g., LPS. Typically, the antigen-binding region of an antibody molecule includes at least one or two CDRs and/or hypervariable loops, or more typically at least three, four, five or six CDRs and/or hypervariable loops.

The terms "compete" or "cross-compete" are used interchangeably herein to refer to the ability of an antibody molecule to interfere with binding of an anti-LPS antibody molecule, e.g., an anti-LPS antibody molecule provided herein, to a target, e.g., LPS on a Gram-negative bacterium. The interference with binding can be direct or indirect (e.g., through an allosteric modulation of the antibody molecule or the target). The extent to which an antibody molecule is able to interfere with the binding of another antibody molecule to the target, and therefore whether it can be said to compete, can be determined using a competition binding assay, for example, a FACS assay, an ELISA, an SPR assay, or an OCTET® assay (ForteBio). In an embodiment, a competition binding assay is a quantitative competition assay. In an embodiment, a first anti-LPS antibody molecule is said to compete for binding to the target with a second anti-LPS antibody molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.*, 32:180-190 (1990)) and also because of potential allergic reactions (see, e.g., LoBuglio et al., *Hybridoma*, 5:5117-5123 (1986)).

The antibody molecule can be a polyclonal or a monoclonal antibody. In an embodiment, the antibody can be recombinantly produced, e.g., produced by any suitable phage display or combinatorial methods.

Various phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al.

International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In an embodiment, the antibody molecule is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. In an embodiment, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by any suitable recombinant DNA technique. Several are known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immunoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to lipopolysaccharide. In an embodiment, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In an embodiment, the donor immunoglobulin is a non-human (e.g., rodent). The acceptor framework is typically a naturally-occurring (e.g., a human) framework or a consensus framework, or a sequence about 85% or higher, e.g., 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by any suitable method, and several such methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare humanized antibodies (UK Patent Application GB 2188638A, filed on Mar. 26, 1987; Winter U.S. Pat. No. 5,225,539), the contents of which is expressly incorporated by reference.

Also provided are humanized antibodies in which specific amino acids have been substituted, deleted or added. Criteria for selecting amino acids from the donor are described in, e.g., U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

In an embodiment, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the heavy chain constant regions (e.g., the human heavy chain constant regions) of IgG1, IgG2, IgG3, and IgG4. In another embodiment, the antibody molecule has a light chain constant region chosen from, e.g., the light chain constant regions (e.g., the human light chain constant regions) of kappa or lambda. The constant region can be altered, e.g., mutated, to modify the properties of the antibody molecule (e.g., to increase or decrease one or more of: Fc receptor binding, antibody glycosylation, the number of cysteine residues, effector cell function, and/or complement function). In an embodiment, the antibody molecule has effector function and can fix complement. In another embodiment, the antibody molecule does not recruit effector cells or fix complement. In an embodiment, the antibody molecule has reduced or no ability to bind an Fc receptor. For example, it may be an isotype or subtype, fragment or other mutant, which does not support binding to an Fc receptor, e.g., it has a mutagenized or deleted Fc receptor binding region. In an embodiment, the antibody molecule comprises an Fc region that is altered to increase an ADCC activity. In an embodiment, the ADCC activity is increased by 10-fold or more, e.g., 25-fold or more, 50-fold or more, 100-fold or more, 200-fold or more, 400-fold or more, 600-fold or more, 800-fold or more, or 1000-fold or more, e.g., between 100-fold and 1000-fold or between 250-fold and 750-fold. In an embodiment, the antibody molecule comprises an Fc region that is altered to modulate engagement with an Fcγ receptor or an opsonophagocytosis activity. In an embodiment, the antibody molecule comprises an Fc region that is altered to modulate engagement with an FcRn receptor.

In an embodiment, a constant region of the antibody molecule is altered. Methods for altering an antibody constant region are known in the art. Antibody molecules with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Amino acid mutations which stabilize antibody structure, such as S228P (EU nomenclature, S241P in Kabat nomenclature) in human IgG4 are also contemplated. Similar type of alterations could be described which if applied to the murine, or other species immunoglobulin would reduce or eliminate these functions.

In an embodiment, the antibody molecule is engineered for optimal engagement with an Fc receptor, e.g., FcγRIIa, FcγRII, C1q, or a combination thereof, e.g., for enhanced opsonophagocytic activity (OPA), complement dependent cytotoxicity (CDC), or both. Without wishing to be bound by theory, it is believed that in an embodiment, OPA can be mediated by engagement of Fc region of the antibody with activating receptor FcγRIIa and inhibitory receptor FcγRIIb. In an embodiment, mutations on the Fc that selectively enhance engagement with FcγRIIa over FcγRIIb can be identified, e.g., using the solved crystal structures of Fc with FcγRIIa and FcγRIIb. Antibody molecules or ADCs harboring one or more Fc engagement enhancing mutations can be evaluated in OPA assays. In another embodiment, Fc mutations for increased binding to C1q complex can be identified, e.g., to promote complement deposition on bacteria and CDC mediated killing of bacteria. Antibody molecules or ADCs harboring one or more C1q affinity enhancing mutations can be evaluated in CDC assays.

In an embodiment, the only amino acids in the antibody molecule are canonical amino acids. In an embodiment, the antibody molecule comprises naturally-occurring amino acids; analogs, derivatives and congeners thereof; amino acid analogs having variant side chains; and/or all stereoisomers of any of any of the foregoing. The antibody molecule may comprise the D- or L-optical isomers of amino acids and peptidomimetics.

A polypeptide of an antibody molecule described herein may be linear or branched, it may comprise modified amino acids, and it may be interrupted by non-amino acids. The antibody molecule may also be modified; for example, by disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The antibody molecule described herein can be used alone in unconjugated form, or can be bound to a substance, e.g., a toxin or moiety (e.g., a therapeutic drug (e.g., an antibiotic); a compound emitting radiation; molecules of plant, fungal, or bacterial origin; or a biological protein (e.g., a protein toxin) or particle (e.g., a recombinant viral particle, e.g., via a viral coat protein). For example, the anti-LPS antibody can be coupled to a radioactive isotope such as an α-, β-, or γ-emitter, or a β- and γ-emitter.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a toxin, a pharmaceutical agent, and/or a protein or peptide that can mediate association of the antibody or antibody portion with another molecule (such as a streptavidin core region or a polyhistidine tag).

Some types of derivatized antibody molecule are produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an anti-LPS antibody molecule may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody molecule may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibody molecule can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An antibody molecule may be conjugated to another molecular entity, typically a label or a therapeutic (e.g., antimicrobial (e.g., antibacterial or bactericidal), immunomodulatory, immunostimularoty, cytotoxic, or cytostatic) agent or moiety. Radioactive isotopes can be used in diagnostic or therapeutic applications. Radioactive isotopes that can be coupled to the antibody molecules include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In), technetium ($^{99}$mTc), phosphorus ($^{32}$P), carbon ($^{14}$c), and tritium ($^{3}$H), or one or more of the therapeutic isotopes listed above.

The present disclosure provides radiolabeled antibody molecules and methods of labeling the same. In an embodiment, a method of labeling an antibody molecule is disclosed. The method includes contacting an antibody molecule, with a chelating agent, to thereby produce a conjugated antibody. The conjugated antibody is radiolabeled with a radioisotope, e.g., $^{111}$Indium, $^{90}$Yttrium and $^{177}$Lutetium, to thereby produce a labeled antibody molecule.

As is discussed above, the antibody molecule can be conjugated to a therapeutic agent. Therapeutically active radioisotopes have already been mentioned. Examples of other therapeutic agents include antimicrobial (e.g., antibacterial) agents, e.g., antimicrobial peptides. In an embodiment, an antimicrobial peptide can be coupled (e.g., fused) to the antibody molecule, e.g., a heavy chain or light chain of the antibody molecule. In an embodiment, the antimicrobial peptide is coupled (e.g., fused) to the N-terminus of the heavy chain or light chain or a functional fragment thereof. In an embodiment, the antimicrobial peptide is coupled (e.g., fused) to the C-terminus of the heavy chain or light chain or a functional fragment thereof. In an embodiment, the antimicrobial peptide is coupled (e.g., fused) to a constant region or a portion thereof. In an embodiment, the heavy chain or light chain, or a portion thereof, and the antimicrobial peptide, forms a fusion polypeptide, e.g., encoded by an open reading frame (ORF). One or more antimicrobial peptides can be coupled (e.g., fused) to the antibody molecule. In an embodiment, at least two of the antimicrobial peptides are identical or substantially identical. In another embodiment, at least two of the antimicrobial peptides are different. In an embodiment, all of the antimicrobial peptides are identical or substantially identical.

In some aspects, this disclosure provides a method of making an antibody molecule disclosed herein. The method includes: providing an antigen, e.g., a bacteria (e.g., a Gram-negative bacteria) or LPS; obtaining an antibody molecule that specifically binds to the antigen; evaluating efficacy of the antibody molecule in modulating activity of the antigen and/or organism expressing the antigen, e.g., a bacterium (e.g., a Gram-negative bacterium). The method can further include administering the antibody molecule, including a derivative thereof (e.g., a humanized antibody molecule) to a subject, e.g., a human.

This disclosure provides an isolated nucleic acid molecule encoding the above antibody molecule, vectors and host cells thereof. The nucleic acid molecule includes, but is not limited to, RNA, genomic DNA and cDNA.

Exemplary sequences of antibody molecules are described in Tables 1-3 below.

TABLE 1

Amino acid sequences of heavy chain variable regions (VHs), light chain variable regions (VLs), heavy chain CDRs (HCDRs), and light chain CDRs (LCDRs) of exemplary antibody molecules. Heavy and light chain CDRs defined according to Chothia system and Kabat system are shown.

| Antibody | SEQ ID NO | VH | | Chothia CDR | SEQ ID NO | Kabat CDR | SEQ ID NO |
|---|---|---|---|---|---|---|---|
| A001-25 | 1 | EVQLQQSGPVLVKPGASVKMSCKASGYTFTDHYINWVKQSH GKSLEWIGGIYPYHGITKYNRNFKDKATLTVDKSSSTAYME LNSLTSELSAVYYCASGSRRYFDVWGTGTTVTVSS | HCDR1<br>HCDR2<br>HCDR3 | GYTFTDH<br>YPYHGI<br>GGSRRYFDV | 14<br>15<br>16 | DHYIN<br>GIYPYHGITKYNRNFKD<br>GGSRRYFDV | 17<br>18<br>16 |
| hwN01 | 2 | EVQLVESGGGLVQPGGSLRLSCAASGFTFSDYMTWVRQAP GKGLEWLGLIRNKRNGDTAEYSASVKGRFTISRDDSKNSLY LQMNSLKTEDTAVYYCARQRGRYTLDYWGQGTLVTVSS | HCDR1<br>HCDR2<br>HCDR3 | GFTFSDY<br>RNKRNGDT<br>QGRGYTLDY | 19<br>20<br>21 | DYYMT<br>LIRNKRNGDTAEYSASVKG<br>QGRGYTLDY | 22<br>23<br>21 |
| hwNv1 | 3 | EVQLVESGGGLVQPGGSLRLSCAASGFTFSDYMTWVRQAP GKGLEWLGLIRAKANGDTAEYSASVKGRFTISRDDSKNSLY LQMNSLKTEDTAVYYCARQRGRYTLDYWGQGTLVTVSS | HCDR1<br>HCDR2<br>HCDR3 | GFTFSDY<br>RAKANGDT<br>QGRGYTLDY | 19<br>25<br>21 | DYYMT<br>LIRAKANGDTAEYSASVKG<br>QGRGYTLDY | 27<br>28<br>21 |
| 3E7 | 4 | QVQLQQSGAELVKPGASVKMSCKASGYTFTSYWITWVKQRP GQGLEWIGDIYPGSGSTNNNEKFKSKATLTVDTSSSTAYMQ LSSLTSEDSAVYYCARGSYSLDYWGQGTLVTVSS | HCDR1<br>HCDR2<br>HCDR3 | GYTFTSY<br>YPGSGS<br>GSYSLDY | 29<br>30<br>31 | SYWIT<br>DIYPGSGSTNYNEKFKS<br>GSYSLDY | 32<br>33<br>31 |
| 3G1 | 5 | EVQLVESGGGLVRPGASVKLSCTASGFNIKNTYMHWVKQRP EQGLEWIGRIDPANGNTKYAPKFQGKATITADTSNTAYLQ LSSLTSEDTAIYYCAPSNYHAMDYWGQGTSVTVSS | HCDR1<br>HCDR2<br>HCDR3 | GFNIKNT<br>DPANGN<br>SNYHAMDY | 34<br>35<br>36 | NTYMH<br>RIDPANGNTKYAPKFQG<br>SNYHAMDY | 37<br>38<br>36 |
| 2C7 | 6 | DVQLQESGPGLVKPSQSLSLTCSVTGYSITSGYWNWIRQF PGNKLEWMGYISYDGSNNYNPSLKNRISITRDTSKNQFFLK LNSVTTEDTATYYCARWNGNYFDYWGQGTTLTVSS | HCDR1<br>HCDR2<br>HCDR3 | GYSITSGY<br>SYDGS<br>WNGNYFDY | 39<br>40<br>41 | SGYYWN<br>YISYDGSNNYNPSLKN<br>WNGNYFDY | 42<br>43<br>41 |
| 3D6 | 7 | EVKLVESGGGLVKPGASVKMSCAASEFTFSDYAMSWVRQTP GKSLEWIGVINPYNGGTSYNQKFKGKATLTVDKSSSTAYME LNSLRSEDTAMYYCARTRQLGLRWFAYWGQGTLVTVSA | HCDR1<br>HCDR2<br>HCDR3 | GYTFTDY<br>NPYNGG<br>TRQLGLRWFAY | 44<br>45<br>46 | DYYMN<br>VINPYNGGTSYNQKFKG<br>TRQLGLRWFAY | 47<br>48<br>46 |
| mAb001 | 103 | EVKLVESGGGLVKPGGSLRLSCAASEFTFSDYAMSWVRQTP AKRLEWVAYISSDGDSTYYPDNIKGRFTISRDNAKNTLYLQ MNSLRSEDTAMYFCAREIRLRGYFDVWGAGTTVTVSS | HCDR1<br>HCDR2<br>HCDR3 | EFTFSDY<br>SSDGDS<br>EIRLRGYFDV | 105<br>106<br>107 | DYAMS<br>YISSDGDSTYYPDNIKG<br>EIRLRGYFDV | 108<br>109<br>107 |

| Antibody | SEQ ID NO | VL | | Chothia CDR | SEQ ID NO | Kabat CDR | SEQ ID NO |
|---|---|---|---|---|---|---|---|
| A001-25 | 8 | DVVMTQTPLSLPVSLGDQASISCRSSQRLVHSNGNTYLHWY LQKPGQSPKLLIYKVSNRFSGVPDRFSGSGSGTDFTLKISR VEAEDLGVYFCSQSTHVPYTFGGGTKLEIK | LCDR1<br>LCDR2<br>LCDR3 | RSSQRLVHSNGNTYLH<br>KVSNRFS<br>SQSTHVPYT | 49<br>50<br>51 | RSSQRLVHSNGNTYLH<br>KVSNRFS<br>SQSTHVPYT | 49<br>50<br>51 |
| hwN01 | 9 | DIQMTQSPSSVSASVGDRVTITCRASQNINIWLSWYQQKPG KAPKLLIYKASNLHTGVPSRFSGSGSGTDFTLTISSLQPED FATYYCLQQSYPRTFGQGTKVEIK | LCDR1<br>LCDR2<br>LCDR3 | RASQNINIWLS<br>KASNLHT<br>LQQSYPRT | 52<br>53<br>54 | RASQNINIWLS<br>KASNLHT<br>LQQSYPRT | 52<br>53<br>54 |

TABLE 1-continued

Amino acid sequences of heavy chain variable regions (VHs), light chain variable regions (VLs), heavy chain CDRs (HCDRs), and light chain CDRs (LCDRs) of exemplary antibody molecules. Heavy and light chain CDRs defined according to Chothia system and Kabat system are shown.

| | | | | | | | |
|---|---|---|---|---|---|---|---|
| hWNv1 | DIQMTQSPSSVSASVGDRVTITCRASQNINIWLSWYQQKPG KAPKLLIYKASNLHTGVPSRFSGSGSGTDFTLTISSLQPED FATYYCLQGQSYPRTFGGGTKVEIK | 9 | LCDR1 LCDR2 LCDR3 | RASQNINIWLS KASNLHT LQGQSYPRT | 52 53 54 | LCDR1 LCDR2 LCDR3 | RASQNINIWLS KASNLHT LQGQSYPRT | 52 53 54 |
| 3E7 | DIVMTQAAPSVPVTPGESVSISCRSSKSLLHSNGNTYLYWF LQRPGQSPQRLLIYMSNLASGVPDRFSGRGSGTDFTLRISR VEAEDVGVYYCMQSLEYPLTFGAGTKLELK | 10 | LCDR1 LCDR2 LCDR3 | RSSKSLLHSNGNTYLY YMSNLAS MQSLEYPLT | 55 56 57 | LCDR1 LCDR2 LCDR3 | RSSKSLLHSNGNTYLY YMSNLAS MQSLEYPLT | 55 56 57 |
| 3G1 | DIVMTQAAPSVPVTPGESVSISCRSSKSLLHSNGNTYLYWF LQRPGQSPQLLIYRMSNLASGVPDRFSGSGSGTAFTLRISR VEAEDVGVYYCMQHLEYPYTFGGGTKLEIK | 11 | LCDR1 LCDR2 LCDR3 | RSSKSLLHSNGNTYLY RMSNLAS MQHLEYPYT | 58 59 60 | LCDR1 LCDR2 LCDR3 | RSSKSLLHSNGNTYLY RMSNLAS MQHLEYPYT | 58 59 60 |
| 2C7 | DIVMSQSPSSLAVSAGEKVTMSCKSSQSLLNSRTRKNYLAW YQQKPGQSPKLLIYWASTRESGVPDRFTGSGSGTDFTLTIS SVQAEDLAVYYCKQSYNLWTFGGGTKLEIK | 12 | LCDR1 LCDR2 LCDR3 | KSSQSLLNSRTRKNYLA WASTRES KQSYNLWT | 61 62 63 | LCDR1 LCDR2 LCDR3 | KSSQSLLNSRTRKNYLA WASTRES KQSYNLWT | 61 62 63 |
| 3D6 | DIQMTQSPASQSASLGESVTITCLASQTIGTWLAWYQQKPG KSPQLLIYAATSLADGVPSRFSGSGSGTTKFSFKISSLQAED FVSYYCQQLYSTPWTFGGGTKLEIK | 13 | LCDR1 LCDR2 LCDR3 | LASQTIGTWLA AATSLAD QQLYSTPWT | 64 65 66 | LCDR1 LCDR2 LCDR3 | LASQTIGTWLA AATSLAD QQLYSTPWT | 64 65 66 |
| mAb001 | DIVLTQSPASLAVSLGQRATISCRASESVFGHGISPMHWYQ QKPGQPPKLLIYRASNLKFGIPARFSGSGSRTDFTLTINPV EADDVATYYCQQSNEYPRTFGGGTKLEIK | 104 | LCDR1 LCDR2 LCDR3 | RASESVFGHGISPMH RASNLKF QQSNEYPRT | 110 111 112 | LCDR1 LCDR2 LCDR3 | RASESVFGHGISPMH RASNLKF QQSNEYPRT | 110 111 112 |

TABLE 2

Nucleotide sequences of heavy chain variable regions (VHs) and light chain variable regions (VLs) of exemplary antibody molecules.

| Antibody | VH | SEQ ID NO |
|---|---|---|
| A001-25 | GAGGTCCAGCTCGAGCAGTCTGGACCTGCTGCTGGTGAAGCCTCGGGCTTCAGTGAAGATGTCCTGTAAGGCTTCTGGATACACATTCACTGACC ACTATATAAACTGGGTGAAGCAGAGGCCATGGAAAGAGCCTTGAGTGGATTGGATATTATTCTTACCACGTATTACTAAGTACAACCGGAA TTTCAAGGACAAGGCCACATTGACTGTTGACAAGTCTTCGATGTCAGAGCCTACATGGAGCTCCAGCACAGACAGGCCTACATGGAGCTCTAGCTCTGAGGCAGCTCTGCGC TACTGTGCAAGCGGGGAAGTCGCCGGTACTCGAAGTCTCGATGTCAGGACTATTCTATGGTCGCAGGCACCACGTCACCGTCTCCTCA | 81 |
| hwN01 | GAAGTGCAGCTCGTGGAATCTGGAGGAGGACTTGTGCAACCTGGAGGTTCCCTGCGACTGTGTGCCGCATCGGTTTCACCTTTTCCGACT ACTACATGACCTGGGTCCGACAGGCCCCAGGGAAGGGGAACCTGGAGTGGGTCCGGTTCGATCCGAACAACAGAGAAGGCCGTATCTGCTGAATACTC GGCCAGCGTGAAGGGCCGGTTCACCATCTCAGAGATGACAGCAAGAACTCCCTGTACCTCCAAATGAACTCCCTGAGAGCCGAGGACACTGCG GTGTACTACTGCGCCCCCGCCAGGGTCGCCGGTACACGCTGGACTATTGGGGCCAGGGCACCCTGGTCACTGTGTCAAGC | 82 |
| hwNv3 | GAAGTGCAGCTCGTGGAATCTGGAGGAGGACTTGTGCAACCTGGAGGTTCCCTGCGACTGTGTGCCGCATCGGTTTCACCTTTTCCGACT ACTGGATGACCTGGGTCAGACAGGCGCCGGGAAGGACTGGAGTGGGTCGGTTCGATCCGAACAACAGAGAAGGCCGTATCTGCTGAATACTC GGCCAGCGTGAAGGGCCGGTTCACCATCTCAGAGATGACAGCAAGAACTCCCTGTACCTCCAAATGAACTCCCTGAGAGCCGAGGACACTGCG GTGTACTACTGCGCCCCCGCCAGGGTCGCCGGTACACGCTGGACTATTGGGGCCAGGGCACCCTGGTCACTGTGTCAAGC | 83 |
| 3E7 | CAGGTCCAACTGCAGCTCGAGTCTGGGGCTGAGCTTGTGAAGCCTGGGGCTTCAGTGAAGATGTCCTGCAAGGCTTCTGGCTACACCTTCACCAGCT ACTGGATAACCTGGGTGAAGCAGAGGCCTGGAACAGGCCTTGAGTGGATTGGAGATATTTATCCTGGTAGTGGTAGTACTAACTACAATGAGAA GTTCAAGGACAAGGCCACACTGACTGTAGACACATCCTCCAGCACAGCCTACATGCAGCTCAGCAGCCTGACATCTGAGGACTCTGCGGTCTAT TACTGTGCAAGAGAGTAGTAGCTACTTTGACTACTGGGGCCAAGGCACCACTCTCACAGTCTCCTCA | 84 |
| 3G1 | GAGGTCCAGCTGCAGCAGTCTGGGCCTGAGCTTGTGCAGCCTGGGGCTTCAGTGAAGTTGTCCTGCAAGGTTCTGCACAGTTCTGCAGTAATATCAAAACA CCTATATGCACTGGGTGAAGCAGAGGCCTGAACAGGCCTTGAGTGGATTGGAAAGATTGATCCTGAGAATGGTAATACTAAATATGCCCCGAA GTTCCAAGGCCAAGGCCACTATACTGCAGACACAATCTCCAGCACACCTACTGCAGCTCAGCAGCCTGACATCTGAGGACTCTGCCATCTAT TACTGTGCTCCTAGTAACTACCAGACTTTGACTACTGGGGCCAAGGGACCACGGTCACCGTCTCCTCA | 85 |
| 2C7 | GATGTACAGCTTCAGGAGTCAGGACCTCGCCTGGTGAAACCTTCTCAGTCTCTGTCTCTCACCTGCTCTGTCACTGGCTACTCCATCACCAGTG GTTATTACTGGAACTGGATCCGGCAGTTTCCAGGAAACAAACTGGAGTGGATGGGCTACATAAGCTACGATGGTAGCAATAACTACAACCCATC TCTCAAAAATCGAATCTCCATCACTCGTGACACATCTAAGAACCAGTTTTTCCTGAAGTTGAATTCTGTGACTACTGAGGACACAGCCACATAT TACTGTGCAAGATGGAATGGTAACTACTTTGACTACTGGGGCCAAGGCACCACTCTCACAGTCTCCTCA | 86 |
| 3D6 | GAGGTCCAGCTGCAACAGTCTGACCTGTCGTGCTGGACCCTGGAGCCTCGGGCTTCGGGGCTTCAGTGAAGATGTCCTGTAAGGCTTCTGGATACACATTCACTGACT ACTATATGAACTGGGTGAAGCAGAGCCATGGAAAGAGCCTTGAGTGGATTATTAATCCTTACAACGGTGTATTACTAGCTACAACCAGAA GTTCAAGGGCAAGGCCACATTGACTGTTGACAAGTCCTCCAGCACAGCCTACATGGAGCTCCAGCAGCCTGACATCTGAGGACTCTGCAGTCTAT TACTGTGCAAGAGAACCAGACCAGCTCGGGTTCGGTTTGCTTAGTGGGGCCAAGGGACTCTGGTCACTGTCTCTGCA | 87 |
| mAb001 | GAAGTGAAGTTGGTGGAGTCTGGGGGAGACTTGGTGAAACCTGGAGGGTCCCTGAAAGCCTCCGGAGACTCTCCGCATATTAGTAGTGATAATACCTGCATAGTGTTCGGACAA ATGCCATGTCTTGGGTTCGCAGACTCTCCAGAGCACCATCTCCAGAGACAATGCCAAGAACACCCTATACCTGCAAATGAACAGTCTGAGGTCTGAGGACACGGCCATGTAT TATTGTGTGCAAGAAAATCGGCTAAGGGGGTACTTCGATGTCTGGGGCGCAGGGACCACGGTCACCGTCTCCTCA | 113 |

| Antibody | VL | SEQ ID NO |
|---|---|---|
| A001-25 | GATGTTGTGATGACCCAAACTCCACTCTCCCTGCCTGTCAGTCTTGGAGATCAAGCCTCCATCTCTTGCAGATCTAGTCAGAGACTTGTACACA GTAATGGAAACACCTATTTACATTGGTACCTGCAGAAGCCAGGCCAGTCTCCAAAGCTCCTGATCTACAAAGTTCAACCAGTTTTCGGGGT CCCAGACAGGTTCAGTGGCAGTGGATCAGGGACAGATTTCACACTCAAGATCAGCAGAGTGGAGGCTGAGGATCTGGGAGTTTATTTCTGCTCT CAAAGTACACACGTTCCGTACACGTTCGGAGGGGGGACCAAGCTGGAAATAAAA | 88 |

TABLE 2-continued

Nucleotide sequences of heavy chain variable regions (VHs) and light chain variable regions (VLs) of exemplary antibody molecules.

| | | |
|---|---|---|
| hWN01 | GACATCCAGATGACTCAGTCCCCGTCCTCAGTCTCCGATCCGTGGGAGATCGCGTGACGATTACTTGCCGGGCGTCCAGAACATCAACATCT GGCTGTCGTGGTACCACCAGAAGCCCGGAAGCTCCGGAAGCTCTGAATCTACAAGCGTGCTAATCTCAAACTTGCACACCGGCGTGCCTTCCCGCTTTC TGGTTCGGGCTCCGGGACTGACTTCACCCTGACCATCAGCAGCCTGCAACCCGAGGACTTCGCCACCTATTACTGCCTCCAAGGACAGTCCTAC CCAAGAACCTTCGGCGAGGAACCAAGGTCGAAATCAAA | 89 |
| hWNv1 | GACATCCAGATGACTCAGTCCCCGTCCTCAGTCTCCGATCCGTGGGAGATCGCGTGACGATTACTTGCCGGGCGTCCAGAACATCAACATCT GGCTGTCGTGGTACCACCAGAAGCCCGGGAAGCTCTGAATCTACAAGCGTGCTAATCTACAAGCTTGCACACCGGCGTGCCTTCCCGCTTTC TGGTTCGGGCTCCGGGACTGACTTCACCCTGACCATCAGCAGCCTGCAACCCGAGGACTTCGCCACCTATTACTGCCTCCAAGGACAGTCCTAC CCAAGAACCTTCGGCGAGGAACCAAGGTCGAAATCAAA | 89 |
| 3E7 | GATATTGTGATGACTCAGGCTGCACCCTCTGTACCTGTCACTCCTGGAGAGTCAGTATCCAGCCTCCTGCAGGTCTAGTAAGAGTCTTCTGCATA GTAATGGCAACACTTACTTGTATTGGTTCCTGCAGAGGCCAGGCCAGTCTCCAGAGCTCCTGATCTATCGGATGTCCAACCTTGCCTCAGGAGT CCCAGACAGGTTCAGTGGCAGAGGGTCAGGGACTGAATTTCACACTGAAGATCAGTAGAGTGGAGGCTGAGGATGTGGGTGTTTATTACTGTATG CAAAGTCTAGAATATCCTCACGTTCGGTGCTCGGAGGGGACCAAGCTGGAGCTGAAA | 90 |
| 3G1 | GATATTGTGATGACTCAGGCTGCACCCTCTGTACCTGTCACTCCTGGAGAGTCAGTATCCAGCCTCCTGCAGGTCTAGTAAGAGTCTCTGCATA GTAATGGCAACACTTACTTGTATTGGTTCCTGCAGAGGCCAGGCCAGTCTCCAGCCTCCTGATGTCCAACCTTGCCTCAGGAGT CCCAGACAGGTTCAGTGGCAGAGGGTCAGGGACTGAATTTCACACTGAAGATCAGTAGAGTGGAGGCTGAGGATGTGGGTGTTTATTACTGTATG CAACATCTAGAATATCCGTACGTTCGGAGGGGGACCAAGCTGGAGCTGAAATAAAA | 91 |
| 2C7 | GACATTGTGATGTCACAGTCTCATCCTCCCTGCTGTGTCAGCAGGAGAGAAGGTCACTATGAGCTGCAAATCCAGTCAGAGTCTGCTCAACA GTAGAACCCGAAAGAACTACTTGGCTTGGTACCAGCAGAAACCAGGGCAGTCTCCTAAACATGCTGATCTACTGGGCATCCACTAGGGAATCTGG GGTCCCTGATCCGTTCACAGGCAGTGGATCTGGGACAGATTTCACTCTCACCATCAGCAGTGTGCAGGCTGAAGACCTGGCAGTTATTACTGC AAGCAATCTTATATCCTCGTGGACGTTCGGTGGAGGCACCAAGCTGGAAATCAAA | 92 |
| 3D6 | GACATTCAGATGACCCAGTCTCCTGCCTCCCAGTCTGCATCTGTGGGAGAAACTGTCACCATCACATGCCTGGCAAGTCAGACCATTGGTACAT GGTTAGCATGGTATCAGCAGAAACCAGGGAAATCTCCTCAGCTCCTGATTTATGCTGCAACCAGCTTGGCAGATGGGGTCCCATCAAGGTTCAG TGGTAGTGGATCTGGCACAAATTTTCTTCAAGATCAGCAGCCTACAGCCTGAAGATTTTGTAAGTTATTACTGTCAACAACTTTACAGTACT CCGTGGACGTTCGGTGGAGGCACCAAGCTGGAAATCAAA | 93 |
| mAb001 | GACATTGTGCTGACCCAATCTCCAGCTTCTTTGGCTGTGTCTCTAGGGCAGAGGGCCACCATCTCCTGCAGAGCCAGTGAAAGTGTTTTGGTC ATGGCATTAGTCACTGGTACCTATGCCATGCACTGGTACCAGCAGAAACCAGGACAGCCACCCAAACTCCTCATCTATCTGTCATCCAACCTAGAATTTGGATCC TGCCAGGTTCAGTGGCAGTGGGTCTAGGACAGACTTCACCCTCACCATTAATCCTGTGGAGGCTGATGATGTTGCAACCTATTACTGTCAGCAA AGTAATGAATATCCTCGGACGTTCGGTGGAGGCACCAAGCTGGAGATCAAA | 114 |

TABLE 3

Amino acid sequences of heavy chain variable regions (VHs), light chain variable regions (VLs), heavy chain CDRs (HCDRs), and light chain CDRs (LCDRs) of exemplary humanized antibody molecules. Heavy and light chain CDRs defined according to Chothia system and Kabat system are shown.

| Antibody/Chain | VH | SEQ ID NO | | Chothia CDR | SEQ ID NO | | Kabat CDR | SEQ ID NO |
|---|---|---|---|---|---|---|---|---|
| mAb001_VH1 | EVKLVESGGGLVQPGGSLRLSCAASEFTFSDYAMSWVRQAPGKGLEWVSYISSDGDSTYYPDNIKGRFTISRDNSKNTLYVQMSSLRAEDTAVYFCAREIRLRGYFDVWGQGTTVTVSS | 115 | HCDR1<br>HCDR2<br>HCDR3 | EFTFSDY<br>SSDGDS<br>EIRLRGYFDV | 105<br>106<br>107 | HCDR1<br>HCDR2<br>HCDR3 | DYAMS<br>YISSDGDSTYYPDNIKG<br>EIRLRGYFDV | 108<br>109<br>107 |
| mAb001_VH2 | EVKLVESGGGLVKPGGSLRLSCAASEFTFSDYAMSWVRQAPGKGLEWVAYISSDGDSIYYPDNIKGRFTISRDNAKNSLYLQMNSLRAEDTAMYFCAREIRLRGYFDVWGQGTTVTVSS | 116 | HCDR1<br>HCDR2<br>HCDR3 | EFTFSDY<br>SSDGDS<br>EIRLRGYFDV | 105<br>106<br>107 | HCDR1<br>HCDR2<br>HCDR3 | DYAMS<br>YISSDGDSIYYPDNIKG<br>EIRLRGYFDV | 108<br>145<br>107 |
| mAb001_VH3 | EVKLVESGGGLVQPGGSLRLSCAASEFTFSDYAMSWVRQAPGKRLEWVAYISSDGDSTYYPDSVKGRFTISRDNAKNSLYLQMNSLRAEDTAMYFCAREIRLRGYFDVWGQGTTVTVSS | 117 | HCDR1<br>HCDR2<br>HCDR3 | EFTFSDY<br>SSDGDS<br>EIRLRGYFDV | 105<br>106<br>107 | HCDR1<br>HCDR2<br>HCDR3 | DYAMS<br>YISSDGDSTYYPDSVKG<br>EIRLRGYFDV | 108<br>146<br>107 |
| mAb001_VH4 | EVKLVESGEGLVQPGGSLRLSCAASEFTFSDYAMSWVRQAPGKRLEWVAYISSDGDSTYYPDNIKGRFTISRDNSKNTLYLQMGSLRAEDMAMYFCAREIRLRGYFDVWGQGTTVTVSS | 118 | HCDR1<br>HCDR2<br>HCDR3 | EFTFSDY<br>SSDGDS<br>EIRLRGYFDV | 105<br>106<br>107 | HCDR1<br>HCDR2<br>HCDR3 | DYAMS<br>YISSDGDSTYYPDNIKG<br>EIRLRGYFDV | 108<br>109<br>107 |

| Antibody/Chain | VL | SEQ ID NO | | Chothia CDR | SEQ ID NO | | Kabat CDR | SEQ ID NO |
|---|---|---|---|---|---|---|---|---|
| mAb001_VL1 | EIVMTQSPATLSVSPGERATLSCRASESVFGHGISPLHWYQQKPGQAPKLLIYRASNRKTGIPARFSGSGSGTEFTLTISSLQSEDFAVYYCQQSNEYPRTFGGGTKVEIK | 119 | LCDR1<br>LCDR2<br>LCDR3 | RASESVFGHGISPLH<br>RASNRKT<br>QQSNEYPRT | 138<br>139<br>112 | LCDR1<br>LCDR2<br>LCDR3 | RASESVFGHGISPLH<br>RASNRKT<br>QQSNEYPRT | 138<br>139<br>112 |
| mAb001_VL2 | DIQMTQSPSTLSASVGDRVTITCRASESVFGHGISPLHWYQQKPGKAPKLLIYRASNLKFGVPSRFSGSGSGTEFTLTISSLQPDDFATYYCQQSNEYPRTFGGGTKVEIK | 120 | LCDR1<br>LCDR2<br>LCDR3 | RASESVFGHGISPLH<br>RASNLKF<br>QQSNEYPRT | 138<br>111<br>112 | LCDR1<br>LCDR2<br>LCDR3 | RASESVFGHGISPLH<br>RASNLKF<br>QQSNEYPRT | 138<br>111<br>112 |
| mAb001_VL3 | EIVMTQSPATLSVSPGERATLSCRASESVFGHGISPLHWYQQKPGQPPRLLIYRASNRKTGIPARFSGSGSGTEFTLTISSLQSEDFAVYYCQQSNEYPRTFGGGTKVEIK | 121 | LCDR1<br>LCDR2<br>LCDR3 | RASESVFGHGISPLH<br>RASNRKT<br>QQSNEYPRT | 138<br>139<br>112 | LCDR1<br>LCDR2<br>LCDR3 | RASESVFGHGISPLH<br>RASNRKT<br>QQSNEYPRT | 138<br>139<br>112 |
| mAb001_VLr2_1 | DIQMTQSPSTLSASVGDRVTITCRASESVFGHGISPLHWYQQKPGKAPKLLIYRASNLKFGVPSRFSGSGSRTDFTLTISSLQPDDFATYYCQQSNEYPRTFGGGTKVEIK | 122 | LCDR1<br>LCDR2<br>LCDR3 | RASESVFGHGISPLH<br>RASNLKF<br>QQSNEYPRT | 138<br>111<br>112 | LCDR1<br>LCDR2<br>LCDR3 | RASESVFGHGISPLH<br>RASNLKF<br>QQSNEYPRT | 138<br>111<br>112 |

TABLE 3-continued

Amino acid sequences of heavy chain variable regions (VHs), light chain variable regions (VLs), heavy chain CDRs (HCDRs), and light chain CDRs (LCDRs) of exemplary humanized antibody molecules. Heavy and light chain CDRs defined according to Chothia system and Kabat system are shown.

| | | | | | | |
|---|---|---|---|---|---|---|
| mAb001_VLr2_2 | DIQMTQSPSTLSASVGDRVTITCRASESVFGHGISPLHWYQ QKPGKAPKLLIYRASNLKFGIPSRFSGSGSRTDFTLTISSL QPDDFATYYCQQSNEYPRTFGGGTKVEIK | 123 | LCDR1 LCDR2 LCDR3 | RASESVFGHGISPLH RASNLKF QQSNEYPRT | 138 111 112 | LCDR1 LCDR2 LCDR3 | RASESVFGHGISPLH RASNLKF QQSNEYPRT | 138 111 112 |
| mAb001_VLr2_3 | DIQMTQSPSTLSASVGDRVTITCRASESVFGHGISPLHWYQ QKPGQPPKLLIYRASNLKFGIPSRFSGSGSGTEFTLTISSL QPDDFATYYCQQSNEYPRTFGGGTKVEIK | 124 | LCDR1 LCDR2 LCDR3 | RASESVFGHGISPLH RASNLKF QQSNEYPRT | 138 111 112 | LCDR1 LCDR2 LCDR3 | RASESVFGHGISPLH RASNLKF QQSNEYPRT | 138 111 112 |
| mAb001_VLr2_4 | DIVLTQSPSTLSASVGDRVTITCRASESVFGHGISPMHWYQ QKPGKAPKLLIYRASNLKFGVPSRFSGSGSGTEFTLTISSL QPDDFATYYCQQSNEYPRTFGGGTKVEIK | 125 | LCDR1 LCDR2 LCDR3 | RASESVFGHGISPMH RASNLKF QQSNEYPRT | 110 111 112 | LCDR1 LCDR2 LCDR3 | RASESVFGHGISPMH RASNLKF QQSNEYPRT | 110 111 112 |
| mAb001_VLr2_5 | DIQMTQSPSTLSASVGDRVTITCRASESVFGHGISPLHWYQ QKPGKAPKLLIYRASNLKFGIPARFSGSGSGTEFTLTISSL QPDDFATYYCQQSNEYPRTFGGGTKVEIK | 126 | LCDR1 LCDR2 LCDR3 | RASESVFGHGISPLH RASNLKF QQSNEYPRT | 138 111 112 | LCDR1 LCDR2 LCDR3 | RASESVFGHGISPLH RASNLKF QQSNEYPRT | 138 111 112 |
| mAb001_VLr2_6 | DIVLTQSPASLAVSLGQRATISCRASESIFGHGISPMHWYQ QKPGQPPKLLIYRASNLKFGIPARFSGSGSGTDFTLTINPV EADDVATYYCQQSNEYPRTFGGGTKLEIK | 127 | LCDR1 LCDR2 LCDR3 | RASESIFGHGISPMH RASNLKF QQSNEYPRT | 140 111 112 | LCDR1 LCDR2 LCDR3 | RASESIFGHGISPMH RASNLKF QQSNEYPRT | 140 111 112 |
| mAb001_VLr2_7 | DIVLTQSPASLAVSLGQRATISCRASESVFGHGTSPMHWYQ QKPGQPPKLLIYRASSLKFGIPARFSGSGSGTDFTLTINPV EADDVATYYCQQSNEYPRTFGGGTKLEIK | 128 | LCDR1 LCDR2 LCDR3 | RASESVFGHGTSPMH RASSLKF QQSNEYPRT | 110 141 112 | LCDR1 LCDR2 LCDR3 | RASESVFGHGTSPMH RASSLKF QQSNEYPRT | 110 141 112 |
| mAb001_VLr2_8 | DIVLTQSPASLAVSLGQRATISCRASESVFGHGTSPMHWYQ QKPGQPPKLLIYRASNLKSGIPARFSGSGSGTDFTLTINPV EADDVATYYCQQSNEYPRTFGGGTKLEIK | 129 | LCDR1 LCDR2 LCDR3 | RASESVFGHGTSPMH RASNLKS QQSNEYPRT | 110 142 112 | LCDR1 LCDR2 LCDR3 | RASESVFGHGTSPMH RASNLKS QQSNEYPRT | 110 142 112 |
| mAb001_VLr2_9 | DIVMTQSPATLSVSPGERATLSCRASESVFGHGTSPLHWYQ QKPGQAPKLLIYRASNLKTGIPARFSGSGSRTDFTLTISSL QSEDFATYYCQQSNEYPRTFGGGTKVEIK | 130 | LCDR1 LCDR2 LCDR3 | RASESVFGHGTSPLH RASNLKT QQSNEYPRT | 138 143 112 | LCDR1 LCDR2 LCDR3 | RASESVFGHGTSPLH RASNLKT QQSNEYPRT | 138 143 112 |
| mAb001_VLr2_10 | EIVMTQSPATLSVSPGERATISCRASESVFGHGTSPLHWYQ QKPGQAPKLLIYRASNRKTGIPARFSGSGSGTEFTLTISPV QSEDFAVYYCQQSNEYPRTFGGGTKLEIK | 131 | LCDR1 LCDR2 LCDR3 | RASESVFGHGTSPLH RASNRKT QQSNEYPRT | 138 139 112 | LCDR1 LCDR2 LCDR3 | RASESVFGHGTSPLH RASNRKT QQSNEYPRT | 138 139 112 |

TABLE 3-continued

Amino acid sequences of heavy chain variable regions (VHs), light chain variable regions (VLs), heavy chain CDRs (HCDRs), and light chain CDRs (LCDRs) of exemplary humanized antibody molecules. Heavy and light chain CDRs defined according to Chothia system and Kabat system are shown.

| | | | | | | | |
|---|---|---|---|---|---|---|---|
| mAb001_VLr3_1 | DIQMTQSPSTLSASVGDRVTITCRASESIFGHGTSPLHWYQ QKPGKAPKLLIYRASNLKSGIPSRFSGSGSRTEFTLTISSL QPDDFATYYCQQSNEYPRTFGGGTKVEIK | 132 | LCDR1 LCDR2 LCDR3 | RASESIFGHGTSPLH RASNLKS QQSNEYPRT | 144 142 112 | LCDR1 LCDR2 LCDR3 | RASESIFGHGISPLH RASNLKS QQSNEYPRT | 144 142 112 |
| mAb001_VLr3_2 | DIQMTQSPSTLSASVGDRVTITCRASESIFGHGTSPLHWYQ QKPGKAPKLLIYRASNLKSGVPSRFSGSGSRTEFTLTISSL QPDDFATYYCQQSNEYPRTFGGGTKVEIK | 133 | LCDR1 LCDR2 LCDR3 | RASESIFGHGTSPLH RASNLKS QQSNEYPRT | 144 142 112 | LCDR1 LCDR2 LCDR3 | RASESIFGHGISPLH RASNLKS QQSNEYPRT | 144 142 112 |
| mAb001_VLr3_3 | DIQMTQSPSTLSASVGDRVTITCRASESIFGHGTSPLHWYQ QKPGKAPKLLIYRASNLKSGVPARFSGSGSRTEFTLTISSL QPDDFATYYCQQSNEYPRTFGGGTKVEIK | 134 | LCDR1 LCDR2 LCDR3 | RASESIFGHGTSPLH RASNLKS QQSNEYPRT | 144 142 112 | LCDR1 LCDR2 LCDR3 | RASESIFGHGISPLH RASNLKS QQSNEYPRT | 144 142 112 |
| mAb001_VLr3_4 | DIQMTQSPSTLSASVGDRVTITCRASESVFGHGTSPLHWYQ QKPGKAPKLLIYRASNLKSGVPSRFSGSGSRTEFTLTISSL QPDDFATYYCQQSNEYPRTFGGGTKVEIK | 135 | LCDR1 LCDR2 LCDR3 | RASESVFGHGTSPLH RASNLKS QQSNEYPRT | 138 142 112 | LCDR1 LCDR2 LCDR3 | RASESVFGHGISPLH RASNLKS QQSNEYPRT | 138 142 112 |
| mAb001_VLr3_5 | DIQMTQSPSTLSASVGDRVTITCRASESIFGHGTSPLHWYQ QKPGKAPKLLIYRASNLKSGVPSRFSGSGSRTDFTLTISSL QPDDFATYYCQQSNEYPRTFGGGTKVEIK | 136 | LCDR1 LCDR2 LCDR3 | RASESIFGHGTSPLH RASNLKS QQSNEYPRT | 144 142 112 | LCDR1 LCDR2 LCDR3 | RASESIFGHGISPLH RASNLKS QQSNEYPRT | 144 142 112 |
| mAb001_VLr3_6 | DIQMTQSPSTLSASVGDRVTITCRASESIFGHGTSPLHWYQ QKPGKAPKLLIYRASNLKSGIPSRFSGSGSRTDFTLTISSL QPDDFATYYCQQSNEYPRTFGGGTKVEIK | 137 | LCDR1 LCDR2 LCDR3 | RASESIFGHGTSPLH RASNLKS QQSNEYPRT | 144 142 112 | LCDR1 LCDR2 LCDR3 | RASESIFGHGISPLH RASNLKS QQSNEYPRT | 144 142 112 |

In an embodiment, the antibody molecule comprises one, two, or three CDRs of the VH region of an antibody molecule described in Table 1 or 3 (e.g., mAb001, A001-25, hWN01, hWNv1, 3E7, 3G1, 2C7, or 3D6, or any of the humanized mAb001), using the Kabat or Chothia definitions of CDRs. In an embodiment, the antibody molecule comprises one, two, or three CDRs of the VL region of an antibody molecule described in Table 1 or 3 (e.g., mAb001, A001-25, hWN01, hWNv1, 3E7, 3G1, 2C7, or 3D6, or any of the humanized mAb001), using the Kabat or Chothia definitions of CDRs. In an embodiment, the antibody molecule comprises one or more (e.g., two or three) CDRs of the VH region and/or one or more (e.g., two or three) CDRs of the VL region of an antibody molecule described in Table 1 or 3 (e.g., mAb001, A001-25, hWN01, hWNv1, 3E7, 3G1, 2C7, or 3D6, or any of the humanized mAb001), using the Kabat or Chothia definitions of CDRs.

In an embodiment, the antibody molecule comprises one, two, or three HCDRs described in Table 1 or 3. In an embodiment, the antibody molecule comprises one, two, or three LCDRs described in Table 1 or 3. In an embodiment, the antibody molecule comprises one or more (e.g., two or three) HCDRs and/or one or more (e.g., two or three) LCDRs described in Table 1 or 3.

In an embodiment, the antibody molecule comprises one, two, three, or four frameworks of the VH region of an antibody molecule described in Table 1 or 3 (e.g., mAb001, A001-25, hWN01, hWNv1, 3E7, 3G1, 2C7, or 3D6, or any of the humanized mAb001). In an embodiment, the antibody molecule comprises one, two, three, or four frameworks of the VL region of an antibody molecule described in Table 1 or 3 (e.g., mAb001, A001-25, hWN01, hWNv1, 3E7, 3G1, 2C7, or 3D6, or any of the humanized mAb001). In an embodiment, the antibody molecule comprises one or more (e.g., two, three, or four) frameworks of the VH region and/or one or more (e.g., two, three, or four) frameworks of the VL region of an antibody molecule described in Table 1 or 3 (e.g., mAb001, A001-25, hWN01, hWNv1, 3E7, 3G1, 2C7, or 3D6, or any of the humanized mAb001).

In an embodiment, the antibody molecule comprises a heavy chain variable region of an antibody molecule described in Table 1 or 3 (e.g., mAb001, A001-25, hWN01, hWNv1, 3E7, 3G1, 2C7, or 3D6, or any of the humanized mAb001). In an embodiment, the antibody molecule comprises a light chain variable region of an antibody molecule described in Table 1 or 3 (e.g., mAb001, A001-25, hWN01, hWNv1, 3E7, 3G1, 2C7, or 3D6, or any of the humanized mAb001). In an embodiment, the antibody molecule comprises a heavy chain variable region and a light chain variable region of an antibody molecule described in Table 1 or 3 (e.g., mAb001, A001-25, hWN01, hWNv1, 3E7, 3G1, 2C7, or 3D6, or any of the humanized mAb001).

In an embodiment, the antibody molecule comprises a heavy chain variable region having an amino acid sequence described in Table 1 or 3. In an embodiment, the antibody molecule comprises a light chain variable region having an amino acid sequence described in Table 1 or 3. In an embodiment, the antibody molecule comprises a heavy chain variable region having an amino acid sequence described in Table 1 or 3 and a light chain variable region having an amino acid sequences described in Table 1 or 3.

In an embodiment, an antibody molecule or ADC as described herein comprises one or more (e.g., 1, 2, or 3) conservative substitutions of VL residue R100 and/or VH residues R101 and/or R103. In an embodiment, one or more of the conservative substitutions comprises a mutation to a positively charged amino acid other than arginine (e.g., lysine or histidine). In an embodiment, the antibody molecule or ADC comprises a conservative substitution of VL residue R100 (e.g., a mutation to a positively charged amino acid other than arginine, e.g., lysine or histidine). In an embodiment, the antibody molecule or ADC comprises a conservative substitution of VH residue R101 (e.g., a mutation to a positively charged amino acid other than arginine, e.g., lysine or histidine). In an embodiment, the antibody molecule or ADC comprises a conservative substitution of VH residue R103 (e.g., a mutation to a positively charged amino acid other than arginine, e.g., lysine or histidine).

In an embodiment, the antibody molecule comprises a heavy chain variable region encoded by a nucleotide sequence described in Table 2. In an embodiment, the antibody molecule comprises a light chain variable region encoded by a nucleotide sequence described in Table 2. In an embodiment, the antibody molecule comprises a heavy chain variable region encoded by a nucleotide sequence described in Table 2 and a light chain variable region encoded by a nucleotide sequence described in Table 2.

In an embodiment, the antibody molecule further comprises a heavy chain constant region. In an embodiment, the antibody molecule further comprises a light chain constant region. In an embodiment, the antibody molecule further comprises a heavy chain constant region and a light chain constant region. In an embodiment, the antibody molecule comprises a heavy chain constant region, a light chain constant region, and heavy and light chain variable regions of an antibody molecule described in Table 1 or 3. In an embodiment, the antibody molecule comprises a heavy chain constant region, a light chain constant region, and variable regions that comprise one, two, three, four, five, or six CDRs of an antibody molecule described in Table 1 or 3.

In an embodiment, the antibody molecule binds to a core pentasaccharide region of the LPS. In an embodiment, the core pentasaccharide region comprises one or more (e.g., two) Kdo residues and one or more (e.g., two or three) Hep residues. In an embodiment, the antibody molecule binds to one or more (e.g., two) Kdo residues, or one or more (e.g., two or three) Hep residues, or any combination thereof.

In an embodiment, the ADC or antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody mAb001 (e.g., SEQ ID NO: 108); an HCDR2 comprising an amino acid sequence that differs by no more than 1, 2, or 3 amino acid residues from, or has at least 85, 90, 95, 99 or 100% homology with, the amino acid sequence of the HCDR2 of antibody mAb001 (e.g., SEQ ID NO: 109); or an HCDR3 comprising an amino acid sequence that differs by no more than 1, 2, or 3 amino acid residues from, or has at least 85, 90, 95, 99 or 100% homology with, the amino acid sequence of the HCDR3 of antibody mAb001 (e.g., SEQ ID NO: 107).

In an embodiment, the heavy chain variable region comprises one, two, or all of the following: an HCDR1 comprising the amino acid sequence of the HCDR1 of antibody mAb001 (e.g., SEQ ID NO: 108); an HCDR2 comprising the amino acid sequence of the HCDR2 of antibody mAb001 (e.g., SEQ ID NO: 109); or an HCDR3 comprising the amino acid sequence of the HCDR3 of antibody mAb001 (e.g., SEQ ID NO: 107).

In an embodiment, the heavy chain variable region comprises an HCDR1 comprising the amino acid sequence of the HCDR1 of antibody mAb001 (e.g., SEQ ID NO: 108); an HCDR2 comprising the amino acid sequence of the HCDR2 of antibody mAb001 (e.g., SEQ ID NO: 109); and an HCDR3 comprising the amino acid sequence of the HCDR3 of antibody mAb001 (e.g., SEQ ID NO: 107).

In an embodiment, the ADC or antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody mAb001 (e.g., SEQ ID NO: 110); an LCDR2 comprising an amino acid sequence that differs by no more than 1, 2, or 3 amino acid residues from, or has at least 85, 90, 95, 99 or 100% homology with, the amino acid sequence of the LCDR2 of antibody mAb001 (e.g., SEQ ID NO: 111); or an LCDR3 comprising an amino acid sequence that differs by no more than 1, 2, or 3 amino acid residues from, or has at least 85, 90, 95, 99 or 100% homology with, the amino acid sequence of the LCDR3 of antibody mAb001 (e.g., SEQ ID NO: 112).

In an embodiment, the light chain variable region comprises one, two, or all of the following: an LCDR1 comprising the amino acid sequence of the LCDR1 of antibody mAb001 (e.g., SEQ ID NO: 110); an LCDR2 comprising the amino acid sequence of the LCDR2 of antibody mAb001 (e.g., SEQ ID NO: 111); or an LCDR3 comprising the amino acid sequence of the LCDR3 of antibody mAb001 (e.g., SEQ ID NO: 112).

In an embodiment, the light chain variable region comprises an LCDR1 comprising the amino acid sequence of the LCDR1 of antibody mAb001 (e.g., SEQ ID NO: 110); an LCDR2 comprising the amino acid sequence of the LCDR2 of antibody mAb001 (e.g., SEQ ID NO: 111); and an LCDR3 comprising the amino acid sequence of the LCDR3 of antibody mAb001 (e.g., SEQ ID NO: 112).

In an embodiment, the ADC or antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody mAb001 (e.g., SEQ ID NO: 108); an HCDR2 comprising an amino acid sequence that differs by no more than 1, 2, or 3 amino acid residues from, or has at least 85, 90, 95, 99 or 100% homology with, the amino acid sequence of the HCDR2 of antibody mAb001 (e.g., SEQ ID NO: 109); or an HCDR3 comprising an amino acid sequence that differs by no more than 1, 2, or 3 amino acid residues from, or has at least 85, 90, 95, 99 or 100% homology with, the amino acid sequence of the HCDR3 of antibody mAb001 (e.g., SEQ ID NO: 107), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody mAb001 (e.g., SEQ ID NO: 110); an LCDR2 comprising an amino acid sequence that differs by no more than 1, 2, or 3 amino acid residues from, or has at least 85, 90, 95, 99 or 100% homology with, the amino acid sequence of the LCDR2 of antibody mAb001 (e.g., SEQ ID NO: 111); or an LCDR3 comprising an amino acid sequence that differs by no more than 1, 2, or 3 amino acid residues from, or has at least 85, 90, 95, 99 or 100% homology with, the amino acid sequence of the LCDR3 of antibody mAb001 (e.g., SEQ ID NO: 112).

In an embodiment, the heavy chain variable region comprises one, two, or all of the following: an HCDR1 comprising the amino acid sequence of the HCDR1 of antibody mAb001 (e.g., SEQ ID NO: 108); an HCDR2 comprising the amino acid sequence of the HCDR2 of antibody mAb001 (e.g., SEQ ID NO: 109); or an HCDR3 comprising the amino acid sequence of the HCDR3 of antibody mAb001 (e.g., SEQ ID NO: 107), and the light chain variable region comprises one, two, or all of the following: an LCDR1 comprising the amino acid sequence of the LCDR1 of antibody mAb001 (e.g., SEQ ID NO: 110); an LCDR2 comprising the amino acid sequence of the LCDR2 of antibody mAb001 (e.g., SEQ ID NO: 111); or an LCDR3 comprising the amino acid sequence of the LCDR3 of antibody mAb001 (e.g., SEQ ID NO: 112).

In an embodiment, the heavy chain variable region comprises an HCDR1 comprising the amino acid sequence of the HCDR1 of antibody mAb001 (e.g., SEQ ID NO: 108); an HCDR2 comprising the amino acid sequence of the HCDR2 of antibody mAb001 (e.g., SEQ ID NO: 109); and an HCDR3 comprising the amino acid sequence of the HCDR3 of antibody mAb001 (e.g., SEQ ID NO: 107), and the light chain variable region comprises an LCDR1 comprising the amino acid sequence of the LCDR1 of antibody mAb001 (e.g., SEQ ID NO: 110); an LCDR2 comprising the amino acid sequence of the LCDR2 of antibody mAb001 (e.g., SEQ ID NO: 111); and an LCDR3 comprising the amino acid sequence of the LCDR3 of antibody mAb001 (e.g., SEQ ID NO: 112).

In an embodiment, the ADC or antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody mAb001 (e.g., SEQ ID NO: 105); an HCDR2 comprising an amino acid sequence that differs by no more than 1, 2, or 3 amino acid residues from, or has at least 85, 90, 95, 99 or 100% homology with, the amino acid sequence of the HCDR2 of antibody mAb001 (e.g., SEQ ID NO: 106); or an HCDR3 comprising an amino acid sequence that differs by no more than 1, 2, or 3 amino acid residues from, or has at least 85, 90, 95, 99 or 100% homology with, the amino acid sequence of the HCDR3 of antibody mAb001 (e.g., SEQ ID NO: 107).

In an embodiment, the heavy chain variable region comprises one, two, or all of the following: an HCDR1 comprising the amino acid sequence of the HCDR1 of antibody mAb001 (e.g., SEQ ID NO: 105); an HCDR2 comprising the amino acid sequence of the HCDR2 of antibody mAb001 (e.g., SEQ ID NO: 106); or an HCDR3 comprising the amino acid sequence of the HCDR3 of antibody mAb001 (e.g., SEQ ID NO: 107).

In an embodiment, the heavy chain variable region comprises an HCDR1 comprising the amino acid sequence of the HCDR1 of antibody mAb001 (e.g., SEQ ID NO: 105); an HCDR2 comprising the amino acid sequence of the HCDR2 of antibody mAb001 (e.g., SEQ ID NO: 106); and an HCDR3 comprising the amino acid sequence of the HCDR3 of antibody mAb001 (e.g., SEQ ID NO: 107).

In an embodiment, the ADC or antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody mAb001 (e.g., SEQ ID NO: 110); an LCDR2 comprising an amino acid sequence that differs by no more than 1, 2, or 3 amino acid residues from, or has at least 85, 90, 95, 99 or 100% homology with, the amino acid sequence of the LCDR2 of antibody mAb001 (e.g., SEQ ID NO: 111); or an LCDR3 comprising an amino acid sequence that differs by no more than 1, 2, or 3 amino acid residues from, or has at least 85, 90, 95, 99 or 100% homology with, the amino acid sequence of the LCDR3 of antibody mAb001 (e.g., SEQ ID NO: 112).

In an embodiment, the light chain variable region comprises one, two, or all of the following: an LCDR1 comprising the amino acid sequence of the LCDR1 of antibody mAb001 (e.g., SEQ ID NO: 110); an LCDR2 comprising the amino acid sequence of the LCDR2 of antibody mAb001 (e.g., SEQ ID NO: 111); or an LCDR3 comprising the amino acid sequence of the LCDR3 of antibody mAb001 (e.g., SEQ ID NO: 112).

In an embodiment, the light chain variable region comprises an LCDR1 comprising the amino acid sequence of the LCDR1 of antibody mAb001 (e.g., SEQ ID NO: 110); an LCDR2 comprising the amino acid sequence of the LCDR1 of antibody mAb001 (e.g., SEQ ID NO: 111); and an LCDR3 comprising the amino acid sequence of the LCDR1 of antibody mAb001 (e.g., SEQ ID NO: 112).

In an embodiment, the ADC or antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody mAb001 (e.g., SEQ ID NO: 105); an HCDR2 comprising an amino acid sequence that differs by no more than 1, 2, or 3 amino acid residues from, or has at least 85, 90, 95, 99 or 100% homology with, the amino acid sequence of the HCDR2 of antibody mAb001 (e.g., SEQ ID NO: 106); or an HCDR3 comprising an amino acid sequence that differs by no more than 1, 2, or 3 amino acid residues from, or has at least 85, 90, 95, 99 or 100% homology with, the amino acid sequence of the HCDR3 of antibody mAb001 (e.g., SEQ ID NO: 107), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody mAb001 (e.g., SEQ ID NO: 110); an LCDR2 comprising an amino acid sequence that differs by no more than 1, 2, or 3 amino acid residues from, or has at least 85, 90, 95, 99 or 100% homology with, the amino acid sequence of the LCDR2 of antibody mAb001 (e.g., SEQ ID NO: 111); or an LCDR3 comprising an amino acid sequence that differs by no more than 1, 2, or 3 amino acid residues from, or has at least 85, 90, 95, 99 or 100% homology with, the amino acid sequence of the LCDR3 of antibody mAb001 (e.g., SEQ ID NO: 112).

In an embodiment, the heavy chain variable region comprises one, two, or all of the following: an HCDR1 comprising the amino acid sequence of the HCDR1 of antibody mAb001 (e.g., SEQ ID NO: 105); an HCDR2 comprising the amino acid sequence of the HCDR2 of antibody mAb001 (e.g., SEQ ID NO: 106); or an HCDR3 comprising the amino acid sequence of the HCDR3 of antibody mAb001 (e.g., SEQ ID NO: 107), and the light chain variable region comprises one, two, or all of the following: an LCDR1 comprising the amino acid sequence of the LCDR1 of antibody mAb001 (e.g., SEQ ID NO: 110); an LCDR2 comprising the amino acid sequence of the LCDR2 of antibody mAb001 (e.g., SEQ ID NO: 111); or an LCDR3 comprising the amino acid sequence of the LCDR3 of antibody mAb001 (e.g., SEQ ID NO: 112).

In an embodiment, the heavy chain variable region comprises an HCDR1 comprising the amino acid sequence of the HCDR1 of antibody mAb001 (e.g., SEQ ID NO: 105); an HCDR2 comprising the amino acid sequence of the HCDR2 of antibody mAb001 (e.g., SEQ ID NO: 106); and an HCDR3 comprising the amino acid sequence of the HCDR3 of antibody mAb001 (e.g., SEQ ID NO: 107), and the light chain variable region comprises an LCDR1 comprising the amino acid sequence of the LCDR1 of antibody mAb001 (e.g., SEQ ID NO: 110); an LCDR2 comprising the amino acid sequence of the LCDR2 of antibody mAb001 (e.g., SEQ ID NO: 111); and an LCDR3 comprising the amino acid sequence of the LCDR3 of antibody mAb001 (e.g., SEQ ID NO: 112).

In an embodiment, the ADC or antibody molecule further comprises one or more human or human derived heavy or light chain variable region frameworks.

In an embodiment, the ADC or antibody molecule comprises a heavy chain variable region (VH), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of antibody mAb001 (e.g., SEQ ID NO: 103). In an embodiment, the heavy chain variable region comprises the amino acid sequence of the VH of antibody mAb001 (e.g., SEQ ID NO: 103).

In an embodiment, the ADC or antibody molecule comprises a light chain variable region (VL), wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of antibody mAb001 (e.g., SEQ ID NO: 104). In an embodiment, the light chain variable region comprises the amino acid sequence of the VL of antibody mAb001 (e.g., SEQ ID NO: 104).

In an embodiment, the ADC or antibody molecule comprises a heavy chain variable region (VH) and a light chain variable region (VL), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of antibody mAb001 (e.g., SEQ ID NO: 103), and wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of antibody mAb001 (e.g., SEQ ID NO: 104).

In an embodiment, the heavy chain variable region comprises the amino acid sequence of the VH of antibody mAb001 (e.g., SEQ ID NO: 103) and the light chain variable region comprises the amino acid sequence of the VL of antibody mAb001 (e.g., SEQ ID NO: 104).

In an embodiment, the heavy chain variable region comprises an amino acid sequence encoded by a nucleotide sequence from Table 2 (e.g., SEQ ID NO: 113). In an embodiment, the light chain variable region comprises and amino acid sequence encoded by a nucleotide sequence from Table 2 (e.g., SEQ ID NO: 114).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody A001-25 (e.g., SEQ ID NO: 17); an HCDR2 comprising an amino acid sequence that differs by no more than 1, 2, or 3 amino acid residues from, or has at least 85, 90, 95, 99 or 100% homology with, the amino acid sequence of the HCDR2 of antibody A001-25 (e.g., SEQ ID NO: 18); or an HCDR3 comprising an amino acid sequence that differs by no more than 1, 2, or 3 amino acid residues from, or has at least 85, 90, 95, 99 or 100% homology with, the amino acid sequence of the HCDR3 of antibody A001-25 (e.g., SEQ ID NO: 16).

In an embodiment, the heavy chain variable region comprises one, two, or all of the following: an HCDR1 comprising the amino acid sequence of the HCDR1 of antibody A001-25 (e.g., SEQ ID NO: 17); an HCDR2 comprising the amino acid sequence of the HCDR2 of antibody A001-25 (e.g., SEQ ID NO: 18); or an HCDR3 comprising the amino acid sequence of the HCDR3 of antibody A001-25 (e.g., SEQ ID NO: 16).

In an embodiment, the heavy chain variable region comprises an HCDR1 comprising the amino acid sequence of the HCDR1 of antibody A001-25 (e.g., SEQ ID NO: 17); an HCDR2 comprising the amino acid sequence of the HCDR2 of antibody A001-25 (e.g., SEQ ID NO: 18); and an HCDR3 comprising the amino acid sequence of the HCDR3 of antibody A001-25 (e.g., SEQ ID NO: 16).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody A001-25 (e.g., SEQ ID NO: 49); an LCDR2 comprising an amino acid sequence that differs by no more than 1, 2, or 3 amino acid residues from, or has at least 85, 90, 95, 99 or 100% homology with, the amino acid sequence of the LCDR2 of antibody A001-25 (e.g., SEQ ID NO: 50); or an LCDR3 comprising an amino acid sequence that differs by no more than 1, 2, or 3 amino acid residues from, or has at least 85, 90, 95, 99 or 100% homology with, the amino acid sequence of the LCDR3 of antibody A001-25 (e.g., SEQ ID NO: 51).

In an embodiment, the light chain variable region comprises one, two, or all of the following: an LCDR1 comprising the amino acid sequence of the LCDR1 of antibody A001-25 (e.g., SEQ ID NO: 49); an LCDR2 comprising the amino acid sequence of the LCDR2 of antibody A001-25 (e.g., SEQ ID NO: 50); or an LCDR3 comprising the amino acid sequence of the LCDR3 of antibody A001-25 (e.g., SEQ ID NO: 51).

In an embodiment, the light chain variable region comprises an LCDR1 comprising the amino acid sequence of the LCDR1 of antibody A001-25 (e.g., SEQ ID NO: 49); an LCDR2 comprising the amino acid sequence of the LCDR2 of antibody A001-25 (e.g., SEQ ID NO: 50); and an LCDR3 comprising the amino acid sequence of the LCDR3 of antibody A001-25 (e.g., SEQ ID NO: 51).

In an embodiment, the antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody A001-25 (e.g., SEQ ID NO: 17); an HCDR2 comprising an amino acid sequence that differs by no more than 1, 2, or 3 amino acid residues from, or has at least 85, 90, 95, 99 or 100% homology with, the amino acid sequence of the HCDR2 of antibody A001-25 (e.g., SEQ ID NO: 18); or an HCDR3 comprising an amino acid sequence that differs by no more than 1, 2, or 3 amino acid residues from, or has at least 85, 90, 95, 99 or 100% homology with, the amino acid sequence of the HCDR3 of antibody A001-25 (e.g., SEQ ID NO: 16), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody A001-25 (e.g., SEQ ID NO: 49); an LCDR2 comprising an amino acid sequence that differs by no more than 1, 2, or 3 amino acid residues from, or has at least 85, 90, 95, 99 or 100% homology with, the amino acid sequence of the LCDR2 of antibody A001-25 (e.g., SEQ ID NO: 50); or an LCDR3 comprising an amino acid sequence that differs by no more than 1, 2, or 3 amino acid residues from, or has at least 85, 90, 95, 99 or 100% homology with, the amino acid sequence of the LCDR3 of antibody A001-25 (e.g., SEQ ID NO: 51).

In an embodiment, the heavy chain variable region comprises one, two, or all of the following: an HCDR1 comprising the amino acid sequence of the HCDR1 of antibody A001-25 (e.g., SEQ ID NO: 17); an HCDR2 comprising the amino acid sequence of the HCDR2 of antibody A001-25 (e.g., SEQ ID NO: 18); or an HCDR3 comprising the amino acid sequence of the HCDR3 of antibody A001-25 (e.g., SEQ ID NO: 16), and the light chain variable region comprises one, two, or all of the following: an LCDR1 comprising the amino acid sequence of the LCDR1 of antibody A001-25 (e.g., SEQ ID NO: 49); an LCDR2 comprising the amino acid sequence of the LCDR2 of antibody A001-25 (e.g., SEQ ID NO: 50); or an LCDR3 comprising the amino acid sequence of the LCDR3 of antibody A001-25 (e.g., SEQ ID NO: 51).

In an embodiment, the heavy chain variable region comprises an HCDR1 comprising the amino acid sequence of the HCDR1 of antibody A001-25 (e.g., SEQ ID NO: 17); an HCDR2 comprising the amino acid sequence of the HCDR2 of antibody A001-25 (e.g., SEQ ID NO: 18); and an HCDR3 comprising the amino acid sequence of the HCDR3 of antibody A001-25 (e.g., SEQ ID NO: 16), and the light chain variable region comprises an LCDR1 comprising the amino acid sequence of the LCDR1 of antibody A001-25 (e.g., SEQ ID NO: 49); an LCDR2 comprising the amino acid sequence of the LCDR2 of antibody A001-25 (e.g., SEQ ID NO: 50); and an LCDR3 comprising the amino acid sequence of the LCDR3 of antibody A001-25 (e.g., SEQ ID NO: 51).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody A001-25 (e.g., SEQ ID NO: 14); an HCDR2 comprising an amino acid sequence that differs by no more than 1, 2, or 3 amino acid residues from, or has at least 85, 90, 95, 99 or 100% homology with, the amino acid sequence of the HCDR2 of antibody A001-25 (e.g., SEQ ID NO: 15); or an HCDR3 comprising an amino acid sequence that differs by no more than 1, 2, or 3 amino acid residues from, or has at least 85, 90, 95, 99 or 100% homology with, the amino acid sequence of the HCDR1 of antibody A001-25 (e.g., SEQ ID NO: 16).

In an embodiment, the heavy chain variable region comprises one, two, or all of the following: an HCDR1 comprising the amino acid sequence of the HCDR1 of antibody A001-25 (e.g., SEQ ID NO: 14); an HCDR2 comprising the amino acid sequence of the HCDR2 of antibody A001-25 (e.g., SEQ ID NO: 15); or an HCDR3 comprising the amino acid sequence of the HCDR3 of antibody A001-25 (e.g., SEQ ID NO: 16).

In an embodiment, the heavy chain variable region comprises an HCDR1 comprising the amino acid sequence of the HCDR1 of antibody A001-25 (e.g., SEQ ID NO: 14); an HCDR2 comprising the amino acid sequence of the HCDR2 of antibody A001-25 (e.g., SEQ ID NO: 15); and an HCDR3 comprising the amino acid sequence of the HCDR3 of antibody A001-25 (e.g., SEQ ID NO: 16).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody A001-25 (e.g., SEQ ID NO: 49); an LCDR2 comprising an amino acid sequence that differs by no more than 1, 2, or 3 amino acid residues from, or has at least 85, 90, 95, 99 or 100% homology with, the amino acid sequence of the LCDR2 of antibody A001-25 (e.g., SEQ ID NO: 50); or an LCDR3 comprising an amino acid sequence that differs by no more than 1, 2, or 3 amino acid residues from, or has at least 85, 90, 95, 99 or 100% homology with, the amino acid sequence of the LCDR3 of antibody A001-25 (e.g., SEQ ID NO: 51).

In an embodiment, the light chain variable region comprises one, two, or all of the following: an LCDR1 comprising the amino acid sequence of the LCDR1 of antibody A001-25 (e.g., SEQ ID NO: 49); an LCDR2 comprising the amino acid sequence of the LCDR2 of antibody A001-25 (e.g., SEQ ID NO: 50); or an LCDR3 comprising the amino acid sequence of the LCDR3 of antibody A001-25 (e.g., SEQ ID NO: 51).

In an embodiment, the light chain variable region comprises an LCDR1 comprising the amino acid sequence of the LCDR1 of antibody A001-25 (e.g., SEQ ID NO: 49); an LCDR2 comprising the amino acid sequence of the LCDR1 of antibody A001-25 (e.g., SEQ ID NO: 50); and an LCDR3 comprising the amino acid sequence of the LCDR1 of antibody A001-25 (e.g., SEQ ID NO: 51).

In an embodiment, the antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody A001-25 (e.g., SEQ ID NO: 14); an HCDR2 comprising an amino acid sequence that differs by no more than 1, 2, or 3 amino acid residues from, or has at least 85, 90, 95, 99 or 100% homology with, the amino acid sequence of the HCDR2 of antibody A001-25 (e.g., SEQ ID NO: 15); or an HCDR3 comprising an amino acid sequence that differs by no more than 1, 2, or 3 amino acid residues from, or has at least 85, 90, 95, 99 or 100% homology with, the amino acid sequence of the HCDR3 of antibody A001-25 (e.g., SEQ ID NO: 16), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody A001-25 (e.g., SEQ ID NO: 49); an LCDR2 comprising an amino acid sequence that differs by no more than 1, 2, or 3 amino acid residues from, or has at least 85, 90, 95, 99 or 100% homology with, the amino acid sequence of the LCDR2 of antibody A001-25 (e.g., SEQ ID NO: 50); or an LCDR3 comprising an amino acid sequence that differs by no more than 1, 2, or 3 amino acid residues from, or has at least 85, 90, 95, 99 or 100% homology with, the amino acid sequence of the LCDR3 of antibody A001-25 (e.g., SEQ ID NO: 51).

In an embodiment, the heavy chain variable region comprises one, two, or all of the following: an HCDR1 comprising the amino acid sequence of the HCDR1 of antibody A001-25 (e.g., SEQ ID NO: 14); an HCDR2 comprising the amino acid sequence of the HCDR2 of antibody A001-25 (e.g., SEQ ID NO: 15); or an HCDR3 comprising the amino acid sequence of the HCDR3 of antibody A001-25 (e.g., SEQ ID NO: 16), and the light chain variable region comprises one, two, or all of the following: an LCDR1 comprising the amino acid sequence of the LCDR1 of antibody A001-25 (e.g., SEQ ID NO: 49); an LCDR2 comprising the amino acid sequence of the LCDR2 of antibody A001-25 (e.g., SEQ ID NO: 50); or an LCDR3 comprising the amino acid sequence of the LCDR3 of antibody A001-25 (e.g., SEQ ID NO: 51).

In an embodiment, the heavy chain variable region comprises an HCDR1 comprising the amino acid sequence of the HCDR1 of antibody A001-25 (e.g., SEQ ID NO: 14); an HCDR2 comprising the amino acid sequence of the HCDR2 of antibody A001-25 (e.g., SEQ ID NO: 15); and an HCDR3 comprising the amino acid sequence of the HCDR3 of antibody A001-25 (e.g., SEQ ID NO: 16), and the light chain variable region comprises an LCDR1 comprising the amino acid sequence of the LCDR1 of antibody A001-25 (e.g., SEQ ID NO: 49); an LCDR2 comprising the amino acid sequence of the LCDR2 of antibody A001-25 (e.g., SEQ ID NO: 50); and an LCDR3 comprising the amino acid sequence of the LCDR3 of antibody A001-25 (e.g., SEQ ID NO: 51).

In an embodiment, the antibody molecule further comprises one or more human or human derived heavy or light chain variable region frameworks.

In an embodiment, the antibody molecule comprises a heavy chain variable region (VH), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of antibody A001-25 (e.g., SEQ ID NO: 1). In an embodiment, the heavy chain variable region comprises the amino acid sequence of the VH of antibody A001-25 (e.g., SEQ ID NO: 1).

In an embodiment, the antibody molecule comprises a light chain variable region (VL), wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of antibody A001-25 (e.g., SEQ ID NO: 8). In an embodiment, the light chain variable region comprises the amino acid sequence of the VL of antibody A001-25 (e.g., SEQ ID NO: 8).

In an embodiment, the antibody molecule comprises a heavy chain variable region (VH) and a light chain variable region (VL), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of antibody A001-25 (e.g., SEQ ID NO: 1), and wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of antibody A001-25 (e.g., SEQ ID NO: 8).

In an embodiment, the heavy chain variable region comprises the amino acid sequence of the VH of antibody A001-25 (e.g., SEQ ID NO: 1) and the light chain variable region comprises the amino acid sequence of the VL of antibody A001-25 (e.g., SEQ ID NO: 8).

In an embodiment, the heavy chain variable region comprises an amino acid sequence encoded by a nucleotide sequence from Table 2 (e.g., SEQ ID NO: 81). In an embodiment, the light chain variable region comprises and amino acid sequence encoded by a nucleotide sequence from Table 2 (e.g., SEQ ID NO: 88).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody hWN01 (e.g., SEQ ID NO: 22); an HCDR2 comprising an amino acid sequence that differs by no more than 1, 2, or 3 amino acid residues from, or has at least 85, 90, 95, 99 or 100% homology with, the amino acid sequence of the HCDR2 of antibody hWN01 (e.g., SEQ ID NO: 23); or an HCDR3 comprising an amino acid sequence that differs by no more than 1, 2, or 3 amino acid residues from, or has at least 85, 90, 95, 99 or 100% homology with, the amino acid sequence of the HCDR3 of antibody hWN01 (e.g., SEQ ID NO: 21).

In an embodiment, the heavy chain variable region comprises one, two, or all of the following: an HCDR1 comprising the amino acid sequence of the HCDR1 of antibody hWN01 (e.g., SEQ ID NO: 22); an HCDR2 comprising the amino acid sequence of the HCDR2 of antibody hWN01 (e.g., SEQ ID NO: 23); or an HCDR3 comprising the amino acid sequence of the HCDR3 of antibody hWN01 (e.g., SEQ ID NO: 21).

In an embodiment, the heavy chain variable region comprises an HCDR1 comprising the amino acid sequence of the HCDR1 of antibody hWN01 (e.g., SEQ ID NO: 22); an HCDR2 comprising the amino acid sequence of the HCDR2 of antibody hWN01 (e.g., SEQ ID NO: 23); and an HCDR3 comprising the amino acid sequence of the HCDR3 of antibody hWN01 (e.g., SEQ ID NO: 21).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody hWN01 (e.g., SEQ ID NO: 52); an LCDR2 comprising an amino acid sequence that differs by no more than 1, 2, or 3 amino acid residues from, or has at least 85, 90, 95, 99 or 100% homology with, the amino acid sequence of the LCDR2 of antibody hWN01 (e.g., SEQ ID NO: 53); or an LCDR3 comprising an amino acid sequence that differs by no more than 1, 2, or 3 amino acid residues from, or has at least 85, 90, 95, 99 or 100% homology with, the amino acid sequence of the LCDR3 of antibody hWN01 (e.g., SEQ ID NO: 54).

In an embodiment, the light chain variable region comprises one, two, or all of the following: an LCDR1 comprising the amino acid sequence of the LCDR1 of antibody hWN01 (e.g., SEQ ID NO: 52; an LCDR2 comprising the amino acid sequence of the LCDR2 of antibody hWN01 (e.g., SEQ ID NO: 53; or an LCDR3 comprising the amino acid sequence of the LCDR3 of antibody hWN01 (e.g., SEQ ID NO: 54.

In an embodiment, the light chain variable region comprises an LCDR1 comprising the amino acid sequence of the LCDR1 of antibody hWN01 (e.g., SEQ ID NO: 52); an LCDR2 comprising the amino acid sequence of the LCDR2 of antibody hWN01 (e.g., SEQ ID NO: 53); and an LCDR3 comprising the amino acid sequence of the LCDR3 of antibody hWN01 (e.g., SEQ ID NO: 54).

In an embodiment, the antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody hWN01 (e.g., SEQ ID NO: 22); an HCDR2 comprising an amino acid sequence that differs by no more than 1, 2, or 3 amino acid residues from, or has at least 85, 90, 95, 99 or 100% homology with, the amino acid sequence of the HCDR2 of antibody hWN01 (e.g., SEQ ID NO: 23); or an HCDR3 comprising an amino acid sequence that differs by no more than 1, 2, or 3 amino acid residues from, or has at least 85, 90, 95, 99 or 100% homology with, the amino acid sequence of the HCDR3 of antibody hWN01 (e.g., SEQ ID NO: 21), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody hWN01 (e.g., SEQ ID NO: 52); an LCDR2 comprising an amino acid sequence that differs by no more than 1, 2, or 3 amino acid residues from, or has at least 85, 90, 95, 99 or 100% homology with, the amino acid sequence of the LCDR2 of antibody hWN01 (e.g., SEQ ID NO: 53); or an LCDR3 comprising an amino acid sequence that differs by no more than 1, 2, or 3 amino acid residues from, or has at least 85, 90, 95, 99 or 100% homology with, the amino acid sequence of the LCDR3 of antibody hWN01 (e.g., SEQ ID NO: 54).

In an embodiment, the heavy chain variable region comprises one, two, or all of the following: an HCDR1 comprising the amino acid sequence of the HCDR1 of antibody hWN01 (e.g., SEQ ID NO: 22); an HCDR2 comprising the amino acid sequence of the HCDR2 of antibody hWN01 (e.g., SEQ ID NO: 23); or an HCDR3 comprising the amino acid sequence of the HCDR3 of antibody hWN01 (e.g., SEQ ID NO: 21), and the light chain variable region comprises one, two, or all of the following: an LCDR1 comprising the amino acid sequence of the LCDR1 of antibody hWN01 (e.g., SEQ ID NO: 52); an LCDR2 comprising the amino acid sequence of the LCDR2 of antibody hWN01 (e.g., SEQ ID NO: 53); or an LCDR3 comprising the amino acid sequence of the LCDR3 of antibody hWN01 (e.g., SEQ ID NO: 54).

In an embodiment, the heavy chain variable region comprises an HCDR1 comprising the amino acid sequence of the HCDR1 of antibody hWN01 (e.g., SEQ ID NO: 22); an HCDR2 comprising the amino acid sequence of the HCDR2 of antibody hWN01 (e.g., SEQ ID NO: 23); and an HCDR3 comprising the amino acid sequence of the HCDR3 of antibody hWN01 (e.g., SEQ ID NO: 21), and the light chain variable region comprises an LCDR1 comprising the amino acid sequence of the LCDR1 of antibody hWN01 (e.g., SEQ ID NO: 52); an LCDR2 comprising the amino acid sequence of the LCDR2 of antibody hWN01 (e.g., SEQ ID NO: 53); and an LCDR3 comprising the amino acid sequence of the LCDR3 of antibody hWN01 (e.g., SEQ ID NO: 54).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody hWN01 (e.g., SEQ ID NO: 19); an HCDR2 comprising an amino acid sequence that differs by no more than 1, 2, or 3 amino acid residues from, or has at least 85, 90, 95, 99 or 100% homology with, the amino acid sequence of the HCDR2 of antibody hWN01 (e.g., SEQ ID NO: 20); or an HCDR3 comprising an amino acid sequence that differs by no more than 1, 2, or 3 amino acid residues from, or has at least 85, 90, 95, 99 or 100% homology with, the amino acid sequence of the HCDR3 of antibody hWN01 (e.g., SEQ ID NO: 21).

In an embodiment, the heavy chain variable region comprises one, two, or all of the following: an HCDR1 comprising the amino acid sequence of the HCDR1 of antibody hWN01 (e.g., SEQ ID NO: 19); an HCDR2 comprising the amino acid sequence of the HCDR2 of antibody hWN01 (e.g., SEQ ID NO: 20); or an HCDR3 comprising the amino acid sequence of the HCDR3 of antibody hWN01 (e.g., SEQ ID NO: 21).

In an embodiment, the heavy chain variable region comprises an HCDR1 comprising the amino acid sequence of the hCDR1 of antibody hWN01 (e.g., SEQ ID NO: 19); an HCDR2 comprising the amino acid sequence of the HCDR2 of antibody hWN01 (e.g., SEQ ID NO: 20); and an HCDR3 comprising the amino acid sequence of the HCDR3 of antibody hWN01 (e.g., SEQ ID NO: 21).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody hWN01 (e.g., SEQ ID NO: 52); an LCDR2 comprising an amino acid sequence that differs by no more than 1, 2, or 3 amino acid residues from, or has at least 85, 90, 95, 99 or 100% homology with, the amino acid sequence of the LCDR2 of antibody hWN01 (e.g., SEQ ID NO: 53); or an LCDR3 comprising an amino acid sequence that differs by no more than 1, 2, or 3 amino acid residues from, or has at least 85, 90, 95, 99 or 100% homology with, the amino acid sequence of the LCDR3 of antibody hWN01 (e.g., SEQ ID NO: 54).

In an embodiment, the light chain variable region comprises one, two, or all of the following: an LCDR1 comprising the amino acid sequence of the LCDR1 of antibody hWN01 (e.g., SEQ ID NO: 52); an LCDR2 comprising the amino acid sequence of the LCDR2 of antibody hWN01 (e.g., SEQ ID NO: 53); or an LCDR3 comprising the amino acid sequence of the LCDR3 of antibody hWN01 (e.g., SEQ ID NO: 54).

In an embodiment, the light chain variable region comprises an LCDR1 comprising the amino acid sequence of the LCDR1 of antibody hWN01 (e.g., SEQ ID NO: 52); an LCDR2 comprising the amino acid sequence of the LCDR2 of antibody hWN01 (e.g., SEQ ID NO: 53); and an LCDR3 comprising the amino acid sequence of the LCDR3 of antibody hWN01 (e.g., SEQ ID NO: 54).

In an embodiment, the antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody hWN01 (e.g., SEQ ID NO: 19); an HCDR2 comprising an amino acid sequence that differs by no more than 1, 2, or 3 amino acid residues from, or has at least 85, 90, 95, 99 or 100% homology with, the amino acid sequence of the HCDR2 of antibody hWN01 (e.g., SEQ ID NO: 20); or an HCDR3 comprising an amino acid sequence that differs by no more than 1, 2, or 3 amino acid residues from, or has at least 85, 90, 95, 99 or 100% homology with, the amino acid sequence of the HCDR3 of antibody hWN01 (e.g., SEQ ID NO: 21), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody hWN01 (e.g., SEQ ID NO: 52); an LCDR2 comprising an amino acid sequence that differs by no more than 1, 2, or 3 amino acid residues from, or has at least 85, 90, 95, 99 or 100% homology with, the amino acid sequence of the LCDR2 of antibody hWN01 (e.g., SEQ ID NO: 53); or an LCDR3 comprising an amino acid sequence that differs by no more than 1, 2, or 3 amino acid residues from, or has at least 85, 90, 95, 99 or 100% homology with, the amino acid sequence of the HCDR3 of antibody hWN01 (e.g., SEQ ID NO: 54).

In an embodiment, the heavy chain variable region comprises one, two, or all of the following: an HCDR1 comprising the amino acid sequence of the HCDR1 of antibody hWN01 (e.g., SEQ ID NO: 19); an HCDR2 comprising the amino acid sequence of the HCDR2 of antibody hWN01 (e.g., SEQ ID NO: 20); or an HCDR3 comprising the amino acid sequence of the HCDR3 of antibody hWN01 (e.g., SEQ ID NO: 21), and the light chain variable region comprises one, two, or all of the following: an LCDR1 comprising the amino acid sequence of the LCDR1 of antibody hWN01 (e.g., SEQ ID NO: 52); an LCDR2 comprising the amino acid sequence of the LCDR2 of antibody hWN01 (e.g., SEQ ID NO: 53); or an LCDR3 comprising the amino acid sequence of the LCDR3 of antibody hWN01 (e.g., SEQ ID NO: 54).

In an embodiment, the heavy chain variable region comprises an HCDR1 comprising the amino acid sequence of SEQ ID NO: 19; an HCDR2 comprising the amino acid sequence of SEQ ID NO: 20; and an HCDR3 comprising the amino acid sequence of SEQ ID NO: 21, and the light chain variable region comprises an LCDR1 comprising the amino acid sequence of SEQ ID NO: 52; an LCDR2 comprising the amino acid sequence of SEQ ID NO: 53; and an LCDR3 comprising the amino acid sequence of SEQ ID NO: 54.

In an embodiment, the antibody molecule further comprises one or more human or human derived heavy or light chain variable region frameworks.

In an embodiment, the antibody molecule comprises a heavy chain variable region (VH), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of antibody hWN01 (e.g., SEQ ID NO: 2). In an embodiment, the heavy chain variable region comprises the amino acid sequence of the VH of antibody hWN01 (e.g., SEQ ID NO: 2).

In an embodiment, the antibody molecule comprises a light chain variable region (VL), wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of antibody hWN01 (e.g., SEQ ID NO: 9). In an embodiment, the light chain variable region comprises the amino acid sequence of the VL of antibody hWN01 (e.g., SEQ ID NO: 9).

In an embodiment, the antibody molecule comprises a heavy chain variable region (VH) and a light chain variable region (VL), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of antibody hWN01 (e.g., SEQ ID NO: 2), and wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of antibody hWN01 (e.g., SEQ ID NO: 9). In an embodiment, the heavy chain variable region comprises the amino acid sequence of the VH of antibody hWN01 (e.g., SEQ ID NO: 2), and the light chain variable region comprises the amino acid sequence of the VL of antibody hWN01 (e.g., SEQ ID NO: 9).

In an embodiment, the heavy chain variable region comprises an amino acid sequence encoded by a nucleotide sequence from Table 2 (e.g., SEQ ID NO: 82). In an embodiment, the light chain variable region comprises and amino acid sequence encoded by a nucleotide sequence from Table 2 (e.g., SEQ ID NO: 89).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody hWNv1 (e.g., SEQ ID NO: 27); an HCDR2 comprising an amino acid sequence that differs by no more than 1, 2, or 3 amino acid residues from, or has at least 85, 90, 95, 99 or 100% homology with, the amino acid sequence of the HCDR2 of antibody hWNv1 (e.g., SEQ ID NO: 28); or an HCDR3 comprising an amino acid sequence that differs by no more than 1, 2, or 3 amino acid residues from, or has at least 85, 90, 95, 99 or 100% homology with, the amino acid sequence of the HCDR3 of antibody hWNv1 (e.g., SEQ ID NO: 21).

In an embodiment, the heavy chain variable region comprises one, two, or all of the following: an HCDR1 comprising the amino acid sequence of the HCDR1 of antibody hWNv1 (e.g., SEQ ID NO: 27); an HCDR2 comprising the amino acid sequence of the HCDR2 of antibody hWNv1

(e.g., SEQ ID NO: 28); or an HCDR3 comprising the amino acid sequence of the HCDR3 of antibody hWNv1 (e.g., SEQ ID NO: 21).

In an embodiment, the heavy chain variable region comprises an HCDR1 comprising the amino acid sequence of the HCDR1 of antibody hWNv1 (e.g., SEQ ID NO: 27); an HCDR2 comprising the amino acid sequence of the HCDR2 of antibody hWNv1 (e.g., SEQ ID NO: 28); and an HCDR3 comprising the amino acid sequence of the HCDR3 of antibody hWNv1 (e.g., SEQ ID NO: 21).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody hWNv1 (e.g., SEQ ID NO: 52); an LCDR2 comprising an amino acid sequence that differs by no more than 1, 2, or 3 amino acid residues from, or has at least 85, 90, 95, 99 or 100% homology with, the amino acid sequence of the LCDR2 of antibody hWNv1 (e.g., SEQ ID NO: 53); or an LCDR3 comprising an amino acid sequence that differs by no more than 1, 2, or 3 amino acid residues from, or has at least 85, 90, 95, 99 or 100% homology with, the amino acid sequence of the LCDR3 of antibody hWNv1 (e.g., SEQ ID NO: 54).

In an embodiment, the light chain variable region comprises one, two, or all of the following: an LCDR1 comprising the amino acid sequence of the LCDR1 of antibody hWNv1 (e.g., SEQ ID NO: 52); an LCDR2 comprising the amino acid sequence of the LCDR2 of antibody hWNv1 (e.g., SEQ ID NO: 53); or an LCDR3 comprising the amino acid sequence of the LCDR3 of antibody hWNv1 (e.g., SEQ ID NO: 54).

In an embodiment, the light chain variable region comprises an LCDR1 comprising the amino acid sequence of the LCDR1 of antibody hWNv1 (e.g., SEQ ID NO: 52); an LCDR2 comprising the amino acid sequence of the LCDR2 of antibody hWNv1 (e.g., SEQ ID NO: 53); and an LCDR3 comprising the amino acid sequence of the LCDR3 of antibody hWNv1 (e.g., SEQ ID NO: 54).

In an embodiment, the antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody hWNv1 (e.g., SEQ ID NO: 27); an HCDR2 comprising an amino acid sequence that differs by no more than 1, 2, or 3 amino acid residues from, or has at least 85, 90, 95, 99 or 100% homology with, the amino acid sequence of the HCDR2 of antibody hWNv1 (e.g., SEQ ID NO: 28); or an HCDR3 comprising an amino acid sequence that differs by no more than 1, 2, or 3 amino acid residues from, or has at least 85, 90, 95, 99 or 100% homology with, the amino acid sequence of the HCDR3 of antibody hWNv1 (e.g., SEQ ID NO: 21), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody hWNv1 (e.g., SEQ ID NO: 52); an LCDR2 comprising an amino acid sequence that differs by no more than 1, 2, or 3 amino acid residues from, or has at least 85, 90, 95, 99 or 100% homology with, the amino acid sequence of the LCDR2 of antibody hWNv1 (e.g., SEQ ID NO: 53); or an LCDR3 comprising an amino acid sequence that differs by no more than 1, 2, or 3 amino acid residues from, or has at least 85, 90, 95, 99 or 100% homology with, the amino acid sequence of the LCDR3 of antibody hWNv1 (e.g., SEQ ID NO: 54).

In an embodiment, the heavy chain variable region comprises one, two, or all of the following: an HCDR1 comprising the amino acid sequence of the HCDR1 of antibody hWNv1 (e.g., SEQ ID NO: 27); an HCDR2 comprising the amino acid sequence of the HCDR2 of antibody hWNv1 (e.g., SEQ ID NO: 28); or an HCDR3 comprising the amino acid sequence of the HCDR3 of antibody hWNv1 (e.g., SEQ ID NO: 21), and the light chain variable region comprises one, two, or all of the following: an LCDR1 comprising the amino acid sequence of the LCDR1 of antibody hWNv1 (e.g., SEQ ID NO: 52); an LCDR2 comprising the amino acid sequence of the LCDR2 of antibody hWNv1 (e.g., SEQ ID NO: 53); or an LCDR3 comprising the amino acid sequence of the LCDR3 of antibody hWNv1 (e.g., SEQ ID NO: 54).

In an embodiment, the heavy chain variable region comprises an HCDR1 comprising the amino acid sequence of the HCDR1 of antibody hWNv1 (e.g., SEQ ID NO: 27); an HCDR2 comprising the amino acid sequence of the HCDR2 of antibody hWNv1 (e.g., SEQ ID NO: 28); and an HCDR3 comprising the amino acid sequence of the HCDR3 of antibody hWNv1 (e.g., SEQ ID NO: 21), and the light chain variable region comprises an LCDR1 comprising the amino acid sequence of the LCDR1 of antibody hWNv1 (e.g., SEQ ID NO: 52); an LCDR2 comprising the amino acid sequence of the LCDR2 of antibody hWNv1 (e.g., SEQ ID NO: 53); and an LCDR3 comprising the amino acid sequence of the LCDR3 of antibody hWNv1 (e.g., SEQ ID NO: 54).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody hWNv1 (e.g., SEQ ID NO: 19); an HCDR2 comprising an amino acid sequence that differs by no more than 1, 2, or 3 amino acid residues from, or has at least 85, 90, 95, 99 or 100% homology with, the amino acid sequence of the HCDR2 of antibody hWNv1 (e.g., SEQ ID NO: 25); or an HCDR3 comprising an amino acid sequence that differs by no more than 1, 2, or 3 amino acid residues from, or has at least 85, 90, 95, 99 or 100% homology with, the amino acid sequence of the HCDR3 of antibody hWNv1 (e.g., SEQ ID NO: 21).

In an embodiment, the heavy chain variable region comprises one, two, or all of the following: an HCDR1 comprising the amino acid sequence of the HCDR1 of antibody hWNv1 (e.g., SEQ ID NO: 19); an HCDR2 comprising the amino acid sequence of the HCDR2 of antibody hWNv1

(e.g., SEQ ID NO: 25); or an HCDR3 comprising the amino acid sequence of the HCDR3 of antibody hWNv1 (e.g., SEQ ID NO: 21).

In an embodiment, the heavy chain variable region comprises an HCDR1 comprising the amino acid sequence of the HCDR1 of antibody hWNv1 (e.g., SEQ ID NO: 19); an HCDR2 comprising the amino acid sequence of the HCDR2 of antibody hWNv1 (e.g., SEQ ID NO: 25); and an HCDR3 comprising the amino acid sequence of the HCDR3 of antibody hWNv1 (e.g., SEQ ID NO: 21).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody hWNv1 (e.g., SEQ ID NO: 52); an LCDR2 comprising an amino acid sequence that differs by no more than 1, 2, or 3 amino acid residues from, or has at least 85, 90, 95, 99 or 100% homology with, the amino acid sequence of the LCDR2 of antibody hWNv1 (e.g., SEQ ID NO: 53); or an LCDR3 comprising an amino acid sequence that differs by no more than 1, 2, or 3 amino acid residues from, or has at least 85, 90, 95, 99 or 100% homology with, the amino acid sequence of the LCDR3 of antibody hWNv1 (e.g., SEQ ID NO: 54).

In an embodiment, the light chain variable region comprises one, two, or all of the following: an LCDR1 comprising the amino acid sequence of the LCDR1 of antibody hWNv1 (e.g., SEQ ID NO: 52); an LCDR2 comprising the amino acid sequence of the LCDR2 of antibody hWNv1 (e.g., SEQ ID NO: 53); or an LCDR3 comprising the amino acid sequence of the LCDR3 of antibody hWN01 (e.g., SEQ ID NO: 54).

In an embodiment, the light chain variable region comprises an LCDR1 comprising the amino acid sequence of the LCDR1 of antibody hWN01 (e.g., SEQ ID NO: 52); an LCDR2 comprising the amino acid sequence of the LCDR2 of antibody hWN01 (e.g., SEQ ID NO: 53); and an LCDR3 comprising the amino acid sequence of the LCDR3 of antibody hWN01 (e.g., SEQ ID NO: 54).

In an embodiment, the antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody hWNv1 (e.g., SEQ ID NO: 19); an HCDR2 comprising an amino acid sequence that differs by no more than 1, 2, or 3 amino acid residues from, or has at least 85, 90, 95, 99 or 100% homology with, the amino acid sequence of the HCDR2 of antibody hWNv1 (e.g., SEQ ID NO: 25); or an HCDR3 comprising an amino acid sequence that differs by no more than 1, 2, or 3 amino acid residues from, or has at least 85, 90, 95, 99 or 100% homology with, the amino acid sequence of the HCDR3 of antibody hWNv1 (e.g., SEQ ID NO: 21), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody hWNv1 (e.g., SEQ ID NO: 52); an LCDR2 comprising an amino acid sequence that differs by no more than 1, 2, or 3 amino acid residues from, or has at least 85, 90, 95, 99 or 100% homology with, the amino acid sequence of the LCDR2 of antibody hWNv1 (e.g., SEQ ID NO: 53); or an LCDR3 comprising an amino acid sequence that differs by no more than 1, 2, or 3 amino acid residues from, or has at least 85, 90, 95, 99 or 100% homology with, the amino acid sequence of the LCDR3 of antibody hWNv1 (e.g., SEQ ID NO: 54).

In an embodiment, the heavy chain variable region comprises one, two, or all of the following: an HCDR1 comprising the amino acid sequence of the HCDR1 of antibody hWNv1 (e.g., SEQ ID NO: 19); an HCDR2 comprising the amino acid sequence of the HCDR2 of antibody hWNv1 (e.g., SEQ ID NO: 25); or an HCDR3 comprising the amino acid sequence of the HCDR3 of antibody hWNv1 (e.g., SEQ ID NO: 21), and the light chain variable region comprises one, two, or all of the following: an LCDR1 comprising the amino acid sequence of the LCDR1 of antibody hWNv1 (e.g., SEQ ID NO: 52); an LCDR2 comprising the amino acid sequence of the LCDR2 of antibody hWNv1 (e.g., SEQ ID NO: 53); or an LCDR3 comprising the amino acid sequence of the LCDR3 of antibody hWNv1 (e.g., SEQ ID NO: 54).

In an embodiment, the heavy chain variable region comprises an HCDR1 comprising the amino acid sequence of the HCDR1 of antibody hWNv1 (e.g., SEQ ID NO: 19); an HCDR2 comprising the amino acid sequence of the HCDR2 of antibody hWNv1 (e.g., SEQ ID NO: 25); and an HCDR3 comprising the amino acid sequence of the HCDR3 of antibody hWNv1 (e.g., SEQ ID NO: 21), and the light chain variable region comprises an LCDR1 comprising the amino acid sequence of the LCDR1 of antibody hWNv1 (e.g., SEQ ID NO: 52); an LCDR2 comprising the amino acid sequence of the LCDR2 of antibody hWNv1 (e.g., SEQ ID NO: 53); and an LCDR3 comprising the amino acid sequence of the LCDR3 of antibody hWNv1 (e.g., SEQ ID NO: 54).

In an embodiment, the antibody molecule further comprises one or more human or human derived heavy or light chain variable region frameworks.

In an embodiment, the antibody molecule comprises a heavy chain variable region (VH), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of hWNv1 (e.g., SEQ ID NO: 3). In an embodiment, the heavy chain variable region comprises the amino acid sequence of the VH of hWNv1 (e.g., SEQ ID NO: 3).

In an embodiment, the antibody molecule comprises a light chain variable region (VL), wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of hWNv1 (e.g., SEQ ID NO: 9). In an embodiment, the light chain variable region comprises the amino acid sequence of the VL of hWNv1 (e.g., SEQ ID NO: 9).

In an embodiment, the antibody molecule comprises a heavy chain variable region (VH) and a light chain variable region (VL), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of hWNv1 (e.g., SEQ ID NO: 3), and wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of hWNv1 (e.g., SEQ ID NO: 9).

In an embodiment, the heavy chain variable region comprises the amino acid sequence of the VH of hWNv1 (e.g., SEQ ID NO: 3), and wherein the light chain variable region comprises the amino acid sequence of the VL of hWNv1 (e.g., SEQ ID NO: 9).

In an embodiment, the heavy chain variable region comprises an amino acid sequence encoded by a nucleotide sequence from Table 2 (e.g., SEQ ID NO: 83). In an embodiment, the light chain variable region comprises and amino acid sequence encoded by a nucleotide sequence from Table 2 (e.g., SEQ ID NO: 89).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody 3E7 (e.g., SEQ ID NO: 32); an HCDR2 comprising an amino acid sequence that differs by no more than 1, 2, or 3 amino acid residues from, or has at least 85, 90, 95, 99 or 100% homology with, the amino acid sequence of the HCDR2 of antibody 3E7 (e.g., SEQ ID NO: 33); or an HCDR3 comprising an amino acid sequence that differs by no more than 1, 2, or 3 amino acid residues from, or has at least 85, 90, 95, 99 or 100% homology with, the amino acid sequence of the HCDR3 of antibody 3E7 (e.g., SEQ ID NO: 31).

In an embodiment, the heavy chain variable region comprises one, two, or all of the following: an HCDR1 comprising the amino acid sequence of the HCDR1 of antibody 3E7 (e.g., SEQ ID NO: 32); an HCDR2 comprising the amino acid sequence of the HCDR2 of antibody 3E7 (e.g., SEQ ID NO: 33); or an HCDR3 comprising the amino acid sequence of the HCDR3 of antibody 3E7 (e.g., SEQ ID NO: 31).

In an embodiment, the heavy chain variable region comprises an HCDR1 comprising the amino acid sequence of the HCDR1 of antibody 3E7 (e.g., SEQ ID NO: 32); an HCDR2 comprising the amino acid sequence of the HCDR2 of antibody 3E7 (e.g., SEQ ID NO: 33); and an HCDR3 comprising the amino acid sequence of the HCDR3 of antibody 3E7 (e.g., SEQ ID NO: 31).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody 3E7 (e.g., SEQ ID NO: 55); an LCDR2 comprising an amino acid sequence that differs by no more than 1, 2, or 3 amino acid residues from, or has at least 85, 90, 95, 99 or 100% homology with, the amino acid sequence of the LCDR2 of antibody 3E7 (e.g., SEQ ID NO: 56); or an LCDR3 comprising an amino acid sequence that differs by no more than 1, 2, or 3 amino acid residues from, or has at least 85, 90, 95, 99 or 100% homology with, the amino acid sequence of the LCDR3 of antibody 3E7 (e.g., SEQ ID NO: 57).

In an embodiment, the light chain variable region comprises one, two, or all of the following: an LCDR1 comprising the amino acid sequence of the LCDR1 of antibody 3E7 (e.g., SEQ ID NO: 55); an LCDR2 comprising the amino acid sequence of the LCDR2 of antibody 3E7 (e.g., SEQ ID NO: 56); or an LCDR3 comprising the amino acid sequence of the LCDR3 of antibody 3E7 (e.g., SEQ ID NO: 57).

In an embodiment, the light chain variable region comprises an LCDR1 comprising the amino acid sequence of the LCDR1 of antibody 3E7 (e.g., SEQ ID NO: 55); an LCDR2 comprising the amino acid sequence of the LCDR2 of antibody 3E7 (e.g., SEQ ID NO: 56); and an LCDR3 comprising the amino acid sequence of the LCDR3 of antibody 3E7 (e.g., SEQ ID NO: 57).

In an embodiment, the antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody 3E7 (e.g., SEQ ID NO: 32); an HCDR2 comprising an amino acid sequence that differs by no more than 1, 2, or 3 amino acid residues from, or has at least 85, 90, 95, 99 or 100% homology with, the amino acid sequence of the HCDR2 of antibody 3E7 (e.g., SEQ ID NO: 33); or an HCDR3 comprising an amino acid sequence that differs by no more than 1, 2, or 3 amino acid residues from, or has at least 85, 90, 95, 99 or 100% homology with, the amino acid sequence of the HCDR3 of antibody 3E7 (e.g., SEQ ID NO: 31), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody 3E7 (e.g., SEQ ID NO: 55); an LCDR2 comprising an amino acid sequence that differs by no more than 1, 2, or 3 amino acid residues from, or has at least 85, 90, 95, 99 or 100% homology with, the amino acid sequence of the LCDR2 of antibody 3E7 (e.g., SEQ ID NO: 56); or an LCDR3 comprising an amino acid sequence that differs by no more than 1, 2, or 3 amino acid residues from, or has at least 85, 90, 95, 99 or 100% homology with, the amino acid sequence of the LCDR3 of antibody 3E7 (e.g., SEQ ID NO: 57).

In an embodiment, the heavy chain variable region comprises one, two, or all of the following: an HCDR1 comprising the amino acid sequence of the HCDR1 of antibody 3E7 (e.g., SEQ ID NO: 32); an HCDR2 comprising the amino acid sequence of the HCDR2 of antibody 3E7 (e.g., SEQ ID NO: 33); or an HCDR3 comprising the amino acid sequence of the HCDR3 of antibody 3E7 (e.g., SEQ ID NO: 31), and the light chain variable region comprises one, two, or all of the following: an LCDR1 comprising the amino acid sequence of the LCDR1 of antibody 3E7 (e.g., SEQ ID NO: 55); an LCDR2 comprising the amino acid sequence of the LCDR2 of antibody 3E7 (e.g., SEQ ID NO: 56); or an LCDR3 comprising the amino acid sequence of the LCDR3 of antibody 3E7 (e.g., SEQ ID NO: 57).

In an embodiment, the heavy chain variable region comprises an HCDR1 comprising the amino acid sequence of the HCDR1 of antibody 3E7 (e.g., SEQ ID NO: 32); an HCDR2 comprising the amino acid sequence of the HCDR2 of antibody 3E7 (e.g., SEQ ID NO: 33); and an HCDR3 comprising the amino acid sequence of the HCDR3 of antibody 3E7 (e.g., SEQ ID NO: 31), and the light chain variable region comprises an LCDR1 comprising the amino acid sequence of the LCDR1 of antibody 3E7 (e.g., SEQ ID NO: 55); an LCDR2 comprising the amino acid sequence of the LCDR2 of antibody 3E7 (e.g., SEQ ID NO: 56); and an LCDR3 comprising the amino acid sequence of the LCDR3 of antibody 3E7 (e.g., SEQ ID NO: 57).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody 3E7 (e.g., SEQ ID NO: 29); an HCDR2 comprising an amino acid sequence that differs by no more than 1, 2, or 3 amino acid residues from, or has at least 85, 90, 95, 99 or 100% homology with, the amino acid sequence of the HCDR2 of antibody 3E7 (e.g., SEQ ID NO: 30); or an HCDR3 comprising an amino acid sequence that differs by no more than 1, 2, or 3 amino acid residues from, or has at least 85, 90, 95, 99 or 100% homology with, the amino acid sequence of the HCDR3 of antibody 3E7 (e.g., SEQ ID NO: 31).

In an embodiment, the heavy chain variable region comprises one, two, or all of the following: an HCDR1 comprising the amino acid sequence of the HCDR1 of antibody 3E7 (e.g., SEQ ID NO: 29); an HCDR2 comprising the amino acid sequence of the HCDR2 of antibody 3E7 (e.g., SEQ ID NO: 30); or an HCDR3 comprising the amino acid sequence of the HCDR3 of antibody 3E7 (e.g., SEQ ID NO: 31).

In an embodiment, the heavy chain variable region comprises an HCDR1 comprising the amino acid sequence of the HCDR1 of antibody 3E7 (e.g., SEQ ID NO: 29); an HCDR2 comprising the amino acid sequence of the HCDR2 of antibody 3E7 (e.g., SEQ ID NO: 30); and an HCDR3 comprising the amino acid sequence of the HCDR3 of antibody 3E7 (e.g., SEQ ID NO: 31).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody 3E7 (e.g., SEQ ID NO: 55); an LCDR2 comprising an amino acid sequence that differs by no more than 1, 2, or 3 amino acid residues from, or has at least 85, 90, 95, 99 or 100% homology with, the amino acid sequence of the LCDR2 of antibody 3E7 (e.g., SEQ ID NO: 56); or an LCDR3 comprising an amino acid sequence that differs by no more than 1, 2, or 3 amino acid residues from, or has at least 85, 90, 95, 99 or 100% homology with, the amino acid sequence of the LCDR3 of antibody 3E7 (e.g., SEQ ID NO: 57).

In an embodiment, the light chain variable region comprises one, two, or all of the following: an LCDR1 comprising the amino acid sequence of the LCDR1 of antibody 3E7 (e.g., SEQ ID NO: 55); an LCDR2 comprising the amino acid sequence of the LCDR2 of antibody 3E7 (e.g., SEQ ID NO: 56); or an LCDR3 comprising the amino acid sequence of the LCDR3 of antibody 3E7 (e.g., SEQ ID NO: 57).

In an embodiment, the light chain variable region comprises an LCDR1 comprising the amino acid sequence of the LCDR1 of antibody 3E7 (e.g., SEQ ID NO: 55); an LCDR2 comprising the amino acid sequence of the LCDR2 of antibody 3E7 (e.g., SEQ ID NO: 56); and an LCDR3 comprising the amino acid sequence of the LCDR3 of antibody 3E7 (e.g., SEQ ID NO: 57).

In an embodiment, the antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody 3E7 (e.g., SEQ ID NO: 29); an HCDR2 comprising an amino acid sequence that differs by no more than 1, 2, or 3 amino acid residues from, or has at least 85, 90, 95, 99 or 100% homology with, the amino acid sequence of the HCDR2 of antibody 3E7 (e.g., SEQ ID NO: 30); or an HCDR3 comprising an amino acid sequence that differs by no more than 1, 2, or 3 amino acid residues from, or has at least 85, 90, 95, 99 or 100% homology with, the amino acid sequence of the HCDR3 of antibody 3E7 (e.g., SEQ ID NO: 31), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody 3E7 (e.g., SEQ ID NO: 55); an LCDR2 comprising an amino acid sequence that differs by no more than 1, 2, or 3 amino acid residues from, or has at least 85, 90, 95, 99 or 100% homology with, the amino acid sequence of the LCDR2 of antibody 3E7 (e.g., SEQ ID NO: 56); or an LCDR3 comprising an amino acid sequence that differs by no more than 1, 2, or 3 amino acid residues from, or has at least 85, 90, 95, 99 or 100% homology with, the amino acid sequence of the LCDR3 of antibody 3E7 (e.g., SEQ ID NO: 57).

In an embodiment, the heavy chain variable region comprises one, two, or all of the following: an HCDR1 comprising the amino acid sequence of the HCDR1 of antibody 3E7 (e.g., SEQ ID NO: 29); an HCDR2 comprising the amino acid sequence of the HCDR2 of antibody 3E7 (e.g., SEQ ID NO: 30); or an HCDR3 comprising the amino acid sequence of the HCDR3 of antibody 3E7 (e.g., SEQ ID NO: 31), and the light chain variable region comprises one, two, or all of the following: an LCDR1 comprising the amino acid sequence of the LCDR1 of antibody 3E7 (e.g., SEQ ID NO: 55); an LCDR2 comprising the amino acid sequence of the LCDR2 of antibody 3E7 (e.g., SEQ ID NO: 56); or an LCDR3 comprising the amino acid sequence of the LCDR3 of antibody 3E7 (e.g., SEQ ID NO: 57).

In an embodiment, the heavy chain variable region comprises an HCDR1 comprising the amino acid sequence of the HCDR1 of antibody 3E7 (e.g., SEQ ID NO: 29); an HCDR2 comprising the amino acid sequence of the HCDR2 of antibody 3E7 (e.g., SEQ ID NO: 30); and an HCDR3 comprising the amino acid sequence of the HCDR3 of antibody 3E7 (e.g., SEQ ID NO: 31), and the light chain variable region comprises an LCDR1 comprising the amino acid sequence of the LCDR1 of antibody 3E7 (e.g., SEQ ID NO: 55); an LCDR2 comprising the amino acid sequence of the LCDR2 of antibody 3E7 (e.g., SEQ ID NO: 56); and an LCDR3 comprising the amino acid sequence of the LCDR3 of antibody 3E7 (e.g., SEQ ID NO: 57).

In an embodiment, the antibody molecule further comprises one or more human or human derived heavy or light chain variable region frameworks.

In an embodiment, the antibody molecule comprises a heavy chain variable region (VH), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of 3E7 (e.g., SEQ ID NO: 4). In an embodiment, the heavy chain variable region comprises the amino acid sequence of the VH of 3E7 (e.g., SEQ ID NO: 4).

In an embodiment, the antibody molecule comprises a light chain variable region (VL), wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of 3E7 (e.g., SEQ ID NO: 10). In an embodiment, the light chain variable region comprises the amino acid sequence of the VL of 3E7 (e.g., SEQ ID NO: 10).

In an embodiment, the antibody molecule comprises a heavy chain variable region (VH) and a light chain variable region (VL), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of 3E7 (e.g., SEQ ID NO: 4), and wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of 3E7 (e.g., SEQ ID NO: 10).

In an embodiment, the heavy chain variable region comprises the amino acid sequence of the VH of 3E7 (e.g., SEQ ID NO: 4), and wherein the light chain variable region comprises the amino acid sequence of the VL of 3E7 (e.g., SEQ ID NO: 10).

In an embodiment, the heavy chain variable region comprises an amino acid sequence encoded by a nucleotide sequence from Table 2 (e.g., SEQ ID NO: 84). In an embodiment, the light chain variable region comprises and amino acid sequence encoded by a nucleotide sequence from Table 2 (e.g., SEQ ID NO: 90).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody 3G1 (e.g., SEQ ID NO: 37); an HCDR2 comprising an amino acid sequence that differs by no more than 1, 2, or 3 amino acid residues from, or has at least 85, 90, 95, 99 or 100% homology with, the amino acid sequence of the HCDR2 of antibody 3G1 (e.g., SEQ ID NO: 38); or an HCDR3 comprising an amino acid sequence that differs by no more than 1, 2, or 3 amino acid residues from, or has at least 85, 90, 95, 99 or 100% homology with, the amino acid sequence of the HCDR3 of antibody 3G1 (e.g., SEQ ID NO: 36).

In an embodiment, the heavy chain variable region comprises one, two, or all of the following: an HCDR1 comprising the amino acid sequence of the HCDR1 of antibody 3G1 (e.g., SEQ ID NO: 37); an HCDR2 comprising the amino acid sequence of the HCDR2 of antibody 3G1 (e.g., SEQ ID NO: 38); or an HCDR3 comprising the amino acid sequence of the HCDR3 of antibody 3G1 (e.g., SEQ ID NO: 36).

In an embodiment, the heavy chain variable region comprises an HCDR1 comprising the amino acid sequence of the HCDR1 of antibody 3G1 (e.g., SEQ ID NO: 37); an HCDR2 comprising the amino acid sequence of the HCDR2 of antibody 3G1 (e.g., SEQ ID NO: 38); and an HCDR3 comprising the amino acid sequence of the HCDR3 of antibody 3G1 (e.g., SEQ ID NO: 36).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody 3G1 (e.g., SEQ ID NO: 58); an LCDR2 comprising an amino acid sequence that differs by no more than 1, 2, or 3 amino acid residues from, or has at least 85, 90, 95, 99 or 100% homology with, the amino acid sequence of the LCDR2 of antibody 3G1 (e.g., SEQ ID NO: 59); or an LCDR3 comprising an amino acid sequence that differs by no more than 1, 2, or 3 amino acid residues from, or has at least 85, 90, 95, 99 or 100% homology with, the amino acid sequence of the LCDR3 of antibody 3G1 (e.g., SEQ ID NO: 60).

In an embodiment, the light chain variable region comprises one, two, or all of the following: an LCDR1 comprising the amino acid sequence of the LCDR1 of antibody 3G1 (e.g., SEQ ID NO: 58); an LCDR2 comprising the amino acid sequence of the LCDR2 of antibody 3G1 (e.g., SEQ ID NO: 59); or an LCDR3 comprising the amino acid sequence of the LCDR3 of antibody 3G1 (e.g., SEQ ID NO: 60).

In an embodiment, the light chain variable region comprises an LCDR1 comprising the amino acid sequence of the LCDR1 of antibody 3G1 (e.g., SEQ ID NO: 58); an LCDR2 comprising the amino acid sequence of the LCDR2 of antibody 3G1 (e.g., SEQ ID NO: 59); and an LCDR3 comprising the amino acid sequence of the LCDR3 of antibody 3G1 (e.g., SEQ ID NO: 60).

In an embodiment, the antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody 3G1 (e.g., SEQ ID NO: 37); an HCDR2 comprising an amino acid sequence that differs by no more than 1, 2, or 3 amino acid residues from, or has at least 85, 90, 95, 99 or 100% homology with, the amino acid sequence of the HCDR2 of antibody 3G1 (e.g., SEQ ID NO: 38); or an HCDR3 comprising an amino acid sequence that differs by no more than 1, 2, or 3 amino acid residues from, or has at least 85, 90, 95, 99 or 100% homology with, the amino acid sequence of the HCDR3 of antibody 3G1 (e.g., SEQ ID NO: 36), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody 3G1 (e.g., SEQ ID NO: 58); an LCDR2 comprising an amino acid sequence that differs by no more than 1, 2, or 3 amino acid residues from, or has at least 85, 90, 95, 99 or 100% homology with, the amino acid sequence of the LCDR2 of antibody 3G1 (e.g., SEQ ID NO: 59); or an LCDR3 comprising an amino acid sequence that differs by no more than 1, 2, or 3 amino acid residues from, or has at least 85, 90, 95, 99 or 100% homology with, the amino acid sequence of the LCDR3 of antibody 3G1 (e.g., SEQ ID NO: 60).

In an embodiment, the heavy chain variable region comprises one, two, or all of the following: an HCDR1 comprising the amino acid sequence of the HCDR1 of antibody 3G1 (e.g., SEQ ID NO: 37); an HCDR2 comprising the amino acid sequence of the HCDR2 of antibody 3G1 (e.g., SEQ ID NO: 38); or an HCDR3 comprising the amino acid sequence of the HCDR3 of antibody 3G1 (e.g., SEQ ID NO: 36), and the light chain variable region comprises one, two, or all of the following: an LCDR1 comprising the amino acid sequence of the LCDR1 of antibody 3G1 (e.g., SEQ ID NO: 58); an LCDR2 comprising the amino acid sequence of the LCDR2 of antibody 3G1 (e.g., SEQ ID NO: 59); or an LCDR3 comprising the amino acid sequence of the LCDR3 of antibody 3G1 (e.g., SEQ ID NO: 60).

In an embodiment, the heavy chain variable region comprises an HCDR1 comprising the amino acid sequence of the HCDR1 of antibody 3G1 (e.g., SEQ ID NO: 37); an HCDR2 comprising the amino acid sequence of the HCDR2 of antibody 3G1 (e.g., SEQ ID NO: 38); and an HCDR3 comprising the amino acid sequence of the HCDR3 of antibody 3G1 (e.g., SEQ ID NO: 36), and the light chain variable region comprises an LCDR1 comprising the amino acid sequence of the LCDR1 of antibody 3G1 (e.g., SEQ ID NO: 58); an LCDR2 comprising the amino acid sequence of the LCDR2 of antibody 3G1 (e.g., SEQ ID NO: 59); and an LCDR3 comprising the amino acid sequence of the LCDR3 of antibody 3G1 (e.g., SEQ ID NO: 60).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody 3G1 (e.g., SEQ ID NO: 34); an HCDR2 comprising an amino acid sequence that differs by no more than 1, 2, or 3 amino acid residues from, or has at least 85, 90, 95, 99 or 100% homology with, the amino acid sequence of the HCDR2 of antibody 3G1 (e.g., SEQ ID NO: 35); or an HCDR3 comprising an amino acid sequence that differs by no more than 1, 2, or 3 amino acid residues from, or has at least 85, 90, 95, 99 or 100% homology with, the amino acid sequence of the HCDR3 of antibody 3G1 (e.g., SEQ ID NO: 36).

In an embodiment, the heavy chain variable region comprises one, two, or all of the following: an HCDR1 comprising the amino acid sequence of the HCDR1 of antibody 3G1 (e.g., SEQ ID NO: 34); an HCDR2 comprising the amino acid sequence of the HCDR2 of antibody 3G1 (e.g., SEQ ID NO: 35); or an HCDR3 comprising the amino acid sequence of the HCDR3 of antibody 3G1 (e.g., SEQ ID NO: 36).

In an embodiment, the heavy chain variable region comprises an HCDR1 comprising the amino acid sequence of the HCDR1 of antibody 3G1 (e.g., SEQ ID NO: 34); an HCDR2 comprising the amino acid sequence of the HCDR2 of antibody 3G1 (e.g., SEQ ID NO: 35); and an HCDR3 comprising the amino acid sequence of the HCDR3 of antibody 3G1 (e.g., SEQ ID NO: 36).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody 3G1 (e.g., SEQ ID NO: 58); an LCDR2 comprising an amino acid sequence that differs by no more than 1, 2, or 3 amino acid residues from, or has at least 85, 90, 95, 99 or 100% homology with, the amino acid sequence of the LCDR2 of antibody 3G1 (e.g., SEQ ID NO: 59); or an LCDR3 comprising an amino acid sequence that differs by no more than 1, 2, or 3 amino acid residues from, or has at least 85, 90, 95, 99 or 100% homology with, the amino acid sequence of the LCDR3 of antibody 3G1 (e.g., SEQ ID NO: 60).

In an embodiment, the light chain variable region comprises one, two, or all of the following: an LCDR1 comprising the amino acid sequence of the LCDR1 of antibody 3G1 (e.g., SEQ ID NO: 58); an LCDR2 comprising the amino acid sequence of the LCDR2 of antibody 3G1 (e.g., SEQ ID NO: 59); or an LCDR3 comprising the amino acid sequence of the LCDR3 of antibody 3G1 (e.g., SEQ ID NO: 60).

In an embodiment, the light chain variable region comprises an LCDR1 comprising the amino acid sequence of the LCDR1 of antibody 3G1 (e.g., SEQ ID NO: 58); an LCDR2 comprising the amino acid sequence of the LCDR2 of antibody 3G1 (e.g., SEQ ID NO: 59); and an LCDR3 comprising the amino acid sequence of the LCDR3 of antibody 3G1 (e.g., SEQ ID NO: 60).

In an embodiment, the antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody 3G1 (e.g., SEQ ID NO: 34); an HCDR2 comprising an amino acid sequence that differs by no more than 1, 2, or 3 amino acid residues from, or has at least 85, 90, 95, 99 or 100% homology with, the amino acid sequence of the HCDR2 of antibody 3G1 (e.g., SEQ ID NO: 35); or an HCDR3 comprising an amino acid sequence that differs by no more than 1, 2, or 3 amino acid residues from, or has at least 85, 90, 95, 99 or 100% homology with, the amino acid sequence of the HCDR3 of antibody 3G1 (e.g., SEQ ID NO: 36), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody 3G1 (e.g., SEQ ID NO: 58); an LCDR2 comprising an amino acid sequence that differs by no more than 1, 2, or 3 amino acid residues from, or has at least 85, 90, 95, 99 or 100% homology with, the amino acid sequence of the LCDR2 of antibody 3G1 (e.g., SEQ ID NO: 59); or an LCDR3 comprising an amino acid sequence that differs by no more than 1, 2, or 3 amino acid residues from, or has at least 85, 90, 95, 99 or 100% homology with, the amino acid sequence of the LCDR3 of antibody 3G1 (e.g., SEQ ID NO: 60).

In an embodiment, the heavy chain variable region comprises one, two, or all of the following: an HCDR1 comprising the amino acid sequence of the HCDR1 of antibody 3G1 (e.g., SEQ ID NO: 34); an HCDR2 comprising the amino acid sequence of the HCDR2 of antibody 3G1 (e.g., SEQ ID NO: 35); or an HCDR3 comprising the amino acid sequence of the HCDR3 of antibody 3G1 (e.g., SEQ ID NO: 36), and the light chain variable region comprises one, two, or all of the following: an LCDR1 comprising the amino acid sequence of the LCDR1 of antibody 3G1 (e.g., SEQ ID NO: 58); an LCDR2 comprising the amino acid sequence of the LCDR2 of antibody 3G1 (e.g., SEQ ID NO: 59); or an LCDR3 comprising the amino acid sequence of the LCDR3 of antibody 3G1 (e.g., SEQ ID NO: 60).

In an embodiment, the heavy chain variable region comprises an HCDR1 comprising the amino acid sequence of the HCDR1 of antibody 3G1 (e.g., SEQ ID NO: 34); an HCDR2 comprising the amino acid sequence of the HCDR2 of antibody 3G1 (e.g., SEQ ID NO: 35); and an HCDR3 comprising the amino acid sequence of the HCDR3 of antibody 3G1 (e.g., SEQ ID NO: 36), and the light chain variable region comprises an LCDR1 comprising the amino acid sequence of the LCDR1 of antibody 3G1 (e.g., SEQ ID NO: 58); an LCDR2 comprising the amino acid sequence of the LCDR2 of antibody 3G1 (e.g., SEQ ID NO: 59); and an LCDR3 comprising the amino acid sequence of the LCDR3 of antibody 3G1 (e.g., SEQ ID NO: 60).

In an embodiment, the antibody molecule further comprises one or more human or human derived heavy or light chain variable region frameworks.

In an embodiment, the antibody molecule comprises a heavy chain variable region (VH), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of 3G1 (e.g., SEQ ID NO: 5). In an embodiment, the heavy chain variable region comprises the amino acid sequence of the VH of 3G1 (e.g., SEQ ID NO: 5).

In an embodiment, the antibody molecule comprises a light chain variable region (VL), wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of 3G1 (e.g., SEQ ID NO: 11). In an embodiment, the light chain variable region comprises the amino acid sequence of the VL of 3G1 (e.g., SEQ ID NO: 11).

In an embodiment, the antibody molecule comprises a heavy chain variable region (VH) and a light chain variable region (VL), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of 3G1 (e.g., SEQ ID NO: 5), and wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of 3G1 (e.g., SEQ ID NO: 11).

In an embodiment, the heavy chain variable region comprises the amino acid sequence of the VH of 3G1 (e.g., SEQ ID NO: 5), and wherein the light chain variable region comprises the amino acid sequence of the VL of 3G1 (e.g., SEQ ID NO: 11).

In an embodiment, the heavy chain variable region comprises an amino acid sequence encoded by a nucleotide sequence from Table 2 (e.g., SEQ ID NO: 85). In an embodiment, the light chain variable region comprises and amino acid sequence encoded by a nucleotide sequence from Table 2 (e.g., SEQ ID NO: 91).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody 2C7 (e.g., SEQ ID NO: 42); an HCDR2 comprising an amino acid sequence that differs by no more than 1, 2, or 3 amino acid residues from, or has at least 85, 90, 95, 99 or 100% homology with, the amino acid sequence of the HCDR2 of antibody 2C7 (e.g., SEQ ID NO: 43); or an HCDR3 comprising an amino acid sequence that differs by no more than 1, 2, or 3 amino acid residues from, or has at least 85, 90, 95, 99 or 100% homology with, the amino acid sequence of the HCDR3 of antibody 2C7 (e.g., SEQ ID NO: 41).

In an embodiment, the heavy chain variable region comprises one, two, or all of the following: an HCDR1 comprising the amino acid sequence of the HCDR1 of antibody 2C7 (e.g., SEQ ID NO: 42); an HCDR2 comprising the amino acid sequence of the HCDR2 of antibody 2C7 (e.g., SEQ ID NO: 43); or an HCDR3 comprising the amino acid sequence of the HCDR3 of antibody 2C7 (e.g., SEQ ID NO: 41).

In an embodiment, the heavy chain variable region comprises an HCDR1 comprising the amino acid sequence of the HCDR1 of antibody 2C7 (e.g., SEQ ID NO: 42); an HCDR2 comprising the amino acid sequence of the HCDR2 of antibody 2C7 (e.g., SEQ ID NO: 43); and an HCDR3 comprising the amino acid sequence of the HCDR3 of antibody 2C7 (e.g., SEQ ID NO: 41).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody 2C7 (e.g., SEQ ID NO: 61); an LCDR2 comprising an amino acid sequence that differs by no more than 1, 2, or 3 amino acid residues from, or has at least 85, 90, 95, 99 or 100% homology with, the amino acid sequence of the LCDR2 of antibody 2C7 (e.g., SEQ ID NO: 62); or an LCDR3 comprising an amino acid sequence that differs by no more than 1, 2, or 3 amino acid residues from, or has at least 85, 90, 95, 99 or 100% homology with, the amino acid sequence of the LCDR3 of antibody 2C7 (e.g., SEQ ID NO: 63).

In an embodiment, the light chain variable region comprises one, two, or all of the following: an LCDR1 comprising the amino acid sequence of the LCDR1 of antibody 2C7 (e.g., SEQ ID NO: 61); an LCDR2 comprising the amino acid sequence of the LCDR2 of antibody 2C7 (e.g., SEQ ID NO: 62); or an LCDR3 comprising the amino acid sequence of the LCDR3 of antibody 2C7 (e.g., SEQ ID NO: 63).

In an embodiment, the light chain variable region comprises an LCDR1 comprising the amino acid sequence of the LCDR1 of antibody 2C7 (e.g., SEQ ID NO: 61); an LCDR2 comprising the amino acid sequence of the LCDR2 of antibody 2C7 (e.g., SEQ ID NO: 62); and an LCDR3 comprising the amino acid sequence of the LCDR3 of antibody 2C7 (e.g., SEQ ID NO: 63).

In an embodiment, the antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody 2C7 (e.g., SEQ ID NO: 42); an HCDR2 comprising an amino acid sequence that differs by no more than 1, 2, or 3 amino acid residues from, or has at least 85, 90, 95, 99 or 100% homology with, the amino acid sequence of the HCDR2 of antibody 2C7 (e.g., SEQ ID NO: 43); or an HCDR3 comprising an amino acid sequence that differs by no more than 1, 2, or 3 amino acid residues from, or has at least 85, 90, 95, 99 or 100% homology with, the amino acid sequence of the HCDR3 of antibody 2C7 (e.g., SEQ ID NO: 41), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody 2C7 (e.g., SEQ ID NO: 61); an LCDR2 comprising an amino acid sequence that differs by no more than 1, 2, or 3 amino acid residues from, or has at least 85, 90, 95, 99 or 100% homology with, the amino acid sequence of the LCDR2 of antibody 2C7 (e.g., SEQ ID NO: 62); or an LCDR3 comprising an amino acid sequence that differs by no more than 1, 2, or 3 amino acid residues from, or has at least 85, 90, 95, 99 or 100% homology with, the amino acid sequence of the LCDR3 of antibody 2C7 (e.g., SEQ ID NO: 63).

In an embodiment, the heavy chain variable region comprises one, two, or all of the following: an HCDR1 comprising the amino acid sequence of the HCDR1 of antibody 2C7 (e.g., SEQ ID NO: 42); an HCDR2 comprising the amino acid sequence of the HCDR2 of antibody 2C7 (e.g., SEQ ID NO: 43); or an HCDR3 comprising the amino acid sequence of the HCDR3 of antibody 2C7 (e.g., SEQ ID NO: 41), and the light chain variable region comprises one, two, or all of the following: an LCDR1 comprising the amino acid sequence of the LCDR1 of antibody 2C7 (e.g., SEQ ID NO: 61); an LCDR2 comprising the amino acid sequence of the LCDR2 of antibody 2C7 (e.g., SEQ ID NO: 62); or an LCDR3 comprising the amino acid sequence of the LCDR3 of antibody 2C7 (e.g., SEQ ID NO: 63).

In an embodiment, the heavy chain variable region comprises an HCDR1 comprising the amino acid sequence of the HCDR1 of antibody 2C7 (e.g., SEQ ID NO: 42); an HCDR2 comprising the amino acid sequence of the HCDR2 of antibody 2C7 (e.g., SEQ ID NO: 43); and an HCDR3 comprising the amino acid sequence of the HCDR3 of antibody 2C7 (e.g., SEQ ID NO: 41), and the light chain variable region comprises an LCDR1 comprising the amino acid sequence of the LCDR1 of antibody 2C7 (e.g., SEQ ID NO: 61); an LCDR2 comprising the amino acid sequence of the LCDR2 of antibody 2C7 (e.g., SEQ ID NO: 62); and an LCDR3 comprising the amino acid sequence of the LCDR3 of antibody 2C7 (e.g., SEQ ID NO: 63).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody 2C7 (e.g., SEQ ID NO: 39); an HCDR2 comprising an amino acid sequence that differs by no more than 1, 2, or 3 amino acid residues from, or has at least 85, 90, 95, 99 or 100% homology with, the amino acid sequence of the HCDR2 of antibody 2C7 (e.g., SEQ ID NO: 40); or an HCDR3 comprising an amino acid sequence that differs by no more than 1, 2, or 3 amino acid residues from, or has at least 85, 90, 95, 99 or 100% homology with, the amino acid sequence of the HCDR3 of antibody 2C7 (e.g., SEQ ID NO: 41).

In an embodiment, the heavy chain variable region comprises one, two, or all of the following: an HCDR1 comprising the amino acid sequence of the HCDR1 of antibody 2C7 (e.g., SEQ ID NO: 39); an HCDR2 comprising the amino acid sequence of the HCDR2 of antibody 2C7 (e.g., SEQ ID NO: 40); or an HCDR3 comprising the amino acid sequence of the HCDR3 of antibody 2C7 (e.g., SEQ ID NO: 41).

In an embodiment, the heavy chain variable region comprises an HCDR1 comprising the amino acid sequence of the HCDR1 of antibody 2C7 (e.g., SEQ ID NO: 39); an HCDR2 comprising the amino acid sequence of the HCDR2 of antibody 2C7 (e.g., SEQ ID NO: 40); and an HCDR3 comprising the amino acid sequence of the HCDR3 of antibody 2C7 (e.g., SEQ ID NO: 41).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody 2C7 (e.g., SEQ ID NO: 61); an LCDR2 comprising an amino acid sequence that differs by no more than 1, 2, or 3 amino acid residues from, or has at least 85, 90, 95, 99 or 100% homology with, the amino acid sequence of the LCDR2 of antibody 2C7 (e.g., SEQ ID NO: 62); or an LCDR3 comprising an amino acid sequence that differs by no more than 1, 2, or 3 amino acid residues from, or has at least 85, 90, 95, 99 or 100% homology with, the amino acid sequence of the LCDR3 of antibody 2C7 (e.g., SEQ ID NO: 63).

In an embodiment, the light chain variable region comprises one, two, or all of the following: an LCDR1 comprising the amino acid sequence of the LCDR1 of antibody 2C7 (e.g., SEQ ID NO: 61); an LCDR2 comprising the amino acid sequence of the LCDR2 of antibody 2C7 (e.g., SEQ ID NO: 62); or an LCDR3 comprising the amino acid sequence of the LCDR3 of antibody 2C7 (e.g., SEQ ID NO: 63).

In an embodiment, the light chain variable region comprises an LCDR1 comprising the amino acid sequence of the LCDR1 of antibody 2C7 (e.g., SEQ ID NO: 61); an LCDR2 comprising the amino acid sequence of the LCDR2 of antibody 2C7 (e.g., SEQ ID NO: 62); and an LCDR3 comprising the amino acid sequence of the LCDR3 of antibody 2C7 (e.g., SEQ ID NO: 63).

In an embodiment, the antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody 2C7 (e.g., SEQ ID NO: 39); an HCDR2 comprising an amino acid sequence that differs by no more than 1, 2, or 3 amino acid residues from, or has at least 85, 90, 95, 99 or 100% homology with, the amino acid sequence of the HCDR2 of antibody 2C7 (e.g., SEQ ID NO: 40); or an HCDR3 comprising an amino acid sequence that differs by no more than 1, 2, or 3 amino acid residues from, or has at least 85, 90, 95, 99 or 100% homology with, the amino acid sequence of the HCDR3 of antibody 2C7 (e.g., SEQ ID NO: 41), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody 2C7 (e.g., SEQ ID NO: 61); an LCDR2 comprising an amino acid sequence that differs by no more than 1, 2, or 3 amino acid residues from, or has at least 85, 90, 95, 99 or 100% homology with, the amino acid sequence of the LCDR2 of antibody 2C7 (e.g., SEQ ID NO: 62); or an LCDR3 comprising an amino acid sequence that differs by no more than 1, 2, or 3 amino acid residues from, or has at least 85, 90, 95, 99 or 100% homology with, the amino acid sequence of the LCDR3 of antibody 2C7 (e.g., SEQ ID NO: 63).

In an embodiment, the heavy chain variable region comprises one, two, or all of the following: an HCDR1 comprising the amino acid sequence of the HCDR1 of antibody 2C7 (e.g., SEQ ID NO: 39); an HCDR2 comprising the amino acid sequence of the HCDR2 of antibody 2C7 (e.g., SEQ ID NO: 40); or an HCDR3 comprising the amino acid sequence of the HCDR3 of antibody 2C7 (e.g., SEQ ID NO: 41), and the light chain variable region comprises one, two, or all of the following: an LCDR1 comprising the amino acid sequence of the LCDR1 of antibody 2C7 (e.g., SEQ ID NO: 61); an LCDR2 comprising the amino acid sequence of the LCDR2 of antibody 2C7 (e.g., SEQ ID NO: 62); or an LCDR3 comprising the amino acid sequence of the LCDR3 of antibody 2C7 (e.g., SEQ ID NO: 63).

In an embodiment, the heavy chain variable region comprises an HCDR1 comprising the amino acid sequence of the HCDR1 of antibody 2C7 (e.g., SEQ ID NO: 39); an HCDR2 comprising the amino acid sequence of the HCDR2 of antibody 2C7 (e.g., SEQ ID NO: 40); and an HCDR3 comprising the amino acid sequence of the HCDR3 of antibody 2C7 (e.g., SEQ ID NO: 41), and the light chain variable region comprises an LCDR1 comprising the amino acid sequence of the LCDR1 of antibody 2C7 (e.g., SEQ ID NO: 61); an LCDR2 comprising the amino acid sequence of the LCDR2 of antibody 2C7 (e.g., SEQ ID NO: 62); and an LCDR3 comprising the amino acid sequence of the LCDR3 of antibody 2C7 (e.g., SEQ ID NO: 63).

In an embodiment, the antibody molecule further comprises one or more human or human derived heavy or light chain variable region frameworks.

In an embodiment, the antibody molecule comprises a heavy chain variable region (VH), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of 2C7 (e.g., SEQ ID NO: 6). In an embodiment, the heavy chain variable region comprises the amino acid sequence of the VH of 2C7 (e.g., SEQ ID NO: 6).

In an embodiment, the antibody molecule comprises a light chain variable region (VL), wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of 2C7 (e.g., SEQ ID NO: 12). In an embodiment, the light chain variable region comprises the amino acid sequence of the VL of 2C7 (e.g., SEQ ID NO: 12).

In an embodiment, the antibody molecule comprises a heavy chain variable region (VH) and a light chain variable region (VL), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of 2C7 (e.g., SEQ ID NO: 6), and wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of 2C7 (e.g., SEQ ID NO: 12).

In an embodiment, the heavy chain variable region comprises the amino acid sequence of the VH of 2C7 (e.g., SEQ ID NO: 6), and wherein the light chain variable region comprises the amino acid sequence of the VL of 2C7 (e.g., SEQ ID NO: 12).

In an embodiment, the heavy chain variable region comprises an amino acid sequence encoded by a nucleotide sequence from Table 2 (e.g., SEQ ID NO: 86). In an embodiment, the light chain variable region comprises and amino acid sequence encoded by a nucleotide sequence from Table 2 (e.g., SEQ ID NO: 92).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody 3D6 (e.g., SEQ ID NO: 47); an HCDR2 comprising an amino acid sequence that differs by no more than 1, 2, or 3 amino acid residues from, or has at least 85, 90, 95, 99 or 100% homology with, the amino acid sequence of the HCDR2 of antibody 3D6 (e.g., SEQ ID NO: 48); or an HCDR3 comprising an amino acid sequence that differs by no more than 1, 2, or 3 amino acid residues from, or has at least 85, 90, 95, 99 or 100% homology with, the amino acid sequence of the HCDR3 of antibody 3D6 (e.g., SEQ ID NO: 46).

In an embodiment, the heavy chain variable region comprises one, two, or all of the following: an HCDR1 comprising the amino acid sequence of the HCDR1 of antibody 3D6 (e.g., SEQ ID NO: 47); an HCDR2 comprising the amino acid sequence of the HCDR2 of antibody 3D6 (e.g., SEQ ID NO: 48); or an HCDR3 comprising the amino acid sequence of the HCDR3 of antibody 3D6 (e.g., SEQ ID NO: 46).

In an embodiment, the heavy chain variable region comprises an HCDR1 comprising the amino acid sequence of the HCDR1 of antibody 3D6 (e.g., SEQ ID NO: 47); an HCDR2 comprising the amino acid sequence of the HCDR2 of antibody 3D6 (e.g., SEQ ID NO: 48); and an HCDR3 comprising the amino acid sequence of the HCDR3 of antibody 3D6 (e.g., SEQ ID NO: 46).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody 3D6 (e.g., SEQ ID NO: 64); an LCDR2 comprising an amino acid sequence that differs by no more than 1, 2, or 3 amino acid residues from, or has at least 85, 90, 95, 99 or 100% homology with, the amino acid sequence of the LCDR2 of antibody 3D6 (e.g., SEQ ID NO: 65); or an LCDR3 comprising an amino acid sequence that differs by no more than 1, 2, or 3 amino acid residues from, or has at least 85, 90, 95, 99 or 100% homology with, the amino acid sequence of the LCDR3 of antibody 3D6 (e.g., SEQ ID NO: 66).

In an embodiment, the light chain variable region comprises one, two, or all of the following: an LCDR1 comprising the amino acid sequence of the LCDR1 of antibody 3D6 (e.g., SEQ ID NO: 64); an LCDR2 comprising the amino acid sequence of the LCDR2 of antibody 3D6 (e.g., SEQ ID NO: 65); or an LCDR3 comprising the amino acid sequence of the LCDR3 of antibody 3D6 (e.g., SEQ ID NO: 66).

In an embodiment, the light chain variable region comprises an LCDR1 comprising the amino acid sequence of the LCDR1 of antibody 3D6 (e.g., SEQ ID NO: 64); an LCDR2 comprising the amino acid sequence of the LCDR2 of antibody 3D6 (e.g., SEQ ID NO: 65); and an LCDR3 comprising the amino acid sequence of the LCDR3 of antibody 3D6 (e.g., SEQ ID NO: 66).

In an embodiment, the antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody 3D6 (e.g., SEQ ID NO: 47); an HCDR2 comprising an amino acid sequence that differs by no more than 1, 2, or 3 amino acid residues from, or has at least 85, 90, 95, 99 or 100% homology with, the amino acid sequence of the HCDR2 of antibody 3D6 (e.g., SEQ ID NO: 48); or an HCDR3 comprising an amino acid sequence that differs by no more than 1, 2, or 3 amino acid residues from, or has at least 85, 90, 95, 99 or 100% homology with, the amino acid sequence of the HCDR3 of antibody 3D6 (e.g., SEQ ID NO: 46), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody 3D6 (e.g., SEQ ID NO: 64); an LCDR2 comprising an amino acid sequence that differs by no more than 1, 2, or 3 amino acid residues from, or has at least 85, 90, 95, 99 or 100% homology with, the amino acid sequence of the LCDR2 of antibody 3D6 (e.g., SEQ ID NO: 65); or an LCDR3 comprising an amino acid sequence that differs by no more than 1, 2, or 3 amino acid residues from, or has at least 85, 90, 95, 99 or 100% homology with, the amino acid sequence of the LCDR3 of antibody 3D6 (e.g., SEQ ID NO: 66).

In an embodiment, the heavy chain variable region comprises one, two, or all of the following: an HCDR1 comprising the amino acid sequence of the HCDR1 of antibody 3D6 (e.g., SEQ ID NO: 47); an HCDR2 comprising the amino acid sequence of the HCDR2 of antibody 3D6 (e.g., SEQ ID NO: 48); or an HCDR3 comprising the amino acid sequence of the HCDR3 of antibody 3D6 (e.g., SEQ ID NO: 46), and the light chain variable region comprises one, two, or all of the following: an LCDR1 comprising the amino acid sequence of the LCDR1 of antibody 3D6 (e.g., SEQ ID NO: 64); an LCDR2 comprising the amino acid sequence of the LCDR2 of antibody 3D6 (e.g., SEQ ID NO: 65); or an LCDR3 comprising the amino acid sequence of the LCDR3 of antibody 3D6 (e.g., SEQ ID NO: 66).

In an embodiment, the heavy chain variable region comprises an HCDR1 comprising the amino acid sequence of the HCDR1 of antibody 3D6 (e.g., SEQ ID NO: 47); an HCDR2 comprising the amino acid sequence of the HCDR2 of antibody 3D6 (e.g., SEQ ID NO: 48); and an HCDR3 comprising the amino acid sequence of the HCDR3 of antibody 3D6 (e.g., SEQ ID NO: 46), and the light chain variable region comprises an LCDR1 comprising the amino acid sequence of the LCDR1 of antibody 3D6 (e.g., SEQ ID NO: 64); an LCDR2 comprising the amino acid sequence of the LCDR2 of antibody 3D6 (e.g., SEQ ID NO: 65); and an LCDR3 comprising the amino acid sequence of the LCDR3 of antibody 3D6 (e.g., SEQ ID NO: 66).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody 3D6 (e.g., SEQ ID NO: 44); an HCDR2 comprising an amino acid sequence that differs by no more than 1, 2, or 3 amino acid residues from, or has at least 85, 90, 95, 99 or 100% homology with, the amino acid sequence of the HCDR2 of antibody 3D6 (e.g., SEQ ID NO: 45); or an HCDR3 comprising an amino acid sequence that differs by no more than 1, 2, or 3 amino acid residues from, or has at least 85, 90, 95, 99 or 100% homology with, the amino acid sequence of the HCDR3 of antibody 3D6 (e.g., SEQ ID NO: 46).

In an embodiment, the heavy chain variable region comprises one, two, or all of the following: an HCDR1 comprising the amino acid sequence of the HCDR1 of antibody 3D6 (e.g., SEQ ID NO: 44); an HCDR2 comprising the amino acid sequence of the HCDR2 of antibody 3D6 (e.g., SEQ ID NO: 45); or an HCDR3 comprising the amino acid sequence of the HCDR3 of antibody 3D6 (e.g., SEQ ID NO: 46).

In an embodiment, the heavy chain variable region comprises an HCDR1 comprising the amino acid sequence of the HCDR1 of antibody 3D6 (e.g., SEQ ID NO: 44); an HCDR2 comprising the amino acid sequence of the HCDR2 of antibody 3D6 (e.g., SEQ ID NO: 45); and an HCDR3 comprising the amino acid sequence of the HCDR3 of antibody 3D6 (e.g., SEQ ID NO: 46).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody 3D6 (e.g., SEQ ID NO: 64); an LCDR2 comprising an amino acid sequence that differs by no more than 1, 2, or 3 amino acid residues from, or has at least 85, 90, 95, 99 or 100% homology with, the amino acid sequence of the LCDR2 of antibody 3D6 (e.g., SEQ ID NO: 65); or an LCDR3 comprising an amino acid sequence that differs by no more than 1, 2, or 3 amino acid residues from, or has at least 85, 90, 95, 99 or 100% homology with, the amino acid sequence of the LCDR3 of antibody 3D6 (e.g., SEQ ID NO: 66).

In an embodiment, the light chain variable region comprises one, two, or all of the following: an LCDR1 comprising the amino acid sequence of the LCDR1 of antibody 3D6 (e.g., SEQ ID NO: 64); an LCDR2 comprising the amino acid sequence of the LCDR2 of antibody 3D6 (e.g., SEQ ID NO: 65); or an LCDR3 comprising the amino acid sequence of the LCDR3 of antibody 3D6 (e.g., SEQ ID NO: 66).

In an embodiment, the light chain variable region comprises an LCDR1 comprising the amino acid sequence of the LCDR1 of antibody 3D6 (e.g., SEQ ID NO: 64); an LCDR2 comprising the amino acid sequence of the LCDR2 of antibody 3D6 (e.g., SEQ ID NO: 65); and an LCDR3 comprising the amino acid sequence of the LCDR3 of antibody 3D6 (e.g., SEQ ID NO: 66).

In an embodiment, the antibody molecule comprises a heavy chain variable region (VH) and a light chain variable region (VL), wherein the heavy chain variable region comprises three heavy chain complementarity determining regions (HCDR1, HCDR2, and HCDR3), and the light chain variable region comprises three light chain complementarity determining regions (LCDR1, LCDR2, and LCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of antibody 3D6 (e.g., SEQ ID NO: 44); an HCDR2 comprising an amino acid sequence that differs by no more than 1, 2, or 3 amino acid residues from, or has at least 85, 90, 95, 99 or 100% homology with, the amino acid sequence of the HCDR2 of antibody 3D6 (e.g., SEQ ID NO: 45); or an HCDR3 comprising an amino acid sequence that differs by no more than 1, 2, or 3 amino acid residues from, or has at least 85, 90, 95, 99 or 100% homology with, the amino acid sequence of the HCDR3 of antibody 3D6 (e.g., SEQ ID NO: 46), and wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of antibody 3D6 (e.g., SEQ ID NO: 64); an LCDR2 comprising an amino acid sequence that differs by no more than 1, 2, or 3 amino acid residues from, or has at least 85, 90, 95, 99 or 100% homology with, the amino acid sequence of the LCDR2 of antibody 3D6 (e.g., SEQ ID NO: 65); or an LCDR3 comprising an amino acid sequence that differs by no more than 1, 2, or 3 amino acid residues from, or has at least 85, 90, 95, 99 or 100% homology with, the amino acid sequence of the LCDR3 of antibody 3D6 (e.g., SEQ ID NO: 66).

In an embodiment, the heavy chain variable region comprises one, two, or all of the following: an HCDR1 comprising the amino acid sequence of the HCDR1 of antibody 3D6 (e.g., SEQ ID NO: 44); an HCDR2 comprising the amino acid sequence of the HCDR2 of antibody 3D6 (e.g., SEQ ID NO: 45); or an HCDR3 comprising the amino acid sequence of the HCDR3 of antibody 3D6 (e.g., SEQ ID NO: 46), and the light chain variable region comprises one, two, or all of the following: an LCDR1 comprising the amino acid sequence of the LCDR1 of antibody 3D6 (e.g., SEQ ID NO: 64); an LCDR2 comprising the amino acid sequence of the LCDR2 of antibody 3D6 (e.g., SEQ ID NO: 65); or an LCDR3 comprising the amino acid sequence of the LCDR3 of antibody 3D6 (e.g., SEQ ID NO: 66).

In an embodiment, the heavy chain variable region comprises an HCDR1 comprising the amino acid sequence of the HCDR1 of antibody 3D6 (e.g., SEQ ID NO: 44); an HCDR2 comprising the amino acid sequence of the HCDR2 of antibody 3D6 (e.g., SEQ ID NO: 45); and an HCDR3 comprising the amino acid sequence of the HCDR3 of antibody 3D6 (e.g., SEQ ID NO: 46), and the light chain variable region comprises an LCDR1 comprising the amino acid sequence of the LCDR1 of antibody 3D6 (e.g., SEQ ID NO: 64); an LCDR2 comprising the amino acid sequence of the LCDR2 of antibody 3D6 (e.g., SEQ ID NO: 65); and an LCDR3 comprising the amino acid sequence of the LCDR3 of antibody 3D6 (e.g., SEQ ID NO: 66).

In an embodiment, the antibody molecule further comprises one or more human or human derived heavy or light chain variable region frameworks.

In an embodiment, the antibody molecule comprises a heavy chain variable region (VH), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of 3D6 (e.g., SEQ ID NO: 7). In an embodiment, the heavy chain variable region comprises the amino acid sequence of the VH of 3D6 (e.g., SEQ ID NO: 7).

In an embodiment, the antibody molecule comprises a light chain variable region (VL), wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of 3D6 (e.g., SEQ ID NO: 13). In an embodiment, the light chain variable region comprises the amino acid sequence of the VL of 3D6 (e.g., SEQ ID NO: 13).

In an embodiment, the antibody molecule comprises a heavy chain variable region (VH) and a light chain variable region (VL), wherein the heavy chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of 3D6 (e.g., SEQ ID NO: 7), and wherein the light chain variable region comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of 3D6 (e.g., SEQ ID NO: 13).

In an embodiment, the heavy chain variable region comprises the amino acid sequence of the VH of 3D6 (e.g., SEQ ID NO: 7), and wherein the light chain variable region comprises the amino acid sequence of the VL of 3D6 (e.g., SEQ ID NO: 13).

In an embodiment, the heavy chain variable region comprises an amino acid sequence encoded by a nucleotide sequence from Table 2 (e.g., SEQ ID NO: 87). In an embodiment, the light chain variable region comprises and amino acid sequence encoded by a nucleotide sequence from Table 2 (e.g., SEQ ID NO: 93).

In an embodiment, the antibody molecule comprises a heavy chain variable region (VH), wherein the VH comprises three heavy chain complementarity determining regions (HCDR1, HCDR2, and HCDR3), wherein the VH comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of a VH described in Table 3 (e.g., any of SEQ ID NOS: 115-118); an HCDR2 comprising an amino acid sequence that differs by no more than 1, 2, or 3 amino acid residues from, or has at least 85, 90, 95, 99 or 100% homology with, the amino acid sequence of the HCDR2 of a VH described in Table 3 (e.g., any of SEQ ID NOS: 115-118); or an HCDR3 comprising an amino acid sequence that differs by no more than 1, 2, or 3 amino acid residues from, or has at least 85, 90, 95, 99 or 100% homology with, the amino acid sequence of the HCDR3 of a VH described in Table 3 (e.g., any of SEQ ID NOS: 115-118).

In an embodiment, the VH comprises one, two, or all of the following: an HCDR1 comprising the amino acid sequence of the HCDR1 of a VH described in Table 3 (e.g., any of SEQ ID NOS: 115-118); an HCDR2 comprising the amino acid sequence of the HCDR2 of a VH described in Table 3 (e.g., any of SEQ ID NOS: 115-118); or an HCDR3 comprising the amino acid sequence of the HCDR3 of a VH described in Table 3 (e.g., any of SEQ ID NOS: 115-118).

In an embodiment, the VH comprises: an HCDR1 comprising the amino acid sequence of the HCDR1 of a VH described in Table 3 (e.g., any of SEQ ID NOS: 115-118); an HCDR2 comprising the amino acid sequence of the HCDR2 of a VH described in Table 3 (e.g., any of SEQ ID NOS: 115-118); and an HCDR3 comprising the amino acid sequence of the HCDR3 of a VH described in Table 3 (e.g., any of SEQ ID NOS: 115-118).

In an embodiment, the antibody molecule comprises a light chain variable region (VL), wherein the VL comprises three light chain complementarity determining regions (LCDR1, LCDR2, and LCDR3), wherein the VL comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of a VL described in Table 3 (e.g., any of SEQ ID NOS: 119-137); an LCDR2 comprising an amino acid sequence that differs by no more than 1, 2, or 3 amino acid residues from, or has at least 85, 90, 95, 99 or 100% homology with, the amino acid sequence of the LCDR2 of a VL described in Table 3 (e.g., any of SEQ ID NOS: 119-137); or an LCDR3 comprising an amino acid sequence that differs by no more than 1, 2, or 3 amino acid residues from, or has at least 85, 90, 95, 99 or 100% homology with, the amino acid sequence of the LCDR3 of a VL described in Table 3 (e.g., any of SEQ ID NOS: 119-137).

In an embodiment, the VL comprises one, two, or all of the following: an LCDR1 comprising the amino acid sequence of the LCDR1 of a VL described in Table 3 (e.g., any of SEQ ID NOS: 119-137); an LCDR2 comprising the amino acid sequence of the LCDR2 of a VL described in Table 3 (e.g., any of SEQ ID NOS: 119-137); or an LCDR3 comprising the amino acid sequence of the LCDR3 of a VL described in Table 3 (e.g., any of SEQ ID NOS: 119-137).

In an embodiment, the VL comprises: an LCDR1 comprising the amino acid sequence of the LCDR1 of a VL described in Table 3 (e.g., any of SEQ ID NOS: 119-137); an LCDR2 comprising the amino acid sequence of the LCDR2 of a VL described in Table 3 (e.g., any of SEQ ID NOS: 119-137); and an LCDR3 comprising the amino acid sequence of the LCDR3 of a VL described in Table 3 (e.g., any of SEQ ID NOS: 119-137).

In an embodiment, the antibody molecule comprises a heavy chain variable region (VH) and a light chain variable region (VL), wherein the VH comprises three heavy chain complementarity determining regions (HCDR1, HCDR2, and HCDR3), and the VL comprises three light chain complementarity determining regions (LCDR1, LCDR2, and LCDR3), wherein the VH comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of a VH described in Table 3 (e.g., any of SEQ ID NOS: 115-118); an HCDR2 comprising an amino acid sequence that differs by no more than 1, 2, or 3 amino acid residues from, or has at least 85, 90, 95, 99 or 100% homology with, the amino acid sequence of the HCDR2 of a VH described in Table 3 (e.g., any of SEQ ID NOS: 115-118); or an HCDR3 comprising an amino acid sequence that differs by no more than 1, 2, or 3 amino acid residues from, or has at least 85, 90, 95, 99 or 100% homology with, the amino acid sequence of the HCDR3 of a VH described in Table 3 (e.g., any of SEQ ID NOS: 115-118); and wherein the VL comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of a VL described in Table 3 (e.g., any of SEQ ID NOS: 119-137); an LCDR2 comprising an amino acid sequence that differs by no more than 1, 2, or 3 amino acid residues from, or has at least 85, 90, 95, 99 or 100% homology with, the amino acid sequence of the LCDR2 of a VL described in Table 3 (e.g., any of SEQ ID NOS: 119-137); or an LCDR3 comprising an amino acid sequence that differs by no more than 1, 2, or 3 amino acid residues from, or has at least 85, 90, 95, 99 or 100% homology with, the amino acid sequence of the LCDR3 of a VL described in Table 3 (e.g., any of SEQ ID NOS: 119-137).

In an embodiment, the VH comprises one, two, or all of the following: an HCDR1 comprising the amino acid sequence of the HCDR1 of a VH described in Table 3 (e.g., any of SEQ ID NOS: 115-118); an HCDR2 comprising the amino acid sequence of the HCDR2 of a VH described in Table 3 (e.g., any of SEQ ID NOS: 115-118); or an HCDR3 comprising the amino acid sequence of the HCDR3 of a VH described in Table 3 (e.g., any of SEQ ID NOS: 115-118); and the VL comprises one, two, or all of the following: an LCDR1 comprising the amino acid sequence of the LCDR1 of a VL described in Table 3 (e.g., any of SEQ ID NOS: 119-137); an LCDR2 comprising the amino acid sequence of the LCDR2 of a VL described in Table 3 (e.g., any of SEQ ID NOS: 119-137); or an LCDR3 comprising the amino acid sequence of the LCDR3 of a VL described in Table 3 (e.g., any of SEQ ID NOS: 119-137).

In an embodiment, the VH comprises: an HCDR1 comprising the amino acid sequence of the HCDR1 of a VH described in Table 3 (e.g., any of SEQ ID NOS: 115-118); an HCDR2 comprising the amino acid sequence of the HCDR2 of a VH described in Table 3 (e.g., any of SEQ ID NOS: 115-118); and an HCDR3 comprising the amino acid sequence of the HCDR3 of a VH described in Table 3 (e.g., any of SEQ ID NOS: 115-118); and the VL comprises: an LCDR1 comprising the amino acid sequence of the LCDR1 of a VL described in Table 3 (e.g., any of SEQ ID NOS: 119-137); an LCDR2 comprising the amino acid sequence of the LCDR2 of a VL described in Table 3 (e.g., any of SEQ ID NOS: 119-137); and an LCDR3 comprising the amino acid sequence of the LCDR3 of a VL described in Table 3 (e.g., any of SEQ ID NOS: 119-137).

In an embodiment, the antibody molecule further comprises one or more human or human derived heavy or light chain variable region frameworks.

In an embodiment, the antibody molecule comprises a heavy chain variable region (VH), wherein the VH comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of a VH described in Table 3 (e.g., any of SEQ ID NOS: 115-118). In an embodiment, the VH comprises the amino acid sequence of a VH described in Table 3 (e.g., any of SEQ ID NOS: 115-118).

In an embodiment, the antibody molecule comprises a light chain variable region (VL), wherein the VL comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of a VL described in Table 3 (e.g., any of SEQ ID NOS: 119-137). In an embodiment, the VL comprises the amino acid sequence of a VL described in Table 3 (e.g., any of SEQ ID NOS: 119-137).

In an embodiment, the antibody molecule comprises a heavy chain variable region (VH) and a light chain variable region (VL), wherein the VH comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of a VH described in Table 3 (e.g., any of SEQ ID NOS: 115-118), and wherein the VL comprises an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of a VL described in Table 3 (e.g., any of SEQ ID NOS: 119-137). In an embodiment, the VH comprises the amino acid sequence of a VH described in Table 3 (e.g., any of SEQ ID NOS: 115-118), and the VL comprises the amino acid sequence of a VL described in Table 3 (e.g., any of SEQ ID NOS: 119-137).

In an embodiment, the HCCDR1, HCCDR2, and HCCDR3 are from the same VH described in Table 3. In an embodiment, the LCCDR1, LCCDR2, and LCCDR3 are from the same VL described in Table 3.

Any of the VH amino acid sequences (or the amino acid sequences of HCDR1, HCDR2, and HCDR3 thereof) disclosed in Table 3 (or a sequence that differs by no more than 1, 2, 3, 4, 5, 6, 7, 8, 9, 10, 11, 12, 13, 14, or 15 amino acid residues therefrom, or has at least 85, 90, 95, 96, 97, 98, 99, or 100% homology therewith) can be combined with any of the VL amino acid sequences (or the amino acid sequences of LCDR1, LCDR2, and LCDR3 thereof) disclosed in Table 3 (or a sequence that differs by no more than 1, 2, 3, 4, 5, 6, 7, 8, 9, 10, 11, 12, 13, 14, or 15 amino acid residues therefrom, or has at least 85, 90, 95, 96, 97, 98, 99, or 100% homology therewith), e.g., to form a humanized antibody molecule. Exemplary combinations include:

SEQ ID NOS: 103 and 104; SEQ ID NOS: 103 and 119; SEQ ID NOS: 103 and 120; SEQ ID NOS: 103 and 121; SEQ ID NOS: 103 and 122; SEQ ID NOS: 103 and 123; SEQ ID NOS: 103 and 124; SEQ ID NOS: 103 and 125; SEQ ID NOS: 103 and 126; SEQ ID NOS: 103 and 127; SEQ ID NOS: 103 and 128; SEQ ID NOS: 103 and 129; SEQ ID NOS: 103 and 130; SEQ ID NOS: 103 and 131; SEQ ID NOS: 103 and 132; SEQ ID NOS: 103 and 133; SEQ ID NOS: 103 and 134; SEQ ID NOS: 103 and 135; SEQ ID NOS: 103 and 136; SEQ ID NOS: 103 and 137; SEQ ID NOS: 115 and 104; SEQ ID NOS: 115 and 119; SEQ ID NOS: 115 and 120; SEQ ID NOS: 115 and 121; SEQ ID NOS: 115 and 122; SEQ ID NOS: 115 and 123; SEQ ID NOS: 115 and 124; SEQ ID NOS: 115 and 125; SEQ ID NOS: 115 and 126; SEQ ID NOS: 115 and 127;

SEQ ID NOS: 115 and 128; SEQ ID NOS: 115 and 129;
SEQ ID NOS: 115 and 130; SEQ ID NOS: 115 and 131;
SEQ ID NOS: 115 and 132; SEQ ID NOS: 115 and 133;
SEQ ID NOS: 115 and 134; SEQ ID NOS: 115 and 135;
SEQ ID NOS: 115 and 136; SEQ ID NOS: 115 and 137;
SEQ ID NOS: 116 and 104; SEQ ID NOS: 116 and 119;
SEQ ID NOS: 116 and 120; SEQ ID NOS: 116 and 121;
SEQ ID NOS: 116 and 122; SEQ ID NOS: 116 and 123;
SEQ ID NOS: 116 and 124; SEQ ID NOS: 116 and 125;
SEQ ID NOS: 116 and 126; SEQ ID NOS: 116 and 127;
SEQ ID NOS: 116 and 128; SEQ ID NOS: 116 and 129;
SEQ ID NOS: 116 and 130; SEQ ID NOS: 116 and 131;
SEQ ID NOS: 116 and 132; SEQ ID NOS: 116 and 133;
SEQ ID NOS: 116 and 134; SEQ ID NOS: 116 and 135;
SEQ ID NOS: 116 and 136; SEQ ID NOS: 116 and 137;
SEQ ID NOS: 117 and 104; SEQ ID NOS: 117 and 119;
SEQ ID NOS: 117 and 120; SEQ ID NOS: 117 and 121;
SEQ ID NOS: 117 and 122; SEQ ID NOS: 117 and 123;
SEQ ID NOS: 117 and 124; SEQ ID NOS: 117 and 125;
SEQ ID NOS: 117 and 126; SEQ ID NOS: 117 and 127;
SEQ ID NOS: 117 and 128; SEQ ID NOS: 117 and 129;
SEQ ID NOS: 117 and 130; SEQ ID NOS: 117 and 131;
SEQ ID NOS: 117 and 132; SEQ ID NOS: 117 and 133;
SEQ ID NOS: 117 and 134; SEQ ID NOS: 117 and 135;
SEQ ID NOS: 117 and 136; SEQ ID NOS: 117 and 137;
SEQ ID NOS: 118 and 104; SEQ ID NOS: 118 and 119;
SEQ ID NOS: 118 and 120; SEQ ID NOS: 118 and 121;
SEQ ID NOS: 118 and 122; SEQ ID NOS: 118 and 123;
SEQ ID NOS: 118 and 124; SEQ ID NOS: 118 and 125;
SEQ ID NOS: 118 and 126; SEQ ID NOS: 118 and 127;
SEQ ID NOS: 118 and 128; SEQ ID NOS: 118 and 129;
SEQ ID NOS: 118 and 130; SEQ ID NOS: 118 and 131;
SEQ ID NOS: 118 and 132; SEQ ID NOS: 118 and 133;
SEQ ID NOS: 118 and 134; SEQ ID NOS: 118 and 135;
SEQ ID NOS: 118 and 136; or SEQ ID NOS: 118 and 137.

In an embodiment, the ADC antibody molecule comprises a VH comprising the amino acid sequence of SEQ ID NO: 117, or a sequence having at least 80% (e.g., at least 80%, 85%, 90%, 95%, 96%, 97%, 98%, or 99%) sequence identity thereto, and a VL comprising the amino acid sequence of SEQ ID NO: 135, or a sequence having at least 80% (e.g., at least 80%, 85%, 90%, 95%, 96%, 97%, 98%, or 99%) sequence identity thereto.

In an embodiment, the ADC or antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising the amino acid sequence of SEQ ID NO: 108; an HCDR2 comprising the amino acid sequence of YISSDGDSX$_1$YYPD X$_2$ X$_3$ KG (SEQ ID NO: 165), wherein X$_1$ is I or T; X$_2$ is N or S; X$_3$ is I or V; or an HCDR3 comprising the amino acid sequence of SEQ ID NO: 107.

In an embodiment, the ADC or antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising the amino acid sequence of RASESX$_1$FGHGISPX$_2$H (SEQ ID NO: 166), wherein X$_1$ is V or I; X$_2$ is M or L; an LCDR2 comprising the amino acid sequence of RASX$_1$X$_2$KX$_3$ (SEQ ID NO: 167), wherein X$_1$ is N or S; X$_2$ is L or R; X$_3$ is F, T or S; or an LCDR3 comprising the amino acid sequence of SEQ ID NO: 112.

In an embodiment, the ADC or antibody molecule comprises a VH and a VL, wherein the VH comprises three heavy chain complementarity determining regions (HCDR1, HCDR2, and HCDR3), and the VL comprises three light chain complementarity determining regions (LCDR1, LCDR2, and LCDR3),
wherein the VH comprises one, two, or all of the following: an HCDR1 comprising the amino acid sequence of SEQ ID NO: 108; an HCDR2 comprising the amino acid sequence of YISSDGDSX$_1$YYPD X$_2$ X$_3$ KG (SEQ ID NO: 165), wherein X$_1$ is I or T; X$_2$ is N or S; X$_3$ is I or V; or an HCDR3 comprising the amino acid sequence of SEQ ID NO: 107, and
wherein the VL comprises one, two, or all of the following: an LCDR1 comprising the amino acid sequence of RASESX$_1$FGHGISPX$_2$H (SEQ ID NO: 166), wherein X$_1$ is V or I; X$_2$ is M or L; an LCDR2 comprising the amino acid sequence of RASX$_1$X$_2$KX$_3$ (SEQ ID NO: 167), wherein X$_1$ is N or S; X$_2$ is L or R; X$_3$ is F, T or S; or an LCDR3 comprising the amino acid sequence of SEQ ID NO: 112.

In an embodiment, the ADC or antibody molecule comprises a VH and a VL, wherein the VH comprises three heavy chain complementarity determining regions (HCDR1, HCDR2, and HCDR3), and the VL comprises three light chain complementarity determining regions (LCDR1, LCDR2, and LCDR3),
wherein the VH comprises: an HCDR1 comprising the amino acid sequence of SEQ ID NO: 108; an HCDR2 comprising the amino acid sequence of YISSDGDSX$_1$YYPD X$_2$ X$_3$ KG (SEQ ID NO: 165), wherein X$_1$ is I or T; X$_2$ is N or S; X$_3$ is I or V; and an HCDR3 comprising the amino acid sequence of SEQ ID NO: 107, and
wherein the VL comprises: an LCDR1 comprising the amino acid sequence of RASESX$_1$FGHGISPX$_2$H (SEQ ID NO: 166), wherein X$_1$ is V or I; X$_2$ is M or L; an LCDR2 comprising the amino acid sequence of RASX$_1$X$_2$KX$_3$ (SEQ ID NO: 167), wherein X$_1$ is N or S; X$_2$ is L or R; X$_3$ is F, T or S; and an LCDR3 comprising the amino acid sequence of SEQ ID NO: 112.

In an embodiment, the antibody molecule comprises or consists of two heavy chain variable regions and two light chain variable regions.

In an embodiment, the antibody molecule further comprises a heavy chain constant region, a light chain constant region, or both.

In an embodiment, the antibody molecule is an IgG antibody molecule, e.g., IgG1, IgG2, IgG3, or IgG4 antibody molecule. In an embodiment, the antibody molecule is not an IgM antibody molecule.

In an embodiment, the antibody molecule comprises a light chain constant region from a kappa or lambda light chain.

In an embodiment, the antibody molecule is capable of binding to two or more Gram-negative strains. Antibody molecules capable of binding to two or more Gram-negative bacterial strains have several advantageous properties. For example, one therapy can be used to treat, prevent, or diagnose multiple bacterial infections. In addition, a physician need not determine which bacterial strain infected a patient in order to determine the appropriate therapy.

According, in an embodiment, the antibody molecule binds to one or more bacteria, e.g., one or more Gram-negative bacteria, e.g., of different genera, species, subspecies, and/or strains.

In an embodiment, the one or more Gram-negative bacteria are selected from a species of Enterobacteriaceae (e.g., a species in *Klebsiella, Enterobacter, Shigella, Escherichia, Salmonella, Yersinia,* or *Citrobacter*, e.g., pan-resistant Enterobacteriaceae), a species of *Pseudomonas*, a species of *Acinetobacter*, or any combination thereof.

In an embodiment, the antibody molecule binds to one or more of: *Klebsiella pneumonia* (e.g., *Klebsiella pneumoniae* subsp. *ozaenae, Klebsiella pneumoniae* subsp. *pneumoniae,* or *Klebsiella pneumoniae* subsp. *rhinoscleromatis*), *Enterobacter cancerogenous, Enterobacter cloacae, Enterobacter hormaechei, Enterobacter asburiae, Shigella boydii, Shigella dysenteriae, Shigella flexneri, Shigella sonnei, Escherichia coli* (e.g., *Escherichia coli* ATCC 11775, *Escherichia coli* ATCC 25922, *Escherichia coli* ATCC 35401, or *Escherichia coli* ATCC 43895), *Escherichia fergusonii, Salmonella choleraesuis, Salmonella choleraesuis* subsp. *indica, Salmonella enteritidis, Salmonella virchow, Salmonella paratyphi* B, *Salmonella typhimurium, Salmonella paratyphi* A, *Salmonella typhi, Salmonella choleraesuis* subsp. *arizonae, Salmonella choleraesuis* subsp. *diarizonae, Salmonella choleraesuis* subsp. *houtenae, Salmonella bongori, Citrobacter sedlakii, Citrobacter braakii, Citrobacter werkmanii, Citrobacter freundii, Citrobacter youngae, Citrobacter amalonaticus, Yersinia enterocolitica, Yersinia frederiksenii, Yersinia pestis, Yersinia pseudotuberculosis,* or any combination thereof.

In an embodiment, the antibody molecule binds to *Pseudomonas*, e.g., *P. aeruginosa*.

In an embodiment, the one or more bacteria are one or more antibiotic-resistant bacteria, e.g., one or more multidrug-resistant Gram-negative bacteria.

In an embodiment, the one or more antibiotic-resistant bacteria are selected from *Pseudomonas* (e.g., *P. aeruginosa*), Enterobacteriaceae (e.g., *Klebsiella pneumonia* or *E. coli*), or *Acinetobacter* (e.g., *A. baumannii*).

In an embodiment, the antibody molecule binds to one or more of: *Enterococcus faecium* (e.g., vancomycin-resistant (VRE) *Enterococcus faecium*), *Staphylococcus aureus* (e.g., methicillin-resistant (MRSA) *Staphylococcus aureus*), *Clostridium difficile, Acinetobacter baumannii* (e.g., multidrug resistant (MDR) *Acinetobacter*), *Pseudomonas aeruginosa* (e.g., multidrug resistant (MDR) *P. aeruginosa*, e.g., carbapenem-resistant *P. aeruginosa*), Enterobacteriaceae (e.g., *E. coli, K pneumoniae,* or *Enterobacter* spp., e.g., carbapenem-resistant Enterobacteriaceae (CRE)), *N. gonorrhoaeae* (e.g., drug-resistant *N. gonorrhoaeae*), *Salmonella* (e.g., drug resistant *Salmonella*), *Shigella* (e.g., drug-resistant *Shigella*), a bacterium producing an extended spectrum p-lactamase (ESBL), or *Mycobacterium tuberculosis* (e.g., drug-resistant *M. tuberculosis*).

In an embodiment, the antibody molecule binds to one or more (e.g., 2, 3, 4, 5, 6, 7, 8, 9, 10, or more) *P. aeruginosa* strains. In another embodiment, the antibody molecule binds to one or more (e.g., 2, 3, 4, 5, 6, or more) multidrug-resistant *P. aeruginosa* strains.

In an embodiment, the antibody molecule binds to LPS with high affinity, e.g., with a $K_D$ that is less than about 10 nM, e.g., measured by an ELISA method.

In an embodiment, the antibody molecule binds to LPS with a $K_{off}$ slower than $1\times10^{-4}$, $5\times10^{-5}$, or $1\times10^{-5}$ s$^{-1}$. In an embodiment, the antibody molecule binds to LPS with a $K_{on}$ faster than $1\times10^4$, $5\times10^4$, $1\times10^5$, or $5\times10^5$ M$^{-1}$s$^{-1}$.

In an embodiment, the antibody molecule has opsonophagocytic activity, e.g., as determined by an OPA assay, e.g., as described herein.

In an embodiment, the antibody molecule binds to an epitope comprising one or more (e.g., two) Kdo residues and/or one or more (e.g., two or three) Hep residues in LPS.

In an embodiment, a) the antibody molecule that binds to lipopolysaccharide (LPS) is coupled (e.g., fused) to b) the antimicrobial peptide, e.g., an antimicrobial peptide described herein, e.g., to form an antibody molecule-drug conjugate (ADC).

In an embodiment, the antibody molecule comprises a heavy chain variable region (VH), wherein the heavy chain variable region is coupled (e.g., fused) to the antimicrobial peptide, e.g., wherein the heavy chain variable region is N-terminal to the antimicrobial peptide.

In an embodiment, the heavy chain variable region is coupled (e.g., fused) to the antimicrobial peptide indirectly, e.g., wherein the C-terminus of the heavy chain variable region is coupled (e.g., fused) to the N-terminus of the antimicrobial peptide via a constant region.

In an embodiment, the antibody molecule comprises a light chain variable region (VL), wherein the light chain variable region is coupled (e.g., fused) to the antimicrobial peptide, e.g., wherein the light chain variable region is N-terminal to the antimicrobial peptide.

In an embodiment, the light chain variable region is coupled (e.g., fused) to the antimicrobial peptide indirectly, e.g., wherein the C-terminus of the light chain variable region is coupled (e.g., fused) to the N-terminus of the antimicrobial peptide via a constant region.

In an embodiment, the antibody molecule is coupled (e.g., fused) to two or more (e.g., three, four, five, six, seven, eight, or more, e.g., four) antimicrobial peptides, e.g., by enzymatic conjugation or chemical conjugation. In an embodiment, at least two of the antimicrobial peptides are identical. In an embodiment, at least two of the antimicrobial peptides are different.

In an embodiment, the antibody molecule is coupled (e.g., fused) to two identical antimicrobial peptides, each is coupled (e.g., fused) to a heavy chain variable region, e.g., indirectly, e.g., via a constant region.

In an embodiment, the antimicrobial peptide coupled (e.g., fused) to the antibody molecule is more effective in inhibiting, e.g., inhibiting the growth, virulence, or infectivity of, a Gram-negative bacterium (e.g., a Gram-negative bacterium described herein) than the antimicrobial peptide or antibody molecule alone, e.g., having a minimum inhibitory concentration (MIC) that is lower, e.g., at least 2, 3, 4, 5, 6, 7, 8, 9, 10, 20, 30, 40, 50, 60, 70, 80, 90, or 100 fold lower, than the MIC of the antimicrobial peptide alone.

In an embodiment, the antimicrobial peptide coupled (e.g., fused) to the antibody molecule is more effective in reducing the viability of, e.g., killing, a Gram-negative bacterium (e.g., a Gram-negative bacterium described herein) than the antimicrobial peptide or antibody molecule alone, e.g., having a minimum bactericidal concentration (MBC) that is lower, e.g., at least 2, 3, 4, 5, 6, 7, 8, 9, 10, 20, 30, 40, 50, 60, 70, 80, 90, or 100 fold lower, than the MBC of the antimicrobial peptide alone.

In an embodiment, the antibody molecule has opsonophagocytic activity (e.g., is phagocytized when bound to the Fc receptor (FcR) of a neutrophil), e.g., as determined by an OPA assay, e.g., as described herein.

In an embodiment, the antimicrobial peptide coupled (e.g., fused) to the antibody molecule does not inhibit, e.g., does not inhibit the growth, virulence, or infectivity of, a Gram-positive bacterium (e.g., a Gram-positive bacterium described herein), e.g., having a minimum inhibitory concentration (MIC) for a Gram-negative bacterium (e.g., a Gram-negative bacterium) that is lower, e.g., at least 2, 5, 10, 20, 50, 100, 200, 500, or 1000 fold lower, than a MIC for a Gram-positive bacterium (e.g., a Gram-positive bacterium).

In an embodiment, the antimicrobial peptide coupled (e.g., fused) to the antibody molecule does not reduce the viability of, e.g., does not kill, a Gram-positive bacterium (e.g., a Gram-positive bacterium described herein), e.g., having a minimum bactericidal concentration (MBC) for a Gram-negative bacterium (e.g., a Gram-negative bacterium) that is lower, e.g., at least 2, 5, 10, 20, 50, 100, 200, 500, or 1000 fold lower fold lower, than a MBC for a Gram-positive bacterium (e.g., a Gram-positive bacterium).

In an embodiment, the Gram-positive bacterium is *Staphylococcus aureus*.

In an embodiment, the antibody molecule binds to a linear or conformational epitope on a Gram-negative bacterium or on LPS.

In an embodiment, the antibody molecule binds to low MW LPS and high MW LPS, e.g., as determined by Western analysis. In an embodiment, the antibody molecule binds to a highly phosphorylated heptose region of *P. aeruginosa* core LPS. In an embodiment, the antibody molecule binds to phosphorylated (e.g., hyper-phosphorylated, e.g., biphosphorylated) Hep I residue of core LPS. In an embodiment, the antibody molecule binds to a region in core LPS (e.g., in *P. aeruginosa*) that is essential for outer membrane formation (as described, e.g., in DeLucia et al. *MBio*. 2011; 2(4). pii: e00142-11, the content of which is incorporated herein by reference).

In an embodiment, the antibody molecule binds to biphosphorylated heptose with high affinity, e.g., with an apparent K D equal to or less than about 20 nM, e.g., as determined by a method described herein. In an embodiment, the antibody molecule preferentially binds to phosphorylated (e.g., hyper-phosphorylated) heptose, compared to non-phosphorylated heptose. In an embodiment, the antibody molecule preferentially binds to hyper-phosphorylated (e.g., biphosphorylated) heptose, compared to heptose with single phosphorylation. In an embodiment, the antibody molecule preferentially binds to hyper-phosphorylated (e.g., biphosphorylated) heptose, compared to biphosphorylated mannose, mannose with single phosphorylation, or non-phosphorylated mannose.

In an embodiment, the antibody molecule having the binding properties described herein comprises a sulfatase motif (e.g., a modified sulfatase motif), e.g., as described herein.

Antimicrobial Peptides

As used herein, the term "antimicrobial peptide" refers to a peptide that has an antimicrobial activity, e.g., an antibacterial activity. While not wishing to be bound by theory, it is believed that, in an embodiment, the antimicrobial peptides can have variable length, sequence and structure with broad spectrum activity against a number of microorganisms, e.g., bacteria, and optionally low levels of induced resistance. In an embodiment, the antimicrobial peptide is an antibacterial peptide.

Antimicrobial peptides are a diverse group of molecules, which are divided into subgroups on the basis of their amino acid composition and structure. Typically, these peptides include two or more positively charged residues provided by arginine, lysine or, in acidic environments, histidine, and a large proportion (e.g., more than 50%) of hydrophobic residues. The secondary structures of these molecules include, e.g., i) α-helical, ii) β-stranded due to the presence of 2 or more disulfide bonds, iii) β-hairpin or loop due to the presence of a single disulfide bond and/or cyclization of the peptide chain, and iv) extended. Some of these peptides can be unstructured in free solution, and fold into their final configuration upon partitioning into biological membranes. Antimicrobial peptides can contain hydrophilic amino acid residues aligned along one side and hydrophobic amino acid residues aligned along the opposite side of a helical molecule. This amphipathicity of the antimicrobial peptides allows them to partition into the membrane lipid bilayer. While not wishing to be bound by theory, it is believed that in an embodiment, the ability to associate with membranes is a typical feature of antimicrobial peptides although membrane permeabilization may not be required.

Types of antimicrobial peptides include, e.g., anionic peptides (e.g., rich in glutamic and aspartic acids), linear cationic α-helical peptides (e.g., lacking cysteine), cationic peptides (e.g., rich in proline, arginine, phenylalanine, glycine, or tryptophan), and anionic and cationic peptides that contain cysteine and form disulfide bonds (e.g., containing 1-3 disulfide bonds).

The modes of action by which antimicrobial peptides kill microbes are varied, and may differ for different bacterial species. The cytoplasmic membrane is a frequent target, but peptides may also interfere with DNA and protein synthesis, protein folding, and cell wall synthesis. The initial contact between the peptide and the target organism can be electrostatic, as most bacterial surfaces are anionic, or hydrophobic. Their amino acid composition, amphipathicity, cationic charge and size allow them to attach to and insert into membrane bilayers to form pores by "barrel-stave," "carpet" or "toroidal-pore" mechanisms. Alternately, they may penetrate into the cell to bind intracellular molecules which are crucial to cell living. Intracellular binding models includes inhibition of cell wall synthesis, alteration of the cytoplasmic membrane, activation of autolysin, inhibition of DNA, RNA, and protein synthesis, and inhibition of certain enzymes. These peptides can be bactericidal and/or bacteriostatic. Typically, the antimicrobial (e.g., antibacterial) activity of these peptides is determined by measuring the minimal inhibitory concentration (MIC).

Antimicrobial peptides have been demonstrated to kill Gram-negative and Gram-positive bacteria, viruses, fungi, and transformed or cancerous cells (Reddy et al. (2004) *International Journal of Antimicrobial Agents* 24 (6): 536-547). Antimicrobial peptides may also have an immunomodulatory activity. For example, the immunomodulatory activities may be involved in the clearance of infection, e.g., the ability to alter host gene expression, act as chemokines and/or induce chemokine production, inhibiting lipopolysaccharide induced pro-inflammatory cytokine production, promoting wound healing, or modulating the responses of dendritic cells and cells of the adaptive immune response.

Several methods can be used to determine the mechanisms of antimicrobial peptide activity. These methods include, e.g., solid-state NMR spectroscopy, microscopy, atomic emission spectroscopy, fluorescent dyes, ion channel formation, circular dichroism and orientated circular dichroism, dual polarization interferometry, or neutron and X-ray diffraction.

In an embodiment, the antimicrobial peptide is under 10 kDa, e.g., under 8 kDa, 6 kDa, 4 kDa, 2 kDa, or 1 kDa. In an embodiment, the antimicrobial peptide comprises or consists of from about 6 to about 100 amino acids, e.g., from about 6 to about 75 amino acids, about 6 to about 50 amino acids, about 6 to about 25 amino acids, about 25 to about 100 amino acids, about 50 to about 100 amino acids, or about 75 to about 100 amino acids. In an embodiment, the anti-bacterial peptide comprises or consists of from about 12 to about 50 amino acids. In an embodiment, the anti-bacterial peptide comprises or consists of from about 15 to about 45 amino acids. In an embodiment, the antimicrobial peptide is substantially cationic. In an embodiment, the antimicrobial peptide is substantially amphipathic. In an embodiment, the antimicrobial peptide is substantially cationic and amphipathic. In an embodiment, the antimicrobial peptide is cytostatic to a Gram-negative bacterium. In an embodiment, the antimicrobial peptide is cytotoxic to a Gram-negative bacterium. In an embodiment, the antimicrobial peptide is cytostatic and cytotoxic to a Gram-positive bacterium. In an embodiment, the antimicrobial peptide is broad-spectrum antimicrobial peptide, e.g., cytostatic and/or cytotoxic to two or more bacteria of different genera, species, subspecies, and/or strains. In an embodiment, the antimicrobial peptide is a secreted polypeptide.

Antimicrobial peptides have been isolated and described from a wide range of animals: microorganisms, invertebrates, plants, amphibians, birds, fish, and mammals (Wang et al., *Nucleic Acids Res.* 2009; 37 (Database issue):D933-7). For example, antimicrobial polypeptides are described in Antimicrobial Peptide Database (; Wang et al., *Nucleic Acids Res.* 2009; 37 (Database issue):D933-7), CAMP: Collection of Anti-Microbial Peptides (; Thomas et al., *Nucleic Acids Res.* 2010; 38 (Database issue):D774-80), U.S. Pat. Nos. 5,221,732, 5,447,914, 5,519,115, 5,607,914, 5,714,577, 5,734,015, 5,798,336, 5,821,224, 5,849,490, 5,856,127, 5,905,187, 5,994,308, 5,998,374, 6,107,460, 6,191,254, 6,211,148, 6,300,489, 6,329,504, 6,399,370, 6,476,189, 6,478,825, 6,492,328, 6,514,701, 6,573,361, 6,573,361, 6,576,755, 6,605,698, 6,624,140, 6,638,531, 6,642,203, 6,653,280, 6,696,238, 6,727,066, 6,730,659, 6,743,598, 6,743,769, 6,747,007, 6,790,833, 6,794,490, 6,818,407, 6,835,536, 6,835,713, 6,838,435, 6,872,705, 6,875,907, 6,884,776, 6,887,847, 6,906,035, 6,911,524, 6,936,432, 7,001,924, 7,071,293, 7,078,380, 7,091,185, 7,094,759, 7,166,769, 7,244,710, 7,314,858, and 7,582,301, the contents of which are incorporated by references.

The antimicrobial peptides described herein may inhibit or reduce the viability of one or more bacteria species, e.g., one or more bacteria (e.g., Gram-negative bacteria) of different genera, species, subspecies, and/or strains. In an embodiment, the antimicrobial peptide is capable of inhibiting and/or reducing the viability of 2, 3, 4, 5, 6, 7, 8, 9, 10, or more Gram-negative bacterial strains. For instance, the antibody molecule may inhibit and/or reduce the viability of one or more bacteria of different species, subspecies, and/or strains from Enterobacteriaceae (e.g., *Klebsiella, Enterobacter, Shigella, Escherichia, Salmonella, Yersinia,* or *Citrobacter*, e.g., pan-resistant Enterobacteriaceae), one or more bacteria of different species, subspecies, and/or strains from *Pseudomonas*, one or more bacteria of different species, subspecies, and/or strains from *Acinetobacter*, or any combination thereof. In an embodiment, the antimicrobial peptide is capable of inhibiting or reducing the viability of *Klebsiella pneumonia* (e.g., *Klebsiella pneumoniae* subsp. *ozaenae, Klebsiella pneumoniae* subsp. *pneumoniae*, or *Klebsiella pneumoniae* subsp. *rhinoscleromatis*), *Enterobacter cancerogenous, Enterobacter cloacae, Enterobacter hormaechei, Enterobacter asburiae, Shigella boydii, Shigella dysenteriae, Shigella flexneri, Shigella sonnei, Escherichia coli* (e.g., *Escherichia coli* ATCC 11775, *Escherichia coli* ATCC 25922, *Escherichia coli* ATCC 35401, or *Escherichia coli* ATCC 43895), *Escherichia fergusonii, Salmonella choleraesuis, Salmonella choleraesuis* subsp. *indica, Salmonella enteritidis, Salmonella virchow, Salmonella paratyphi* B, *Salmonella typhimurium, Salmonella paratyphi* A, *Salmonella typhi, Salmonella choleraesuis* subsp. *arizonae, Salmonella choleraesuis* subsp. *diarizonae, Salmonella choleraesuis* subsp. *houtenae, Salmonella bongori, Citrobacter sedlakii, Citrobacter braakii, Citrobacter werkmanii, Citrobacter freundii, Citrobacter youngae, Citrobacter amalonaticus, Yersinia enterocolitica, Yersinia frederiksenii, Yersinia pestis, Yersinia pseudotuberculosis*, or any combination thereof.

In an embodiment, the antimicrobial peptide is capable of inhibit and/or reduce the viability of one or more: *Enterococcus faecium* (e.g., vancomycin-resistant (VRE) *Enterococcus faecium*), *Staphylococcus aureus* (e.g., methicillin-resistant (MRSA) *Staphylococcus aureus*), *Clostridium Acinetobacter haumannii* (e.g., multidrug resistant (MDR) *Acinetobacter*), *Pseudomonas aeruginosa* (e.g., multidrug resistant (MDR) *P. aeruginosa*, e.g., carbapenem-resistant *P. aeruginosa*), Enterobacteriaceae (e.g., *E. coli, K. pneumoniae*, or *Enterobacter* spp., e.g., carbapenem-resistant Enterobacteriaceae (CRE)), *N. gonorrhoaeae* (e.g., drug-resistant *N. gonorrhoaeae*), *Salmonella* (e.g., drug resistant *Salmonella*), *Shigella* (e.g., drug-resistant *Shigella*), a bacterium producing an extended spectrum β-lactamase (ESBL), or *Mycobacterium tuberculosis* (e.g., drug-resistant *M. tuberculosis*). The antimicrobial peptides described herein can have one or more (e.g., two, three or all) of the following properties: strong bacterial inhibition activity, strong bactericidal activity, low red blood cell (RBC) hemolytic activity, or low cytotoxicity (e.g., off-target toxicity). In an embodiment, the antimicrobial peptide has a minimum inhibitory concentration (MIC) of less than 100 g/ml, e.g., less than 90, 80, 70, 60, 50, 40, 30, 20, 10, or 5 µg/ml, against a bacterial strain described herein, e.g., *Escherichia coli* ATCC 25922, *Pseudomonas aeruginosa* ATCC27853, or both. In an embodiment, the antimicrobial peptide has a minimum bactericidal concentration (MBC) of less than 100 µg/ml, e.g., less than 90, 80, 70, 60, 50, 40, 30, 20, 10, or 5 µg/ml, against a bacterial strain described herein, e.g., *Escherichia coli* ATCC 25922, *Pseudomonas aeruginosa* ATCC27853, or both. In an embodiment, the antimicrobial peptide has low hemolytic activity, e.g., has a PLC to MIC ratio for a Gram-negative bacterium (e.g., a Gram-negative bacterium described herein) which is equal to or greater than 1 (e.g., greater than 4:1, 8:1, 16:1, 24:1, or 32:1), e.g., as determined by a red blood cell hemolysis assay and an MIC assay, respectively. In an embodiment, the PLC is the concentration (e.g., minimum concentration) required or needed to lyse 50% of the red blood cells. In an embodiment, the antimicrobial peptide has low hemolytic activity, e.g., has an MLC to MIC ratio for a Gram-negative bacterium (e.g., a Gram-negative bacterium described herein) which is greater than 4:1 (e.g., greater than 8:1, 16:1, 24:1, or 32:1), e.g., as determined by a red blood cell hemolysis assay and an MIC assay, respectively. In an embodiment, the MLC is the concentration (e.g., minimum concentration) required or needed to lyse 100% of the red blood cells.

In an embodiment, the antimicrobial peptide is an α-helical peptide. In an embodiment, the antimicrobial peptide has two or more amino acid residues cross-linked. For example, two cysteine residues in the antimicrobial peptide can be cross-linked, e.g., chemically cross-linked. While not wishing to be bound by theory, it is believed that in an embodiment, cross-linking two or more amino acid residues in an antimicrobial peptide may enhance α-helical conformation, enhance serum stability, and/or increase antimicrobial potency. In an embodiment, the antimicrobial peptide having two or more amino acid residues cross-linked is at least 2, 3, 4, 5, 6, 7, 8, 9, or 10-fold more stable, e.g., in serum, than an otherwise identical antimicrobial peptide that does not have two or more amino acid residues cross-linked. In an embodiment, the antimicrobial peptide having two or more amino acid residues cross-linked has a MIC that is at least 10%, 20%, 30%, 40%, 50%, 60%, 70%, 80%, 90%, 95%, 98%, or 99% lower than an otherwise identical antimicrobial peptide that does not have two or more amino acid residues cross-linked.

In an embodiment, the antimicrobial peptide is coupled (e.g., fused) to an antibody molecule, e.g., an antibody molecule described herein, e.g., to form an antibody molecule-drug conjugate (ADC).

The following criteria can be used to select a candidate antimicrobial peptide: broad spectrum (e.g., activity against multiple bacterial pathogens), alpha-helical secondary structure (e.g., readily expressed in functional form), mechanism of action by membrane disruption (e.g., bactericidal and/or synergy with small molecules), in vivo stability (e.g., stable in human sera), and adaptable to N-terminal modifications (e.g., to function as C-terminal antibody conjugates).

The antimicrobial peptides described herein can contain a sequence that does not have an antimicrobial activity by itself. In an embodiment, the antimicrobial peptide comprises a linker sequence. In an embodiment, the antimicrobial peptide comprises a sortase donor sequence.

In an embodiment, the antimicrobial peptide alone does not bind to LPS, e.g., a core region of LPS.

In an embodiment, a heavy chain of the antibody molecule comprises a first sortase acceptor sequence and a light chain of the antibody molecule comprises a second sortase acceptor sequence. In an embodiment, the sortase acceptor sequence, e.g., the first sortase recognition sequence, comprises the amino acid sequence of $(GS)_6LPETGGG$ (SEQ ID NO: 24). In another embodiment, the sortase acceptor sequence, e.g., the second sortase acceptor sequence, comprises the amino acid sequence of $P(G_4S)_2LPETGGSG$ (SEQ ID NO: 26).

In an embodiment, the antimicrobial peptide comprises or consists of an amino acid sequence that differs by no more than 1, 2, 3, 4, or 5 amino acid residues from, or has at least 80%, 85%, 90%, 95%, 96%, 97%, 98%, 99%, or 100% homology with, an amino acid sequence described herein, e.g., any of SEQ ID NOS: 67-80, 94-102, 147-156, 158-159, 163-164, or 246-258. In an embodiment, the antimicrobial peptide comprises or consists of an amino acid sequence described herein e.g., any of SEQ ID NOS: 67-80, 94-102, 147-156, 158-159, 163-164, or 246-258, or a portion thereof, e.g., a functional fragment thereof (e.g., one or more (e.g., two, three, four or more) of the N-terminal G residues are omitted). For example, the first three N-terminal G residues in any of SEQ ID NOS: 101, 147, 152-154, 156, or 163-164 can be omitted. In an embodiment, the presence of one or more (e.g., two, three, four or more) of the N-terminal G residues does not reduce, or significantly reduce, the activity of the antimicrobial peptide.

In an embodiment, the peptide comprises the amino acid sequence of:

```
                                        (SEQ ID NO: 68)
RGLRRLGRKIAHGVKKYGPTVLRIIRIAG, (SEQ ID NO: 80)
GGGRGLRRLGRKIAHGVKKYGPTVLRIIRIAG, (SEQ ID NO: 101)
GGGGRFKRFRKKFKKLFKKLSPVIPLLHLG,
or (SEQ ID NO: 102)
GRFKRFRKKFKKLFKKLSPVIPLLHLG.
```

In an embodiment, the antimicrobial peptide is a stapled antimicrobial peptide. Without wishing to be bound by theory, it is believed that in an embodiment, stapling can increase stability, reduce non-specific binding, or both, e.g., in serum. Exemplary stapling methods are described, e.g., in Alexander et al. *J. Am. Chem. Soc.*, 2013, 135 (16), 5946-5949; and Example 7.

In an embodiment, the antimicrobial peptide comprises or consists of an amino acid sequence described in Table 4. In another embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence described in Table 4, or a portion thereof, e.g., a functional fragment thereof. In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NOS: 67-80, 94-102, 147-156, 158-159, 163-164, or 246-258. In an embodiment, the antimicrobial peptide comprises a carboxamide group (e.g., a C-terminal carboxamide functional group).

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 257.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 258.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 101.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 147.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 152.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 153.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 154.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 156.

In an embodiment, an ADC comprising the antimicrobial peptide is capable of reducing P. aeruginosa titers by at least about 3 logs (e.g., about 1.5, 2, 2.5, 3, 3.5, or 4 logs), e.g., at peptide levels of about 4 (e.g., about 2, 3, 4, 5, 6, 7) times the MIC or greater. In an embodiment, an ADC comprising the antimicrobial peptide disrupts the membrane of a bacterium, e.g., P. aeruginosa.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 163.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 164.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of any of SEQ ID NOS: 156 and 246-258.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 246.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 247.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 248.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 249.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 250.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 251.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 252.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 253.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 254.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 255.

In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 256.

In an embodiment, the antimicrobial peptide comprises one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38. 39, 40, or more) D-amino acids. In an embodiment, at least 10%, 20%, 30%, 40%, 50%, 60%, 70%, 80%, 90%, or 100% of the amino acid residues in the antimicrobial peptide are D-amino acids. In an embodiment, all of the amino acid residues in the antimicrobial peptide are D-amino acids. Without wishing to be bound by theory, it is believed that in an embodiment, the presence of one or more (e.g., all) D-amino acids in the antimicrobial peptide can increase the stability of the antimicrobial peptide or ADC, e.g., in serum (e.g., human serum), e.g., compared to an otherwise identical antimicrobial peptide that contains one or more (e.g., all) L-amino acids.

In an embodiment, the antimicrobial peptide comprises one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38. 39, 40, or more) L-amino acids. In an embodiment, at least 10%, 20%, 30%, 40%, 50%, 60%, 70%, 80%, 90%, or 100% of the amino acid residues in the antimicrobial peptide are L-amino acids. In an embodiment, all of the amino acid residues in the antimicrobial peptide are L-amino acids.

In an embodiment, the antimicrobial peptide comprises one or more D-amino acids and one or more L-amino acids. For example, any of the amino acid residues in the antimicrobial peptides described in Table 4 can be a D-amino acid or an L-amino acid.

TABLE 4

Amino acid sequences of exemplary antimicrobial peptides

| Peptide (P) | Amino Acid Sequences | SEQ ID NO |
|---|---|---|
| Peptide 26 | ALWKTLLKKVLKAAAK | 67 |
| Peptide 119 | RGLRRLGRKIAHGVKKYGPTVLRIIRIAG | 68 |
| Peptide 109 | GIGKFLKKAKKFGKAFVKILKK | 69 |
| Peptide 30 | ALWKTLLKKVLKAAAKGGGGSGGGGS | 70 |
| Peptide 24 | GIGKFLKKAKKFGKAFVKILKKGGGGSGGGGS | 71 |
| Peptide 126 | KKLLKWLKKLL | 72 |
| Peptide 21 | (MAL)-(EG3)-GIGKFLKKAKKFGKAFVKILKK | 73 |
| Peptide 128 | RLGNFFRKAKKKIGRGLKKIGQKIKDFLGNLVPRTES | 74 |
| Peptide 23 | GGGGSGGGGSGIGKFLKKAKKFGKAFVKILKK | 75 |
| Peptide 33 | GLRKRLRKFRNKIKEKLKKIGQKIQGLLPKLA | 76 |
| Peptide 29 | GGGGSGGGGSALWKTLLKKVLKAAAK | 77 |
| Peptide 85 | GWKKWFNRAKKVGKTVGGLAVDHYLG | 78 |
| Peptide 70 | GAFGNFLKGVAKKAGLKILSIAQCKLFGTC | 79 |
|  | GGGRGLRRLGRKIAHGVKKYGPTVLRIIRIAG | 80 |
|  | GIGKHVGKALKGLKGLLKGLGES | 94 |
|  | GRRKRKWLRRIGKGVKIIGGAALDHL | 95 |
|  | GGLRSLGRKILRAWKKYGPQATPATRQ | 96 |
|  | IKWKKLLRAAKRIL | 97 |
|  | IGKKWKRIVKRIKKFLRKL | 98 |
|  | ILGKIWKIKKLF | 99 |
|  | RLGDILQKAREKIEGGLKKLVQKIKDFFGKFAPRTES | 100 |
|  | GGGGRFKRFRKKFKKLFKKLSPVIPLLHLG | 101 |
|  | GRFKRFRKKFKKLFKKLSPVIPLLHLG | 102 |
| Peptide 265 | GGGLLGDFFRKSKEKIGKEFKRIVQRIKDFLRNLVPRTES | 147 |
| Peptide 266 | GGGKWKSFIKKLTKAAKKVVTTAKKPLIV | 148 |
| Peptide 267 | GGGGRFKRFRKKFKKLFKKLSPVIPLLHLG | 101 |
| Peptide 268 | GGGVNWKKILGKIIKVVK | 149 |
| Peptide 269 | GGGTLISWIKNKRKQRPRVSRRRRRRGGRRRR | 150 |
| Peptide 270 | GGGGIGAILKVLATGLPTLISWIKNKRKQ | 151 |
| Peptide 271 | GGGGLRKRLRKFRNKIKEKLKKIGQKIQGLLPKLA | 152 |
| Peptide 293 | GGGGLRRLGRKIAHGIKKYGPTILRIIRIAG | 153 |
| Peptide 294 | GGGRGLRRLGRKIAHGVKKYGPTVLRIIKKYG | 154 |
| Peptide 295 | GGGGRFKRFRKKFKKLFKKLSPVIPLLHLG | 101 |
| Peptide 296 | GGGKRFKKFFKKLKNSVKKRAKKFFKKPRVIGVSIPF | 155 |
| Peptide 297 | GGGKFFRKLKKSVKKRAKEFFKKPRVIGVSIPF | 156 |
| Peptide 261 | GGGGIGKFLKKAKKFGKAFVKILKK | 163 |
| Peptide 369 | GGGKLLRKLKKSVKKRAKELLKKPRVIGVSIPL | 257 |
| Peptide 292 | GGGHTASDAAAAAALTAANAAAAAASMA | 258 |

TABLE 4-continued

Amino acid sequences of exemplary antimicrobial peptides

| Peptide (P) | Amino Acid Sequences | SEQ ID NO |
|---|---|---|
| GGG-Octapeptin | GGG-D-Dab-cyclic(L-Dab-L-Dab-D-Leu-L-Phe-L-Dab-L-Dab-L-Leu) | 164 |

MAL: maleimide; EG3: tri(ethylene glycol)

In an embodiment, the ADC comprises a peptide comprising the amino acid sequence of

RGLRRLGRKIAHGVKKYGPTVLRIIRIAG, (SEQ ID NO: 68)

GGGRGLRRLGRKIAHGVKKYGPTVLRIIRIAG, (SEQ ID NO: 80)

GGGGRFKRFRKKFKKLFKKLSPVIPLLHLG, (SEQ ID NO: 101)
or

GRFKRFRKKFKKLFKKLSPVIPLLHLG. (SEQ ID NO: 102)

In an embodiment, the antimicrobial peptide comprises or consists of an amino acid sequence selected from:

RGLRRLGRKIAHGVKKYGPTVLRIIRIAG, (SEQ ID NO: 68)

GIGKFLKKAKKFGKAFVKILKK, (SEQ ID NO: 69)

KKLLKWLKKLL, (SEQ ID NO: 72)

RLGNFFRKAKKKIGRGLKKIGQKIKDFLGNLVPRTES, (SEQ ID NO: 74)

GIGKHVGKALKGLKGLLKGLGES, (SEQ ID NO: 94)

GRRKRKWLRRIGKGVKIIGGAALDHL, (SEQ ID NO: 95)

GGLRSLGRKILRAWKKYGPQATPATRQ, (SEQ ID NO: 96)

IKWKKLLRAAKRIL, (SEQ ID NO: 97)

IGKKWKRIVKRIKKFLRKL, (SEQ ID NO: 98)

ILGKIWKIKKLF, (SEQ ID NO: 99)
or

RLGDILQKAREKIEGGLKKLVQKIKDFFGKFAPRTES. (SEQ ID NO: 100)

In an embodiment, the antimicrobial peptide comprises or consists of an amino acid sequence selected from the peptide sequences described herein (e.g., in Table 4). In an embodiment, the antimicrobial peptide is an analog of an antimicrobial peptide described herein, e.g., to enhance one or more biophysical properties of the antimicrobial peptide. In an embodiment, the antimicrobial peptide is an analog of peptide 297 (P297), e.g., (D)-P297. In an embodiment, the antimicrobial peptide (e.g., a P297 analog) comprises a mutation of a charged residue (e.g., arginine or lysine) to an uncharged residue (e.g., alanine or threonine). In an embodiment, the antimicrobial peptide (e.g., a P297 analog) comprises an R to A, an R to T mutation, an R to S mutation, or a combination thereof. In an embodiment, the antimicrobial peptide (e.g., a P297 analog) comprises a K to A, a K to T mutation, a K to S mutation, or a combination thereof. In an embodiment, the antimicrobial peptide comprises an anionic peptide at the C- or N-terminus, or at a location close to the C- or N-terminus (e.g., no more than 1, 2, 3, 4, 5, or 6 amino acids from the C- or N-terminus). In an embodiment, the length of the anionic peptide is about 2 to 15, 3 to 14, 4 to 13, 5 to 12, 6 to 11, 7 to 10, 8 to 9, 2 to 13, 2 to 11, 2 to 9, 2 to 7, 2 to 5, 12 to 15, 9 to 15, 6 to 15, 3 to 15, 4 to 9, 5 to 8, or 6 to 7 amino acid residues. In an embodiment, the antimicrobial peptide comprises a sequence of AAA, e.g., N-terminal and adjacent to the anionic peptide sequence. In an embodiment, the antimicrobial peptide, e.g., (D)P-297, has about the same activity (e.g., killing *Pseudomonas aeruginosa*) as P297. In an embodiment, the antimicrobial peptide, e.g., (D)P-297, is more stable in serum than P297. In an embodiment, the antimicrobial peptide (e.g., a P297 analog) reduces *Pseudomonas aeruginosa* titers by more than about 3 logs (e.g., 2, 2.5, 3, 3.5, or 4 logs), e.g., at peptide levels of four times the MIC or greater. In an embodiment, the antimicrobial peptide (e.g., a P297 analog) has lytic levels that are more than 10-fold greater than the MIC. In an embodiment, the antimicrobial peptide (e.g., a P297 analog) has a high therapeutic index in in vitro assays. In an embodiment, the antimicrobial peptide (e.g., a P297 analog) shows cytotoxicity of mammalian cells (e.g., 293T) that is about 200-fold greater than the MIC. In an embodiment, the antimicrobial peptide (e.g., a P297 analog) has L-amino acids substituted with D-amino acids (e.g., (D)-P297). In an embodiment, the antimicrobial peptide in which the L-amino acids are substituted with D-amino acids, e.g., (D)-P297, has decreased protease sensitivity and/or increased serum stability relative to (L)-P297. In an embodiment, the antimicrobial peptide in which the L-amino acids are substituted with D-amino acids, e.g., (D)-P297, has about the same, or essentially the same, activity (e.g., killing *Pseudomonas aeruginosa*) as P297.

In an embodiment, the antimicrobial peptide comprises or consists of an amino acid sequence selected from the peptide sequences described in Table 4. In an embodiment, the antimicrobial peptide comprises or consists of an amino acid sequence of Peptide 297 (P297) or Peptide 369 (P369). In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 156. In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 257. In an embodiment, the antimicrobial peptide comprises or consists of D-amino acids, e.g., as described herein. In an embodiment, the antimicrobial peptide (e.g., P369 or P297) is conjugated to an antibody molecule (e.g., VSX). In an embodiment, the ADC (e.g., VSX-1 or VSX-2) has bactericidal activity. In an embodiment, the ADC (e.g., VSX-1 or VSX-2) shows reduced cytotoxicity relative to a reference ADC. In an embodiment, the ADC (e.g., VSX-1 or VSX-2) has improved biodistribution, compared to a reference ADC. In an embodiment, the ADC (e.g., VSX-1 or VSX-2) increases survival in a murine *Pseudomonas aeruginosa* lung infection model relative to a reference antibody, e.g., as described in Example 11.

Antibody Molecule-Drug Conjugates

As used herein, the term "antibody molecule-drug conjugate" or ADC refers to an antibody molecule that is coupled to a non-antibody moiety, e.g., a therapeutic agent or label, e.g., an antimicrobial peptide. The antibody molecule can be coupled to the non-antibody moiety directly, or indirectly, e.g., through a linker.

In an embodiment, the antibody molecule is coupled to the non-antibody moiety by a covalent bond. In an embodiment, the antibody molecule is coupled to the non-antibody moiety by a peptide bond. In an embodiment, the coupling of the antibody molecule to the non-antibody moiety is mediated by a sortase. In an embodiment, the coupling of the antibody molecule and the non-antibody moiety forms a fusion protein. In an embodiment, the antibody molecule and the non-antibody moiety forms a fusion protein. In an embodiment, the fusion protein comprises a linker between the antibody molecule (e.g., a heavy chain, a light chain, or both) and the non-antibody moiety. In an embodiment, the antibody molecule is coupled to the non-antibody moiety by a non-peptide bond. In an embodiment, the antibody molecule is not coupled to the non-antibody moiety by a non-peptide bond. In an embodiment, a non-antibody moiety is also referred to as a "payload."

In an embodiment, the non-antibody moiety is coupled to the backbone of the antibody molecule. In another embodiment, the non-antibody moiety is coupled to a side chain of the antibody molecule. In an embodiment, the non-antibody moiety is a peptide (e.g., an antimicrobial peptide) and the antibody molecule is coupled to the backbone of the peptide (e.g., antimicrobial peptide). In an embodiment, the non-antibody moiety is a peptide (e.g., an antimicrobial peptide) and the antibody molecule is coupled to a side-chain of the peptide (e.g., antimicrobial peptide).

In an embodiment, two or more (e.g., three, four, five, six, seven, eight, or more) non-antibody moieties (e.g., antimicrobial peptides) are coupled to the antibody molecule. In an embodiment, four non-antibody moieties (e.g., antimicrobial peptides) are coupled to the antibody molecule. For example, the non-antibody moieties can be the same, or at least some of the non-antibody moieties are different from each other. In an embodiment, the non-antibody moiety (e.g., antimicrobial peptide) is coupled to the antibody molecule in a bivalent manner. In another embodiment, the non-antibody moiety (e.g., antimicrobial peptide) is coupled to the antibody molecule in a tetravalent manner.

In an embodiment, the ADC comprises an antibody molecule that binds to a bacterium (e.g., a Gram-negative bacterium). In an embodiment, the ADC comprises an antibody molecule that binds to LPS, e.g., on the outer membrane of a Gram-negative bacterium). In an embodiment, the ADC comprises an antibody molecule described herein.

In an embodiment, the ADC comprises one, two, or three CDRs of the VH region of an antibody molecule described in Table 1 or 3 (e.g., mAb001, A001-25, hWN01, hWNv1, 3E7, 3G1, 2C7, or 3D6, or any of the humanized mAb001), using the Kabat or Chothia definitions of CDRs. In an embodiment, the ADC comprises one, two, or three CDRs of the VL region of an antibody molecule described in Table 1 or 3 (e.g., mAb001, A001-25, hWN01, hWNv1, 3E7, 3G1, 2C7, or 3D6, or any of the humanized mAb001), using the Kabat or Chothia definitions of CDRs. In an embodiment, the ADC comprises one or more (e.g., two or three) CDRs of the VH region and/or one or more (e.g., two or three) CDRs of the VL region of an antibody molecule described in Table 1 or 3 (e.g., mAb001, A001-25, hWN01, hWNv1, 3E7, 3G1, 2C7, or 3D6, or any of the humanized mAb001), using the Kabat or Chothia definitions of CDRs.

In an embodiment, the ADC comprises one, two, or three VH CDRs described in Table 1 or 3. In an embodiment, the ADC comprises one, two, or three VL CDRs described in Table 1 or 3. In an embodiment, the ADC comprises one or more (e.g., two or three) VH CDRs and/or one or more (e.g., two or three) VL CDRs described in Table 1 or 3.

In an embodiment, the ADC comprises one, two, three, or four frameworks of the VH region of an antibody molecule described in Table 1 or 3 (e.g., mAb001, A001-25, hWN01, hWNv1, 3E7, 3G1, 2C7, or 3D6, or any of the humanized mAb001). In an embodiment, the ADC comprises one, two, three, or four frameworks of the VL region of an antibody molecule described in Table 1 or 3 (e.g., mAb001, A001-25, hWN01, hWNv1, 3E7, 3G1, 2C7, or 3D6, or any of the humanized mAb001). In an embodiment, the ADC comprises one or more (e.g., two, three, or four) frameworks of the VH region and/or one or more (e.g., two, three, or four) frameworks of the VL region of an antibody molecule described in Table 1 or 3 (e.g., mAb001, A001-25, hWN01, hWNv1, 3E7, 3G1, 2C7, or 3D6, or any of the humanized mAb001).

In an embodiment, the ADC comprises a heavy chain variable region of an antibody molecule described in Table 1 or 3 (e.g., mAb001, A001-25, hWN01, hWNv1, 3E7, 3G1, 2C7, or 3D6, or any of the humanized mAb001). In an embodiment, the ADC comprises a light chain variable region of an antibody molecule described in Table 1 or 3 (e.g., mAb001, A001-25, hWN01, hWNv1, 3E7, 3G1, 2C7, or 3D6, or any of the humanized mAb001). In an embodiment, the ADC comprises a heavy chain variable region and a light chain variable region of an antibody molecule described in Table 1 or 3 (e.g., mAb001, A001-25, hWN01, hWNv1, 3E7, 3G1, 2C7, or 3D6, or any of the humanized mAb001).

In an embodiment, the ADC comprises a heavy chain variable region having an amino acid sequence described in Table 1 or 3. In an embodiment, the ADC comprises a light chain variable region having an amino acid sequence described in Table 1 or 3. In an embodiment, the ADC comprises a heavy chain variable region having an amino acid sequence described in Table 2 and a light chain variable region having an amino acid sequence described in Table 1 or 3. In an embodiment, an antibody molecule or ADC as described herein comprises one or more (e.g., 1, 2, or 3) conservative substitutions of VL residue R100 and/or VH residues R101 and/or R103. In an embodiment, one or more of the conservative substitutions comprises a mutation to a positively charged amino acid other than arginine (e.g., lysine or histidine). In an embodiment, the antibody molecule or ADC comprises a conservative substitution of VL residue R100 (e.g., a mutation to a positively charged amino acid other than arginine, e.g., lysine or histidine). In an embodiment, the antibody molecule or ADC comprises a conservative substitution of VH residue R101 (e.g., a mutation to a positively charged amino acid other than arginine, e.g., lysine or histidine). In an embodiment, the antibody molecule or ADC comprises a conservative substitution of VH residue R103 (e.g., a mutation to a positively charged amino acid other than arginine, e.g., lysine or histidine).

In an embodiment, the antibody molecule comprises a heavy chain variable region encoded by a nucleotide sequence described in Table 2. In an embodiment, the antibody molecule comprises a light chain variable region encoded by a nucleotide sequence described in Table 2. In an embodiment, the antibody molecule comprises a heavy chain variable region encoded by a nucleotide sequence described in Table 2 and a light chain variable region encoded by a nucleotide sequence described in Table 2.

In an embodiment, the ADC comprises a heavy chain constant region. In an embodiment, the ADC comprises a light chain constant region. In an embodiment, the ADC comprises a heavy chain constant region and a light chain constant region. In an embodiment, the ADC comprises a heavy chain constant region, a light chain constant region, and heavy and light chain variable regions of an antibody molecule described in Table 1 or 3. In an embodiment, the ADC comprises a heavy chain constant region, a light chain constant region, and variable regions that comprise one, two, three, four, five, or six CDRs of antibody molecule described in Table 1 or 3.

In an embodiment, the ADC is capable of binding to two or more Gram-negative bacteria of different genera, species, subspecies, and/or strains. Antibody molecules or ADCs capable of binding to two or more Gram-negative bacteria of different genera, species, subspecies, and/or strains have several advantageous properties. For example, one therapy can be used to treat, prevent, or diagnose multiple bacterial infections. In addition, a physician need not determine which bacterial genus, species, subspecies and/or strain infected a patient in order to determine the appropriate therapy. Accordingly, in an embodiment, the ADC is capable of independently binding to 2, 3, 4, 5, 6, 7, 8, 9, 10, or more Gram-negative bacteria of different genera, species, subspecies, and/or strains, with high affinity. For instance, the antibody molecule may independently bind with high affinity to one or more bacteria of different species, subspecies, and/or strains from Enterobacteriaceae (e.g., *Klebsiella, Enterobacter, Shigella, Escherichia, Salmonella, Yersinia,* or *Citrobacter*, e.g., pan-resistant Enterobacteriaceae), one or more bacteria of different species, subspecies, and/or strains from *Pseudomonas*, one or more bacteria of different species, subspecies, and/or strains from *Acinetobacter*, or any combination thereof. In an embodiment, the ADC is capable of binding to *Klebsiella pneumonia* (e.g., *Klebsiella pneumoniae* subsp. *ozaenae, Klebsiella pneumoniae* subsp. *pneumoniae*, or *Klebsiella pneumoniae* subsp. *rhinoscleromatis*), *Enterobacter cancerogenous, Enterobacter cloacae, Enterobacter hormaechei, Enterobacter asburiae, Shigella boydii, Shigella dysenteriae, Shigella flexneri, Shigella sonnei, Escherichia coli* (e.g., *Escherichia coli* ATCC 11775, *Escherichia coli* ATCC 25922, *Escherichia coli* ATCC 35401, or *Escherichia coli* ATCC 43895), *Escherichia fergusonii, Salmonella choleraesuis, Salmonella choleraesuis* subsp. *indica, Salmonella enteritidis, Salmonella virchow, Salmonella paratyphi* B, *Salmonella typhimurium, Salmonella paratyphi* A, *Salmonella typhi, Salmonella choleraesuis* subsp. *arizonae, Salmonella choleraesuis* subsp. *diarizonae, Salmonella choleraesuis* subsp. *houtenae, Salmonella bongori, Citrobacter sedlakii, Citrobacter braakii, Citrobacter werkmanii, Citrobacter freundii, Citrobacter youngae, Citrobacter amalonaticus, Yersinia enterocolitica, Yersinia frederiksenii, Yersinia pestis, Yersinia pseudotuberculosis,* or any combination thereof.

In an embodiment, the ADC is capable of binding to one or more of: *Enterococcus faecium* (e.g., vancomycin-resistant (VRE) *Enterococcus faecium*), *Staphylococcus aureus* (e.g., methicillin-resistant (MRSA) *Staphylococcus aureus*), *Clostridium difficile, Acinetobacter baumannii* (e.g., multidrug resistant (MDR) *Acinetobacter*), *Pseudomonas aeruginosa* (e.g., multidrug resistant (MDR) *P. aeruginosa*, e.g., carbapenem-resistant *P. aeruginosa*), Enterobacteriaceae (e.g., *E. coli, K. pneumoniae,* or *Enterobacter* spp., e.g., carbapenem-resistant Enterobacteriaceae (CRE)), *N. gonorrhoaeae* (e.g., drug-resistant *N. gonorrhoaeae*), *Salmonella* (e.g., drug resistant *Salmonella*), *Shigella* (e.g., drug-resistant *Shigella*), a bacterium producing an extended spectrum β-lactamase (ESBL), or *Mycobacterium tuberculosis* (e.g., drug-resistant *M. tuberculosis*).

In an embodiment, the ADC is capable of binding to one or more (e.g., 2, 3, 4, 5, 6, 7, 8, 9, 10, or more) *P. aeruginosa* strains. In another embodiment, the ADC is capable of binding to one or more (e.g., 2, 3, 4, 5, 6, or more) multidrug-resistant *P. aeruginosa* strains.

In an embodiment, the ADC binds to a linear or conformational epitope on LPS. In another embodiment, the ADC binds to a core pentasaccharide region on LPS. In an embodiment, the ADC has an opsonophagocytic activity, e.g., as determined by an opsonophagocytosis assay described herein. In an embodiment, the ADC has an opsonophagocytic killing activity, e.g., at about 20 µg/mL of the ADC, e.g., in the presence of phagocytes.

In an embodiment, the ADC comprises an antimicrobial peptide, e.g., an antimicrobial peptide described herein, e.g., having an amino acid sequence disclosed in Table 4. In another embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence described in Table 4, or a portion thereof, e.g., a functional fragment thereof (e.g., one or more (e.g., two, three, four or more) of the N-terminal G residues are omitted). In an embodiment, the antimicrobial peptide comprises or consists of an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of any of SEQ ID NO: 67-80, 94-102, 147-156, 158-159, 163-164, or 246-258. In an embodiment, the ADC comprises one or more (e.g., two, three, four, five, six, seven, eight, or more) antimicrobial peptides, each of which has an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of any of SEQ ID NO: 67-80, 94-102, 147-156, 158-159, 163-164, or 246-258. In an embodiment, the ADC comprises four or more antimicrobial peptides, each of which has an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of any of SEQ ID NO: 67-80, 94-102, 147-156, 158-159, 163-164, or 246-258. In an embodiment, the ADC comprises four or more antimicrobial peptides, each of which comprises or consists of the amino acid sequence of any of SEQ ID NO: 67-80, 94-102, 147-156, 158-159, 163-164, or 246-258. In an embodiment, the antimicrobial peptide comprises a carboxamide group (e.g., a C-terminal carboxamide functional group).

In an embodiment, the antimicrobial peptide comprises one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38. 39, 40, or more) D-amino acids. In an embodiment, at least 10%, 20%, 30%, 40%, 50%, 60%, 70%, 80%, 90%, or 100% of the amino acid residues in the antimicrobial peptide are D-amino acids. In an embodiment, all of the amino acid residues in the antimicrobial peptide are D-amino acids.

In an embodiment, the antimicrobial peptide comprises one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38. 39, 40, or more) L-amino acids. In an embodiment, at least 10%, 20%, 30%, 40%, 50%, 60%, 70%, 80%, 90%, or 100% of the amino acid residues in the antimicrobial peptide are L-amino acids. In an embodiment, all of the amino acid residues in the antimicrobial peptide are L-amino acids.

In an embodiment, the antimicrobial peptide comprises one or more D-amino acids and one or more L-amino acids.

In an embodiment, the ADC is capable of inhibiting and/or reducing the viability of 2, 3, 4, 5, 6, 7, 8, 9, 10, or more bacteria (e.g., Gram-negative bacteria) of different genera, species, subspecies, and/or strains. For instance, the antibody molecule may inhibit and/or reduce the viability of one or more bacteria of different species, subspecies, and/or strains from Enterobacteriaceae (e.g., *Klebsiella, Enterobacter, Shigella, Escherichia, Salmonella, Yersinia,* or *Citrobacter*, e.g., pan-resistant Enterobacteriaceae), one or more bacteria of different species, subspecies, and/or strains from *Pseudomonas*, one or more bacteria of different species, subspecies, and/or strains from *Acinetobacter*, or any combination thereof. In an embodiment, the ADC is capable of inhibiting or reducing the viability of *Klebsiella pneumonia* (e.g., *Klebsiella pneumoniae* subsp. *ozaenae*, *Klebsiella pneumoniae* subsp. *pneumoniae*, or *Klebsiella pneumoniae* subsp. *rhinoscleromatis*), *Enterobacter cancerogenous, Enterobacter cloacae, Enterobacter hormaechei, Enterobacter asburiae, Shigella boydii, Shigella dysenteriae, Shigella flexneri, Shigella sonnei, Escherichia coli* (e.g., *Escherichia coli* ATCC 11775, *Escherichia coli* ATCC 25922, *Escherichia coli* ATCC 35401, or *Escherichia coli* ATCC 43895), *Escherichia fergusonii, Salmonella choleraesuis, Salmonella choleraesuis* subsp. *indica, Salmonella enteritidis, Salmonella virchow, Salmonella paratyphi* B, *Salmonella typhimurium, Salmonella paratyphi* A, *Salmonella typhi, Salmonella choleraesuis* subsp. *arizonae, Salmonella choleraesuis* subsp. *diarizonae, Salmonella choleraesuis* subsp. *houtenae, Salmonella bongori, Citrobacter sedlakii, Citrobacter braakii, Citrobacter werkmanii, Citrobacter freundii, Citrobacter youngae, Citrobacter amalonaticus, Yersinia enterocolitica, Yersinia frederiksenii, Yersinia pestis, Yersinia pseudotuberculosis,* or any combination thereof.

In an embodiment, the ADC is capable of inhibiting or reducing the viability of one or more of: *Enterococcus faecium* (e.g., vancomycin-resistant (VRE) *Enterococcus faecium*), *Staphylococcus aureus* (e.g., methicillin-resistant (MRSA) *Staphylococcus aureus*), *Clostridium difficile, Acinetobacter baumannii* (e.g., multidrug resistant (MDR) *Acinetobacter*), *Pseudomonas aeruginosa* (e.g., multidrug resistant (MDR) *P. aeruginosa*, e.g., carbapenem-resistant *P. aeruginosa*), Enterobacteriaceae (e.g., *E. coli, K. pneumoniae,* or *Enterobacter* spp., e.g., carbapenem-resistant Enterobacteriaceae (CRE)), *N. gonorrhoaeae* (e.g., drug-resistant *N. gonorrhoaeae*), *Salmonella* (e.g., drug resistant *Salmonella*), *Shigella* (e.g., drug-resistant *Shigella*), a bacterium producing an extended spectrum β-lactamase (ESBL), or *Mycobacterium tuberculosis* (e.g., drug-resistant *M. tuberculosis*).

In an embodiment, the ADC is capable of binding to one or more (e.g., 2, 3, 4, 5, 6, 7, 8, 9, 10, or more) *P. aeruginosa* strains. In another embodiment, the ADC is capable of binding to one or more (e.g., 2, 3, 4, 5, 6, or more) multidrug-resistant *P. aeruginosa* strains.

While not wishing to be bound by theory, the antimicrobial peptides suitable for the ADCs described herein can be selected, at least in part, based on one or more (e.g., two, three or all) of the following properties: strong bacterial inhibition activity, strong bactericidal activity, low red blood cell (RBC) hemolytic activity, or low cytotoxicity (e.g., off-target toxicity). In an embodiment, the antimicrobial peptide has a minimum inhibitory concentration (MIC) of less than 100 μg/ml, e.g., less than 90, 80, 70, 60, 50, 40, 30, 20, 10, or 5 μg/ml, against a bacterial strain described herein, e.g., *Escherichia coli* ATCC 25922, *Pseudomonas aeruginosa* ATCC27853, or both. In an embodiment, the antimicrobial peptide has a minimum bactericidal concentration (MBC) of less than 100 μg/ml, e.g., less than 90, 80, 70, 60, 50, 40, 30, 20, 10, or 5 μg/ml, against a bacterial strain described herein, e.g., *Escherichia coli* ATCC 25922, *Pseudomonas aeruginosa* ATCC27853, or both. In an embodiment, the antimicrobial peptide has low hemolytic activity, e.g., has a PLC to MIC ratio for a Gram-negative bacterium (e.g., a Gram-negative bacterium described herein) which is equal to or greater than 1 (e.g., greater than 4:1, 8:1, 16:1, 24:1, or 32:1), e.g., as determined by a red blood cell hemolysis assay and an MIC assay, respectively. In an embodiment, the PLC is the concentration (e.g., minimum concentration) required or needed to lyse 50% of the red blood cells. In an embodiment, the antimicrobial peptide has low hemolytic activity, e.g., has an MLC to MIC ratio for a Gram-negative bacterium (e.g., a Gram-negative bacterium described herein) which is greater than 4:1 (e.g., greater than 8:1, 16:1, 24:1, or 32:1), e.g., as determined by a red blood cell hemolysis assay and an MIC assay, respectively. In an embodiment, the MLC is the concentration (e.g., minimum concentration) required or needed to lyse 100% of the red blood cells.

In an embodiment, the antimicrobial peptide is an α-helical peptide. In an embodiment, the antimicrobial peptide has two or more amino acid residues cross-linked. For example, two cysteine residues in the antimicrobial peptide can be cross-linked, e.g., chemically cross-linked. While not wishing to be bound by theory, it is believed that in an embodiment, cross-linking two or more amino acid residues in an antimicrobial peptide may enhance α-helical conformation, enhance serum stability, and/or increase antimicrobial potency. In an embodiment, the antimicrobial peptide having two or more amino acid residues cross-linked is at least 2, 3, 4, 5, 6, 7, 8, 9, or 10-fold more stable, e.g., in serum, than an otherwise identical antimicrobial peptide that does not have two or more amino acid residues cross-linked. In an embodiment, the antimicrobial peptide having two or more amino acid residues cross-linked has a MIC that is at least 10%, 20%, 30%, 40%, 50%, 60%, 70%, 80%, 90%, 95%, 98%, or 99% lower than an otherwise identical antimicrobial peptide that does not have two or more amino acid residues cross-linked.

In an embodiment, the ADC is produced by enzymatic synthesis. For example, ADCs can be produced by expression of an antibody molecule (e.g., a tagged antibody molecule), chemical synthesis of a peptide (e.g., an antimicrobial peptide), and enzymatic ligation of the peptide to the antibody molecule. In an embodiment, 90% or more, e.g., 92% or more, 95% or more, 97% or more, or 99% or more, reaction efficiency is achieved. In another embodiment, the method further comprises purifying the ADC. In an embodiment, the yield is 60% or more (e.g., 70% or more, 75% or more, 80% or more, 90% or more, or 95% or more) after purification.

In an embodiment, the ADC binds to a bacterial surface. In another embodiment, the ADC binds to a secreted vesicle. In yet another embodiment, the ADC binds to both a bacterial surface and a secreted vesicle. In an embodiment, the binding is detected by electron microscopy. In an embodiment, the ADC has enhanced binding to bacteria from a first genus, species, or subspecies, compared to binding to bacteria from a second genus, species, or subspecies. In an embodiment, the ADC has enhanced binding to *P. aeruginosa*, compared to binding to bacteria other than *P. aeruginosa* (e.g., *E. coli* or *Klebsiella* spp.).

In an embodiment, the ADC comprising: a) an antibody molecule that binds to lipopolysaccharide (LPS); and b) an antimicrobial peptide, wherein the antibody molecule comprises a VH and a VL, wherein the VH comprises three heavy chain complementarity determining regions (HCDR1, HCDR2, and HCDR3), and the VL comprises three light chain complementarity determining regions (LCDR1, LCDR2, and LCDR3), and wherein the ADC or antibody molecule comprises:

(a) an HCDR1 comprising the amino acid sequence of SEQ ID NO: 108; an HCDR2 comprising the amino acid sequence of any of SEQ ID NOS: 109, 145, or 146; an HCDR3 comprising the amino acid sequence of SEQ ID NO: 107; an LCDR1 comprising the amino acid sequence of any of SEQ ID NOS: 110, 138, 140, or 144; an LCDR2 comprising the amino acid sequence of any of SEQ ID NOS: 111, 139, 141, 142, or 143; and an LCDR3 comprising the amino acid sequence of any of SEQ ID NO: 112, or (b) an HCDR1 comprising the amino acid sequence of SEQ ID NO: 105; an HCDR2 comprising the amino acid sequence of SEQ ID NO: 106; an HCDR3 comprising the amino acid sequence of SEQ ID NO: 107; an LCDR1 comprising the amino acid sequence of any of SEQ ID NOS: 110, 138, 140, or 144; an LCDR2 comprising the amino acid sequence of any of SEQ ID NOS: 111, 139, 141, 142, or 143; and an LCDR3 comprising the amino acid sequence of any of SEQ ID NO: 112; and wherein the antimicrobial peptide comprises or consists of:

(i) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 101;

(ii) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 147;

(iii) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 152;

(iv) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 153;

(v) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 154;

(vi) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 156;

(vii) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 163;

(viii) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 164;

(ix) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 246;

(x) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 247;

(xi) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 248;

(xii) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 249;

(xiii) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 250;

(xiv) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 251;

(xv) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 252;

(xvi) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 253;

(xvii) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 254;

(xviii) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 255;

(xix) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 256;

(xx) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 257; or (xxi) an amino acid sequence that differs by no more than 1, 2, 3, 4, 5, 6, 7, 8, 9, or 10 amino acid residues from, or has at least 80%, 85%, 90%, 95%, 97%, or 100% homology with, the amino acid sequence of SEQ ID NO: 258.

In an embodiment, the ADC comprises (a) and (i). In an embodiment, the ADC comprises (a) and (ii). In an embodiment, the ADC comprises (a) and (iii). In an embodiment, the ADC comprises (a) and (iv). In an embodiment, the ADC comprises (a) and (v). In an embodiment, the ADC comprises (a) and (vi). In an embodiment, the ADC comprises (a) and (vii). In an embodiment, the ADC comprises (a) and (viii). In an embodiment, the ADC comprises (a) and (ix). In an embodiment, the ADC comprises (a) and (x). In an embodiment, the ADC comprises (a) and (xi). In an embodiment, the ADC comprises (a) and (xii). In an embodiment, the ADC comprises (a) and (xiii). In an embodiment, the ADC comprises (a) and (xiv). In an embodiment, the ADC comprises (a) and (xv). In an embodiment, the ADC comprises (a) and (xvi). In an embodiment, the ADC comprises (a) and (xvii). In an embodiment, the ADC comprises (a) and (xviii). In an embodiment, the ADC comprises (a) and (xix). In an embodiment, the ADC comprises (a) and (xviii). In an embodiment, the ADC comprises (a) and (xx). In an embodiment, the ADC comprises (a) and (xviii). In an embodiment, the ADC comprises (a) and (xxi).

In an embodiment, the ADC comprises (b) and (i). In an embodiment, the ADC comprises (b) and (ii). In an embodiment, the ADC comprises (b) and (iii). In an embodiment, the ADC comprises (b) and (iv). In an embodiment, the ADC comprises (b) and (v). In an embodiment, the ADC comprises (b) and (vi). In an embodiment, the ADC comprises (b) and (vii). In an embodiment, the ADC comprises (b) and (viii). In an embodiment, the ADC comprises (b) and (ix). In an embodiment, the ADC comprises (b) and (x). In an embodiment, the ADC comprises (b) and (xi). In an embodiment, the ADC comprises (b) and (xii). In an embodiment, the ADC comprises (b) and (xiii). In an embodiment, the ADC comprises (b) and (xiv). In an embodiment, the ADC comprises (b) and (xv). In an embodiment, the ADC comprises (b) and (xvi). In an embodiment, the ADC comprises (b) and (xvii). In an embodiment, the ADC comprises (b) and (xviii). In an embodiment, the ADC comprises (b) and (xix). In an embodiment, the ADC comprises (a) and (xviii). In an embodiment, the ADC comprises (a) and (xx). In an embodiment, the ADC comprises (a) and (xviii). In an embodiment, the ADC comprises (b) and (xxi).

Site-Specific Conjugation

The ADCs described herein can be made by site-specific conjugation methods. Without wishing to be bound by theory, it is believed that in an embodiment, site-specific conjugation can offer certain advantages over conventional conjugation chemistries used to make ADCs. For example, site-specific conjugation, including, e.g., site-specific payload placement, allows for control over the drug-to-antibody ratio and the conjugation site, which can affect the properties of an ADC, e.g., pharmacokinetics (PK), disposition, or efficacy of the ADC. In addition, the linker composition used in site-specific conjugation can also affect the properties of an ADC.

Site-specific conjugation methods for making ADCs can produce homogeneous products, e.g., with controlled drug loading, simplified analytics, and an improved therapeutic index. Typically, these methods introduce reactive amino acids at defined locations on the antibody backbone and use the unique chemical or enzymatic reactivity of these amino acids to conjugate payloads (as described, e.g., in Junutula et al. *Nat Biotechnol.* 2008; 26(8):925-32; Strop et al. *Chem Biol.* 2013; 20(2):161-7; Axup et al. *Proc Natl Acad Sci USA.* 2012; 109(40):16101-6; Kung Sutherland et al. *Blood.* 2013; I22(8):1455-63).

Exemplary site-specific conjugation methods are also described, e.g., in Drake et al. *Bioconjug Chem.* 2014; 25(7):1331-41, U.S. Pat. No. 9,238,878, and International Publication No. WO 2010/096394, the contents of all of which are incorporated by reference herein. For example, a chemoenzymatic approach to the site-selective modification of proteins can use the naturally-occurring formylglycine-generating enzyme (FGE) to introduce a formylglycine (fGly) residue into a protein backbone. Linkers can be designed to selectively react with the aldehyde side chain of fGly to form a stable C—C bond with the protein. Without wishing to be bound by theory, it is believed that in an embodiment, the methods described herein can generate site-specifically conjugated ADCs, e.g., with controlled stoichiometry and clean analytics, which allows for the design of ADCs with desired efficacy and reduced toxicity.

As described herein, in an embodiment, site-specific ADC production is based upon the incorporation of formylglycine (fGly), a non-natural amino acid, into the antibody sequence. For example, to incorporate fGly, a short consensus sequence (e.g., CXPXR, where X is typically serine, threonine, alanine, or glycine), can be inserted at a desired location, e.g., in a conserved region, of an antibody heavy or light chain, using standard molecular biology cloning techniques (Rabuka et al. *Nat Protoc.* 2012; 7(6):1052-67). The consensus sequence can be inserted at a variety locations of the antibody molecule, e.g., in a heavy chain (e.g., in CH1, CH2, or CH3, or at C-terminus), in a light chain (e.g., in the constant region or at C-terminus), or both. A plurality of consensus sequences (e.g., 2, 3, 4, 5, 6, 7, 8, or more identical, similar or different consensus sequences) can be inserted into the antibody molecule.

The tagged antibody molecule can be produced recombinantly in cells that co-express the formylglycine-generating enzyme (FGE). The FGE can co-translationally convert the cysteine within the tag into an fGly residue, resulting in an antibody molecule expressed with an aldehyde tag (Carison et al. *J Biol Chem.* 2008; 283(29):20117-25). The aldehyde functional group in the tag can serve as a chemical handle for bioorthogonal conjugation (Sletten et al. *Angew Chem Int Ed Engl.* 2009; 48(38):6974-98). In an embodiment, Hydrazino-iso-Pictet-Spengler (HIPS) ligation is used to connect the payload to fGly, forming a stable, covalent C—C bond between the drug payload (e.g., an antimicrobial peptide) and the antibody molecule (Agarwal et al. *Bioconjug Chem.* 2013; 24(6):846-51). This C—C bond is typically stable to physiologically relevant challenges encountered by the ADC, e.g., during circulation and FcRn recycling (e.g., proteases, low pH, or reducing reagents). An exemplary conjugation method and related chemistry is described in FIG. 26 of PCT Publication No. WO 2018/136626 (incorporated herein by reference in its entirety).

The disclosure herein provides an ADC comprising an anti-LPS antibody molecule (e.g., an antibody molecule described herein) and a covalently coupled antimicrobial peptide (e.g., an antimicrobial peptide described herein), wherein the antibody molecule comprises a modified sulfatase motif. The disclosure also provides an aldehyde-tagged antibody molecule that can be covalently and site-specifically coupled to an antimicrobial peptide to provide a drug-containing scaffold. The ADCs described herein can be used to treat or prevent a bacterial infection (e.g., an infection associated with a Gram-negative bacterium, e.g., *Pseudomonas aeruginosa*) or a related disorder in accordance with a method described herein. Also described herein are methods of producing the ADCs or aldehyde-tagged antibody molecules described herein.

Aldehyde Tags

Typically, an aldehyde tag can be based on any amino acid sequence derived from a sulfatase motif, which is capable of being converted by a formylglycine generating enzyme (FGE) to contain a formylglycine (FGly). Without wishing to be bound by theory, it is believed that in an embodiment, the action of FGE is directed in a sequence-specific manner, e.g., the FGE acts at a sulfatase motif and this sulfatase motif can be positioned within any region of an antibody molecule. In an embodiment, FGE-mediated conversion of a sulfatase motif is site-specific, e.g., the FGE acts at the amino acid sequence of a sulfatase motif. In another embodiment, the ability of FGE to act upon the sulfatase motif is sequence context-independent, e.g., the ability of the FGE to convert a cysteine/serine of a sulfatase motif is independent of the sequence context in which the sulfatase motif is presented in the antibody molecule.

A minimal sulfatase motif of an aldehyde tag is typically no more than 6 amino acid residues in length, typically about 5 or 6 amino acid residues in length. Aldehyde tags can comprise a minimal sulfatase motif of 5 or 6 residues, or can be longer and comprise a minimal sulfatase motif which can be flanked at the N- and/or C-terminal sides of the motif by one or more additional amino acid residues. Aldehyde tags of, for example, 5 or 6 amino acid residues can be used, as well as longer amino acid sequences of more than 5, 6, 7, 8, 9, 10, 11, 12, 13, 14, 15, 16, 17, 18, 19, 20 or more amino acid residues.

Without wishing to be bound by theory, it is believed that in an embodiment, it is desirable to minimize the extent of modification of the native amino acid sequence of an antibody molecule, by minimizing the number of amino acid residues that are inserted, deleted, substituted (replaced), or added (e.g., to the N- or C-terminus). In an embodiment, the aldehyde tag requires modification (insertion, addition, deletion, substitution/replacement) of less than 16, 15, 14, 13, 12, 11, 10, 9, 8, or 7 amino acid residues of the amino acid sequence of the antibody molecule.

In an embodiment, a sulfatase motif useful in aldehyde tags as described herein has the formula:

$$X_1Z_1X_2Z_2X_3Z_3 \quad (I)$$

where $Z_1$ is cysteine or serine (which can also be represented by (C/S));

$Z_2$ is either a proline or alanine residue (which can also be represented by (P/A));

$Z_3$ is a basic amino acid, and may be arginine (R), lysine (K) or histidine (H), usually lysine), or an aliphatic amino acid (alanine (A), glycine (G), leucine (L), valine (V), isoleucine (I), or proline (P), usually A, G, L, V, or I;

$X_1$ is present or absent and, when present, can be any amino acid, though usually an aliphatic amino acid, a sulfur-containing amino acid, or a polar, uncharged amino acid, (e.g., other than an aromatic amino acid or a charged amino acid), usually L, M, V, S or T, more usually L, M, S or V, with the proviso that when the sulfatase motif is at the N-terminus of an antibody chain, $X_1$ is present; and $X_2$ and $X_3$ independently can be any amino acid, though usually an aliphatic amino acid, a polar, uncharged amino acid, or a sulfur containing amino acid (e.g., other than an aromatic amino acid or a charged amino acid), usually S, T, A, V, G or C, more usually S, T, A, V or G.

In an embodiment, the sulfatase motif has the formula:

$$X_1Z_1X_2Z_2X_3R \quad (Ia).$$

Typically, following action of an FGE on the sulfatase motif, $Z_1$ is oxidized to generate a 2-formylglycine (FGly) residue. Following both FGE-mediated conversion and reaction with a reactive partner of an antimicrobial peptide, FGly position at $Z_1$ in the formula above is covalently bound to the antimicrobial peptide. In an embodiment, the reactive partner is an α-nucleophile, e.g., an aminooxy or hydrazide group, and provides for linkage of the antibody molecule to the antimicrobial peptide, e.g., through an oxime or hydrazone linkage. In an embodiment, the antibody molecule and antimicrobial peptide are not linked through an amide bond, as may be found in other drug conjugates based on recombinant fusion protein technology.

In an embodiment, the aldehyde tag is present at a location other than the N-terminus of an antibody chain, and $X_1$ of the formula above is provided by an amino acid residue of the native amino acid sequence of the antibody molecule. In an embodiment, when present at a location other than the N-terminus of an antibody molecule chain, the sulfatase motif has the formula:

$$(C/S)X_1(P/A)X_2Z_3 \quad (II)$$

where $X_1$ and $X_2$ is independently any amino acid, though typically an aliphatic amino acid, a polar, uncharged amino acid, or a sulfur-containing amino acid (e.g., other than an aromatic amino acid or a charged amino acid), typically S, T, A, V, or C, more typically S, T, A, or V. $Z_3$ in Formula II is defined as above.

In an embodiment, the sulfatase motif has the formula:

$$(C/S)X_1(P/A)X_2R \quad (IIa)$$

The sulfatase motif can contain additional residues at one or both of the N- and C-terminus of the sequence, e.g., such that the aldehyde tag includes both a sulfatase motif and an "auxiliary motif". In one embodiment, the sulfatase motif includes an optional auxiliary motif at the C-terminus (e.g., following the arginine residue in the formula above) 1, 2, 3, 4, 5, 6, or all 7 of the contiguous residues of an amino acid sequence of AALLTGR (SEQ ID NO: 170), SQLLTGR (SEQ ID NO: 171), AAFMTGR (SEQ ID NO: 172), AAFLTGR (SEQ ID NO: 173), SAFLTGR (SEQ ID NO: 174), ASILTGK (SEQ ID NO: 175), VSFLTGR (SEQ ID NO: 176), ASLLTGL (SEQ ID NO: 177), ASILITG (SEQ ID NO: 178), VSFLTGR (SEQ ID NO: 176), SAIMTGR (SEQ ID NO: 179), SAIVTGR (SEQ ID NO: 180), TNLWRG (SEQ ID NO: 181), TNLWRGQ (SEQ ID NO: 182), TNLCAAS (SEQ ID NO: 183), VSLWTGK (SEQ ID NO: 184), SMLLTG (SEQ ID NO: 185), SMLLTGN (SEQ ID NO: 186), SMLLTGT (SEQ ID NO: 187), ASFMAGQ (SEQ ID NO: 188), or ASLLTGL (SEQ ID NO: 177) (see, e.g., Dierks et al. (1999) EMBO J 18(8): 2084-2091), or of GSLFTGR (SEQ ID NO: 189). In an embodiment, the aldehyde tag does not contain an amino acid sequence CGPSR(M/A)S (SEQ ID NO: 190) or CGPSR(M/A) (SEQ ID NO: 191), which may be present as a native amino acid sequence in phosphonate monoester hydrolases.

The sulfatase motif of the aldehyde tag is typically selected to be capable of conversion by a selected FGE. In an embodiment, the FGE is present in a host cell in which the aldehyde tagged antibody molecule is expressed. In another embodiment, the FGE is contacted with the aldehyde tagged antibody molecule in a cell-free method.

Typically, sulfatase motifs susceptible to conversion by a eukaryotic FGE contain a cysteine and a proline (e.g., a cysteine and proline at $Z_1$ and $Z_2$, respectively, in Formula I above (e.g., X1CX2PX3R); CX1PX2R in Formula II above) and are modified by the "SUMF1-type" FGE (as described, e.g., in Cosma et al. *Cell* 2003, 113, (4), 445-56; Dierks et al. *Cell* 2003, 113, (4), 435-44). Sulfatase motifs susceptible to conversion by a prokaryotic FGE contain either a cysteine or a serine, and a proline in the sulfatase motif (e.g., a cysteine or serine at $Z_1$, and a proline at $Z_2$, respectively, in Formula I above (e.g., X1(C/S)X2PX3R); (C/S)X1PX2R in Formula II above) are modified either by the "SUMF1-type" FGE or the "AtsB-type" FGE, respectively (as described e.g., in Szameit et al. *J Biol Chem* 1999, 274, (22), 15375-81). Other sulfatase motifs susceptible to conversion by a prokaryotic FGE contain either a cysteine or a serine, and either a proline or an alanine in the sulfatase motif (e.g., a cysteine or serine at $Z_1$, and a proline or alanine at $Z_2$, respectively, e.g., $SX_1AX_2R$; $X_1CX_2PX_3Z_3$; $X_1SX_2PX_2Z_3$; $X_1CX_2AX_3Z_3$; $X_1SX_2AX_3Z_3$; $CX_1PX_2Z_3$; $SX_1PX_2Z_3$; $CX_1AX_2Z_3$; $SX_1AX_2Z_3$ (in Formula I above); $CX_1PX_2Z_3$ (in Formula II above); $X_1CX_2PX_3R$; $X_1SX_2PX_2R$; $X_1CX_2AX_3R$; $X_1SX_2AX_3R$ (in Formula Ia above); $CX_1PX_2R$; $SX_1PX_2R$; $CX_1AX_2R$; $SX_1AX_2R$ (in Formula IIa above), and are susceptible to modification by, for example, can be modified by an FGE of a Firmicutes (e.g., *Clostridium perfringens*), as described, e.g., in Berteau et al. *J. Biol. Chem.* 2006; 281:22464-22470).

In an embodiment, the FGE is a eukaryotic FGE (e.g., a mammalian FGE, e.g., a human FGE) and the sulfatase motif has the formula:

$$X_1CX_2PX_3Z_3 \qquad (III)$$

where
$X_1$ is present or absent and, when present, is any amino acid, though typically an aliphatic amino acid, a sulfur-containing amino acid, or a polar, uncharged amino acid (e.g., other than an aromatic amino acid or a charged amino acid), typically L, M, S or V, with the proviso that when the sulfatase motif is at the N-terminus of an antibody molecule chain, $X_1$ is present;

$X_2$ and $X_3$ is independently any amino acid, though typically an aliphatic amino acid, a sulfur-containing amino acid, or a polar, uncharged amino acid, (e.g., other than an aromatic amino acid or a charged amino acid), typically S, T, A, V, G, or C, more usually S, T, A, V or G; and $Z_3$ is a basic amino acid (which may be other than arginine (R), and may be lysine (K) or histidine (H), usually lysine), or an aliphatic amino acid (alanine (A), glycine (G), leucine (L), valine (V), isoleucine (I), or proline (P), usually A, G, L, V, or I, where $Z_3$ is arginine (R) in Formula IIIa.

In an embodiment, the sulfatase motif has the formula $$X_1CX_2PX3R \qquad (IIIa).$$

For example, exemplary sulfatase motifs include, but are not limited to, LCTPSR (SEQ ID NO: 169), MCTPSR (SEQ ID NO: 192), VCTPSR (SEQ ID NO: 193), LCSPSR (SEQ ID NO: 194), LCAPSR (SEQ ID NO: 195), LCVPSR (SEQ ID NO: 196), LCGPSR (SEQ ID NO: 197), ICTPAR (SEQ ID NO: 198), LCTPSK (SEQ ID NO: 199), MCTPSK (SEQ ID NO: 200), VCTPSK (SEQ ID NO: 201), LCSPSK (SEQ ID NO: 202), LCAPSK (SEQ ID NO: 203), LCVPSK (SEQ ID NO: 204), LCGPSK (SEQ ID NO: 205), LCTPSA (SEQ ID NO: 206), ICTPAA (SEQ ID NO: 207), MCTPSA (SEQ ID NO: 208), VCTPSA (SEQ ID NO: 209), LCSPSA (SEQ ID NO: 210), LCAPSA (SEQ ID NO: 211), LCVPSA (SEQ ID NO: 212), and LCGPSA (SEQ ID NO: 213).

As described in more detail below, a converted aldehyde tagged antibody molecule is reacted with a reactive partner of a moiety of interest to provide for conjugation between the moiety of interest to the FGly residue of the converted aldehyde tagged antibody molecule, and production of a modified polypeptide (e.g., an ADC described herein). Modified antibody molecules having a modified aldehyde tag are typically described by comprising a modified sulfatase having the formula:

$$X_1(FGly')X_2Z_2X_3Z_3 \qquad (I')$$

where
FGly' is a formylglycine residue having a covalently attached moiety (e.g., an antimicrobial peptide described herein);

$Z_2$ is either a proline or alanine residue (which can also be represented by (P/A));

$Z_3$ in Formula I' is a basic amino acid, and may be arginine (R) (as in Formula Ia'), lysine (K) or histidine (H), usually lysine), or an aliphatic amino acid (alanine (A), glycine (G), leucine (L), valine (V), isoleucine (I), or proline (P), usually A, G, L, V, or I;

$X_1$ is present or absent and, when present, is any amino acid, though typically an aliphatic amino acid, a sulfur-containing amino acid, or a polar, uncharged amino acid (e.g., other than an aromatic amino acid or a charged amino acid), typically L, M, V, S or T, more typically L, M or V, with the proviso that when the sulfatase motif is at the N-terminus of an antibody chain, $X_1$ is present; and $X_2$ and $X_3$ is independently any amino acid, though typically an aliphatic amino acid, a sulfur-containing amino acid, or a polar, uncharged amino acid (e.g., other than an aromatic amino acid or a charged amino acid), typically S, T, A, V, G or C, more typically S, T, A, V or G.

In an embodiment, the modified sulfatase motif has the formula:

$$X_1(FGly')X_2Z_2X_3R \qquad (Ia')$$

Exemplary converted sulfatase motifs include, but are not limited to, L(FGly)TPSR (SEQ ID NO: 214), M(FGly)

TPSR (SEQ ID NO: 215), V(FGly)TPSR (SEQ ID NO: 216), L(FGly)SPSR (SEQ ID NO: 217), L(FGly)APSR (SEQ ID NO: 218), L(FGly)VPSR (SEQ ID NO: 219), L(FGly)GPSR (SEQ ID NO: 220), I(FGly)TPAR (SEQ ID NO: 221), L(FGly)TPSK (SEQ ID NO: 222), M(FGly) TPSK (SEQ ID NO: 223), V(FGly)TPSK (SEQ ID NO: 224), L(FGly)SPSK (SEQ ID NO: 225), L(FGly)APSK (SEQ ID NO: 226), L(FGly)VPSK (SEQ ID NO: 227), L(FGly)GPSK (SEQ ID NO: 228), L(FGly)TPSA (SEQ ID NO: 229), M(FGly)TPSA (SEQ ID NO: 230), V(FGly) TPSA (SEQ ID NO: 231), L(FGly)SPSA (SEQ ID NO: 232), L(FGly)APSA (SEQ ID NO: 233), L(FGly)VPSA (SEQ ID NO: 234), and L(FGly)GPSA (SEQ ID NO: 235).

Exemplary antibody molecules that are covalently coupled to antimicrobial peptide through reaction with the aldehyde of the FGly residue can include those having the amino acid sequences described above, but have the modified FGly (represented above by FGly') in lieu of the unmodified FGly.

Modification of Antibody Molecules to Contain an Aldehyde Tag

An aldehyde tag can be provided in an antibody molecule (e.g., an antibody heavy or light chain, or a fragment thereof) by insertion (e.g., to provide a 5 or 6 amino acid residue insertion within the native amino acid sequence) and/or by addition (e.g., at an N- or C-terminus of an antibody chain). An aldehyde tag can also be provided by complete or partial substitution of native amino acid residues of the antibody molecule with the contiguous amino acid sequence of an aldehyde tag. For example, a heterologous aldehyde tag of 5 or 6 amino acid residues can be provided in an antibody molecule by replacing 1, 2, 3, 4, 5, or 6 amino acid residues of the native amino acid sequence with the corresponding amino acid residues of the aldehyde tag.

Modification of an antibody molecule to include one or more aldehyde tags can be accomplished using recombinant molecular genetic techniques, e.g., to produce a nucleic acid encoding the desired aldehyde tagged polypeptide. Alternatively, an aldehyde tag can be added using non-recombinant techniques, e.g., using native chemical ligation or pseudo-native chemical ligation, e.g., to add an aldehyde tag to a C-terminus of the polypeptide (as described, e.g., in U.S. Pat. Nos. 6,184,344, 6,307,018, 6,451,543, and 6,570,040; and Rush et al. (Jan. 5, 2006) Org Lett. 8(1):131-4).

Aldehyde tags can be positioned at any suitable location within an antibody molecule. In an embodiment, the site of the aldehyde tag is accessible for conversion by an FGE and subsequent modification at the FGly, or can be rendered accessible (e.g., by denaturing the polypeptide). The antibody molecule can include a plurality of aldehyde tags, e.g., 2, 3, 4, 5, 6, 7, 8, or more aldehyde tags. In an embodiment, at least two (e.g., all) of the aldehyde tags of the plurality are identical. In another embodiment, at least one aldehyde tag of the plurality differs from another aldehyde tag of the plurality.

Antibody Molecules Containing Multiple Aldehyde Tags

A plurality of aldehyde tags can be positioned in the aldehyde-tagged antibody molecule, e.g., to distribute the tags over the surface of the antibody molecule.

In an embodiment, the aldehyde tags are spaced apart in the antibody molecule by amino acid residues native to the antibody molecule. In another embodiment, the aldehyde tags are spaced apart by a linker, where the linker has an amino acid sequence heterologous to the antibody molecule.

In an embodiment, the aldehyde tags are provided in the aldehyde-tagged antibody molecule as a concatemeric construct of 2, 3, 4, or more aldehyde tags, where the expression construct thus encodes for 2, 3, 4 or more sulfatase motifs in a contiguous sequence of the modified antibody molecule, wherein the sulfatase motifs are separated by a linker. For example, the linker can be selected to provide flexibility between the aldehyde tags, thus allowing for rotation of covalently-bound antimicrobial peptides, e.g., to enhance presentation of biologically active antimicrobial peptide on the ADC surface. Such linkers can also be used where the aldehyde tags are not provided as a concatamer, e.g., where an aldehyde tag is positioned at a C- or N-terminus of an antibody chain. Aldehyde tags, including those provided as concetemers, can be positioned at or near the C-terminus of an antibody chain, at or near the N-terminus of an antibody chain, and/or in one or more solvent-accessible loops of the antibody molecule.

Linkers can be selected, e.g., according to the aldehyde tag used, the number of aldehyde tags in the concatamer, the degree of flexibility desired, or a combination thereof. The length of the linker can vary, e.g., about 2-50, 3-25, 4-23, 5-20, 6-18, 7-16, 8-14, or 9-12 amino acids. Exemplary flexible linkers include, but are not limited to, glycine polymers $(G)_n$, glycine-serine polymers (including, e.g., $(GS)_n$, $(GSGGS)_n$, (SEQ ID NO: 236) and $(GGGS)_n$ (SEQ ID NO: 237), where n is an integer of at least one), glycine-alanine polymers, alanine-serine polymers, and other flexible linkers such as the tether for the shaker potassium channel. Glycine and glycine-serine polymers are of interest since both of these amino acids are relatively unstructured, and therefore may be able to serve as a neutral tether between components. Glycine polymers are of particular interest since glycine accesses significantly more phi-psi space than even alanine, and is much less restricted tan residues with longer side chains (see Scheraga, Rev. Computational Chem. 11173-142 (1992)). Exemplary flexible linkers include, but are not limited to, GGSGG (SEQ ID NO: 238), GSGSG (SEQ ID NO: 239), GSGGG (SEQ ID NO: 240), GGGSG (SEQ ID NO: 241), or GSSSG (SEQ ID NO: 242). Other linkers may be composed of non-amino acid linkages. Polyethylene glycol (PEG) repeats (e.g., $EG_2$, $EG_3$, $EG_4$, or $EG_6$) are of particular interest since PEG repeats have little non-specific binding to biomolecules.

Concatemeric aldehyde tag constructs containing a linker can be described by the general formula: $T_1$-$L_n$-$T_2$, where $T_1$ and $T_2$ are the same or different aldehyde tags as described herein (e.g., formulae I, Ia, I', Ia', II, IIIa, III, and IIIa), L is a linker peptide, and n is an integer of 1 or more, e.g., 2, 3, 4, 5, 6, 7, 8, or more. An exemplary amino acid sequence of a concatemeric aldehyde tag containing a linker is LCTPSRGGGGLCTPSR (SEQ ID NO: 243), where the cysteine (C) is modified to an FGly by action of an FGE, and can be reacted with a reactive partner-containing antimicrobial peptide to provide for covalently bound antimicrobial peptide as described herein.

The aldehyde tag(s) can be positioned in the antibody molecule to take into account its structure when folded (e.g., in a cell-free environment, usually a cell-free physiological environment), e.g., to provide the aldehyde tag at a solvent accessible site in the folded antibody molecule. The solvent accessible aldehyde tag can thus be accessed in the folded, unconverted aldehyde-tagged antibody molecule to be accessible to an FGE for conversion of the serine or cysteine to an FGly and/or to a reactive partner reagent for conjugation to an antimicrobial peptide. Where an aldehyde tag is positioned at a solvent accessible site, cell free FGE-mediated conversion and modification with a moiety by reaction with a reactive partner can be performed without the need to denature the protein. Solvent accessible sites can also include polypeptide regions that are exposed at an extracellular or intracellular cell surface when expressed in a host cell.

Accordingly, one or more aldehyde tags can be provided at sites independently selected from, for example, a solvent accessible N-terminus, a solvent accessible N-terminal region, a solvent accessible C-terminus, a solvent accessible C-terminal region, and/or a loop structure. In an embodiment, the aldehyde tag is positioned at a site other than the C-terminus of an antibody chain. In an embodiment, two or more aldehyde tags are located in a heavy chain, e.g., in one, two, or all of CH1, CH2, or CH3. In an embodiment, the light chain of the antibody molecule does not contain an aldehyde tag.

In an embodiment, an aldehyde tag site is located at a site which is post-translationally modified in the parent antibody molecule (e.g., a naturally-occurring site). For example, an aldehyde tag can be introduced at a site of glycosylation (e.g., N-glycosylation, O-glycosylation), phosphorylation, sulfation, ubiquitination, acylation, methylation, prenylation, hydroxylation, or carboxylation, in the native antibody molecule. In an embodiment, the site of post-translational modification is engineered (e.g., by recombinant techniques) and does not occur naturally in the antibody molecule.

In an embodiment, the aldehyde-tagged antibody molecule comprises an aldehyde-tagged Fc fragment. Exemplary aldehyde-tagged mouse IgG1 Fc fragments having single and multiple aldehyde tags, including exemplary aldehyde-tagged Fc fragments containing an aldehyde tag concatemer with two aldehyde tags separated by a linker, are described in U.S. Pat. No. 9,238,878.

Formylglycine Generating Enzymes (FGEs)

A formylglycine generating enzyme (FGE) is an enzyme that oxidizes cysteine or serine in a sulfatase motif to FGly. As used herein, FGEs include enzymes that convert a cysteine (C) to FGly in a sulfatase motif, and enzymes that convert serine (S) to FGly in a sulfatase motif (also known as Ats-B-like).

The FGE used to facilitate conversion of cysteine or serine to FGly in a sulfatase motif of an aldehyde tag of a polypeptide can be selected according to the sulfatase motif present in the aldehyde tag. The FGE can be native to the host cell in which the aldehyde tagged polypeptide is expressed, or the host cell can be genetically modified to express an appropriate FGE. Eukaryotic sulfatases generally contain a cysteine in their sulfatase motif and are modified by the "SUMF1-type" FGE (Cosma et al. *Cell* 2003, 113, (4), 445-56; Dierks et al. *Cell* 2003, 113, (4), 435-44). Prokaryotic sulfatases generally contain either a cysteine or a serine in their sulfatase motif and are modified either by the "SUMF1-type" FGE or the "AtsB-type" FGE, respectively (Szameit et al. *J Biol Chem* 1999, 274, (22), 15375-81). An FGE has been described in *Mycobacterium tuberculosis* (e.g., GenBank Acc. No. NP-215226 (gi:15607852) and International Publication No. WO 2008/036350), in deuterostomia, including vertebrates and echinodermata (e.g., Pepe et al. *Cell* 2003; 113, 445-456, Dierks et al. (2003) *Cell* 113, 435-444; Cosma et al. *Hum. Mutat.* 2004; 23, 576-581). Nucleic acids encoding a number of FGEs are known in the art and readily available (e.g., Preusser et al. *J. Biol. Chem.* 2005; 280(15):14900-10; Fang et al. *J Biol. Chem.* 2004; 79(15):14570-8; Landgrebe et al. *Gene.* 2003; 316:47-56; Dierks et al. *FEBS Lett.* 1998; 423(1):61-5; Dierks et al. *Cell.* 2003; 113(4):435-44; Cosma et al. *Cell* 2003; 113(4):445-56; Baenziger *Cell* 2003; 113(4):421-2 (review); Dierks et al. *Cell.* 2005; 121(4):541-52; Roeser et al. *Proc Natl Acad Sci USA* 2006; 103(1):81-6; Sardiello et al. *Hum Mol. Genet.* 2005; 14(21):3203-17; GenBank Accession No. NM182760; International Publication Nos. WO 2004/072275 and WO 2008/036350). In an embodiment, the sulfatase motif is compatible with a human FGE (e.g., the SUMF1-type FGE, as described, e.g., in Cosma et al. *Cell* 2003; 113, 445-56; Dierks et al. *Cell* 2003; 113, 435-44). In an embodiment, the aldehyde tagged antibody molecule is expressed in a human cell that expresses the FGE or in a host cell, typically a mammalian cell, genetically modified to express a human FGE. When a cell-free method is used to convert a sulfatase motif-containing antibody molecule, an isolated FGE can be used.

Methods for Conversion and Modification of an Aldehyde Tag

Conversion of an aldehyde tag present in an aldehyde tagged antibody molecule can be accomplished by cell-based or cell-free methods.

In an embodiment, conversion of an aldehyde tag of an aldehyde tagged antibody molecule can be accomplished by expression of the aldehyde tagged protein in a cell that contains a suitable FGE. For example, conversion of the cysteine or serine of the aldehyde tag can occur during or following translation in the host cell. The FGE of the host cell can be endogenous to the host cell, or the host cell can be recombinant for a suitable FGE that is heterologous to the host cell. FGE expression can be provided by an expression system endogenous to the FGE gene (e.g., expression is provided by a promoter and other control elements present in the native FGE gene of the host cell), or can be provided by from a recombinant expression system in which the FGE coding sequence is operably linked to a heterologous promoter to provide for constitutive or inducible expression. Conditions suitable for use to accomplish conjugation of a reactive partner moiety to an aldehyde tagged antibody molecule are similar to those described in Mahal et al. *Science* 1997; 276(5315):1125-8.

In another embodiment, cell-free conversion of an aldehyde tag of an aldehyde tagged antibody molecule can be accomplished by contacting an aldehyde tagged antibody molecule with an FGE under conditions suitable for conversion of a cysteine or serine of a sulfatase motif of the aldehyde tag to an FGly. For example, nucleic acid encoding an aldehyde tagged polypeptide can be expressed in an in vitro transcription/translation system in the presence of a suitable FGE to provide for production of converted aldehyde tagged antibody molecule.

Alternatively, isolated, unconverted aldehyde tagged antibody molecule can be isolated following recombinant production in a host cell lacking a suitable FGE or by synthetic production. The isolated aldehyde tagged antibody molecule is then contacted with a suitable FGE under conditions to provide for aldehyde tag conversion. The aldehyde tagged antibody molecule can be unfolded by methods known in the art (e.g., using heat, adjustment of pH, chaotropic agents (e.g., urea), organic solvents (e.g., hydrocarbons: octane, benzene, or chloroform) and the denatured protein contacted with a suitable FGE. The aldehyde-tagged antibody molecule can then be refolded under suitable conditions.

Similarly, modification of a converted aldehyde tag of an aldehyde tagged antibody molecule can be accomplished by cell-based or cell-free methods. For example, converted aldehyde tagged antibody molecule can be isolated from a production source (e.g., recombinant host cell production, synthetic production), and contacted with a reactive partner-containing antimicrobial peptide under conditions suitable to provide for conjugation of a moiety of the reactive partner to the FGly of the aldehyde tag.

Methods for Modification of Peptides to Contain Reactive Partner for Reaction with 2-Formylglycine Antimicrobial peptides to be conjugated to an aldehyde-tagged antibody molecule can be modified to incorporate a reactive partner for reaction with an aldehyde of the FGly residue of the aldehyde-tagged antibody molecule.

Since the methods of aldehyde-tagged antibody modification are compatible with conventional chemical processes, any of a variety of commercially available reagents can be used to accomplish conjugation. For example, aminooxy, hydrazide, hydrazine, or thiosemicarbazide derivatives of a number of moieties of interest are suitable reactive partners, and are readily available or can be generated using standard chemical methods.

In an embodiment, the reactive moiety (e.g., aminooxy or hydrazide) can be positioned at an N-terminal region, the N-terminus, a C-terminal region, the C-terminus, or at a position internal to the peptide. For example, the peptide can be synthesized from a Boc-protected precursor. An amino group of a peptide can react with a compound comprising a carboxylic acid group and oxy-N-Boc group (e.g., 3-(2,5-dioxopyrrolidin-1-yloxy)propanoic acid). Other variations on the compound comprising a carboxylic acid group and oxy-N-protecting group can include different number of carbons in the alkylene linker and substituents on the alkylene linker. The reaction between the amino group of the peptide and the compound comprising a carboxylic acid group and oxy-N-protecting group occurs through standard peptide coupling chemistry. Examples of peptide coupling reagents that can be used include, but not limited to, DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl-3-ethyl-carbodiimide hydrochloride), cyanuric fluoride, cyanuric chloride, TFFH (tetramethyl fluoroformamidinium hexafluorophosphate), DPPA (diphenylphosphorazidate), BOP (benzotriazol-1-yloxytris(dimethylamino)phosphonium hexafluorophosphate), HBTU (O-benzotriazol-1-yl-N,N,N',N'-tetramethyluronium hexafluorophosphate), TBTU (O-benzotriazol-1-yl-N,N,N',N'-tetramethyluronium tetrafluoroborate), TSTU (O—(N-succinimidyl)-N,N,N',N'-tetramethyluronium tetrafluoroborate), HATU (N-[(dimethylamino)-1-H-1,2,3-triazolo[4,5,6]-pyridin-1-ylmethylene]-N-methylmethanaminium hexafluorophosphate N-oxide), BOP-Cl (bis(2-oxo-3-oxazolidinyl)phosphinic chloride), PyBOP ((1-H-1,2,3-benzotriazol-1-yloxy)-tris(pyrrolidino) phosphonium tetrafluorophopsphate), BrOP (bromotris(dimethylamino)phosphonium hexafluorophosphate), DEPBT (3-(diethoxyphosphoryloxy)-1,2,3-benzotriazin-4(3H)-one) PyBrOP (bromotris(pyrrolidino)phosphonium hexafluorophosphate).

Deprotection to expose the amino-oxy functionality can be performed on the peptide comprising an N-protecting group. Deprotection of the N-oxysuccinimide group, for example, occurs according to standard deprotection conditions for a cyclic amide group. Deprotecting conditions can be found in Greene and Wuts, *Protective Groups in Organic Chemistry*, 3rd Ed., 1999, John Wiley & Sons, NY and Harrison et al. Certain deprotection conditions include a hydrazine reagent, amino reagent, or sodium borohydride. For example, the deprotection of the Boc protecting group can occur with TFA. Other reagents for deprotection include, but are not limited to, hydrazine, methylhydrazine, phenylhydrazine, sodium borohydride, and methylamine. The product and intermediates can be purified by conventional means, such as HPLC purification.

In an embodiment, the conjugation reaction is performed at a pH below 7, with a pH of about 5.5, about 6, or about 6.5. Where conjugation is performed with an aldehyde tagged antibody molecule present in a living cell, the conditions are selected to be physiologically compatible. For example, the pH can be dropped temporarily for a time sufficient to allow for the reaction to occur but within a period tolerated by the cell having an aldehyde tag (e.g., from about 30 min to 1 hour). Physiological conditions for conducting modification of aldehyde tagged antibody molecules on a cell surface can be similar to those used in a ketone-azide reaction in modification of cells bearing cell-surface azides (e.g., U.S. Pat. No. 6,570,040).

Exemplary Site-Specific ADCs

In an embodiment, the ADC is site-specifically decorated with one or more covalently coupled antimicrobial peptides. The site-specificity of reaction of a reactive partner-containing antimicrobial peptide with an aldehyde tag of the protein allows for production of proteins having multiple sites for chemical conjugation, thus providing a scaffold for production of ADCs have a desired peptide payload per protein ratio. In an embodiment, the relative position of the aldehyde tags in the aldehyde-tagged protein can be designed to provide for a desired presentation of covalently bound antimicrobial peptides on the surface of the final ADC, thus allowing for control of spatial orientation of the displayed peptide payload.

In an embodiment, the site-specific nature of chemical modification of aldehyde tags to attach antimicrobial peptide to the antibody molecule can be used to provide for a composition comprising a substantially homogenous population ADCs. Such ADCs can provide for control of the stoichiometry of drug delivery. Such homogenous populations include those in which 60% or more, e.g., 70% or more, 75% or more, 80% or more, 85% or more, 90% or more, 95% or more, of the ADCs of the population have the same antimicrobial peptide payload to antibody molecule ratio.

In an embodiment, the ADCs of the present disclosure comprise an anti-LPS antibody molecule (e.g., an anti-LPS antibody molecule described herein) and one or more covalently bound antimicrobial peptides (e.g., antimicrobial peptides described herein), where the antibody molecule comprises a modified sulfatase motif of the formula:

$$X_1(FGly')X_2Z_2X_3Z_3$$

where FGly' has the formula:

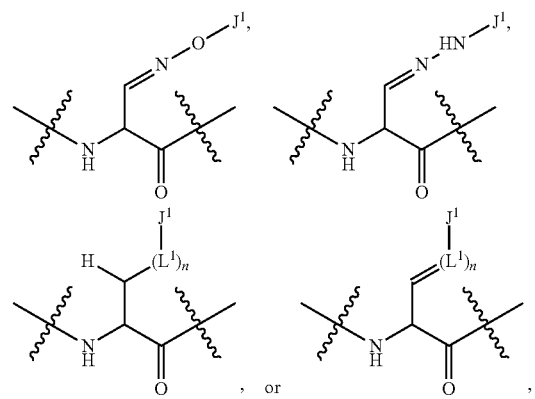

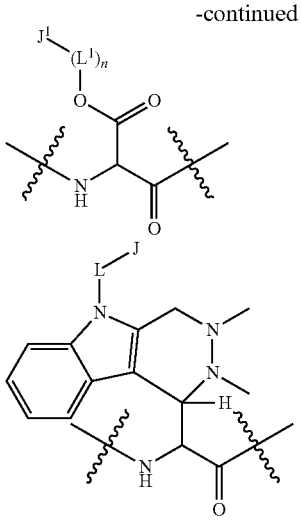

HIPS chemistry,
wherein $J_1$ is the covalently bound antimicrobial peptide;
each $L_1$ is a divalent moiety independently selected from alkylene, substituted alkylene, alkenylene, substituted alkenylene, alkynylene, alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;
n is a number selected from zero to 40;
$Z_2$ is a proline or alanine residue;
$X_1$ is present or absent and, when present, is any amino acid, with the proviso that when the sulfatase motif is at an N-terminus of the polypeptide, $X_1$ is present;
$X_2$ and $X_3$ are each independently any amino acid; and
$Z_3$ is a basic amino acid, and
wherein the antibody molecule presents the covalently bound drug on a solvent-accessible surface when in a folded state. $X_1$, $X_2$, $Z_2$, $X_3$, and $Z_3$ can be further defined as discussed above.

In an embodiment, the ADC is formed by the HIPS chemistry ligation (e.g., as described in PCT Publication No. WO 2018/136626, incorporated herein by reference in its entirety).

In an embodiment, the aldehyde-tagged protein can be designed to provide for multiple sites for chemical conjugation, e.g., to provide a scaffold for production of ADCs having a desired drug payload per protein ratio. The ADCs of the present disclosure typically include at least 2 (e.g., 3, 4, 5, 6, 7, 8, or more) modified sulfatase motifs having covalently bound antimicrobial peptides. The ADCs of the present disclosure can provide for a 4 or more, 5 or more, or 6 or more covalently bound antimicrobial peptides in the ADC. ADCs of the present disclosure thus include those having a peptide payload to antibody molecule ratio of at least 2:1, at least 3:1, at least 4:1, at least 5:1, at least 6:1, at least 7:1, or at least 8:1.

The relative position of the aldehyde tags in the aldehyde-tagged antibody molecule can be designed to provide for a desired presentation of covalently coupled antimicrobial peptides on the surface of the final ADC. This feature allows for control of spatial orientation of the displayed drug payload on the surface of the final ADC. ADCs containing multiple aldehyde tags, which may include concatemeric aldehyde tags separated by flexible linkers as described herein, can provide for, e.g., greater drug payload: antibody molecule ratios and enhanced presentation of drug to a physiological environment in which the ADC is present. In an embodiment, the ADC can be described as a modified antibody molecule "decorated" with antimicrobial peptide covalently coupled to the antibody molecule, e.g., through an oxime or hydrazone linkage to the backbone of the antibody molecule.

For example, the aldehyde tags can be positioned in the ADC at an N-terminus of an antibody chain, a C-terminus of an antibody chain, and a solvent-accessible loop of the antibody molecule. The aldehyde tags can optionally be provided in connection with a linker, e.g., a flexible linker, as described above. The multiple aldehyde tags can be localized to a particular region(s) of the antibody molecule or antibody chain (e.g., provided in one or more of a solvent-accessible loop, N-terminal region (including N-terminus), C-terminal region (including C-terminus)), or can be distributed over the solvent-accessible surface area of the folded modified antibody molecule. In an embodiment, at least one aldehyde tag is located in a heavy chain constant region (e.g., one, two or all of CH1, CH2, or CH3), a light chain constant region, or both.

In an embodiment, the aldehyde tags are spaced so that the final ADC has covalently coupled antimicrobial peptides spaced apart at a distance sufficient to avoid interaction between the covalently coupled antimicrobial peptides, e.g., such that the peptides do not contact one another or otherwise interfere with their respective biological activities.

Methods of Making ADCs

Methods of conjugation of an FGly-containing aldehyde-tagged antibody molecule with a reactive-partner containing-antimicrobial peptide to provide an ADC having a desired peptide payload to antibody molecule ratio are provided by the present disclosure.

In an embodiment, the methods described herein involve combining an FGly-containing, aldehyde-tagged antibody molecule with a reactive partner-containing antimicrobial peptide (e.g., an aminooxy- or hydrazide-containing peptide) in a reaction mixture under conditions suitable to promote reaction between the aldehyde(s) for the FGly(s) of the aldehyde-tagged antibody molecule with the reactive partner of the peptide(s), thereby producing a reaction product of an ADC having peptide covalently coupled to the backbone of the antibody molecule, e.g., through an oxime bond, hydrazide bond, or other aldehyde specific chemistries such as reductive aminations, or Wittig reactions.

After production of the aldehyde-tagged antibody molecule, it is isolated using any of a variety of techniques available in the art (e.g., chromatography, e.g., HPLC, FPLC, or immunoaffinity purification). In an embodiment, the antibody molecule contains an immunotag (e.g., His tag, FLAG tag), typically positioned at an N- or C-terminus to facilitate isolation and purification prior to conjugation with drug. The FGly-containing aldehyde-tagged antibody molecule for use in a conjugation reaction with antimicrobial peptide can be provided in denatured form or can be folder prior to combining in the reaction mixture. Typically, the FGly-containing aldehyde-tagged antibody molecule is provided in folded form in the conjugation reaction mixture. Where obtained from cells expressing the aldehyde-tagged antibody molecule and a compatible FGE, the FGly-containing aldehyde-tagged antibody molecule can be isolated in folded form from cells or, where secreted, from culture supernatant. Where needed, methods for folding of proteins are available in the art, and can be readily applied to the methods described herein.

In an embodiment, the aldehyde-tagged protein having an FGly residue is isolated. In an embodiment, the aldehyde-tagged protein having an FGly residue is purified. In an embodiment, the aldehyde-tagged protein is combined in a reaction mixture (e.g., in a buffered solution) with a reactive partner-containing antimicrobial peptide. The buffered solution can be at a physiological or near physiological pH, e.g., a pH of about 5 to 7, typically a pH of about 6.5. In an embodiment, the reactive partner-containing antimicrobial peptide is provided in the reaction mixture in excess to the aldehyde moieties of the FGly-containing aldehyde-tagged protein, typically at least 2, 3, 4, 5, 6, 7, 8, 9, 10-fold or more excess, e.g., to drive the reaction to completion. After addition of reactive partner-containing antimicrobial peptide to the reaction mixture, the mixture is stirred under suitable conditions of time and temperature (e.g., at room temperature for about 2 h). The resulting ADC is isolated from the reaction mixture and can be further purified using standard techniques (e.g., chromatography, e.g., HPLC or FPLC).

Alternative ADC Ligation Methods

The ADCs described herein can be produced by a number of different methods.

In an embodiment, the antimicrobial peptide is coupled to the antibody molecule by lysine conjugation (e.g., using a surface exposed lysine as an antibody reactive group). In an embodiment, the antibody molecule is directly conjugated to an activated amino acid on the antimicrobial peptide. In another embodiment, a lysine on the antibody molecule is converted to a thiol reactive group and antibody molecule with the thiol reactive group is ligated to a thiolated antimicrobial peptide. In yet another embodiment, a lysine on the antibody molecule is converted to a free thiol and the antibody molecule with the free thiol is ligated to a thiol reactive antimicrobial peptide.

In an embodiment, the antimicrobial peptide is coupled to the antibody molecule by interchain disulfides (e.g., using disulfides linking HC-HC or HC-LC). In an embodiment, interchain disulfides of the antibody molecule are reduced and the antibody molecule with the reduced interchain disulfides is ligated to a thiol reactive antimicrobial peptide.

In an embodiment, the antimicrobial peptide is coupled to the antibody molecule using a non-native amino acid (e.g., an amino acid substituted with aldehyde, azide, or alkyne). In an embodiment, the antibody molecule is ligated to the antimicrobial peptide using click chemistry (Kolb et al. *Angew Chem Int Ed Engl.* 2001; 40(11):2004-2021; Evans *Australian Journal of Chemistry.* 2007; 60 (6): 384-395).

In an embodiment, the antimicrobial peptide is coupled to the antibody molecule using a biodegradable polymer (e.g., lysine or thiol). In an embodiment, the antimicrobial peptide is ligated to a biodegradable polymer and the polymer is ligated to the antibody molecule.

Provided herein are also ADCs made by the methods described herein.

Evaluation of Candidates

The ADCs described herein can be evaluated using a number of in vitro assays, including, e.g., 1) bactericidal activity, 2) opsonophagocytic activity, and 3) membrane disruption.

Without wishing to be bound by theory, it is believed that in an embodiment the dual mechanism of action, direct killing and opsonophagocytic activity (OPA), can allow for the ADCs described herein to be functional in either normal or neutropenic patients. Opsonic antibodies typically function by binding to the bacterial surface, recruiting complement and phagocytic cells (e.g., neutrophils), which then engulf the bacteria. Immune-compromised patients are at the highest risk of infection and often have very low levels of phagocytic cells. An antibacterial approach that offers a direct bactericidal mechanism of action may overcome some of the limitations of antibody-based therapies that focus on opsonophagocytosis or complement-mediated killing as a mechanism of action. It is also believed that in an embodiment, by incorporating a direct, fast-acting bactericidal function, the ADCs described herein can overcome several resistance mechanisms.

Bactericidal assay: Direct killing activity of the ADC can be measured against two well described laboratory strains of *P. aeruginosa* (PA14 and PA01) and no less than three clinical strains of *P. aeruginosa*, including MDR and Pan-resistant strains. These assays are conducted in the absence of complement or effector cells. Activity in this assay can provide insight on the inherent killing activity of the ADC.

Opsonophagocytosis assay: Killing activity of the ADC can be measured against the same *P. aeruginosa* strains as for the bactericidal activity, but this time in the presence of complement and freshly purified polymorphonuclear leukocytes. Activity in this assay can provide information on the ability of the ADC to recruit neutrophils and induce bacterial killing via opsonophagocytosis.

Membrane disruption: A dye release/uptake assay can be performed against the same strains of *P. aeruginosa* used in the bactericidal and opsonophagocytosis assay. The ability of the ADC to disrupt the bacterial outer membrane is measured. Activity in this assay can provide insight into the molecular mechanism of action of the ADC.

Evaluation of Candidates: Opsonophagocytosis Assay (OPA)

The candidates of antibody molecules and antibody molecule-drug conjugates (ADCs) described herein can be evaluated, e.g., in vitro, for their opsonophagocytic activities, by opsonophagocytosis assays.

Assays for antibody-mediated, complement-dependent opsonization are described, e.g., in Hemachandra et al. *Infect Immun.* 2001; 69(4):2223-2229. Briefly, the ability of the antibody molecule or ADC candidates to opsonize bacteria for uptake by human polymorphonuclear leukocytes (PMNs) can be measured by flow cytometry. Bacteria are grown, heat killed, and FITC labeled. Opsonization can be carried out by incubating the labeled bacteria with antibody molecules or antibody molecule-drug conjugates with or without 1% human serum from an agammaglobulinemic patient as the complement source. Bacteria are washed in PBS containing 6% dextran and 0.2% glucose and then are resuspended in Hanks balanced salt solution with 0.1% gelatin. PMNs can be isolated from peripheral human blood via venipuncture of healthy adult volunteers. PMNs are resuspended to achieve a concentration of $10^7$ cells/ml and are activated for 30 min with 10 µl of a $10^{-6}$ dilution of N-formyl-Met-Leu-Phe (FMLP; Peninsula Laboratories, San Carlos, Calif.) per ml of cells. PMNs are added to each opsonized bacterial opsonized bacterial sample, incubated at 37° C., separated from free bacteria by differential centrifugation, and resuspended in PBS. Single-color flow cytometric analysis of PMN can be performed utilizing a FACScan and CellQuest software (Becton Dickinson, Mountain View, Calif.), and phagocytosis is expressed in relative units of mean fluorescence of 10,000 PMN for each sample. To demonstrate that the observed opsonophagocytosis is associated with bacterial killing, an alternative assay can be used in which 25,000 CFU of live bacteria are mixed with agammaglobulinemic human serum, various concentrations of antibody molecules or antibody molecule-drug conjugates, and $10^6$ fresh human PMN obtained as described above in RPMI medium (400-ml final volume). Samples are obtained at the beginning and end of a 90-min 37° C. incubation, after which bacteria are diluted and then plated for bacterial enumeration.

In an embodiment, killing activity of the ADC can be measured against the same *P. aeruginosa* strains as for the bactericidal activity, but this time in the presence of complement and freshly purified polymorphonuclear leukocytes. Activity in this assay can provide information on the ability of the ADC to recruit neutrophils and induce bacterial killing via opsonophagocytosis.

An exemplary opsonophagocytosis assay is also described in Example 1.

Evaluation of Candidates: Minimal Inhibitory Concentration Determination

The candidates of antimicrobial peptides and antibody molecule-drug conjugates (ADCs) described herein can be evaluated, e.g., in vitro, for their microbial inhibitory activities, by determining the minimal inhibitory concentration (MIC).

In an embodiment, the MIC is determined in the presence of human serum (e.g., 50% human serum), and sometimes referred to herein as hsMIC. In an embodiment, the MIC is determined in the presence of phosphate-buffered saline (PBS). In an embodiment, the MIC or hsMIC is determined on per ADC basis. In an embodiment, the MIC or hsMIC is determined on per payload or antimicrobial peptide basis. In an embodiment, the ratio of hsMIC to MIC is equal to or less than 2, e.g., equal to or less than 1.5 or 1.

Methods for determining MIC are also described, e.g., in Clinical and Laboratory Standards Institute. 2012. Methods for dilution antimicrobial susceptibility tests for bacteria that grow aerobically; approved standard, 9th ed. M07-A8, vol 29, no. 2 Clinical and Laboratory Standards Institute, Wayne, PA. For example, MIC can be determined according to CLSI guidelines, using 2-fold serial compound dilutions, in 96-well microtiter plates. Briefly, compounds are diluted in water across a mother plate then 2 μl is stamped to assay plates, one plate for each strain to be tested. Bacterial strains are sub-cultured overnight on agar plates at 37° C. Overnight plates are used to prepare 0.5 McFarland cultures in 0.85% saline. These concentrated cultures are diluted 1:200 in growth media to approximately $5 \times 10^5$ cells/ml. All assay plates receive 100 μl diluted culture per well. All plates are placed at 37° C. overnight. After 18 hours the plates are read using a mirrored plate reader and reflected incandescent light. In an embodiment, the MIC can be defined as the lowest concentration of compound that inhibits growth by at least 80%. Wells at and above the MIC should appear void of growth when read by eye.

An exemplary method for determination of MIC is also described in Example 2.

Evaluation of Candidates: In Vitro Cytokine Release and Fc Function Studies

The ability of the ADC to stimulate cytokine release can be evaluated in an in vitro soluble cytokine release assay. For example, human whole blood from healthy volunteers can be incubated for 24 hours at 37° C. with three concentrations of the antibody molecule and appropriate controls. Upon completion of the incubation, samples can be analyzed for a panel of cytokines. No impact in the cytokine release profile relative to other commercial antibodies can be used as the passing criteria for this study.

Characteristics of the antibody molecule to bind and mediate effector functions, such as antibody dependent cellular cytotoxicity and complement dependent cytotoxicity, can be characterized to confirm that the candidate ADC has the expected Fc effector functions based on its canonical isotype binding characteristics to Fcγ receptors and C1q.

Animal Models

The antibody molecules, antibody molecule-drug conjugates (ADCs), and antimicrobial peptides described herein can be evaluated in vivo, e.g., using various animal models. For example, an animal model can be used to test the efficacy of an antibody molecule, anti-bacterial peptide, or antibody molecule-drug conjugate described herein in reducing or inhibiting bacterial infection. Animal models can also be used, e.g., to investigate for side effects, measure concentrations of antibody molecules, anti-bacterial peptides or antibody molecule-drug conjugates in situ, demonstrate correlations between bacterial infection and bacteria under controlled conditions.

Exemplary animal models that can be used for evaluating an antibody molecule, anti-bacterial peptide, or antibody molecule-drug conjugate described herein include, but are not limited to, basic antimicrobial screening models (e.g., as described in Zak and O'Reilly, *Antimicrob. Agents Chemother.* 1991; 35(8): 1527-1531); primary rodent infection models (e.g., as described in Marra and Girard *Curr. Protoc. Pharmacol.* 2006; Chapter 13: Unit 13A.4); ex vivo models (e.g., as described in Zak and O'Reilly, *Antimicrob. Agents Chemother.* 1991; 35(8): 1527-1531); monoparametric or discriminative models (e.g., as described in Zak and O'Reilly, *Antimicrob. Agents Chemother.* 1991; 35(8): 1527-1531); mice models for wound healing (e.g., as described in Samy et al. *Methods Mol. Biol.* 2011; 716: 245-265); rabbit models for evaluation of bacterial migration and colonization (e.g., as described in Allan et al. *J. Biomed. Biotechnol.* 2012; 2012: 921617). Pharmacokinetic-pharmacodynamic modeling of antimicrobial drugs are described, e.g., in Nielsen and Friberg *Pharmacol. Rev.* 2013; 65(3):1053-1090.

Exemplary types of animals that can be used to evaluate antibody molecules, anti-bacterial peptides, or antibody molecule-drug conjugates described herein include, but are not limited to, mice, rats, rabbits, guinea pigs, and monkeys. Various methods of immunosuppression can be used for enhancement of virulence of bacteria for inoculation. These methods include, e.g., targeting bone marrow (e.g., by irradiation), targeting neutrophils (e.g., using cytostatics), targeting macrophages (e.g., using mucin or baker's yeast), targeting complement (e.g., using cobra venom factor), targeting tuftsin (e.g., by splenectomy), targeting immunoglobulins (e.g., using anti-Ig), targeting T-lymphocytes (e.g., by thymectomy), or targeting interleukins (e.g., using antibodies or chemical compounds). Other considerations that may influence anti-bacterial activity in in vivo tests include, e.g., inoculum size, virulence, growth or generation time in vivo, timing of treatment, method of administration, pharmacokinetics/pharmacodynamics, and development of resistance in vivo.

Pharmaceutical Compositions and Kits

In some aspects, this disclosure provides compositions, e.g., pharmaceutically acceptable compositions, which include an antibody molecule, an antibody molecule-drug conjugate (ADC), or an antimicrobial peptide, as described herein, formulated together with a pharmaceutically acceptable carrier.

As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal, transdermal or epidermal administration (e.g., by injection or infusion). In an embodiment, less than about 5%, e.g., less than about 4%, 3%, 2%, or 1% of the antibody molecules, ADCs, or antimicrobial peptides in the pharmaceutical composition are present as aggregates. In other embodiments, at least about 95%, e.g., at least about 96%, 97%, 98%, 98.5%, 99%, 99.5%, 99.8%, or more of the antibody molecules, ADCs, or antimicrobial peptides in the pharmaceutical composition are present as monomers. In an embodiment, the level of aggregates or monomers is determined by chromatography, e.g., high performance size exclusion chromatography (HP-SEC).

The compositions set out herein may be in a variety of forms. These include, for example, liquid, semi-solid and solid dosage forms, such as liquid solutions (e.g., injectable and infusible solutions), dispersions or suspensions, liposomes, and suppositories. A suitable form depends on the intended mode of administration and therapeutic application. Typical suitable compositions are in the form of injectable or infusible solutions. One suitable mode of administration is parenteral (e.g., intravenous, subcutaneous, intraperitoneal, intramuscular). In an embodiment, the antibody molecule, ADC, or antimicrobial peptide is administered by intravenous infusion or injection. In an embodiment, the antibody, ADC, or antimicrobial peptide is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibody molecules ADC, or antimicrobial peptide can be administered by a variety of methods. Several are known in the art, and for many therapeutic, prophylactic, or diagnostic applications, an appropriate route/mode of administration is intravenous injection or infusion. For example, the antibody molecules, ADC, or antimicrobial peptide can be administered by intravenous infusion at a rate of less than 10 mg/min; preferably less than or equal to 5 mg/min to reach a dose of about 1 to 100 mg/m$^2$, preferably about 5 to 50 mg/m$^2$, about 7 to 25 mg/m$^2$ and more preferably, about 10 mg/m$^2$. As will be appreciated by the skilled artisan, the route and/or mode of administration will vary depending upon the desired results. In an embodiment, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In an embodiment, an antibody molecule, ADC, or antimicrobial peptide can be orally administered, for example, with an inert diluent or an assimilable edible carrier. The antibody molecule, ADC, or antimicrobial peptide (and other ingredients, if desired) may also be enclosed in a hard or soft shell gelatin capsule, compressed into tablets, or incorporated directly into the subject's diet. For oral therapeutic administration, the antibody molecule, ADC, or antimicrobial peptide may be incorporated with excipients and used in the form of ingestible tablets, buccal tablets, troches, capsules, elixirs, suspensions, syrups, wafers, and the like. To administer an antibody molecule, ADC, or antimicrobial peptide by other than parenteral administration, it may be necessary to coat the compound with, or co-administer the compound with, a material to prevent its inactivation. Therapeutic, prophylactic, or diagnostic compositions can also be administered with medical devices, and several are known in the art.

Dosage regimens are adjusted to provide the desired response (e.g., a therapeutic, prophylactic, or diagnostic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the antibody molecule, ADC, or antimicrobial peptide, and the particular therapeutic, prophylactic, or diagnostic effect to be achieved, and (b) the limitations inherent in the art of compounding such an antibody molecule, ADC, or antimicrobial peptide for the treatment of sensitivity in individuals.

In an embodiment, the ADC is administered to a subject as a single dose. In vitro studies of an exemplary ADC described herein demonstrate rapid bactericidal activity at ~10 microgram/mL or lower against *Pseudomonas aeruginosa*, including MDR strains, even in the absence of serum or effector cells. Further, in vivo studies with the exemplary ADC demonstrate a significant reduction in bacterial counts in a neutropenic *P. aeruginosa* lung infection model. Without wishing to be bound by theory, it is believed that in an embodiment, the specificity and half-life of the ADC described herein (e.g., on the order of days) can allow for a single dose administration of the ADC, e.g., as a pathogen-specific antibacterial, for *P. aeruginosa*, including MDR/XDR strains, while promoting antimicrobial stewardship, sparing the gut microbiome, and limiting resistance development.

An exemplary, non-limiting range for a therapeutically, prophylactically, or diagnostically effective amount of an antibody molecule, ADC, or antimicrobial peptide is 0.1-100 mg/kg, e.g., 0.1-50 mg/kg or 0.1-20 mg/kg, e.g., about 1-10, 1-5, 5-10, or 1-3 mg/kg, e.g., about 1, 2, 3, 4, 5, 6, 7, 8, 9, or 10 mg/kg. The antibody molecule, ADC, or antimicrobial peptide can be administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, e.g., about 10 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed compositions.

The pharmaceutical compositions herein may include a "therapeutically effective amount," "prophylactically effective amount," or "diagnostically effectively amount" of an antibody molecule, ADC, or antimicrobial peptide.

A "therapeutically effective amount" refers to an amount effective, at dosages and for periods of time necessary, to achieve the desired therapeutic result. A therapeutically effective amount of the antibody molecule, ADC, or antimicrobial peptide may vary according to factors such as the disease state, age, sex, and weight of the individual, and the ability of the antibody or antibody portion to elicit a desired response in the individual. A therapeutically effective amount is also one in which any toxic or detrimental effects of the antibody molecule, ADC, or antimicrobial peptide is outweighed by the therapeutically beneficial effects. A "therapeutically effective dosage" typically inhibits a measurable parameter by at least about 20%, e.g., by at least about 40%, by at least about 60%, or by at least about 80% relative to untreated subjects. The measurable parameter may be, e.g., bacterial load, fever, headache, muscle or joint pains, skin rash, bleeding, reduced platelet levels, and reduced blood pressure. The ability of an antibody molecule, ADC, or antimicrobial peptide to inhibit a measurable parameter can be evaluated in an animal model system predictive of efficacy in reducing, inhibiting, or preventing a bacterial infection. Alternatively, this property of a composition can be evaluated by examining the ability of the antibody molecule, ADC, or antimicrobial peptide to inhibit or reduce the viability of bacteria, e.g., by an in vitro assay described herein.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A "diagnostically effective amount" refers to an amount effective, at dosages and for periods of time necessary, to achieve the desired diagnostic result. Typically, a diagnostically effective amount is one in which a bacterial infection or a related disorder can be diagnosed in vitro, ex vivo, or in vivo.

Also within this disclosure is a kit that comprises an antibody molecule, ADC, or antimicrobial peptide described herein. The kit can include one or more other elements including: instructions for use; other reagents, e.g., a label, a therapeutic agent, or an agent useful for chelating, or otherwise coupling, an antibody molecule, ADC, or antimicrobial peptide to a label or therapeutic agent, or a radioprotective composition; devices or other materials for preparing the antibody molecule, ADC, or antimicrobial peptide for administration; pharmaceutically acceptable carriers; and devices or other materials for administration to a subject.

Nucleic Acids

The present disclosure also features nucleic acids comprising nucleotide sequences that encode the antibody molecules (e.g., heavy and light chain variable regions and CDRs of the antibody molecules), antibody molecule-drug conjugates (e.g., heavy and light chain variable regions and CDRs of the antibody molecule-drug conjugates), or antimicrobial peptide, as described herein.

For example, the present disclosure features a first and second nucleic acid encoding heavy and light chain variable regions, respectively, of an antibody molecule chosen from one or more of the antibody molecules disclosed herein, e.g., an antibody molecule of Table 1 or 3, or a portion of an antibody molecule, e.g., the variable regions of Table 1 or 3. The nucleic acid can comprise a nucleotide sequence encoding any one of the amino acid sequences in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein).

In an embodiment, the nucleic acid can comprise a nucleotide sequence encoding at least one, two, or three CDRs from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In an embodiment, the nucleic acid can comprise a nucleotide sequence encoding at least one, two, or three CDRs from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In an embodiment, the nucleic acid can comprise a nucleotide sequence encoding at least one, two, three, four, five, or six CDRs from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In an embodiment, the nucleic acid can comprise a nucleotide sequence encoding at least one, two, or three CDRs from a heavy chain variable region having the nucleotide sequence as set forth in Table 2, a sequence substantially homologous thereto (e.g., a sequence at least about 85%, 90%, 95%, 99% or more identical thereto, and/or capable of hybridizing under the stringency conditions described herein). In an embodiment, the nucleic acid can comprise a nucleotide sequence encoding at least one, two, or three CDRs from a light chain variable region having the nucleotide sequence as set forth in Table 2, or a sequence substantially homologous thereto (e.g., a sequence at least about 85%, 90%, 95%, 99% or more identical thereto, and/or capable of hybridizing under the stringency conditions described herein). In an embodiment, the nucleic acid can comprise a nucleotide sequence encoding at least one, two, three, four, five, or six CDRs from heavy and light chain variable regions having the nucleotide sequence as set forth in Table 2, or a sequence substantially homologous thereto (e.g., a sequence at least about 85%, 90%, 95%, 99% or more identical thereto, and/or capable of hybridizing under the stringency conditions described herein).

In an embodiment, the nucleic acid comprises a nucleotide sequence as set forth in Table 2 or a sequence substantially homologous thereto (e.g., a sequence at least about 85%, 90%, 95%, 99% or more identical thereto, and/or capable of hybridizing under the stringency conditions described herein). In an embodiment, the nucleic acid comprises a portion of a nucleotide sequence as set forth in Table 2 or a sequence substantially homologous thereto (e.g., a sequence at least about 85%, 90%, 95%, 99% or more identical thereto, and/or capable of hybridizing under the stringency conditions described herein). The portion may encode, for example, a variable region (e.g., VH or VL); one, two, or three or more CDRs; or one, two, three, or four or more framework regions.

In an embodiment, the nucleic acid comprises a nucleotide sequence encoding an amino acid sequence as set forth in Table 4, or a sequence substantially homologous thereto (e.g., a sequence at least about 80%, 85%, 90%, 95% or more identical thereto, and/or capable of hybridizing under the stringency conditions described herein). In an embodiment, the nucleic acid comprises a portion of a nucleotide sequence encoding an amino acid sequence as set forth in Table 4, or a sequence substantially homologous thereto (e.g., a sequence at least about 80%, 85%, 90%, 95%, or more identical thereto, and/or capable of hybridizing under the stringency conditions described herein).

The nucleic acids disclosed herein include deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

In some aspects, the application features host cells and vectors containing the nucleic acids described herein. The nucleic acids may be present in a single vector or separate vectors present in the same host cell or separate host cell, as described in more detail below.

Vectors

Further provided herein are vectors that comprise nucleotide sequences encoding an antibody molecule, antibody molecule-drug conjugate (ADC), or antimicrobial peptide, described herein. In an embodiment, the vectors comprise nucleotides encoding an antibody molecule described herein. In an embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule, anti-bacterial peptide, or antibody molecule-drug conjugate produced are known to those skilled in the art, and may be varied or optimized depending upon the specific expression vector and mammalian host cell employed, based upon the present description.

Cells

The present disclosure also provides host cells comprising a nucleic acid encoding an antibody molecule, anti-bacterial peptide, or antibody molecule-drug conjugate as described herein. For example, the host cells may comprise a nucleic acid of Table 2, a sequence substantially homologous thereto (e.g., a sequence at least about 85%, 90%, 95%, 99% or more identical thereto, and/or capable of hybridizing under the stringency conditions described herein), or a portion of one of said nucleic acids. Additionally, the host cells may comprise a nucleic acid encoding an amino acid sequence described in Tables 1, 3, or 8, a sequence substantially homologous thereto (e.g., a sequence at least about 80%, 85%, 90%, 95%, 99% or more identical thereto), or a portion of one of said sequences.

In an embodiment, the host cells are genetically engineered to comprise nucleic acids encoding the antibody molecule, ADC, or antimicrobial peptide.

In an embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The disclosure also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

Uses of Antibody Molecules, Antibody Molecule-Drug Conjugates, and Antimicrobial Peptides The antibody molecules, antibody molecule-drug conjugates (ADCs), or antimicrobial peptides disclosed herein, as well as the pharmaceutical compositions disclosed herein, have in vitro, ex vivo, and in vivo therapeutic, prophylactic, and/or diagnostic utilities.

In an embodiment, the antibody molecule, ADC, or antimicrobial peptide, inhibits or reduces the viability of bacteria, e.g., Gram-negative bacteria. For example, these molecules can be administered to cells in culture, in vitro or ex vivo, or to a subject, e.g., a human subject, e.g., in vivo, to inhibit or reduce the viability of bacteria, e.g., Gram-negative bacteria. Accordingly, in an aspect, the disclosure provides a method of treating or preventing a bacterial infection in a subject, comprising administering to the subject an antibody molecule, ADC, or antimicrobial peptide, described herein, such that the bacterial infection is treated or prevented. For example, these antibody molecules can be administered to cells in culture, e.g. in vitro or ex vivo, or in a subject, e.g., in vivo, to treat, prevent, and/or diagnose a bacterial infection, or to inhibit or reduce a bacterial infection.

As used herein, the term "subject" is intended to include human and non-human animals. In an embodiment, the subject is a human subject, e.g., a human patient infected with bacteria, e.g., disease-causing bacteria, e.g., Gram-negative bacteria, or at risk of being infected with bacteria, e.g., disease-causing bacteria, e.g., Gram-negative bacteria. The term "non-human animals" includes mammals and non-mammals, such as non-human primates. In an embodiment, the subject is a human. The methods and compositions described herein are suitable for treating human patients infected with bacteria, e.g., disease-causing bacteria, e.g., Gram-negative bacteria. Patients infected with bacteria, e.g., disease-causing bacteria, e.g., Gram-negative bacteria include those who have been exposed to the bacteria but are (at least temporarily) asymptomatic, patients having a bacterial infection, or patients having a disorder related to a bacterial infection.

Methods of Treating or Preventing Bacterial Infection

Gram-negative bacteria display lipopolysaccharides (LPS) on the outer membrane of the bacteria. While not wishing to be bound by theory, in an embodiment, the antibody molecules, antibody molecule-drug conjugates (ADCs), or antimicrobial peptides described herein can inhibit or reduce the viability of Gram-negative bacteria, at least in part, by binding to LPS.

The antibody molecules, ADCs, and antimicrobial peptides described herein, can be used to treat or prevent bacterial infections, as well as disorders, conditions or symptoms associated with bacterial infections.

In an embodiment, the bacterial infection is caused by one or more of the following bacteria: *Klebsiella pneumonia* (e.g., *Klebsiella pneumoniae* subsp. *ozaenae*, *Klebsiella pneumoniae* subsp. *pneumoniae*, or *Klebsiella pneumoniae* subsp. *rhinoscleromatis*), *Enterobacter cancerogenous*, *Enterobacter cloacae*, *Enterobacter hormaechei*, *Enterobacter asburiae*, *Shigella boydii*, *Shigella dysenteriae*, *Shigella flexneri*, *Shigella sonnei*, *Escherichia coli* (e.g., *Escherichia coli* ATCC 11775, *Escherichia coli* ATCC 25922, *Escherichia coli* ATCC 35401, or *Escherichia coli* ATCC 43895), *Escherichia fergusonii*, *Salmonella choleraesuis*, *Salmonella choleraesuis* subsp. *indica*, *Salmonella enteritidis*, *Salmonella virchow*, *Salmonella paratyphi* B, *Salmonella typhimurium*, *Salmonella paratyphi* A, *Salmonella typhi*, *Salmonella choleraesuis* subsp. *arizonae*, *Salmonella choleraesuis* subsp. *diarizonae*, *Salmonella choleraesuis* subsp. *houtenae*, *Salmonella bongori*, *Citrobacter sedlakii*, *Citrobacter braakii*, *Citrobacter werkmanii*, *Citrobacter freundii*, *Citrobacter youngae*, *Citrobacter amalonaticus*, *Yersinia enterocolitica*, *Yersinia frederiksenii*, *Yersinia pestis*, *Yersinia pseudotuberculosis*, or any combination thereof.

In an embodiment, the bacterial infection is caused by one or more of: *Enterococcus faecium* (e.g., vancomycin-resistant (VRE) *Enterococcus faecium*), *Staphylococcus aureus* (e.g., methicillin-resistant (MRSA) *Staphylococcus aureus*), *Clostridium difficile*, *Acinetobacter baumannii* (e.g., multidrug resistant (MDR) *Acinetobacter*), *Pseudomonas aeruginosa* (e.g., multidrug resistant (MDR) *P. aeruginosa*, e.g., carbapenem-resistant *P. aeruginosa*), Enterobacteriaceae (e.g., *E. coli*, *K. pneumoniae*, or *Enterobacter* spp., e.g., carbapenem-resistant Enterobacteriaceae (CRE)), *N. gonorrhoaeae* (e.g., drug-resistant *N. gonorrhoaeae*), *Salmonella* (e.g., drug resistant *Salmonella*), *Shigella* (e.g., drug-resistant *Shigella*), a bacterium producing an extended spectrum β-lactamase (ESBL), or *Mycobacterium tuberculosis* (e.g., drug-resistant *M. tuberculosis*).

Exemplary disorders or conditions that can be associated with bacterial infections include, but are not limited to pneumonia (e.g., community-acquired pneumonia and hospital-acquired pneumonia), a urinary tract infection (UTI), septicemia, meningitis, diarrhea (e.g., traveler's diarrhea), a soft tissue infection, a skin infection, bacteremia, a respiratory system infection (e.g., a lower respiratory tract infection), endocarditis, an intra-abdominal infection, septic arthritis, osteomyelitis, a CNS infection, an ophthalmic infection, cholecystitis, cholangitis, meningitis (e.g., neonatal meningitis), typhoid fever, food poisoning, gastroenteritis, enteric fever, shigellosis, a blood stream infection, intra-abdominal sepsis, a brain abscess, meningitis, sepsis (e.g., neonatal sepsis), a joint infection, a bone infection, a gastrointestinal infection, or a wound infection.

Certain antibody molecules, ADCs, and antimicrobial peptides described herein are capable of treating at least 2, 3, 4, 5, 6, 7, 8, 9, 10, 20, 25, 30, 35, 40, 50, 100, 200, or more bacteria (e.g., Gram-negative bacteria) of different genera, species, subspecies, and/or strains. Accordingly, in an embodiment, the antibody molecule, ADC, or antimicrobial peptide is administered to a patient infected with or with a risk of being infected with bacterial infection, when no test has been performed to determine the genus, species. subspecies, and/or strain of the bacteria, e.g., the type of infected or disease-causing bacteria may be unknown.

The antibody molecules, ADCs, or antimicrobial peptides are typically administered at a frequency that keeps a therapeutically effective level of antibody molecules, ADCs, or antimicrobial peptides in the patient's system until the patient recovers. For example, the antibody molecules, ADCs, or antimicrobial peptides may be administered at a frequency that achieves a serum concentration sufficient for at least about 1, 2, 5, 10, 20, 30, or 40 antibody molecules, ADCs, or antimicrobial peptides to bind each bacterium. In an embodiment, the antibody molecules, ADCs, or antimicrobial peptides are administered every 1, 2, 3, 4, 5, 6, or 7 days.

Methods of administering various antibody molecules, ADCs, or antimicrobial peptides are known in the art and are described below. Suitable dosages of the antibody molecules, ADCs, or antimicrobial peptides used will depend on the age and weight of the subject and the particular drug used.

The antibody molecules or antimicrobial peptides can be used by themselves or conjugated to a second agent, e.g., an antibacterial agent, toxin, or protein, e.g., a second antibacterial (e.g., anti-LPS) antibody molecule or antimicrobial peptide. This method includes: administering the antibody molecule or antimicrobial peptide, alone or conjugated to a second agent, to a subject requiring such treatment. The antibody molecules can be used to deliver a variety of therapeutic agents, e.g., a toxin or anti-viral agent, or mixtures thereof.

Combination Therapies

The antibody molecules, antibody molecule-drug conjugates (ADCs), and antimicrobial peptides can be used in combination with other therapies. For example, the combination therapy can include an antibody molecule, ADC, or antimicrobial peptide co-formulated with, and/or co-administered with, one or more additional therapeutic agents, e.g., anti-bacterial agents (including antibiotics or other antibacterial antibodies), vaccines, or agents that enhance an immune response. In other embodiments, the antibody molecules, anti-bacterial peptides, or antibody molecule-drug conjugates are administered in combination with other therapeutic treatment modalities, such as intravenous hydration, fever-reducing agents (such as acetaminophen), or blood transfusion. Such combination therapies may advantageously utilize lower dosages of the administered therapeutic agents, thus avoiding possible toxicities or complications associated with the various monotherapies.

Administered "in combination", as used herein, means that two (or more) different treatments are delivered to the subject before, or during the course of the subject's affliction with a bacterial infection or disease. In one embodiment, two or more treatments are delivered prophylactically, e.g., before the subject is infected or diagnosed with bacteria, e.g., Gram-negative bacteria. In another embodiment, the two or more treatments are delivered after the subject has been infected or diagnosed with bacteria, e.g., Gram-negative bacteria. In an embodiment, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In an embodiment of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In an embodiment, delivery is such that the reduction in a symptom, or other parameter related to the bacterial infection or disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiment, the additional antimicrobial agent is an antibiotic. For example, the antibiotic can be a beta-lactam antibiotic (e.g., a penicillin, a cephalosporin, a monobactam, or a carbapenem), a monobactam, a carbapenem, a macrolide, a lincosamide, a streptogramin, an aminoglycoside, a quinolone, a sulfonamide, a tetracycline, a glycopeptide, a lipoglycopeptide, an oxazolidinone, a rifamycin, a polypeptide, or a tuberactinomycin. Exemplary antibiotics include, but are not limited to, amikacin, amoxicillin, ampicillin, azithromycin, aztreonam, bacampicillin, bacitracin, balofloxacin, besifloxacin, capreomycin, carbenicillin, cefacetrile (cephacetrile), cefaclomezine, cefaclor, cefadroxil (cefadroxyl), cefalexin (cephalexin), cefaloglycin (cephaloglycin), cefalonium (cephalonium), cefaloram, cefaloridine (cephaloradine), cefalotin (cephalothin), cefamandole, cefaparole, cefapirin (cephapirin), cefatrizine, cefazaflur, cefazedone, cefazolin (cephazolin), cefcanel, cefcapene, cefclidine, cefdaloxime, cefdinir, cefditoren, cefedrolor, cefempidone, cefepime, cefetamet, cefetrizole, cefivitril, cefixime, cefluprenam, cefmatilen, cefmenoxime, cefmepidium, cefmetazole, cefodizime, cefonicid, cefoperazone, cefoselis, cefotaxime, cefotetan, cefovecin, cefoxazole, cefoxitin, cefozopran, cefpimizole, cefpirome, cefpodoxime, cefprozil (cefproxil), cefquinome, cefradine (cephradine), cefrotil, cefroxadine, cefsumide, ceftaroline, ceftaroline (teflaro), ceftazidime, cefteram, ceftezole, ceftibuten, ceftiofur, ceftiolene, ceftioxide, ceftizoxime, ceftobiprole, ceftriaxone, cefuracetime, cefuroxime, cefuzonam, chloramphenicol, ciprofloxacin, clarithromycin, clinafloxacin, clindamycin, cloxacillin, cycloserine, daptomycin (cubicin), demeclocycline, dicloxacillin, dirithromycin, doripenem, doxycycline, enoxacin, ertapenem, erythromycin, flucloxacillin, flumequine, gatifloxacin, gemifloxacin, gemifloxacin (factive), gentamicin, grepafloxacin, imipenem, imipenem/cilastatin, kanamycin, levofloxacin, lincomycin, linezolid, lomefloxacin, macrocyclics, meropenem, metronidazole, mezlocillin, minocycline, moxifloxacin, nadifloxacin, nafcillin, nalidixic acid, neomycin, netilmicin, nitrofurantoin, norfloxacin, ofloxacin, oxacillin, oxolinic acid, oxytetracycline, paromomycin, pazufloxacin, pefloxacin, penicillin g, penicillin v, pipemidic acid, piperacillin, piromidic acid, pivampicillin, pivmecillinam, polymyxin b, pristinamycin, prulifloxacin, quinupristin/dalfopristin, rifabutin, rifampin, rifapentine, rosoxacin, roxithromycin, rufloxacin, sitafloxacin, sparfloxacin, streptomycin, sulfamethizole, sulfamethoxazole, sulfisoxazole, teicoplanin, telavancin, telavancin (vibativ), telithromycin, temafloxacin, tetracycline, ticarcillin, tigecycline, tinidazole, tobramycin, tosufloxacin, trimethoprim-sulfamethoxazole, trovafloxacin, vancomycin, viomycin, or zeocin.

In an embodiment, the additional anti-bacterial agent is a vaccine. The vaccine may be, e.g., live, attenuated, or inactivated bacteria, e.g., anthrax vaccine (e.g., BIOTHRAX®), DTaP vaccine (e.g., DAPTACEL® or INFANRIX®), DT vaccine, *Haemophilus influenzae* type b (Hib) vaccine (e.g., ACTHIB®, HIBERIX®, or PEDVAXHIB®), meningococcal vaccine (e.g., MENOMUNE®, MENACTRA®, MENVEO®, TRUMENBA®, or BEXSERO®), pneumococcal vaccine (e.g., PNEUMOVAX® 23 or PREVNAR® 13), tetanus/diphtheria vaccine (e.g., DECAVAC® or TENIVAC®), tetanus/diphtheria/pertussis vaccine (e.g., BOOSTRIX® or ADACEL®), typhoid vaccine (e.g., TYPHIM VI® or VIVOTIF®), DTaP/polio vaccine (e.g., KINRIX®), DTaP/hepatitis B/polio vaccine (e.g., PEDIARIX®), DTaP/polio/*Haemophilus* influenza type b vaccine (e.g., PENTACEL®), *Haemophilus* influenza type b/hepatitis B vaccine (e.g., COMVAX®), and *Haemophilus* influenza type b/meningococcal vaccine (e.g., MENHIBRIX®).

In an embodiment, the additional antiviral agent is a second antibody molecule, ADC, or antimicrobial peptide, e.g., an antibody molecule, ADC, or antimicrobial peptide different from a first antibody molecule, ADC, or antimicrobial peptide. Exemplary antibody molecules that can be used in combination include, but are not limited to, any combination of the antibody molecules listed in Table 1 or 3.

In an embodiment, the additional anti-bacterial agent is an antimicrobial (e.g., antibacterial) peptide. Exemplary antimicrobial peptides include, but are not limited to, pexiganan acetate (MSI 78), omiganan (MX-226/MBI-226 or CLS001), iseganan (IB-367), hLF1-11, XOMA 629, PAC-113, CZEN-002, IMX942, OP-145, Ghrelin, PMX-30063, delmitide (RDP58), plectasin, and HB1345.

In an embodiment, the additional anti-bacterial agent is a resistance-modifying agent. Exemplary resistance-modifying agents include, but are not limited to, an efflux inhibitor (e.g., Phe-Arg-β-naphthylamide) and beta-lactamase inhibitor (e.g., clavulanic acid or sulbactam).

Methods of Diagnosis

In some aspects, the present disclosure provides a diagnostic method for detecting the presence of a bacterium in vitro (e.g., in a biological sample, such as a blood sample) or in vivo (e.g., in vivo imaging in a subject). The method includes: (i) contacting the sample with an antibody molecule or antibody molecule-drug conjugate (ADC) described herein, or administering to the subject, the antibody molecule or ADC; (optionally) (ii) contacting a reference sample, e.g., a control sample (e.g., a control biological sample, such as plasma or blood) or a control subject with an antibody molecule or ADC described herein; and (iii) detecting formation of a complex between the antibody molecule or ADC, and the sample or subject, or the control sample or subject, wherein a change, e.g., a statistically significant change, in the formation of the complex in the sample or subject relative to the control sample or subject is indicative of the presence of the bacterium in the sample. The antibody molecule or ADC can be directly or indirectly labeled with a detectable substance to facilitate detection of the bound or unbound antibody. Suitable detectable substances include various enzymes, prosthetic groups, fluorescent materials, luminescent materials and radioactive materials, as described above and described in more detail below.

The term "sample," as it refers to samples used for detecting bacteria includes, but is not limited to, cells, cell lysates, proteins or membrane extracts of cells, body fluids such as blood, or tissue samples.

Complex formation between the antibody molecule or ADC, and a bacterium or lipopolysaccharide, can be detected by measuring or visualizing either the antibody molecule or antibody molecule-drug conjugate bound to the bacterium or lipopolysaccharide or unbound antibody molecule or ADC. Any suitable detection assays can be used, and conventional detection assays include an enzyme-linked immunosorbent assays (ELISA), a fluorescence-activated cell sorting (FACS) assay, a radioimmunoassay (RIA) or tissue immunohistochemistry. Alternative to labeling the antibody molecule or ADC, the presence of a bacterium or lipopolysaccharide can be assayed in a sample by a competition immunoassay utilizing standards labeled with a detectable substance and an unlabeled antibody molecule or ADC. In this assay, the biological sample, the labeled standards and the antibody molecule or ADC are combined and the amount of labeled standard bound to the unlabeled binding molecule is determined. The amount of bacteria or lipopolysaccharides in the sample is inversely proportional to the amount of labeled standard bound to the antibody molecule or ADC.

Additional Aspects and Embodiments are Provided in the Numbered Paragraphs Below.

1. An antibody molecule-drug conjugate (ADC) comprising an antibody molecule and a covalently coupled peptide, wherein the antibody molecule comprises a heavy chain variable region (VH), wherein the VH comprises three heavy chain complementarity determining regions (HCDR1, HCDR2, and HCDR3), and wherein the VH comprises:
    (a) an HCDR1 comprising the amino acid sequence of SEQ ID NO: 105; an HCDR2 comprising the amino acid sequence of SEQ ID NO: 106; and an HCDR3 comprising the amino acid sequence of SEQ ID NO: 107, or
    (b) an HCDR1 comprising the amino acid sequence of SEQ ID NO: 108; an HCDR2 comprising the amino acid sequence of SEQ ID NO: 146; and an HCDR3 comprising the amino acid sequence of SEQ ID NO: 107; and wherein the antibody molecule comprises a light chain variable region (VL), wherein the VL comprises three light chain complementarity determining regions (LCDR1, LCDR2, and LCDR3), and wherein the VL comprises:
    (a) an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112, or
    (b) an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112; and
    wherein the peptide comprises the amino acid sequence of SEQ ID NO: 257 or an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO 257.

2. The ADC of paragraph 1, wherein the VH comprises an HCDR1 comprising the amino acid sequence of SEQ ID NO: 105; an HCDR2 comprising the amino acid sequence of SEQ ID NO: 106; and an HCDR3 comprising the amino acid sequence of SEQ ID NO: 107; and wherein the VL comprises an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112.

3. The ADC of paragraph 1, wherein VH comprises an HCDR1 comprising the amino acid sequence of SEQ ID NO: 108; an HCDR2 comprising the amino acid sequence of SEQ ID NO: 146; and an HCDR3 comprising the amino acid sequence of SEQ ID NO: 107; and wherein the VL comprises an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112

4. The ADC of any of paragraphs 1-3, wherein the VH comprises the amino acid sequence of SEQ ID NO 117, or an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO 117.

5. The ADC of any of paragraphs 1-4, wherein the VH comprises the amino acid sequence of SEQ ID NO 117.

6. The ADC of any of paragraphs 1-5, wherein the VL comprises the amino acid sequence of SEQ ID NO 135, or an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO 135.

7. The ADC of any of paragraphs 1-6, wherein the VL comprises the amino acid sequence of SEQ ID NO: 135.

8. The ADC of any of paragraphs 1-7, wherein the antibody molecule is capable of binding to *Pseudomonas*.

9. The ADC of any of paragraphs 1-8, wherein the antibody molecule is capable of binding to *Pseudomonas aeruginosa*.

10. The ADC of any of paragraphs 1-9, wherein the antibody molecule is capable of binding to lipopolysaccharide (LPS) on *Pseudomonas*.

11. The ADC of any of paragraphs 1-10, wherein the antibody molecule is capable of binding to an inner core glycan moiety on LPS on *Pseudomonas*.

12. The ADC of any of paragraphs 1-11, wherein the antibody molecule does not bind, or does not substantially bind, to *E coli* LPS, e.g., as determined by Western blot.

13. The ADC of any of paragraphs 1-12, wherein the antibody molecule does not bind, or does not substantially bind, to heptose or a mono-phosphorylated heptose analog (e.g., 2-P-Hep or 4-P-Hep), e.g., as determined by a Biolayer Interferometry analysis.

14. The ADC of any of paragraphs 1-13, wherein the antibody molecule binds to di-phosphorylated 2,4-P-Hep monosaccharide, e.g., as determined by a Biolayer Interferometry analysis.

15. The ADC of any of paragraphs 1-14, wherein the antibody molecule binds to di-phosphorylated mannose (2,4-P-Man), e.g., with reduced binding compared to di-phosphorylated 2,4-P-Hep monosaccharide, e.g., as determined by a Biolayer Interferometry analysis.

16. The ADC of any of paragraphs 1-15, wherein the antibody molecule binds to one or more *P. aeruginosa* strains described herein, e.g., one or more strains resistant to carbapenems, anti-*pseudomonas* third generation cephalosporins or fluoroquinolones, e.g., with an apparent avidity of about 20 to about 150 pM (e.g., about 50 to about 120 pM), e.g., as determined by a whole bacterial cell ELISA.

17. The ADC of any of paragraphs 1-16, wherein the antibody molecule does not bind, or does not substantially bind, to one or more of *Escherichia coli, Klebsiella pneumoniae, Salmonella typhimurium*, a gram-positive organism, or a mammalian cell, e.g., as determined by a whole cell ELISA.

18. The ADC of any of paragraphs 1-17, wherein the antibody molecule binds to a *Pseudomonas* species other than *Pseudomonas aeruginosa*, e.g., one or more of *Pseudomonas fluorescens, Pseudomonas putida*, or *Pseudomonas stutzeri*, e.g., as determined by a whole bacterial cell ELISA.

19. The ADC of any of paragraphs 1-18, wherein the antibody molecule is a monoclonal antibody molecule, a humanized antibody molecule, an isolated antibody molecule, or a synthetic antibody molecule.

20. The ADC of any of paragraphs 1-19, wherein the antibody molecule comprises two VHs and two VLs.

21. The ADC of any of paragraphs 1-20, wherein the antibody molecule further comprises a heavy chain constant region of an IgG1, IgG2, IgG3, or IgG4.

22. The ADC of any of paragraphs 1-21, wherein the antibody molecule further comprises a light chain constant region of a kappa or lambda chain.

23. The ADC of any of paragraphs 1-22, wherein the antibody molecule comprises a Fab, a F(ab')2, an Fv, or a single chain Fv fragment (scFv).

24. The ADC of any of paragraphs 1-23, wherein the peptide comprises the amino acid sequence of SEQ ID NO 257.

25. The ADC of any of paragraphs 1-24, wherein the peptide comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33, D-amino acids, or at least 10%, 20%, 30%, 40%, 50%, 60%, 70%, 80%, 90%, 95%, or 100%, of the amino acid residues in the peptide are D-amino acids.

26. The ADC of any of paragraphs 1-25, wherein all of the amino acid residues in the peptide are D-amino acids.

27. The ADC of any of paragraphs 1-26, wherein the peptide is coupled to the VH, e.g., the C-terminus of the VH, e.g., indirectly (e.g., via a constant region, a linker, or both).

28. The ADC of any of paragraphs 1-27, wherein the peptide is coupled to the antibody molecule by an enzymatic ligation, e.g., using Sortase A (SrtA), e.g., via a sortase recognition sequence (e.g., LPETGGG (SEQ ID NO: 244)).

29. The ADC of any of paragraphs 1-28, wherein the peptide comprises a sortase donor sequence, e.g., N-terminal GGG.

30. The ADC of any of paragraphs 1-29, wherein the ADC comprises a linker, e.g., a (Gly-Ser)n linker sequence, where n=2 to 20 (SEQ ID NO: 262), between the antibody molecule and the peptide.

31. The ADC of any of paragraphs 1-30, wherein the ADC has a peptide-to-antibody molecule ratio between about 2 and about 8, e.g., between about 2 and about 4, e.g., as determined by mass spectrometry.

32. The ADC of any of paragraphs 1-31, wherein the ADC has a peptide-to-antibody molecule ratio of about 2, e.g., as determined by mass spectrometry.

33. The ADC of any of paragraphs 1-32, wherein the ADC has an in vitro bactericidal activity against *P. aeruginosa* at a concentration of about 2 µg/mL to about 50 µg/mL, e.g., about 3.1 µg/mL to about 25 µg/mL.

34. The ADC of any of paragraphs 1-33, wherein the ADC has an in vitro bactericidal activity against *P. aeruginosa* at a concentration that differs by 50% or less, e.g., 45%, 40%, 35%, 30%, 25%, 20%, 15%, 10%, or less, compared to a reference ADC, e.g., VSX-1.

35. The ADC of any of paragraphs 1-34, wherein the ADC has a mean lytic concentration (MLC) of about 500 µg/mL or more, e.g., 800 µg/mL or more, for *P. aeruginosa*.

36. The ADC of any of paragraphs 1-35, wherein the ADC has an MLC that differs by 50% or less, e.g., 45%, 40%, 35%, 30%, 25%, 20%, 15%, 10%, or less, compared to a reference ADC, e.g., VSX-1, for *P. aeruginosa*.

37. The ADC of any of paragraphs 1-36, wherein the ADC has a CC50 (the concentration at which 50% cytotoxicity of mammalian cells is observed) of about 500 µg/mL or more, e.g., 800 µg/mL or more, for *P. aeruginosa*.

38. The ADC of any of paragraphs 1-37, wherein the ADC has a CC50 that is higher, e.g., at least 0.5, 1, 2, 3, 4, or 5-fold higher than a reference ADC, e.g., VSX-1, for *P. aeruginosa*.

39. The ADC of any of paragraphs 1-38, wherein the ADC has an improved biodistribution compared to a reference ADC, e.g., VSX-1, e.g., as determined by pharmacokinetics measurements, whole body imaging, in vivo imaging, ELISA, and/or mass spectrometry of blood samples.

40. An ADC comprising an antibody molecule comprising two VHs and two VLs,
  wherein the VH is covalently coupled with a peptide comprises the amino acid sequence of SEQ ID NO: 257; and
  wherein the VH comprises an HCDR1 comprising the amino acid sequence of SEQ ID NO: 105; an HCDR2 comprising the amino acid sequence of SEQ ID NO: 106; and an HCDR3 comprising the amino acid sequence of SEQ ID NO: 107; and
  wherein the VL comprises an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112.

41. An ADC comprising an antibody molecule comprising two VHs and two VLs,
  wherein the VH is covalently coupled with a peptide comprises the amino acid sequence of SEQ ID NO: 257; and
  wherein the VH comprises an HCDR1 comprising the amino acid sequence of SEQ ID NO: 108; an HCDR2 comprising the amino acid sequence of SEQ ID NO: 146; and an HCDR3 comprising the amino acid sequence of SEQ ID NO: 107; and
  wherein the VL comprises an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112.

42. The ADC of paragraph 40 or 41, wherein the VH comprises the amino acid sequence of SEQ ID NO: 117, and wherein the VL comprises the amino acid sequence of SEQ ID NO: 135.

43. The ADC of any of paragraphs 40-42, wherein the peptide is coupled to the C-terminus of the VH via a (Gly-Ser)$_n$ linker.

44. The ADC of any of paragraphs 1-43, wherein the antibody molecule comprises a modified sulfatase motif.

45. The ADC of paragraph 44, wherein the modified sulfatase motif has the formula:

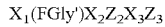

where FGly' has the formula:

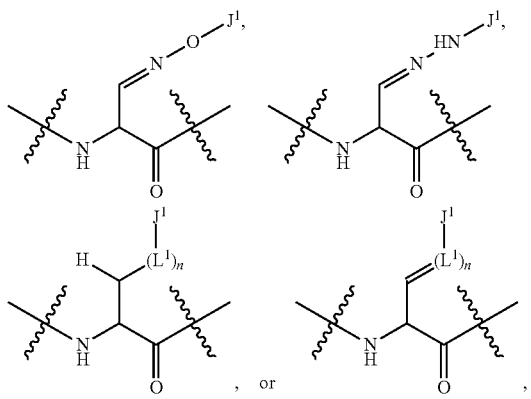

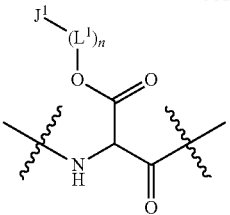

HIPS chemistry
  wherein J$_1$ is the covalently coupled antimicrobial peptide;
  each L$_1$ is a divalent moiety independently selected from alkylene, substituted alkylene, alkenylene, substituted alkenylene, alkynylene, alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;
  n is a number selected from zero to 40;
  Z$_2$ is a proline or alanine residue;
  X$_1$ is present or absent and, when present, is any amino acid, with the proviso that when the sulfatase motif is at an N-terminus of the polypeptide, X$_1$ is present;
  X$_2$ and X$_3$ are each independently any amino acid; and
  Z$_3$ is a basic amino acid.

46. The ADC of paragraph 44 or 45, wherein the antibody molecule presents the covalently coupled antimicrobial peptide on a solvent-accessible surface when in a folded state.

47. The ADC of any of the preceding paragraphs, wherein the modified sulfatase motif is a heterologous modified sulfatase motif.

48. The ADC of any of the preceding paragraphs, wherein the modified sulfatase motif comprises or consists of 12 or less (e.g., 11 or less, 10 or less, 9 or less, 8 or less, 7 or less, or 6 or less) amino acid residues.

49. The ADC of any of the preceding paragraphs, wherein the modified sulfatase motif is located in the ADC at an N-terminus of an antibody molecule chain, a C-terminus of an antibody molecule chain, or a solvent-accessible loop of the antibody molecule.

50. The ADC of any of the preceding paragraphs, wherein the modified sulfatase motif is located in a heavy chain (or a fragment thereof) of the antibody molecule.

51. The ADC of any of the preceding paragraphs, wherein the modified sulfatase motif is located in a constant region of the heavy chain (e.g., CH1, CH2, or CH3), e.g., at a terminus (e.g., C-terminus) of the heavy chain constant region.

52. The ADC of any of the preceding paragraphs, wherein the modified sulfatase motif is located in a light chain (or a fragment thereof) of the antibody molecule.

53. The ADC of any of the preceding paragraphs, wherein the modified sulfatase motif is located in a constant region of a light chain, e.g., at a terminus (e.g., C-terminus) of the light chain constant region.

54. The ADC of any of the preceding paragraphs, wherein the ADC comprises a plurality of modified sulfatase motifs, e.g., two or more (e.g., 3, 4, 5, 6, 7, 8, or more) modified sulfatase motifs.

55. The ADC of paragraph 54, wherein the modified sulfatase motifs are located in a heavy chain (or a fragment thereof), a light chain (or a fragment thereof), or both, of the antibody molecule.

56. The ADC of paragraph 54 or 55, wherein the modified sulfatase motifs are located in a constant region of the heavy chain (e.g., one or more of CH1, CH2, or CH3), a constant region of the light chain, or both.

57. The ADC of any of paragraphs 54-56, comprising two or more heavy chains, each comprising a modified sulfatase motif.

58. The ADC of any of paragraphs 54-57, comprising two or more light chains, each comprising a modified sulfatase motif.

59. The ADC of any of the preceding paragraphs, wherein $Z_3$ is arginine (R).

60. The ADC of any of the preceding paragraphs, wherein $X_1$, when present, $X_2$, and $X_3$ are each independently an aliphatic amino acid, a sulfur-containing amino acid, or a polar, uncharged amino acid.

61. The ADC of any of the preceding paragraphs, wherein $X_1$, when present, is L, M, V, S or T. In an embodiment, $X_2$ and $X_3$ are each independently S, T, A, V, G, or C.

62. A pharmaceutical composition comprising an ADC of any of paragraphs 1-58 and a pharmaceutically acceptable carrier.

63. An ADC of any of paragraphs 1-61, or a pharmaceutical composition of paragraph 62, for use in a method of treating or preventing a bacterial infection associated with *Pseudomonas* in a subject.

64. The ADC or composition for use of paragraph 63, wherein the bacterial infection is associated with *Pseudomonas aeruginosa*.

65. The ADC or composition for use of paragraph 63 or 64, wherein the ADC is administered at a dose of 1-10 mg/kg.

66. The ADC or composition for use of any of paragraphs 63-65, wherein the ADC is administered intravenously, subcutaneously, or intranasally or by inhalation.

67. The ADC or composition for use of any of paragraphs 63-66, wherein the ADC is administered prior to or after onset of a symptom associated with the bacterial infection.

68. The ADC or composition for use of any of paragraphs 63-67, wherein the subject has one or more of: pneumonia, a urinary tract infection (UTI), septicemia, meningitis, diarrhea, a soft tissue infection, a skin infection, bacteremia, a respiratory system infection, endocarditis, an intra-abdominal infection, septic arthritis, osteomyelitis, a CNS infection, an ophthalmic infection, cholecystitis, cholangitis, meningitis, typhoid fever, food poisoning, gastroenteritis, enteric fever, shigellosis, a blood stream infection, intra-abdominal sepsis, a brain abscess, meningitis, sepsis, a joint infection, a bone infection, a gastrointestinal infection, or a wound infection.

69. The ADC or composition for use of any of paragraphs 63-68, wherein the bacterial infection is a nosocomial infection or a hospital-acquired infection.

70. The ADC or composition for use of any of paragraphs 63-69, wherein the subject is a human or an animal.

71. The ADC or composition for use of any of paragraphs 63-70, wherein the subject is an immunocompromised patient or a health professional.

72. The ADC or composition for use of any of paragraphs 63-71, wherein the subject has, or is at risk of having, an HIV infection or AIDS, a cancer, a solid organ transplantation, a stem cell transplantation, a sickle cell disease or asplenia, a congenital immune deficiency, a chronic inflammatory condition, a cochlear implant, malnutrition, or a cerebrospinal fluid leak.

73. The ADC or composition for use of any of paragraphs 63-72, wherein the subject is 18 years old or younger, 15 years old or younger, 12 years old or younger, 9 years old or younger, or 6 years old or younger, or is at least 60 years old, at least 65 years old, at least 70 years old, at least 75 years old, or at least 80 years old.

74. The ADC or composition for use of any of paragraphs 63-73, wherein the method further comprises administering to the subject a second antimicrobial agent or therapy.

75. The ADC or composition for use of paragraph 74, wherein the second antimicrobial agent or therapy comprises an antibiotic or a phage therapy.

76. The ADC or composition for use of paragraph 75, wherein the antibiotic is a polymyxin (e.g., colistin) or (I-lactam (e.g., carbapenem, e.g., meropenem)

77. The ADC or composition for use of paragraph 76, wherein the antibiotic is chosen from an aminoglycoside, an ansamycin, a carbacephem, a carbapenem, a cephalosporin, a glycopeptide, a lincosamide, a lipopeptide, a macrolide, a monobactam, a nitrofuran, an oxazolidinone, a penicillin, a penicillin combination, a polypeptide, a quinolone or fluoroquinolone, a sulfonamide, a tetracycline, or a drug 78. The ADC or composition for use of paragraph 76 or 77, wherein the antibiotic is chosen from amikacin, gentamicin, kanamycin, neomycin, netilmicin, tobramycin, paromomycin, streptomycin, spectinomycin, geldanamycin, herbimycin, or rifaximin, loracarbef, ertapenem, doripenem, imipenem/cilastatin, meropenem, cefadroxil, cefazolin, cefalotin, cefalothin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, penicillin g, temocillin, ticarcillin, amoxicillin/clavulanate, ampicillin/sulbactam, piperacillin/tazobactam, ticarcillin/clavulanate, bacitracin, colistin, polymyxin b, ciprofloxacin, enoxacin, gatifloxacin, gemitloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (co-trimoxazole), sulfonamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, or trimethoprim.

79. The ADC or composition for use of any of paragraphs 76-78, wherein the antibiotic is chosen from levofloxacin, ciprofloxacin, gentamicin, ceftriaxone, ofloxacin, amikacin, tobramycin, aztreonam, or imipenem/cilastatin.

80. The ADC or composition for use of any of paragraphs 74-79, wherein the second antimicrobial agent or therapy is administered before the ADC is administered, concurrently with the administration of the ADC, or after the ADC is administered.

81. A method of inhibiting or reducing a bacterial infection, the method comprising contacting a cell an ADC of any of paragraphs 1-61, or a pharmaceutical composition of paragraph 62, in an amount effective to inhibit or reduce the bacterial infection.

82. The method of paragraph 81, wherein the ADC or pharmaceutical composition is contacted with the cell in vitro, ex vivo, or in vivo.

83. A kit comprising: an ADC of any of paragraphs 1-61 or a pharmaceutical composition of paragraph 62; and instructions for use of the ADC or pharmaceutical composition.

84. A container comprising an ADC of any of paragraphs 1-61 or a pharmaceutical composition of paragraph 62.

85. A nucleic acid molecule encoding:
 (a) a VH, a VL, or both, of the antibody molecule of an ADC of any of paragraphs 1-61;
 (b) the antimicrobial peptide of an ADC of any of paragraphs 1-61;
 (c) both (a) and (b); or
 (d) an ADC of any of paragraphs 1-61.

86. A vector comprising the nucleic acid molecule of paragraph 85.

87. A cell comprising the nucleic acid molecule of 64 or the vector of paragraph 86.

88. A method of producing an ADC, the method comprising culturing the cell of paragraph 66 under conditions that allow production of an ADC, thereby producing the ADC.

89. A method of producing an ADC, the method comprising contacting an antibody molecule that binds to LPS with a peptide comprising an antimicrobial peptide, and optionally, a sortase donor sequence, in the presence of a sortase, under conditions that allow a sortase-mediated reaction to occur, thereby producing the ADC.

90. The method of paragraph 89, wherein the antibody molecule comprises a sortase acceptor sequence comprising a sortase recognition sequence, a linker sequence, or both.

91. A method of treating or preventing a bacterial infection, comprising administering to a subject in need thereof an ADC of any of paragraphs 1-61, or a pharmaceutical composition of paragraph 62, in an amount effective to treat or prevent the bacterial infection.

92. Use of an ADC of any of paragraphs 1-61 in the manufacture of a medicament for treating or preventing a bacterial infection.

93. An aldehyde-tagged anti-LPS antibody molecule (e.g., an anti-LPS antibody molecule described herein) comprising a sulfatase motif having an amino acid sequence of:

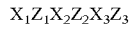

where
 $Z_1$ is a cysteine, a serine, or a 2-formylglycine residue;
 $Z_2$ is a proline or alanine residue;
 $X_1$ is present or absent and, when present, is any amino acid, with the proviso that when the heterologous sulfatase motif is at an N-terminus of the aldehyde tagged polypeptide, $X_1$ is present; and
 $X_2$ and $X_3$ are each independently any amino acid; and
 $Z_3$ is a basic amino acid.

94. The antibody molecule of paragraph 93, which is capable of presenting a covalently coupled antimicrobial peptide on a solvent-accessible surface when in a folded state.

95. The antibody molecule of paragraph 93 or 94, wherein the sulfatase motif is a heterologous sulfatase motif, and/or an unmodified sulfatase motif or a modified sulfatase motif.

96. The antibody molecule of any of paragraphs 93-95, wherein the sulfatase motif comprises or consists of 12 or less (e.g., 11 or less, 10 or less, 9 or less, 8 or less, 7 or less, or 6 or less) amino acid residues.

97. The antibody molecule of any of paragraphs 93-96, wherein the sulfatase motif is located in the ADC at an N-terminus of an antibody molecule chain, a C-terminus of an antibody molecule chain, or a solvent-accessible loop of the antibody molecule.

98. The antibody molecule of any of paragraphs 93-97, wherein the sulfatase motif is located in a heavy chain (or a fragment thereof) of the antibody molecule.

99. The antibody molecule of any of paragraphs 93-98, wherein the sulfatase motif is located in a constant region of the heavy chain (e.g., CH1, CH2, or CH3), e.g., at a terminus (e.g., C-terminus) of the heavy chain constant region.

100. The antibody molecule of any of paragraphs 93-99, wherein the sulfatase motif is located in a light chain (or a fragment thereof) of the antibody molecule.

101. The antibody molecule of any of paragraphs 93-100, wherein the sulfatase motif is located in a constant region of a light chain, e.g., at a terminus (e.g., C-terminus) of the light chain constant region.

102. The antibody molecule of any of paragraphs 93-101, wherein the ADC comprises a plurality of sulfatase motifs, e.g., two or more (e.g., 3, 4, 5, 6, 7, 8, or more) modified sulfatase motifs.

103. The antibody molecule of paragraph 102, wherein the sulfatase motifs are located in a heavy chain (or a fragment thereof), a light chain (or a fragment thereof), or both, of the antibody molecule.

104. The antibody molecule of paragraph 102 or 103, wherein the sulfatase motifs are located in a constant region of the heavy chain (e.g., one or more of CH1, CH2, or CH3), a constant region of the light chain, or both.

105. The antibody molecule of any of paragraphs 102-104, comprising two or more heavy chains, each comprising a sulfatase motif.

106. The antibody molecule of any of paragraphs 102-105, comprising two or more light chains, each comprising a modified sulfatase motif.

107. The antibody molecule of any of paragraphs 93-106, wherein $Z_3$ is arginine (R).

108. The antibody molecule of any of paragraphs 93-106, wherein $X_1$, when present, $X_2$, and $X_3$ are each independently an aliphatic amino acid, a sulfur-containing amino acid, or a polar, uncharged amino acid.

109. The antibody molecule of any of paragraphs 93-108, wherein $X_1$, when present, is L, M, V, S or T. In an embodiment, $X_2$ and $X_3$ are each independently S, T, A, V, G, or C.

110. A method of producing an ADC comprising contacting an aldehyde-tagged anti-LPS antibody molecule (e.g., an aldehyde-tagged anti-LPS antibody molecule described herein) and an antimicrobial peptide (e.g., an antimicrobial peptide described herein) under conditions that allows a reaction between an aldehyde of the antibody molecule and a reactive group of the antimicrobial peptide to occur, thereby producing the ADC.

111. The method of paragraph 110, wherein the aldehyde-tagged antibody molecule comprises a 2-formyl-glycine residue (e.g., FGly' at $Z_1$).

112. The method of paragraph 110 or 111, the antimicrobial peptide comprises an aminooxy or hydrazide reactive group.

113. The method of any of paragraphs 110-112, which comprises combining in a reaction mixture the aldehyde-tagged antibody molecule and the antimicrobial peptide.

114. The method of any of paragraphs 110-113, wherein the antimicrobial peptide is contacted with the antibody molecule, or is provided in a reaction mixture, in an amount sufficient to provide for a desired ratio of antimicrobial peptide to antibody molecule, e.g., the ratio of about 1:1, 2:1, 3:1, 4:1, 5:1, 6:1, 7:1, 8:1, or more.

115. The method of any of paragraphs 110-114, wherein the aldehyde-tagged antibody molecule and antimicrobial peptide is coupled by the Hydrazino-iso-Pictet-Spengler (HIPS) ligation.

116. The method of any of paragraphs 110-114, wherein the aldehyde-tagged antibody molecule and antimicrobial peptide is coupled by conjugation with oximes and hydrazides following by reduction.

117. The method of any of paragraphs 110-116, further comprising isolating (e.g., purifying) the ADC, e.g., from a reaction mixture.

118. The method of any of paragraphs 110-117, wherein the aldehyde-tagged antibody molecule is folded before the aldehyde-tagged antibody molecule is contacted with the antimicrobial peptide (e.g., before the aldehyde-tagged antibody molecule is combined with the antimicrobial peptide in a reaction mixture).

119. A composition (e.g., a pharmaceutical composition) comprising an ADC comprising an anti-LPS antibody molecule (e.g., an anti-LPS antibody molecule described herein) and a covalently coupled antimicrobial peptide (e.g., an antimicrobial peptide described herein) and a pharmaceutically acceptable carrier, wherein the antibody molecule comprises a modified sulfatase motif described herein.

120. A reaction mixture comprising an ADC comprising an anti-LPS antibody molecule (e.g., an anti-LPS antibody molecule described herein) and an antimicrobial peptide (e.g., an antimicrobial peptide described herein) and a pharmaceutically acceptable carrier, wherein the antibody molecule comprises a sulfatase motif (e.g., a modified sulfatase motif) described herein.

121. A method of treating or preventing a bacterial infection or a related disorder, comprising administering to a subject in need thereof an ADC, or a pharmaceutical composition comprising an ADC, in an amount effective to treat or prevent the bacterial infection or related disorder, wherein the ADC comprises an anti-LPS antibody molecule (e.g., an anti-LPS antibody molecule described herein) and a covalently coupled antimicrobial peptide (e.g., an antimicrobial peptide described herein), and wherein the antibody molecule comprises a modified sulfatase motif described herein.

122. The method of paragraph 121, wherein the bacterial infection is associated with a Gram-negative bacterium.

123. The method of paragraph 121 or 122, wherein the bacterial infection is a *Pseudomonas* infection.

124. The method of any of paragraphs 121-123, wherein the bacterial infection is associated with *Pseudomonas aeruginosa*.

125. A nucleic acid comprising a nucleotide sequence encoding an aldehyde-tagged anti-LPS antibody molecule described herein.

126. An anti-LPS antibody molecule or ADC binds to an epitope described herein, wherein the antibody molecule or ADC comprises a modified sulfatase motif (e.g., a modified sulfatase motif described herein).

127. The antibody molecule or ADC of paragraph 126, which binds to a hyper-phosphorylated HepI residue in core LPS of *Pseudomonas aeruginosa*.

128. An ADC comprising an anti-LPS antibody molecule (e.g., an anti-LPS antibody molecule described herein) and a covalently coupled antimicrobial peptide (e.g., an antimicrobial peptide described herein), wherein the antimicrobial peptide is coupled to the antibody molecule via
 (a) lysine conjugation (e.g., using a surface exposed lysine as an antibody reactive group);
 (b) interchain disulfides (e.g., using disulfides linking HC-HC or HC-LC);
 (c) a non-native amino acid (e.g., an amino acid substituted with aldehyde, azide, or alkyne); or
 (d) a biodegradable polymer (e.g., lysine or thiol).

129. The ADC of paragraph 128, wherein the antimicrobial peptide is coupled to the antibody molecule via (a), and wherein the antibody molecule is directly conjugated to an activated amino acid on the antimicrobial peptide.

130. The ADC of paragraph 128, wherein the antimicrobial peptide is coupled to the antibody molecule via (a), and wherein a lysine on the antibody molecule is converted to a thiol reactive group and antibody molecule with the thiol reactive group is ligated to a thiolated antimicrobial peptide.

131. The ADC of paragraph 128, wherein the antimicrobial peptide is coupled to the antibody molecule via (a), and wherein a lysine on the antibody molecule is converted to a free thiol and the antibody molecule with the free thiol is ligated to a thiol reactive antimicrobial peptide.

132. The ADC of paragraph 128, wherein the antimicrobial peptide is coupled to the antibody molecule via (b), and wherein interchain disulfides of the antibody molecule are reduced and the antibody molecule with the reduced interchain disulfides is ligated to a thiol reactive antimicrobial peptide.

133. The ADC of paragraph 128, wherein the antimicrobial peptide is coupled to the antibody molecule via (c), and wherein the antibody molecule is ligated to the antimicrobial peptide using click chemistry.

134. The ADC of paragraph 128, wherein the antimicrobial peptide is coupled to the antibody molecule via (d), and wherein the antimicrobial peptide is ligated to a biodegradable polymer and the polymer is ligated to the antibody molecule.

135. A composition (e.g., a pharmaceutical composition) comprising the ADC of any of paragraphs 128-134.

136. A method of treating or preventing a bacterial infection or a related disorder, comprising administering to a subject in need thereof an ADC of any of paragraphs 128-134, or a pharmaceutical composition of paragraph 135, in an amount effective to treat or prevent the bacterial infection or related disorder.

EXAMPLES

The studies described herein identify antibody-drug conjugates (ADCs) as an important therapeutic strategy that can result in an effective anti-microbial agent. To this end, the examples focused on the pathogenic gram-negative bacteria *Pseudomonas aeruginosa*. An exemplary monoclonal antibody, VSX, that binds to an inner core glycan moiety on lipopolysaccharide (LPS) that is essential for *P. aeruginosa* viability was engineered. Based on its specific binding profile, homology modelling, and NMR analysis, the 2,4-phospho-heptose sugar found in the inner core LPS was identified as its core epitope. An ADC was designed by fusing an antimicrobial peptide at the C-terminal end of the $V_H$ and/or $V_L$-chain of VSX. This ADC rapidly kills *P. aeruginosa* strains, demonstrates low levels of toxicity to mammalian cells and protects mice from *P. aeruginosa* lung infection when administered therapeutically. Furthermore, it was found that the ADC is synergistic with anti-*Pseudomo-*

*nas* classes of antibiotics. This approach can be a widely useful strategy to target specific pathogenic microorganisms and thereby be microbiota sparing.

Example 1: Engineering of VSX

LPS represents an ideal target for construction of an anti-drug conjugate (ADC). First, the antigen is present at high copy number (>$10^7$ copies per cell)(9), which is 10-100 fold higher than typical antigens targeted by tumor-directed ADCs. Second, analysis of available genetic information indicates that several portions of LPS are likely to be highly conserved across *P. aeruginosa* strains, particularly within the inner core. Both the WaaP (4-O phosphorylation) and WapP (2-O phosphorylation) gene products are essential genes for *P. aeruginosa* growth in vitro and in vivo (Skurnik D, et al. 2013. PLoS Pathog 9:e1003582) and are present in all sequenced strains (Winsor G L, et al. 2016. Nucleic Acids Res 44:D646-53). Therefore, selective pressure applied by an antibody targeting the gene products of these proteins will have a decreased probability for escape mutants appearing as to date these mutants have been reported to be non-viable (Delucia A M, et al. 2011. MBio 2). Additionally, these genes are part of an operon unique to *Pseudomonas* spp: glnE-ilvE-waaF-waaC-waaG-waaP-PA5008-PA5007-PA5006 (Winsor G L, et al. 2016. Nucleic Acids Res 44:D646-53); suggesting that specific antibodies should only target *Pseudomonas* spp over other gram-negative bacteria.

To experimentally test this rationale, a mouse antibody that demonstrated strong binding to isolated LPS from *P. aeruginosa* was isolated. Systematic engineering of this antibody—humanization, improvement of drug-like properties, increase of affinity—led to the identification of monoclonal antibody VSX. This antibody is >85% identical to human germline, contains no glycosylation sites (except in the constant region) or unpaired cysteines and expresses well in CHO cells. Antibody binding assessed by Western Blot confirms that VSX binds to isolated *P. aeruginosa* LPS. Specifically, binding to smooth LPS extracted from *P. aeruginosa* was detected, whereas none was detected to *E coli* LPS (FIG. 1B). To further characterize the antibody's epitope, mono-, and di-phosphorylated heptose monosaccharides, mimicking the key Hep I and Hep II residues of the inner core binding epitope (see below) were synthesized (synthesis scheme and characterization in Example 10) and used in binding studies and evaluated by bio-layer interferometry and microcalorimetry (FIG. 2). VSX does not bind to either heptose or mono-phosphorylated heptose analogs (2-P-Hep and 4-P-Hep); binding only to di-phosphorylated 2,4-P-Hep monosaccharide. Of note, this binding was not entirely driven by avidity as the Fab domain also binds with similar affinity. The binding to the 2,4-P-Hep was not primarily due to non-specific interactions since a similar but reduced binding to di-phosphorylated mannose (2,4-P-Man) which lacks the methyl-hydroxyl group at C6 position was observed.

Example 2: VSX Binds to *P. aeruginosa* Surface Antigen LPS

Figure 3A:
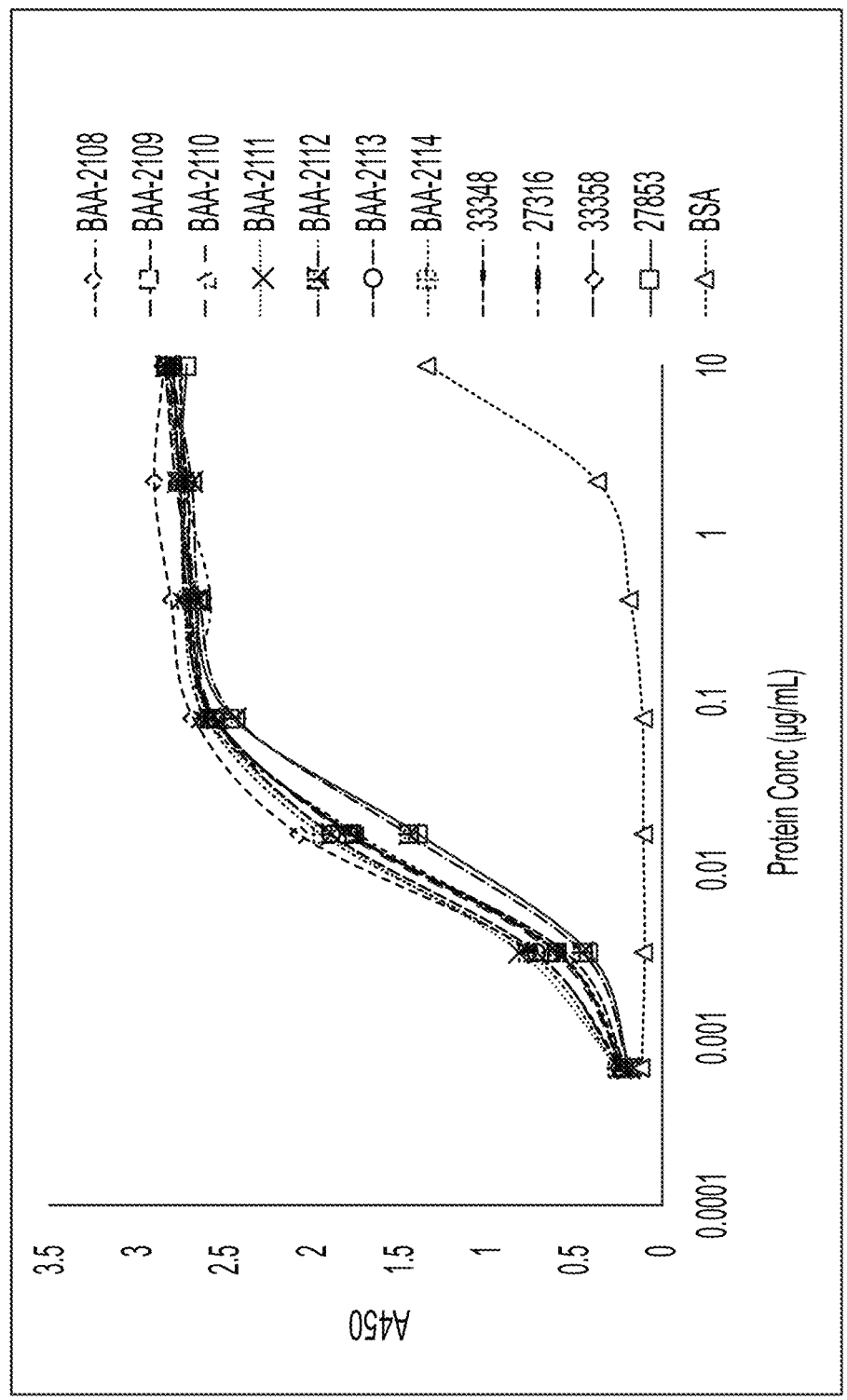
FIG. 3A depicts whole cell ELISA binding of VSX antibody to a plurality of P. aeruginosa strains (as indicated). VSX antibody shows strong binding to multiple P. aeruginosa strains and minimal binding to bovine serum albumin, BSA.
Figure 3B:
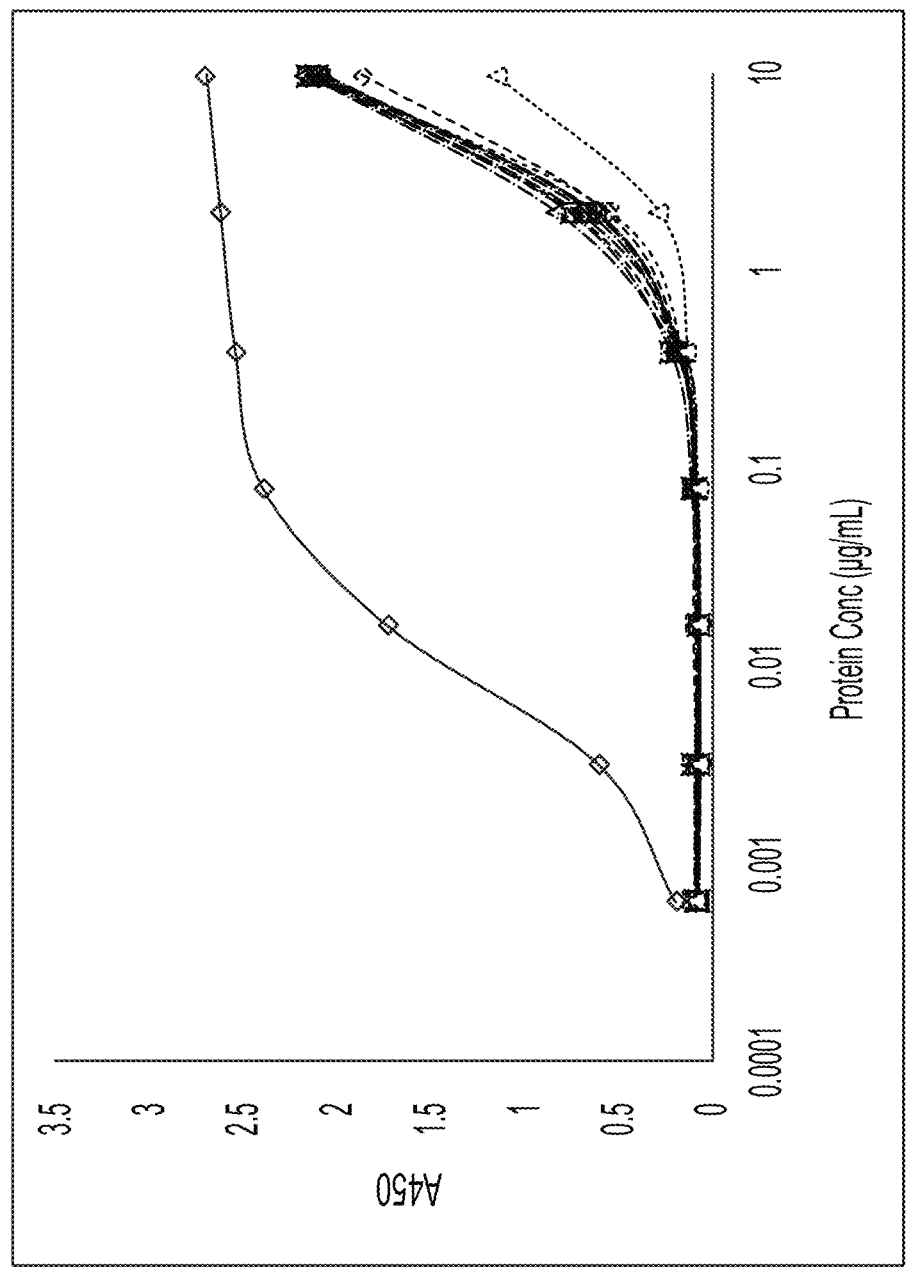
FIG. 3B depicts strong VSX antibody binding to P. aeruginosa strain ATCC 27853 and weak binding to E. coli (dark blue), K. pneumoniae (green), S. typhimurium (light blue), mammalian cells or BSA (red).
Figure 3C:
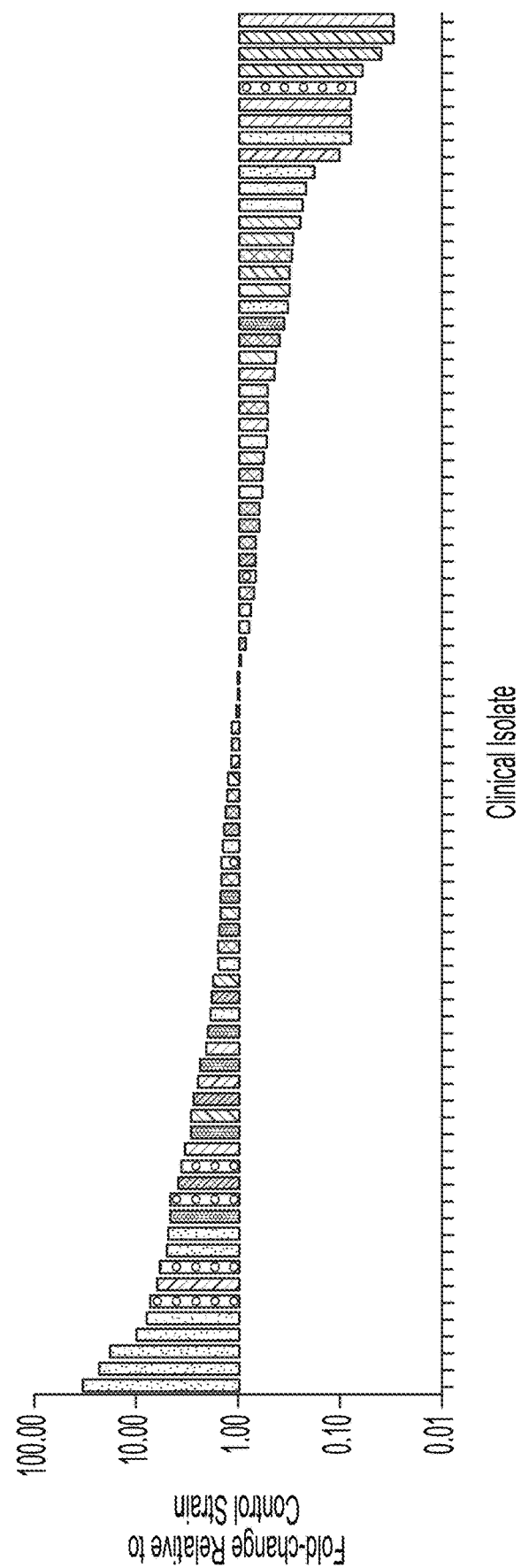
FIG. 3C depicts semi-quantitative analysis of VSX binding in over 100 P. aeruginosa strains from clinical isolates of varying sites of infection using whole cell ELISA. Binding is relative to Pae ATCC 27853.
Figure 17A:
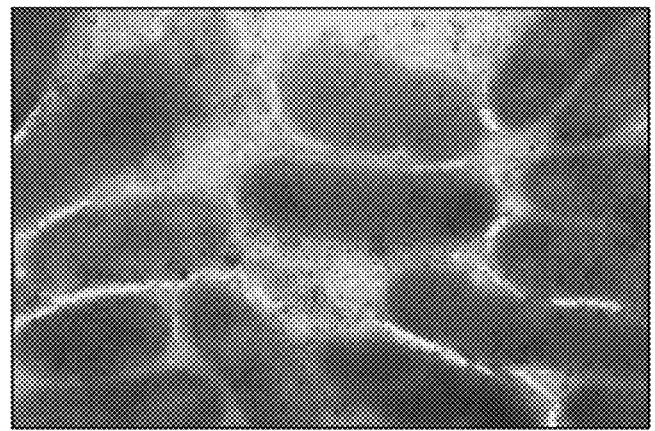
FIGS. 17A-17C depicts electron microscopy of *P. aeruginosa* cells for VSX (A), an anti-alginate antibody (B), and an isotype control antibody (C).
Figure 17B:
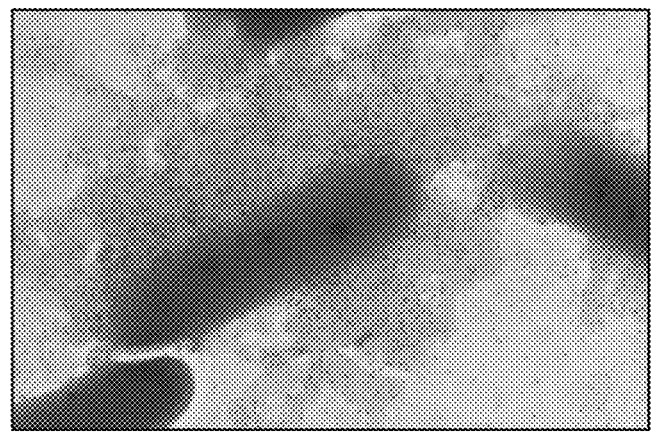
Figure 17C:
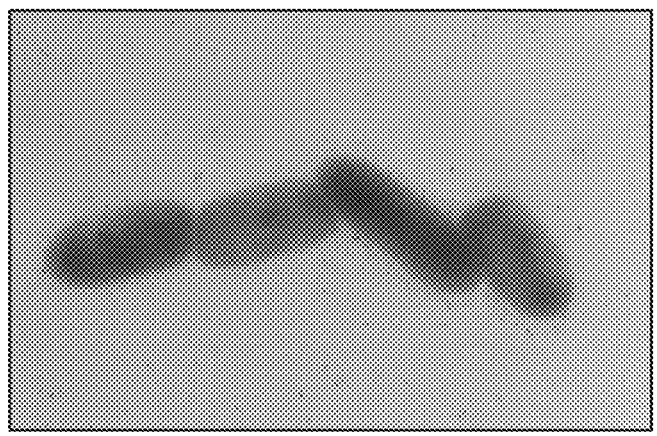

The question of whether the inner core LPS region is accessible at the cell surface of an intact organism and whether this accessibility might be serotype specific is addressed. In a whole bacterial cell ELISA, we find that the epitope is accessible and that VSX binds to 23 diverse *P. aeruginosa* strains including strains resistant to carbapenems, anti-*pseudomonas* third generation cephalosporins or fluoroquinoles (FIG. 3A) suggesting a serotype-independent binding. An apparent avidity of 50-120 pM as determined by ELISA was observed across strains. The antibody does not bind to other common human pathogenic gram-negative bacteria including multiple strains of *Escherichia coli*, *Klebsiella pneumoniae* and *Salmonella typhimurium* (FIG. 3B) or to gram-positive organisms or mammalian cells. Extending this analysis in a semi-quantitative manner, it was found that antibody binding could be detected in over 100 *P. aeruginosa* strains from clinical isolates of varying sites of infection. Furthermore, binding analysis of other *Pseudomonas* species, including *P. fluorescens, P. putida* and *P. stutzeri*, demonstrated binding as well (FIG. 3C). To further confirm these findings, electron microscopy images show that VSX engages proximate to the cell surface in contrast to an antibody that targets alginate (FIGS. 17A-17C). Taken together, these results indicate that VSX binds to the inner core of LPS, present on the outer membrane of *P. aeruginosa*. To confirm these findings and to investigate further the interaction of VSX to the inner core of LPS, additional structural investigations were completed to describe the way by which VSX recognizes the hydrophilic inner core part of LPS.

Example 3: Structural Analysis of Glycan-Fab Interaction

Figure 4A:
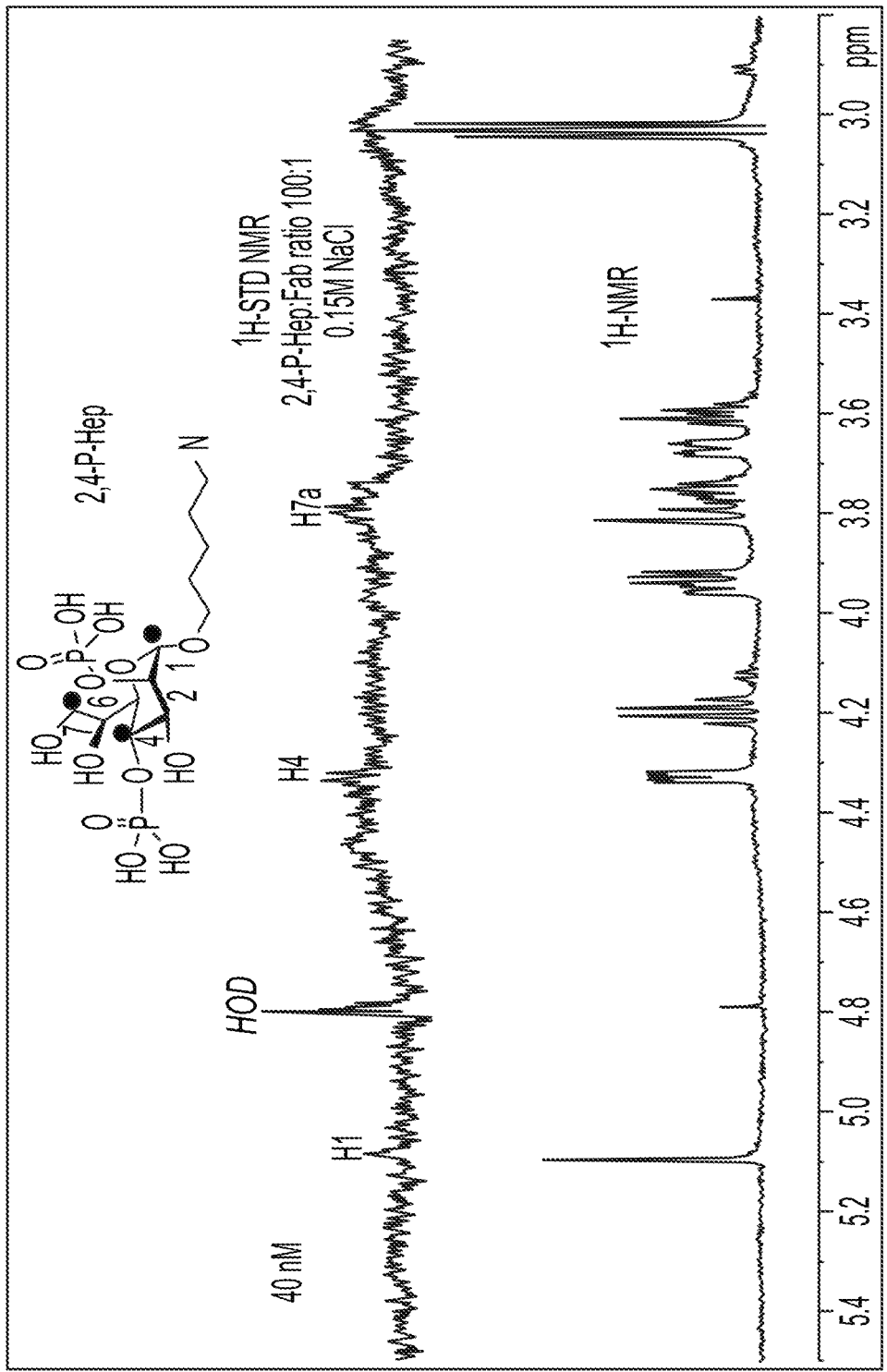
FIG. 4A depicts STD NMR spectrum (A, Top) of 2,4-P-Hep and VSX Fab at 100:1 molar ratio, 0.15M NaCl. VSX binding was shown to bind only to di-phosphorylated heptose (2,4-P-Hep).
Figure 4B:
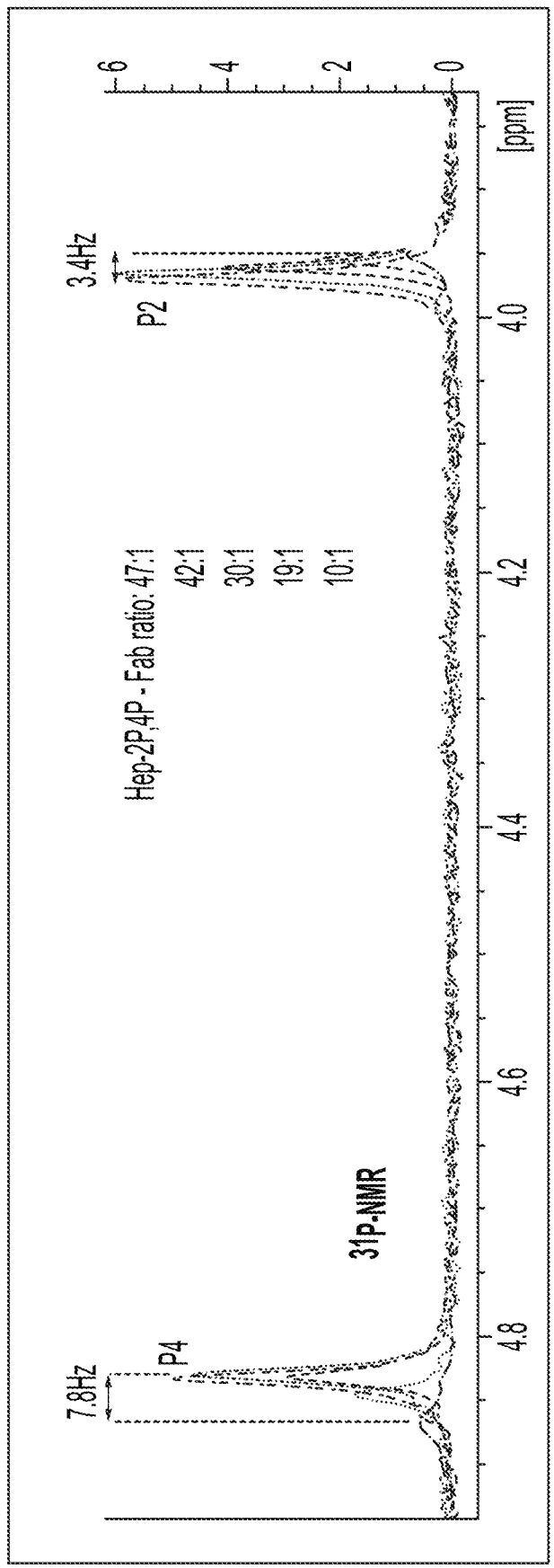
FIG. 4B depicts $^1$H NMR spectrum (A, Bottom) of 2,4-P-Hep, (B) $^{31}$P NMR of 2,4-P-Hep titration in the presence of VSX Fab.
Figure 5A:
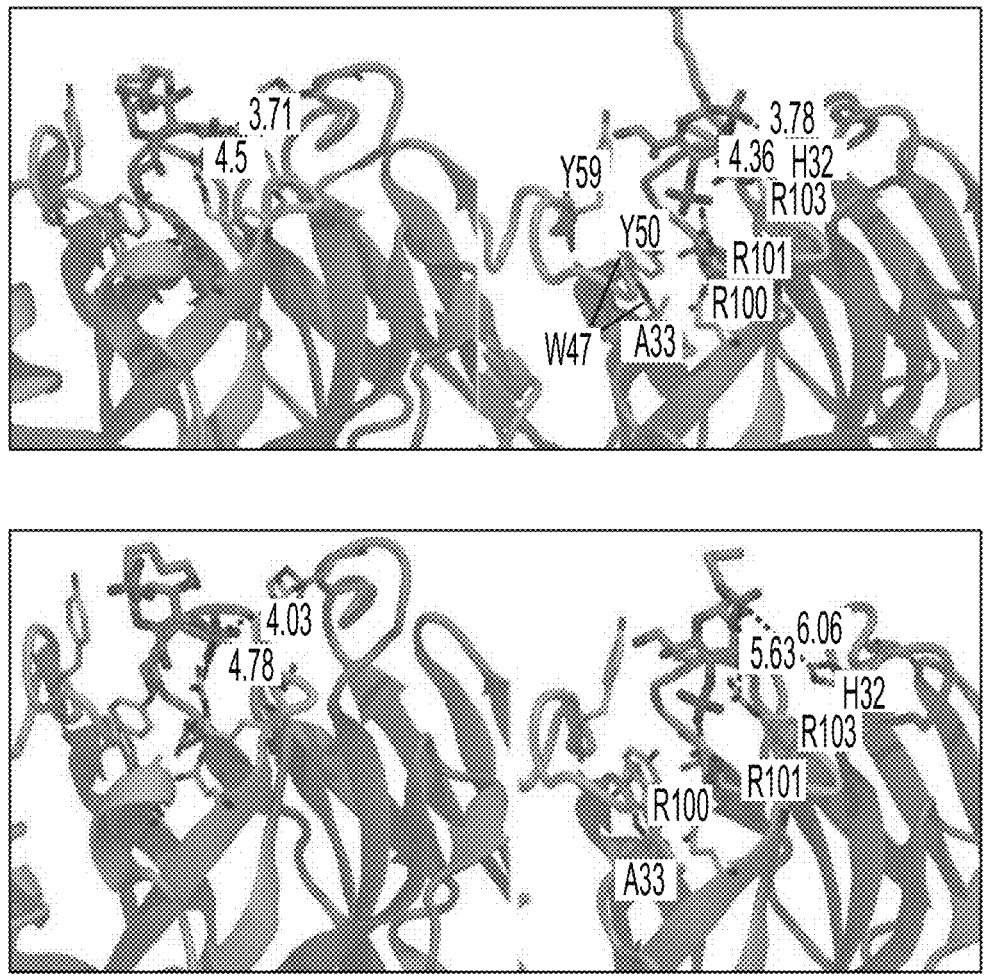
FIG. 5A depicts molecular dynamics (MD) simulation snapshots at 6 and 34 ns of the two docking poses of the 2,4-Hep-VSX complex. The left and right poses orient the monosaccharide with the methyl-hydroxyl group at C6 position and with its 4-phosphate group toward the VSX receptor binding site, respectively.
Figure 18A:
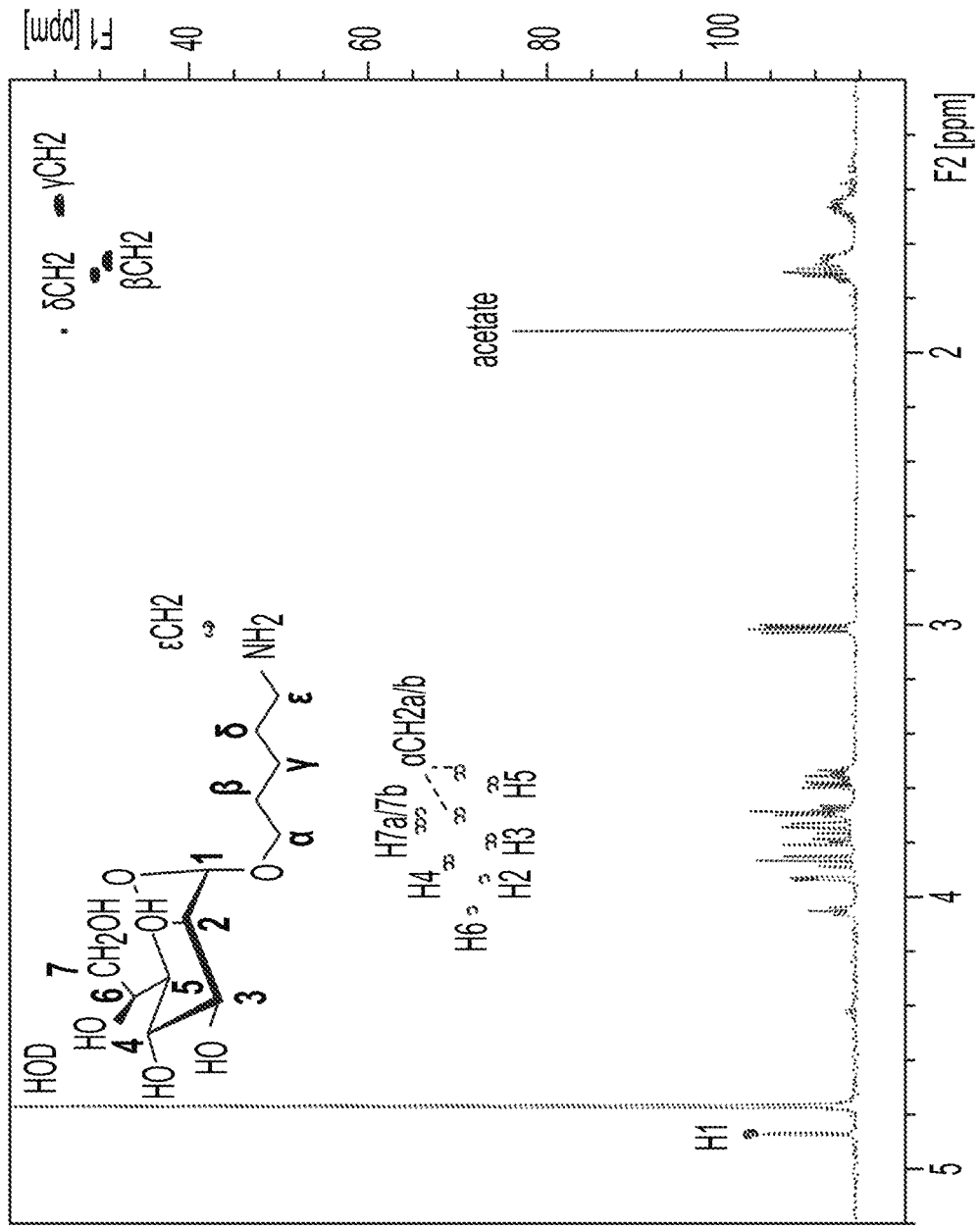
FIGS. 18A-18C Proton and HSQC spectra of Heptose derivatives. Proton (orange) and HSQC spectrum (blue) of (A) Heptose derivative, (B) 4-P-Heptose derivative, and (C) 2,4-P-Heptose derivative with signal assignments.
Figure 18B:
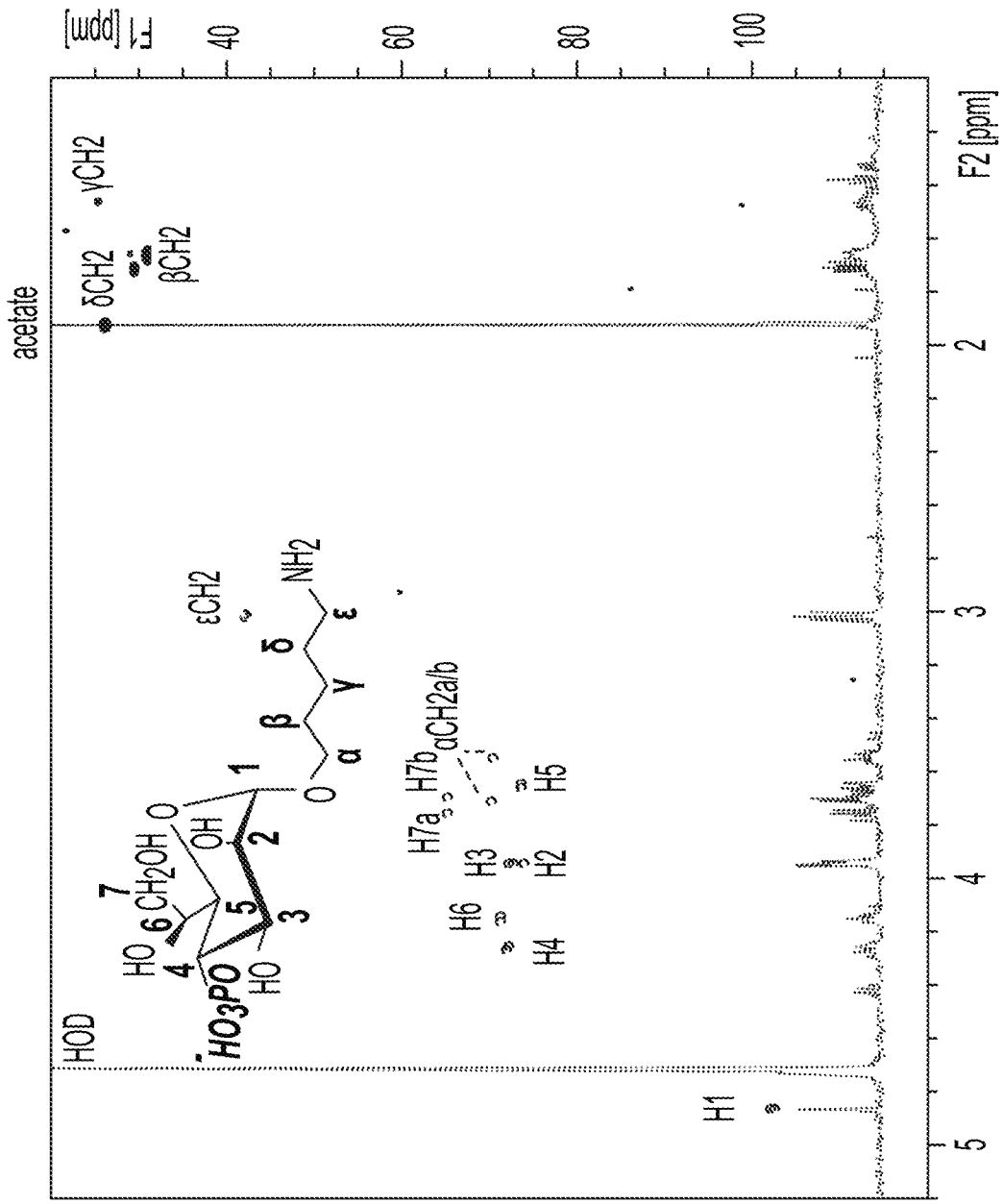
Figure 18C:
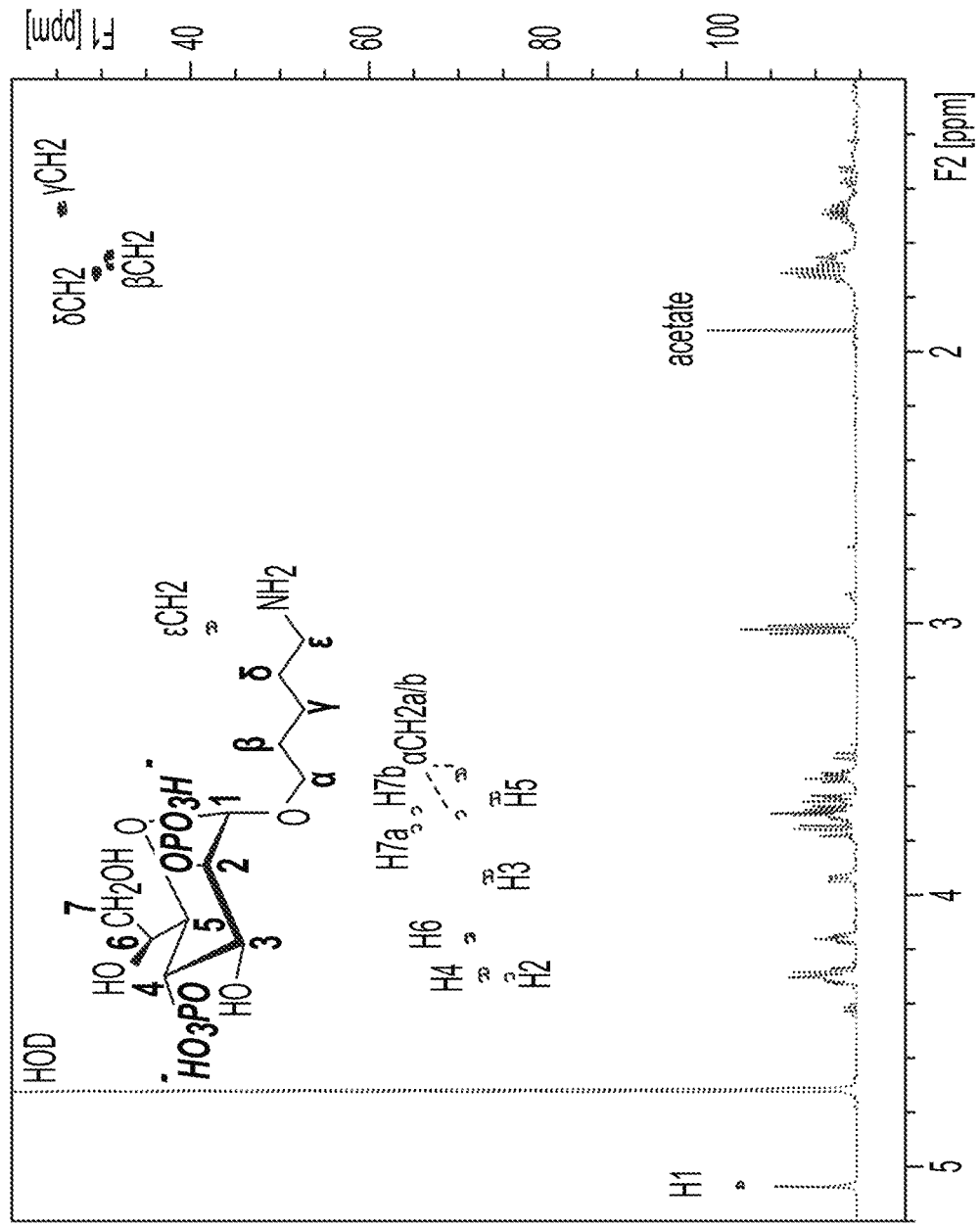
Figure 19:
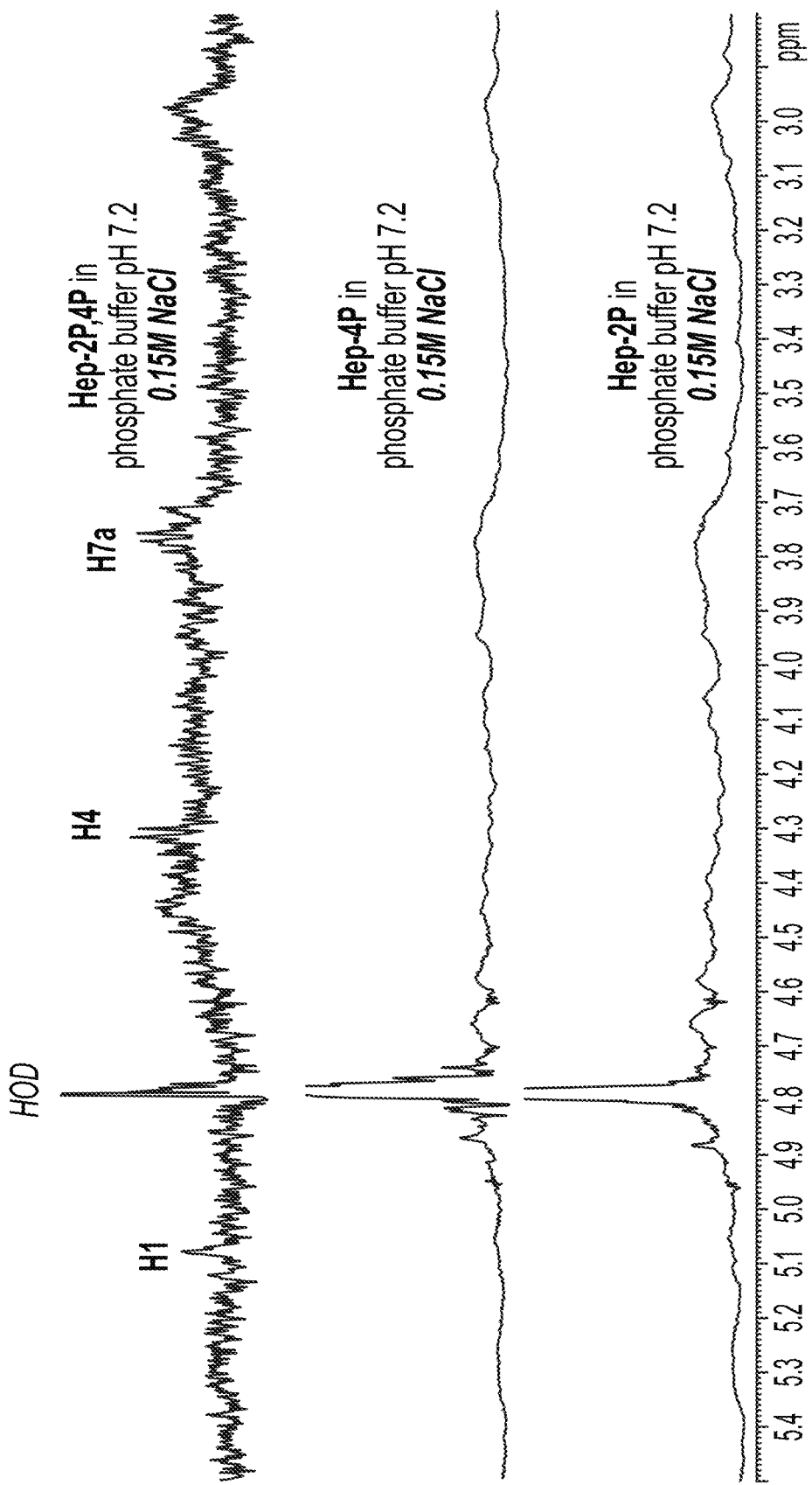
FIG. 19 depicts $^1$H STD NMR spectra of synthetic Heptose derivatives and VSX Fab.
Figure 20:
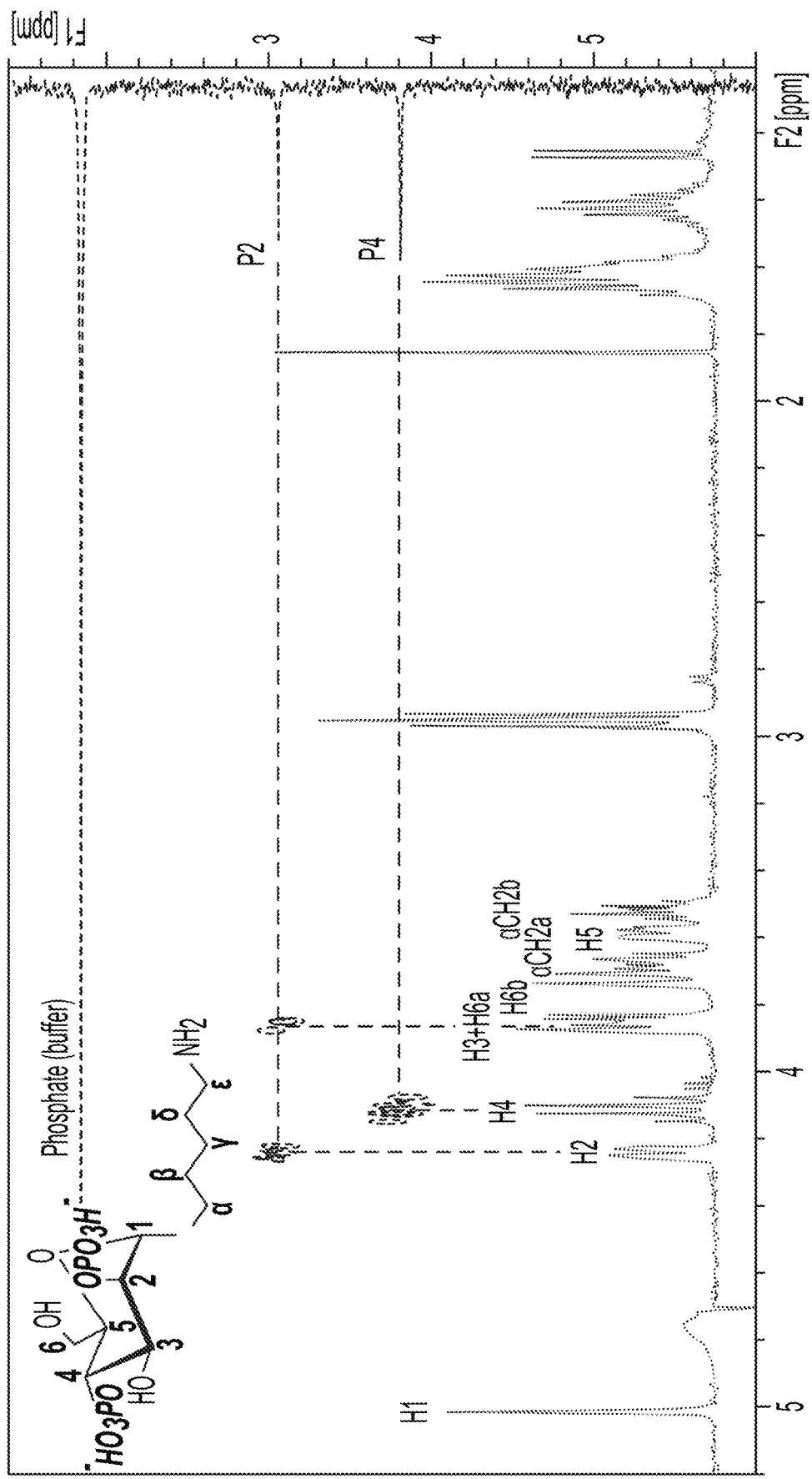
FIG. 20 depicts $^1$H-$^{31}$P HMBC NMR spectrum of 2,4-P-Heptose derivative. Long range correlations between proton and phosphorous signals are shown.

Proton and carbon signals of synthetic monosaccharides were assigned by homo- (COSY and TOCSY, not shown) and heteronuclear NMR spectroscopy (FIGS. 18A-18C). Structural insight into the VSX Fab interactions with the synthetic monosaccharides was studied by $^1$H-STD, $^{31}$P-NMR spectroscopy, molecular modeling and MD simulation. The $^1$H-STD NMR spectra showed that, consistent with previous studies, only the di-phosphorylated heptose (2,4-P-Hep) binds to the VSX Fab domain (FIG. 4A, FIG. 19). Under the measurement conditions the energy transfer from the Fab domain to the H1, H4 and H7a atoms of the 2,4-P-Hep was observed, suggesting their possible spatial proximity to the Fab molecule, in qualitative agreement with the two selected docking poses reported in FIG. 5A left and right. Since $^1$H-NMR does not inform on the role of the phosphate groups, a monosaccharide titration experiment was carried out using $^{31}$P-NMR (FIG. 4B). Prior to the titration experiments, the assignment of the two $^{31}$P signals in the 2,4-P-Hep spectrum was performed by $^1$H-$^{31}$P HMBC NMR as shown in FIG. 20. In the further titration study the 4-P phosphate resonance showed a broader line width and more significant change in chemical shift compared to 2-P phosphate resonance suggesting a stronger binding of 4-P phosphate to the Fab domain compared to 2-P phosphate group.

*P. aeruginosa* core-oligosaccharide has ten sugar residues of which two are anionic Kdo sugars (Kdo I and Kdo II) and two are phosphorylated heptose (Hep I and Hep II) sugars. Together, they form the inner core oligosaccharide bridging the lipid-A and outer core-oligosaccharide moieties. Since the two Kdo sugars are present within most gram-negative LPS molecules and due to the displayed specificity of VSX, this disaccharide is unlikely to be the core epitope of VSX. In most *P. aeruginosa* LPS molecules, the Hep II sugar is mono-phosphorylated at the second position and exhibits strain specific modifications while the Hep I sugar is di-phosphorylated at second and fourth positions with lower levels of modification. Previous studies have demonstrated that the fourth position phosphorylation of Hep I sugar is essential not only for the complete synthesis of LPS but also for bacterial viability (Delucia A M, et al. 2011. MBio 2). Given these constraints, the highly conserved Hep I sugar moiety is likely within the core epitope for VSX. Although the Hep I sugar moiety is also present in *E. coli* LPS, it is mono-phosphorylated at only the second position and is not recognized, further suggesting the importance of a phosphate group in the fourth position to enable VSX binding. Notably, modeling and STD studies suggest that the binding is driven by the simultaneous action of two phosphate groups, thus the relative contribution of the 2-O phosphate group is likely significant.

Figure 5B:
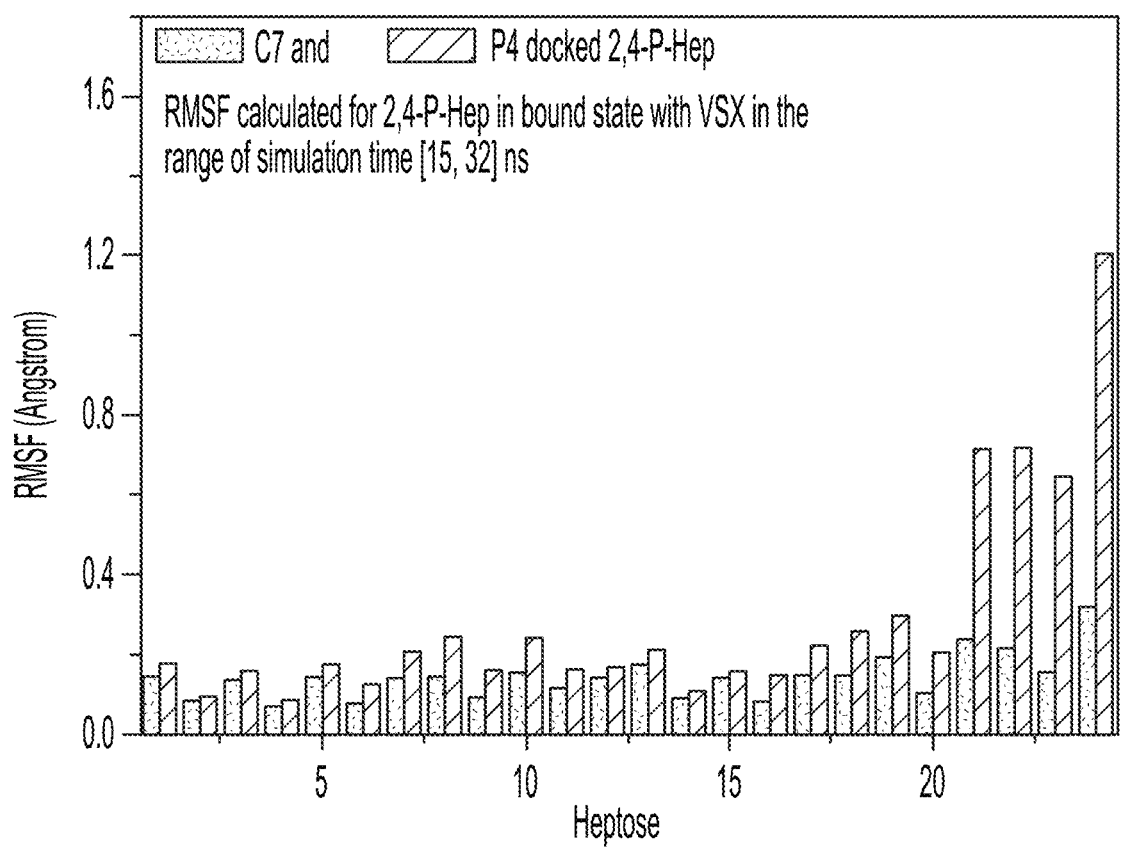
FIG. 5B depicts the Root Mean Square Fluctuation (RMSF) of the Hep residues in the bound state with VSX in two different poses.

Molecular docking of 2,4-P-heptose monosaccharide, a monosaccharide mimic of Hep I, with the Fv domain identified two closely related binding poses wherein the monosaccharide bound either with its 4-phosphate group or with its methyl-hydroxyl group at C6 position (FIG. 5A) interacting with the R100 residue at the bottom of the pocket. These two poses differ by a 60° rotation of the sugar and they both allow the presence of an extended sugar moiety at the reducing and non-reducing end of the bound 2,4-P-Hep monosaccharide. The Autodock 4.2 scoring function gives −3.8 and −6.0 Kcal mol$^{-1}$ as binding energy estimations for the two poses, respectively. To investigate further, MD simulation was applied to refine the geometries of both docking poses, giving rise to a dynamic description of the 2,4-Hep-VSX molecular recognition event, with snapshots completed at both early and later stages (i.e. at 6 and 34 ns, FIG. 5A). The Root Mean Square Fluctuation (RMSF) of the Hep residue in bound state with VSX (FIG. 5B) and the Autodock scoring function indicates that the binding energy is slightly greater when, in addition to the recognition of 2-P and 4-P by R103 and R101, the aliphatic tail of the sugar C6-C7 is recognized by one of the hedges of the VSX binding pocket, formed by Trp47, Tyr50, and Tyr59. This result suggests that dispersive forces also likely contribute to the 2,4-P-Hep-VSX molecular recognition event, suggesting that this binding pose corresponds to a stronger binding interaction, as also supported by shorter distances between ligand and receptor contact sites at later stage of the MD simulation.

To confirm the above analysis, we probed the three CDR Arg residues (VH: R101, R103 and VL: R100) of the antigen binding pocket to confirm that they are central to binding. Mutation of any of these Arg residues to Gln is predicted to eliminate the side chain positive charge and remove a significant portion of the antigen interface area. Consistent with this model, none of the Arg to Gln mutants showed any measurable binding to mono-phosphorylated heptose sugars (2P-Hep or 4P-Hep) suggesting the importance of these Arg residues for binding (FIG. 6A). Additionally, the mutation of monosaccharide contact residues (VH: A33, E99, VL:H32) resulted in abolished binding, whereas mutation of non-contact residues within HCDR2 (VH: D54 and D56) did not demonstrate significant loss of binding. That mutation of any of these CDR Arg residues to Gln abolished antigen binding suggests the importance of the electrostatic interactions. The commonly observed HCDR2 sequon Xaa-Xaa-Gly-Gly-(Ser/Thr/Gly) has been implicated in binding to a negatively charged groups on carbohydrate, DNA and proteins(13). In VSX, this sequon is present with acidic amino acid sequence Ser-Ser-Asp-Gly-Asp (SEQ ID NO: 263); mutation of these Asp residue to Gln does not influence the 2,4-Hep binding.

Example 4: Activity of VSX

Figure 6B:
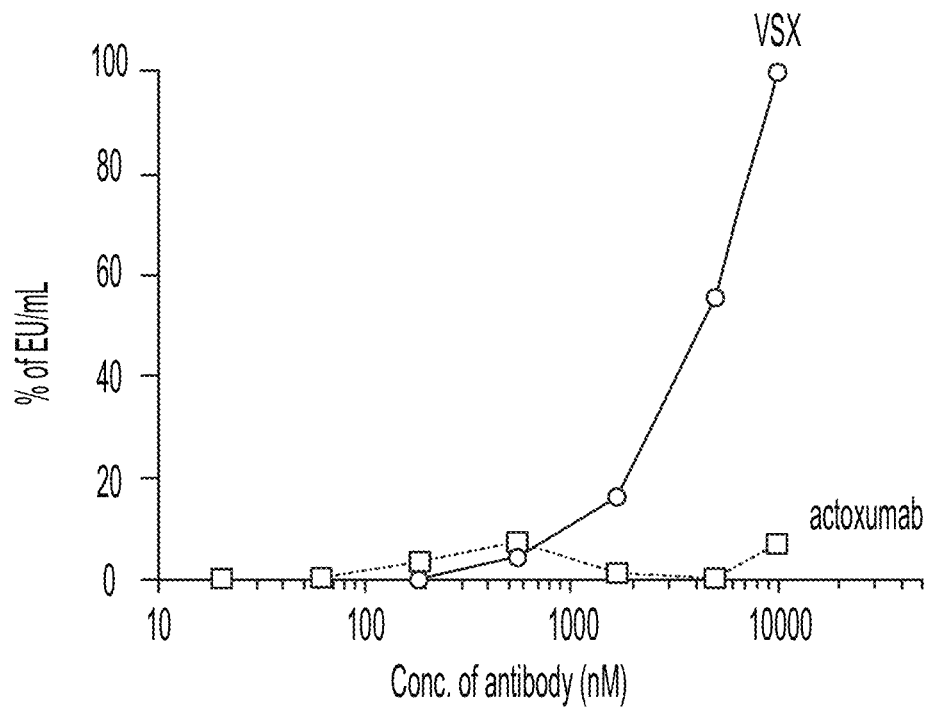
FIG. 6B depicts binding of either VSX (dark colored) or a control antibody (light colored) to LPS.
Figure 6C:
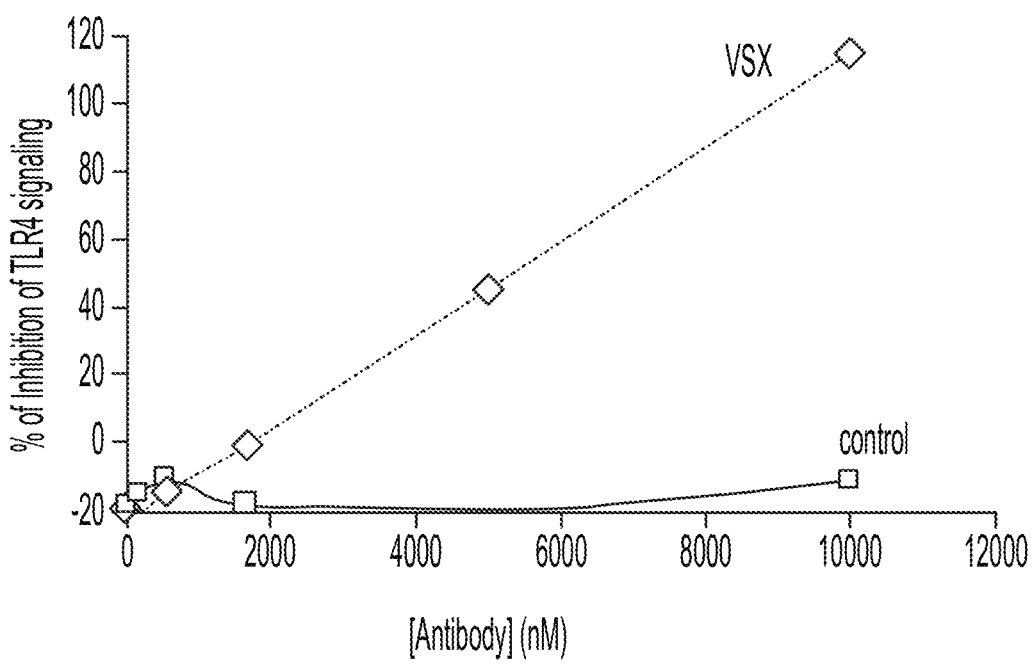
FIG. 6C shows that VSX binding inhibits LPS-mediated (Toll-like receptor 4) TLR4 activation. Diamonds=VSX; Squares=negative control antibody.
Figure 6D:
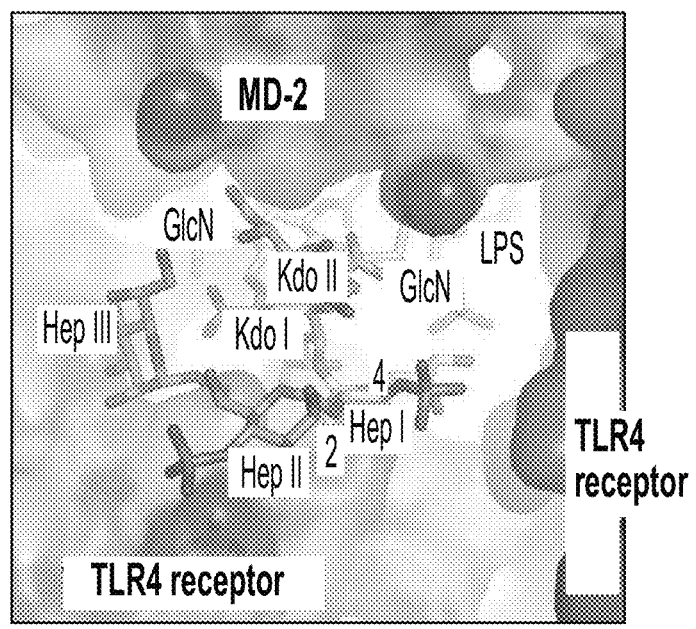
FIG. 6D depicts a structural model of the TLR4 receptor-MD-2-LPS complex.

In the presence of Complement alone, VSX demonstrated some direct bactericidal activity in vitro (~20% killing at 1 μg/mL). When phagocytes were added in the system, opsonophagocytosis killing activity was detected but was not complete at 20 μg/mL. Therefore, other additional mechanisms of protection that could be mediated by VSX were further explored. Specifically, it has been reported that shedding of LPS may cause pathophysiological manifestations upon hyperstimulation of the host immune system—initiated by activation of toll-like receptors (TLRs) which, in turn, can lead to septic shock (Singer M, et al. 2016. JAMA 315:801-10). Given this pathophysiology, an anti-LPS mAb could play a vital role in neutralizing LPS by limiting LPS shedding, promoting its serum clearance and inhibiting the LPS-mediated binding to TLR and concomitant activation of immune system. Consistent with this pathway as well as the binding site of VSX, VSX showed strong binding to LPS relative to control antibody (FIG. 6B). In addition, a HEK-blue reporter assay that measures the activation of TLR4 receptor by free LPS demonstrated that VSX inhibited LPS-mediated TLR4 activation (FIG. 6C).

Example 5: Selection of AMP

VSX armed with direct killing activity, without the need of either complement or phagocytes, was sought through the addition of a bactericidal payload that could also significantly increase the overall level of bacterial killing that may achieve any antibacterial antibody. For this purpose, antimicrobial peptides (AMPs) were chosen due to their rapid killing activity and the proven efficacy of their mechanism of action, very close to the last line of defense of our current antibiotics, the polymyxins (Velkov T, et al. 2016. Future Med Chem 8:1017-25). There are at least four distinct classes of antimicrobial peptides, based on their secondary structures: β-sheet, α-helix, extended, and loop (Bahar A A, Ren D. 2013. Pharmaceuticals (Basel) 6:1543-75). Since AMP activity in the context of covalent addition to an antibody was focused on, the loop class was eliminated, due to the requirement of disulfides to stabilize secondary structure, as well as peptides that require oligomerization to elicit cell killing activity. With these limitations in mind, the class of amphipathic α-helical peptides that act at the cell surface clearly represent a desirable peptide class for formation of an ADC. Furthermore, reports indicate that binding of ~$10^6$ AMPs/cell will induce cell killing; even with a drug-antibody ratio (DAR) of 1:1, binding to 10% of the LPS would be sufficient to induce killing, with lower amount required for higher DARs.

Figure 7A:
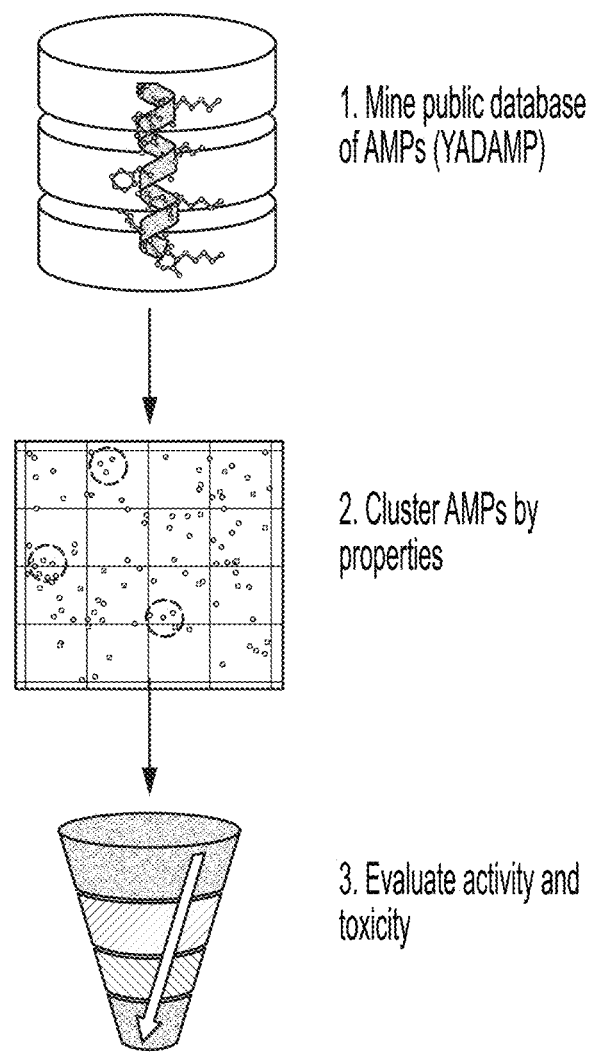
FIG. 7A depicts the workflow for the identification of an antimicrobial peptide (AMP).

To identify an optimal AMP payload for an ADC, a robust structure-activity campaign was completed to identify α-helical AMPs that (1) are active at the cell surface and hence do not require internalization; (2) are bactericidal against *P. aeruginosa* and (3) have low hemolytic and cytotoxic activity. Initially, a bioinformatics-driven workflow (mine public database of AMPs (YADAMP)→cluster AMPs by properties→evaluate activity and toxicity) was utilized to select AMPs for experimental characterization to identify potent payloads with a high therapeutic index (FIG. 7A). Selecting the most potent of these can be a complex process due to the lack of consistency by which each AMP in the database has been characterized. To facilitate identification of AMPs for use in an ADC, a screening strategy that clustered peptides based on their underlying physicochemical properties was implemented, followed by characterization of representative members from each cluster. Here YADAMP, a database of AMPs that contains over 2,500 sequences of peptides with reported antibacterial activity, was used. Clustering was performed by utilizing a K-means algorithm using calculated properties that have been reported to be relevant to antimicrobial activity (peptide length, predicted helicity, predicted hydropathy, percentage of select amino acids [Lys, Arg, Trp, Cys, His], and charge at pH7, pH5, and pH9). An initial set of 100 peptides was selected for experimental characterization through a panel of in vitro assays involving MIC testing against multiple bacterial strains, hemolytic evaluation and cytotoxicity. Once potent peptides with favorable characteristics were identified, the remaining members of the corresponding clusters were then selected for experimental characterization. Using this approach, the number of peptides that required screening was significantly reduced by approximately 10-fold. Over the course of the campaign, ~400 peptides were screened experimentally.

Figure 7B:
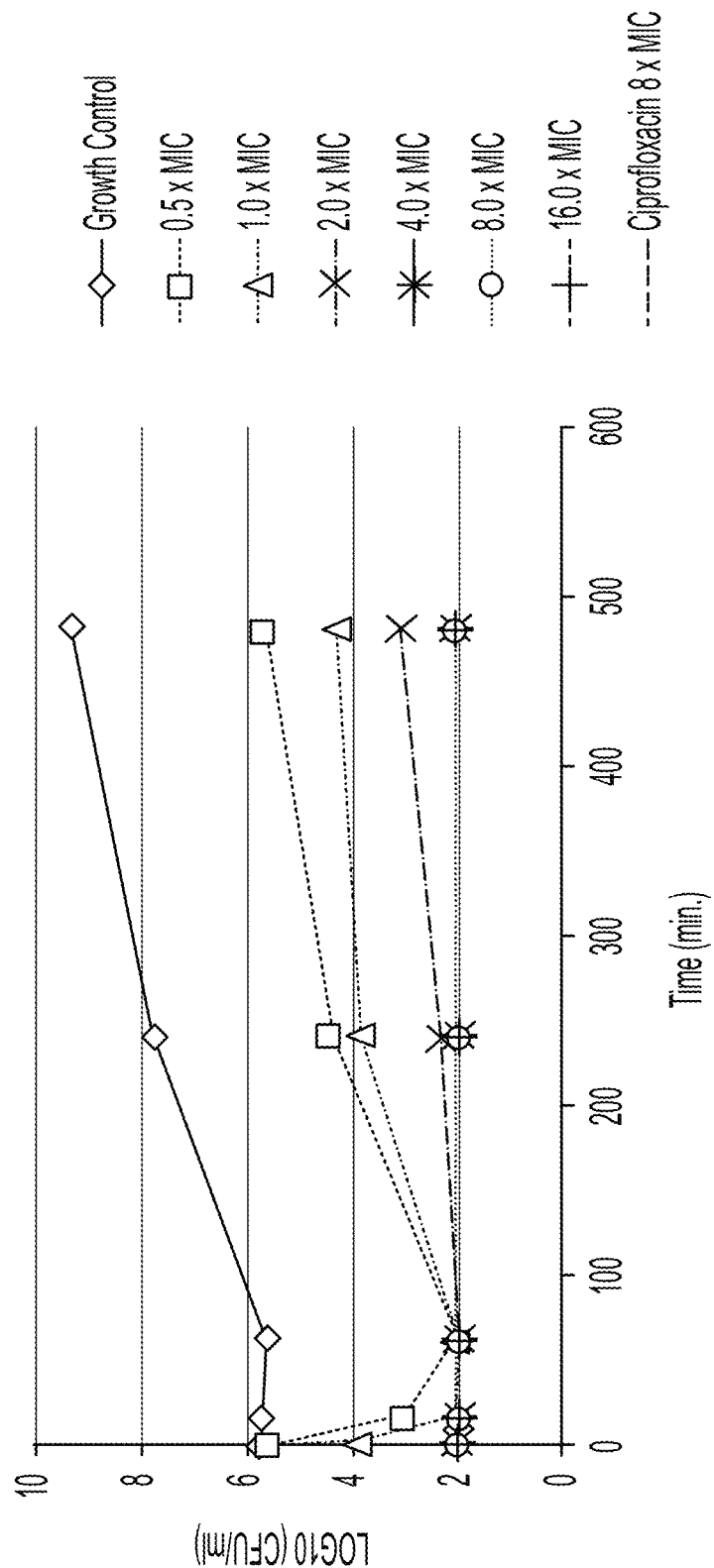
FIG. 7B depicts rapid P297 bactericidal activity in a time-kill assay using *P. aeruginosa* ATCC 27853.
Figure 7C:
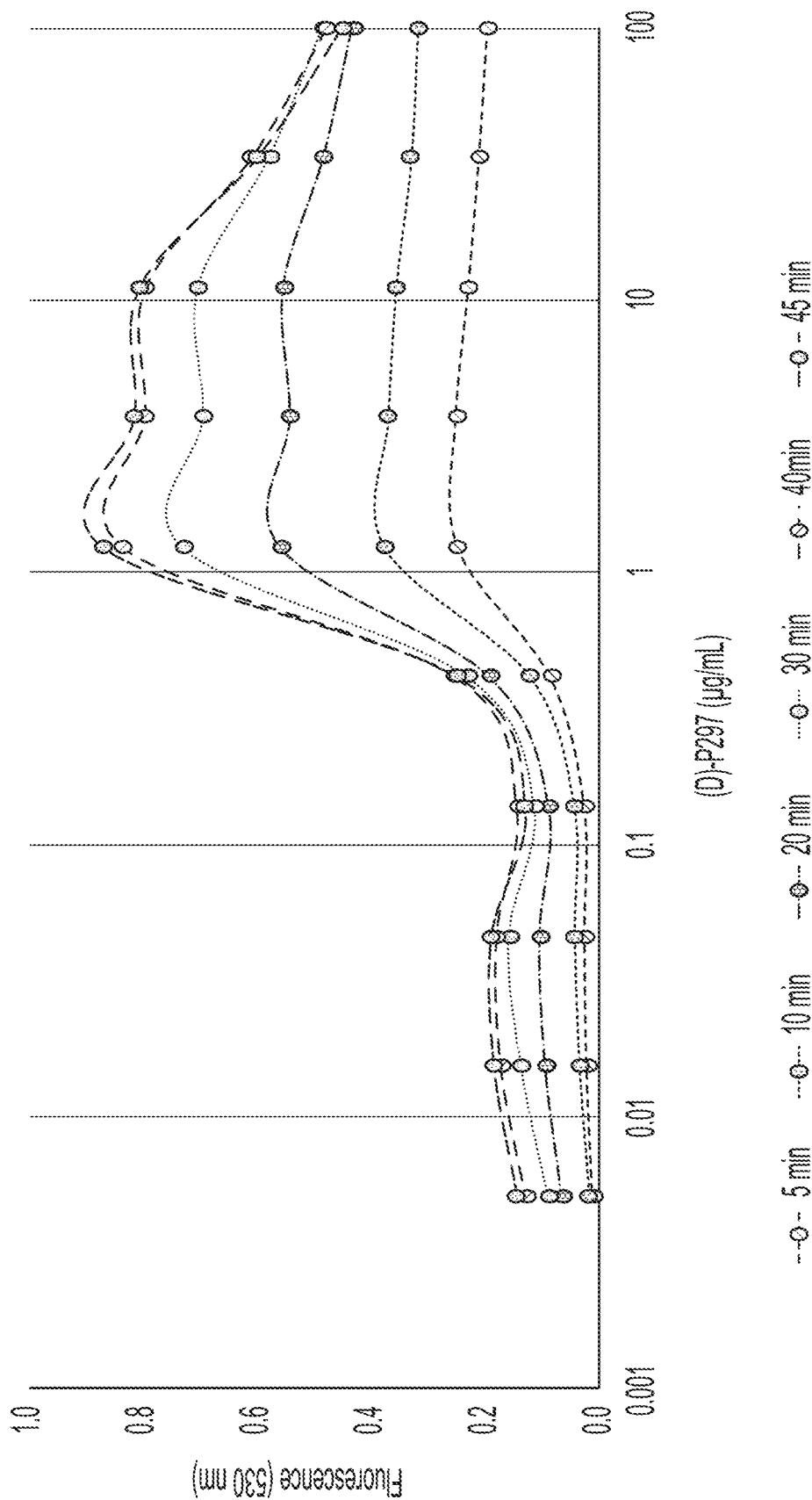
FIG. 7C depicts calcein leakage measurements using DOPE/DOPG liposomes representing model bacterial membranes. The mechanism of action of P297 likely involves membrane disruption.
Figure 7D:
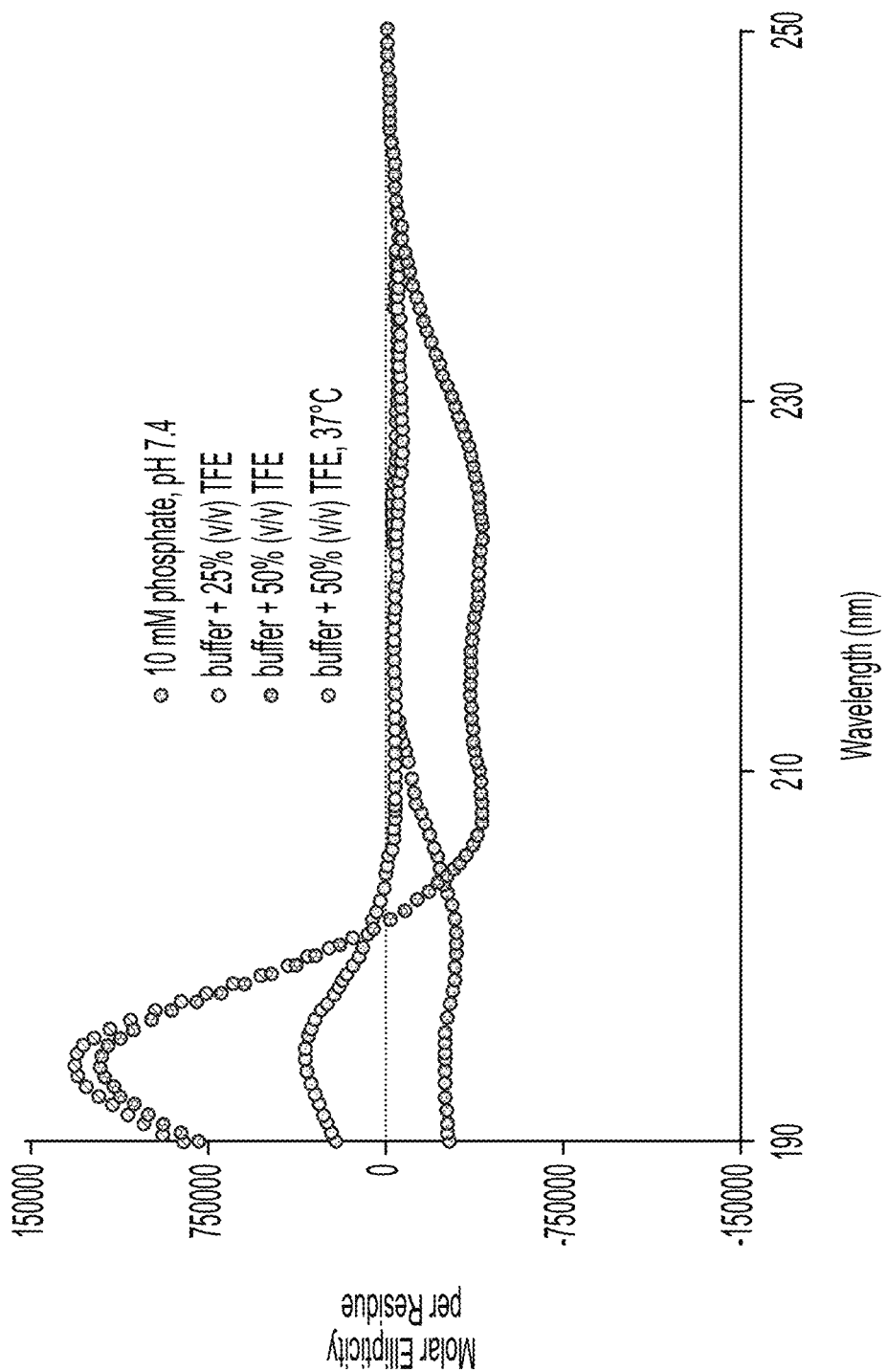
FIG. 7D depicts circular dichroism spectra of P297 in buffer with increasing hydrophobic content. Results show increasing alpha-helical character with hydrophobicity.

The initial screen identified several α-helical AMPs that possessed minimum inhibitory concentrations (MICs) of 1-8 µg/mL against *P. aeruginosa*, some with broad activity against other gram negatives as well. However, several of these initial AMPs also demonstrated lytic activity against human red blood cells. One notable exception to this trend was the α-helical sub-class of the cathelicidin family of AMPs. Cathelicidins are a family of structurally diverse AMPs that exert potent antibacterial activity and act as multifunctional effector molecules of innate immunity. In particular, one member of this class, cathelicidin-BF demonstrated potent MIC values against multiple *P. aeruginosa* strains, low hemolytic activity, and an inability to kill mammalian cells (FIG. 6A). Time-course experiments with one member of this class, P297, indicated that at peptide levels of four times the MIC or greater, the peptide was able to rapidly reduce *P. aeruginosa* titers by >3 logs, confirming that the peptide was bactericidal and not merely bacteriostatic (FIG. 7B). Mechanistic studies confirmed that this peptide family likely works through membrane disruption (FIG. 7C). Additionally, resistance assessment by two different methods and comparison of its frequency to that of polymyxin B (colistin) indicated similar or lower frequency of mutations, on the order of $10^{-8}$ to $10^{-10}$, for P297. Circular dichroism analysis indicated that in aqueous solution, P297 did not adopt appreciable secondary structure; the minimum at approximately 198 nm corresponding to the π-π* transition of a random coil. In contrast, in the presence of 40% 2,2,2-trifluoroethanol, a nonpolar solvent that has been used to promote native-like α-helical structures in peptides with intrinsic α-helix forming properties, there is a strong signal at 196 nm, indicative of α-helix formation (FIG. 7D). These results, taken together, confirm that P297 is an α-helical, bactericidal peptide that is able to rapidly kill *P. aeruginosa* and has a relatively high barrier to resistance development.

Additionally, P297 exhibited a relatively high therapeutic index in our in vitro assays. One key metric that we employed, and that has previously been shown to a sensitive assay of potential toxicity, is red blood cell hemolysis (Oddo A, Hansen P R. 2017. Methods Mol Biol 1548:427-435). For this assessment, both the mean lytic concentration (MLC), that is, the concentration of peptide that induced 100% hemolysis as well as the minimal concentration at which red blood cell hemolysis is first observed (defined as partial lytic concentration, PLC), were employed.

TABLE 5

In vitro activity and toxicity of representative peptide variants.
MIC, minimum inhibitory concentration, numbers in parentheses are molar equivalents; Pae, Pseudomonas; Eco, E. coli; Sau, S. Aureus; MLC, mean lytic concentration; PLC, partial lytic concentration; hsMIC, MIC in human serum; CC50 is the concentration at which 50% cytotoxicity of mammalian cells is observed; ND, not determined; NA, no active in human serum.

| Sample | Sequence | MIC (µg/ml) | | | | Hemolysis | | Human Serum | Cytotox |
| --- | --- | --- | --- | --- | --- | --- | --- | --- | --- |
| | | Pae 27853 | Pae 39324 | Eco 25922 | Sau 29213 | MLC/ MIC | PLC/ MIC | hsMIC/ MIC | $CC_{50}$ (µg/ml) |
| P261 | GGGGIGKFLKKAKKFGKAFVKILKK (SEQ ID NO: 163) | 16 | 8 | 4 | 32 | >8 | >8 | 2 | 250 |
| P265 | GGGLLGDFFRKSKEKIGKEFKRIVQRIKDFL RNLVPRTES (SEQ ID NO: 147) | 32 | 16 | 32 | >128 | >4 | 1 | >4 | 90 |
| P267 | GGGGRFKRFRKKFKKLFKKLSPVIPLLHLG (SEQ ID NO: 101) | 4 | 4 | 4 | 16 | >32 | >32 | 0.5 | 70 |
| P271 | GGGGLRKRLRKFRNKIKEKLKKIGQKIQGL LPKLA (SEQ ID NO: 152) | 16 | 8 | 4 | 16 | >8 | 4 | 2 | 250 |
| P292 | GGGHTASDAAAAAALTAANAAAAAAASM A (SEQ ID NO: 270) | >128 | >128 | >128 | >128 | ND | <1 | ND | 250 |
| P293 | GGGGLRRLGRKIAHGIKKYGPTILRIIRIAG (SEQ ID NO: 153) | 8 | 2 | 4 | 4 | 16 | 4 | 4 | 70 |
| P294 | GGGRGLRRLGRKIAHGVKKYGPTVLRIIKK YG (SEQ ID NO: 154) | 64 | 2 | 4 | 4 | >2 | >2 | 1 | 120 |
| P295 | GGGGRFKRFRKKFKKLFKKLSPVIPLLHLG (SEQ ID NO: 101) | 4 | 4 | 4 | 16 | >32 | >32 | 1 | 95 |
| P296 | GGGKRFKKFFKKLKNSVKKRAKKFFKKPR VIGVSIPF (SEQ ID NO: 155) | 4 | 2 | 4 | 16 | >32 | 32 | NA | 400 |
| P297 | GGGKFFRKLKKSVKKRAKEFFKKPRVIGVS IPF (SEQ ID NO: 156) | 4 (1.0) | 2 (0.5) | 4 (1.0) | 32 (8.3) | >32 | >32 | 2 | 780 |

TABLE 5-continued

In vitro activity and toxicity of representative peptide variants.
MIC, minimum inhibitory concentration, numbers in parentheses are molar equivalents; Pae,
Pseudomonas; Eco, E. coli; Sau, S. Aureus; MLC, mean lytic concentration; PLC, partial
lytic concentration; hsMIC, MIC in human serum; CC50 is the concentration at which 50%
cytotoxicity of mammalian cells is observed; ND, not determined; NA, no active in human serum.

| Sample | Sequence | MIC (µg/ml) | | | | Hemolysis | | Human Serum | Cytotox |
| --- | --- | --- | --- | --- | --- | --- | --- | --- | --- |
| | | Pae 27853 | Pae 39324 | Eco 25922 | Sau 29213 | MLC/ MIC | PLC/ MIC | hsMIC/ MIC | $CC_{50}$ (µg/ml) |
| Ctl. | Ceftazadime | 1 (1.8) | 1 (1.8) | 0.25 (0.5) | 4 (7.3) | 16 | 8 | 1 | 550 |

As shown in Table 5 above, with both measurements, the lytic levels of P297 were >10-fold greater than the MIC. Furthermore, the cytotoxicity of P297 to 293T, as a representative mammalian cell, was ~200-fold greater than the MIC. Therefore, given its potency and relative selectivity for bacteria, P297 was selected for further peptide design.

Figure 8:
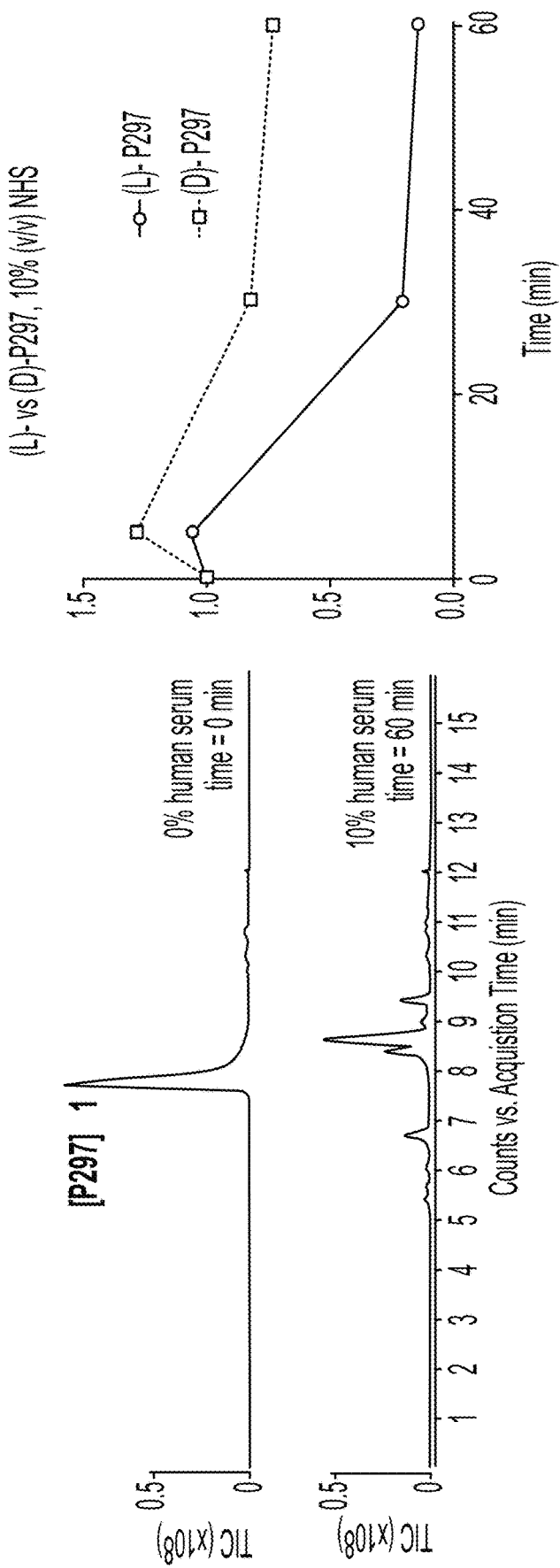

Further analysis of P297 indicated that, while it is highly active and specific in vitro, in the presence of human or mouse serum the activity of P297 decreased substantially over time. LC-MS analysis of P297 in the presence of serum demonstrated that the peptide was likely adsorbing to serum components, presumably proteins, and was also being cleaved by serum proteases—its half-life was on the order of 20 minutes (FIG. 8). Therefore, the properties of P297 were modified to make it more amenable to long exposure times in vivo, especially given that antibody levels can be sustained for days. As a first modification, the L-amino acids of P297 were replaced with D-amino acids (D297), a substitution which can decrease protease sensitivity and increase serum stability. Circular dichroism analysis of D297 confirmed that it adopted a left-handed helix in the presence of 2,2,2-trifluoroethanol. In vitro analysis of D297 indicated that it possessed equivalent potency against P. aeruginosa compared to P297 with the added benefit that the D-version was stable in serum (FIG. 18B). As with P297, D297 had low hemolytic and cytotoxic activity. Thus, by converting to the D-peptide sequence we were able to retain bactericidal activity, enhance serum stability and preserve the lack of hemolytic and cytotoxicity of the AMP.

Example 6: Construction of VSX Conjugates

Figure 9A:
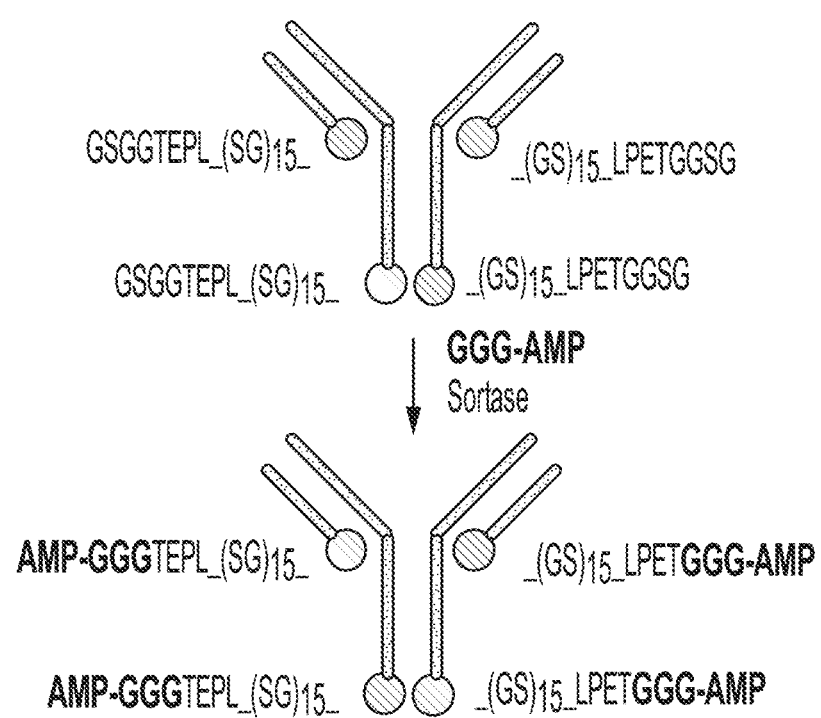
FIG. 9A depicts the synthesis of antibody-AMP conjugates using Sortase ligation.
Figures 1, 9B:
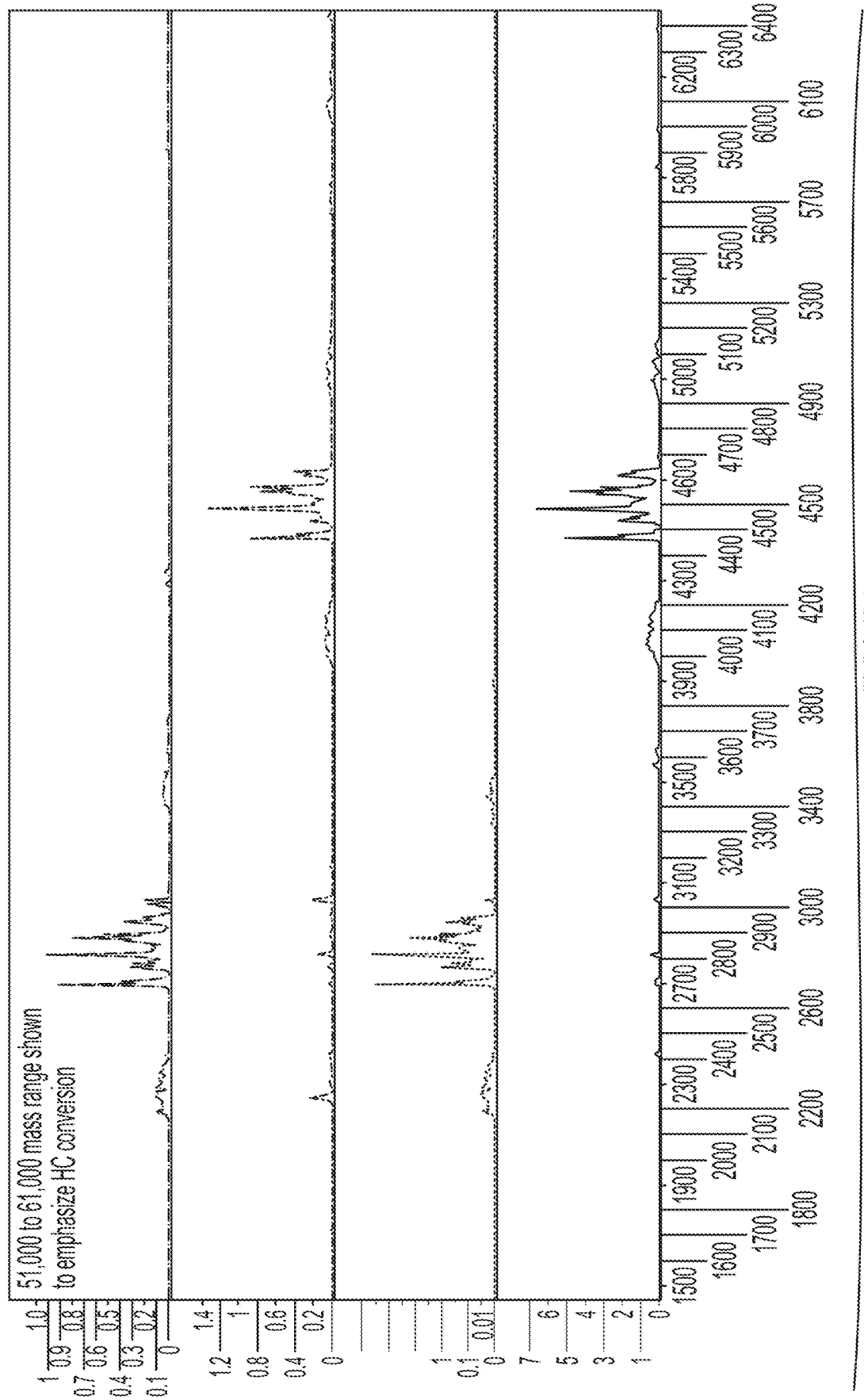
Figure 9C:
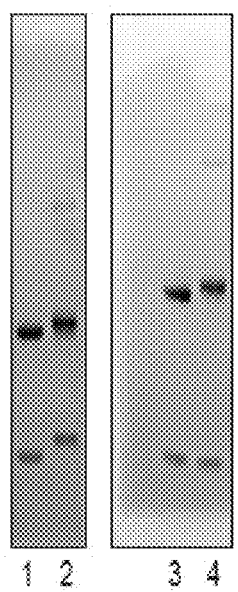
FIG. 9C depicts the Coomassie gel analysis showing robust conversion of starting material to desired D-P297 ADC product. Lanes 1 and 2 are respectively the starting material and product for D-P297 ligation to both heavy and light chains. Lanes 3 and 4 are the starting material and product for D-P297 ligation, respectively, to only the heavy chains (the light chain in the antibody starting material was wild-type lacking the sortase acceptor recognition sequence). Based on this analysis, it is estimated that the drug-antibody ratio (DAR) for material having sortase acceptors on both heavy and light chains is 3.6, and for material having acceptors on only the heavy chains is 1.8.

To produce and test multiple antibody-drug conjugate (ADC) constructs of VSX and D297, we turned to an enzymatic ligation strategy using Sortase A (SrtA) (FIG. 9A). The SrtA method involves expressing antibodies with a SrtA-ligatable tag and then enzymatically coupling them with chemically synthesized AMPs (Mao H, et al. 2004. J. Am Chem Soc 126:2670-1). Constructs were produced as C-terminal variants of the heavy chain (HC), light chain (LC) or both chains (dual). ADCs were analyzed by mass spectrometry, SDS-PAGE gel and SEC-HPLC. The couplings were efficient, routinely converting at >90% per site as determined by LC-MS. For example, the conjugates with HC or LC attachment had a drug-to-antibody ratio (DAR) of ~2 (≥1.8 as assessed by mass spectrometry) or ~4 (≥3.6 as assessed by mass spectrometry) for the Dual conjugate (FIGS. 9B-9C). D297 was attached in all cases with a 30-amino acid-GS$_{15}$-linker (SEQ ID NO: 157), to maintain flexibility, between the terminal HC/LC residue and the sortase signal sequence. Importantly, SEC analysis showed a homogenous product with no signs of aggregation (FIG. 9D), a common concern in the ADC field.

Example 7: In Vitro Activity of VSX-297

Figure 11:
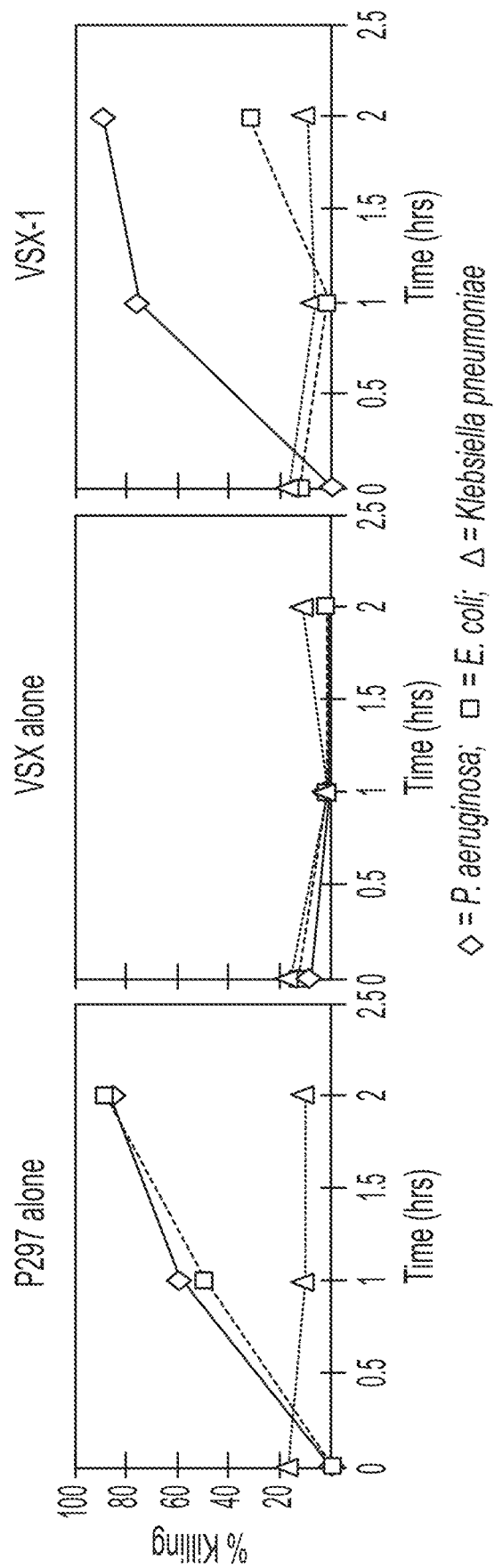
FIG. 11 depicts mixed microbial killing of *P. aeruginosa*, *K. pneumoniae* and *E. coli* by P297 alone (left panel), VSX alone (center panel), and VSX-1 (right panel).

Using the VSX antibody, a series of ADC constructs were evaluated in vitro for direct bactericidal activity against P. aeruginosa (FIG. 10). From these initial constructs, the relative order of activity was concluded to be Dual>HC>LC. The most potent ADC, VSX-1, containing a DAR of four with payload D-297 ligated to the C-terminus of each HC and LC. VSX-1 exhibited potent bactericidal activity in a killing assay against P. aeruginosa including laboratory strains and strains resistant to carbapenems and anti-pseudomonas third generation cephalosporins or fluoroquinoles (1-10 µg/ml or 5-50 nM). Further, the construct was selective for P. aeruginosa in a mixed microbial assay containing P. aeruginosa, K. pneumoniae and E. coli (FIG. 11). Consistent with the results of D297, the construct had minimal hemolytic activity and negligible cytotoxic activity against 293T cells. The killing properties of the ADC were also evaluated in an opsonophagocytic assay to confirm intactness of the antibody. The ADC was highly active at 10 µg/ml, resulting in 1 log bacterial reduction in the presence of heat-inactivated complement and >3 log killing activity with non-heat inactivated complement, in the presence of polymorphonuclear neutrophils (FIG. 12). That VSX-1 is more active than the VSX parental antibody is unsurprising when one considers that the AMP, upon intercalation into the membrane, likely facilitates close contact between the antibody and complement and/or phagocytic immune cells. In all, many of the properties of the parent peptide and the antibody translated to the ADC as well. Finally, given that VSX-1 acts at the outer membrane of P. aeruginosa, it was reasoned that it may demonstrate synergy with existing antibiotics, which must cross the double membrane to target intracellular targets. Indeed, it was found that VSX-1 or peptide constructs appear to increase the potency of classical anti-Pseudomonas antibiotics (e.g. carbapenems or polymyxin), likely by increasing outer membrane permeability.

Example 8: In Vivo Activity of VSX-1

To investigate the in vivo activity of VSX-1, lung infection models was focused on for several reasons. First, the lung is a common site for P. aeruginosa infection, leading to community/hospital-acquired pneumonia, which is associated with problematic outcomes, with high mortality rates, up to 30-60% in some studies (Zavascki A P, et al. 2006. Crit Care 10:R114.). As such, it presents one area of likely clinical use for a pathogen-specific ADC. Second, given the compartmentalization of the lung from the bloodstream, it also represents a high bar to demonstrate efficacy for a systemically administered antimicrobial. Lastly, given suboptimal dosing of AMP equivalents in these studies (i.e., <20% of the effective dose based on mass) and the localized colonization, efficacy would likely require transport of the ADC, mediated by the VSX antibody.

Figures 13A, 13B:
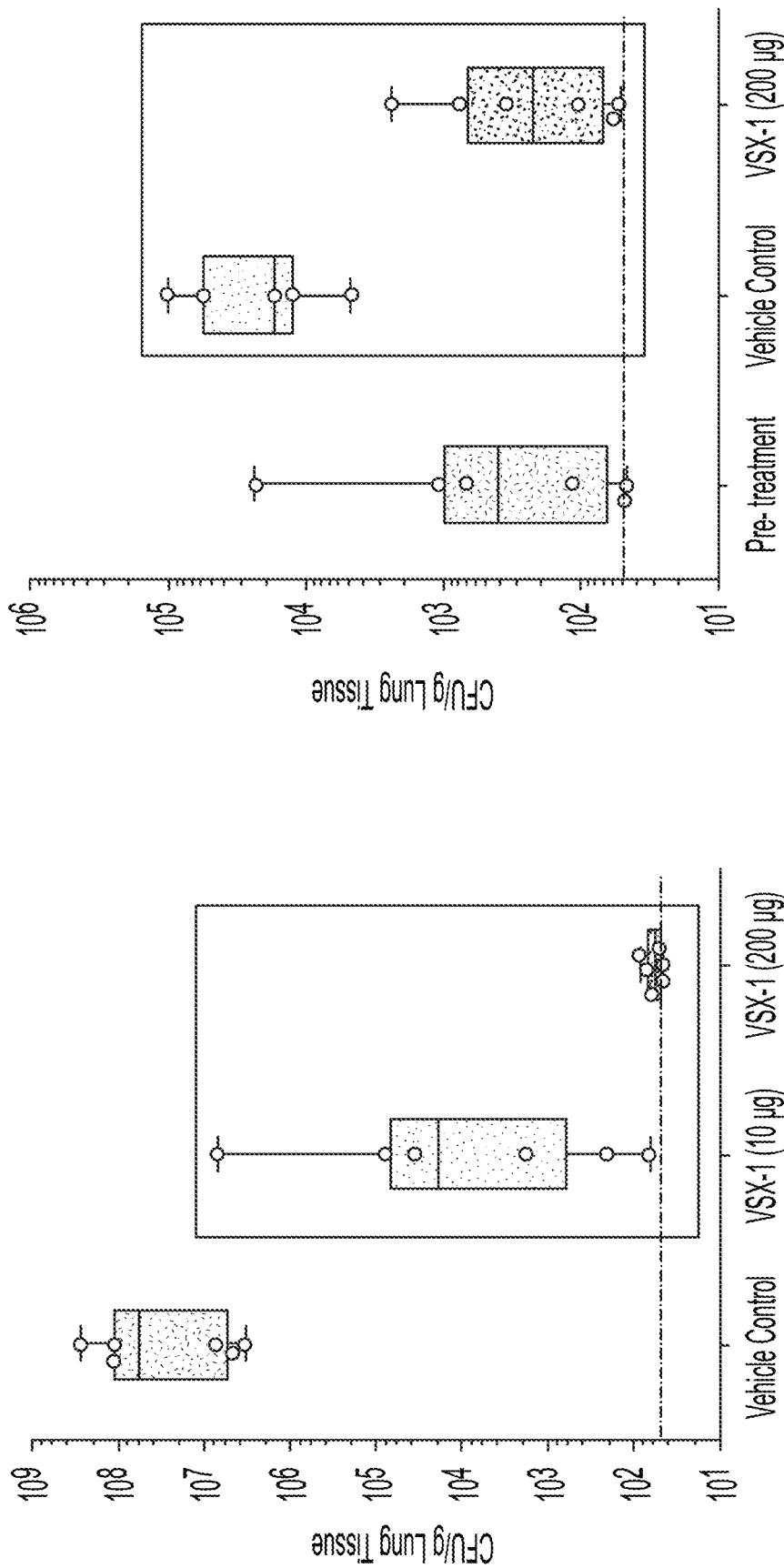
FIGS. 13A-13C depict evaluation of conjugates in in vivo models of *P. aeruginosa* lung infection. (A) Neutropenic animals were co-administered VSX-1 and bacteria (ATCC 27853). CFU burden was measured in the lung at eight hours. (B) Neutropenic animals were treated with VSX-1 one hour post-infection (ATCC 27853). CFU burden was measured in the lung at eight hours. (C) Acute lung infection model with *P. aeruginosa* PA14 ($2 \times 10^6$/animal), C57/Bl16, 10 animals/gp, intranasal inoculation, intraperitoneal dosing four hours post-infection.
Figure 13C:
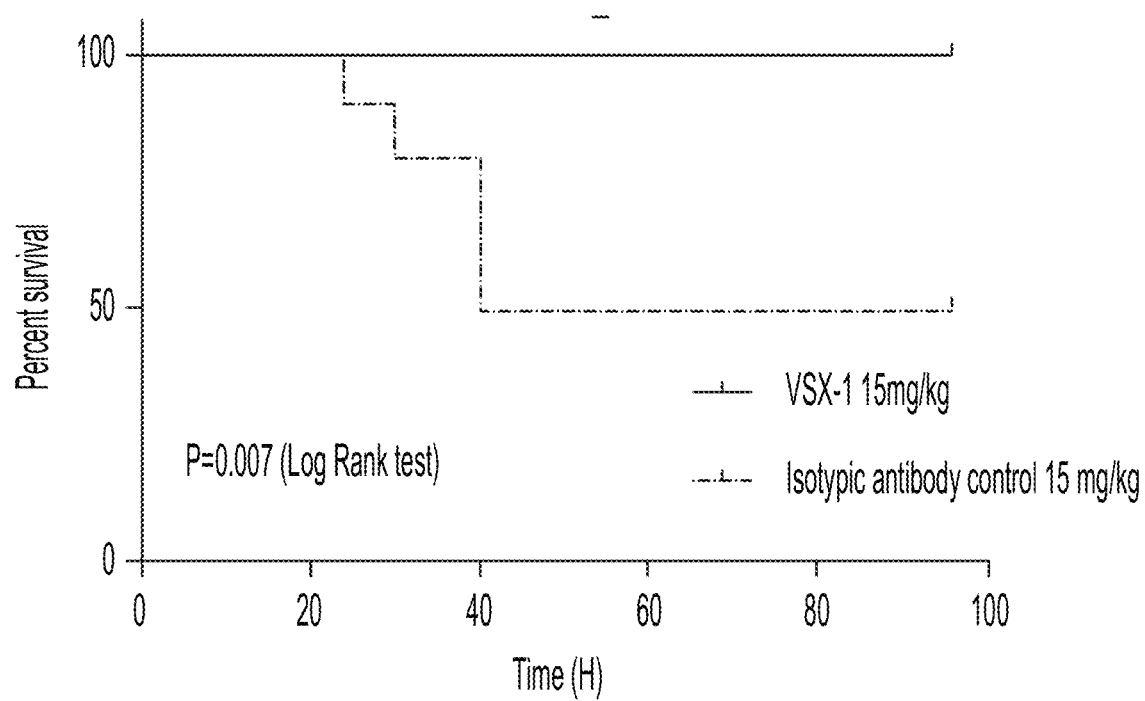

Consistent with the in vitro data, VSX-1 demonstrated in vivo efficacy in multiple animal models of *P. aeruginosa* infection. A murine neutropenic lung infection model with *P. aeruginosa* (ATCC 27853) was initially employed. Infected animals were treated intranasally with VSX-297 construct resulting in statistically significant reduction in the bacterial load in the lung when co-administered (FIG. 13A) or dosed therapeutically (FIG. 13B). Notably, the antibody alone group showed no bacterial reduction, supporting the selection of an ADC with direct bactericidal activity as a preferred mechanism, particularly in an immunocompromised setting. Building on this initial data, VSX-1 was evaluated in a murine immunocompetent lung infection model with the well described PA14 strain of *P. aeruginosa*. Treatment of infected animals three hours post-infection with a single intraperitoneal dose of VSX-297 at 15 mg/kg resulted in statistically significant survival at 100 hours (FIG. 13C). The immunocompetent model used for this experiment is aggressive, with 50-100% of control animals succumbing to infection within 24 hours of infection. To confirm the contribution of the mAb component, a sham-conjugate was prepared using a non-*P. aeruginosa* targeting antibody (actoxumab). The actoxumab-D297 conjugate showed no survival benefit in the immunocompetent lung infection model, validating the selection of a *P. aeruginosa* surface-targeting antibody. In all, the protection observed with the VSX-1 conjugate was highly encouraging and warranted the further exploration of this ADC as a potential treatment for *P. aeruginosa* lung infection.

Example 9: Optimization of VSX Conjugates

Figure 14A:
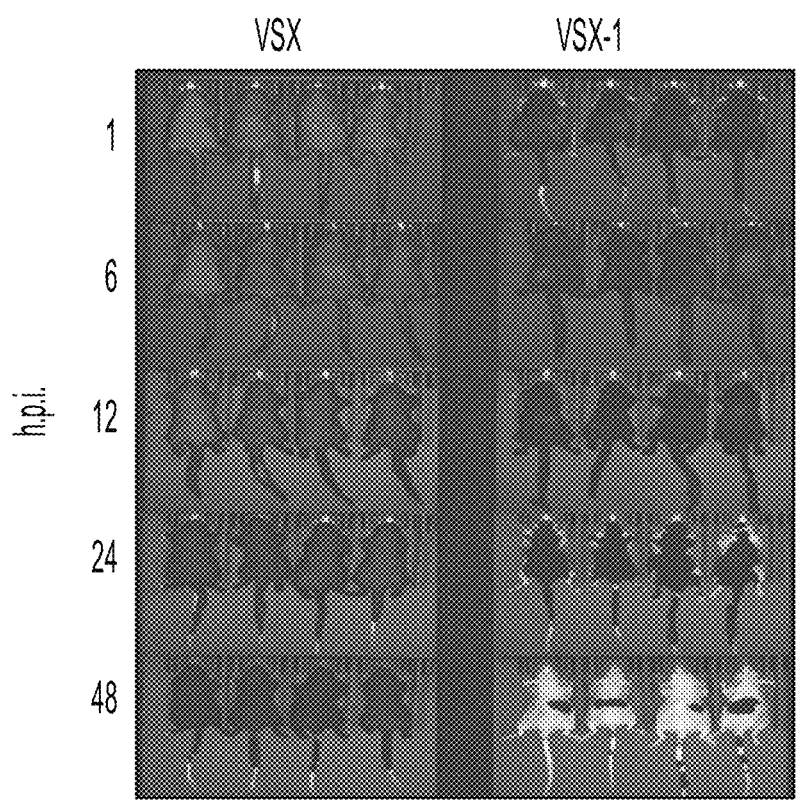
FIG. 14A depicts in vivo imaging of VSX-297 biodistribution.
Figure 15:
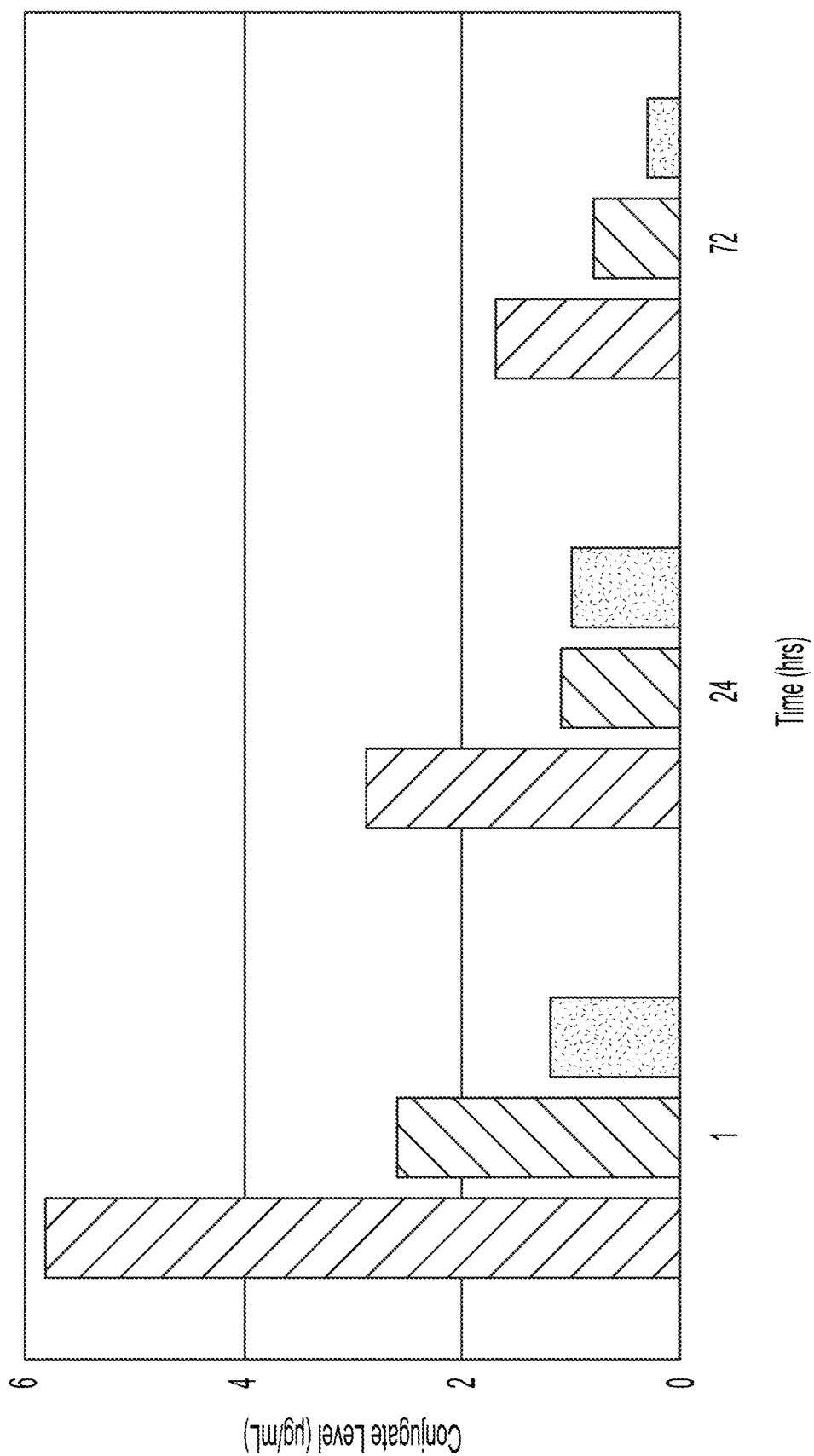
FIG. 15 depicts the blood levels in mice administered VSX-2 or VSX-1. For this experiment, mice were injected with either VSX-1 or VSX-2 and blood samples were drawn 1, 24, or 72 hours post-injection. Levels of conjugate were assessed by mass spectrometry or ELISA.
Figure 16:
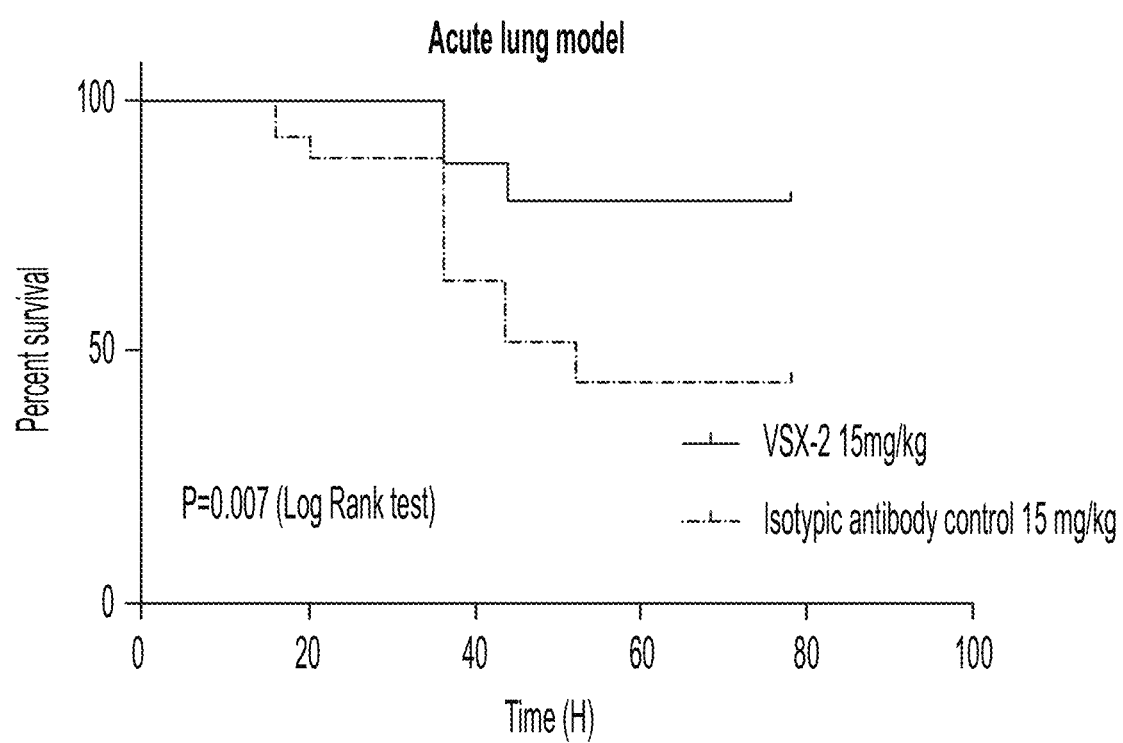
FIG. 16 depicts VSX-2 acute lung infection model with *P. aeruginosa* PA14 ($2 \times 10^6$/animal), C57/Bl6, 25 animals/gp, intranasal inoculation, intraperitoneal dosing 4 h post-infection.

The first generation VSX-1 construct was further evaluated in vivo. Despite complete protection in *P. aeruginosa* infection models, VSX-1 construct was further engineered to improve biodistribution relative to the parent antibody (FIG. 14A). To optimize the biodistribution properties of VSX conjugates as a potential therapeutic a focused set of studies were carried out on: payload charge, payload hydrophobicity and DAR. Starting from the P297 sequence, a set of charge variants and variants with globally reduced hydrophobicity were screened. Unexpectedly, P369 (GGGKLLRKLKKSVKKRAKELLKKPRVIGVSIPL (SEQ ID NO: 257)), containing 5 phenylalanine to leucine substitutions, emerged as a more potent peptide and, when conjugated to the VSX antibody, retained bactericidal activity, demonstrated little cytotoxicity (FIG. 14B). In parallel, a series of DAR2 constructs was evaluated in vivo for biodistribution relative to the parent antibody and demonstrated improved biodistribution (FIG. 15). Indeed, VSX-2, containing a DAR of 2 with payload D369 ligated to the C-terminus of each HC, demonstrated protection in the *P. aeruginosa* lung infection model relative to a control antibody (FIG. 16).

Example 10: Materials and Methods

Materials. The VSX antibody was initially isolated from a mouse hybridoma, humanized, and engineered for stability and high expression. The sequence and attributes of the antibody are listed in FIG. 1A. L-297 and D-297 peptides were synthesized via solid phase synthesis; purity and identity were verified by HPLC and high resolution mass spectrometry (Calc. Mass 3807.29, Obs. Mass 3807.37-3807.38). Bacterial strains were from ATCC and characterized by Evotec. Briefly, these strains, isolated from human sputum, have been tested against a variety of drug classes, including the penicillins, cephalosporins, carbapenems, quinolones, and aminoglycosides. A description of the specific antibiotic resistance phenotype for each strain is described in Table 6 below.

TABLE 6

Exemplary antibiotics and corresponding *P. aeruginosa* strains used

| | | BAA-2108 | BAA-2109 | BAA-2110 | BAA-2111 | BAA-2112 | BAA-2113 | BAA-2114 |
|---|---|---|---|---|---|---|---|---|
| Penicillins | Amoxicillin/Clavulanic Acid | R | R | NT | R | R | R | R |
| | Piperacillin/Tazobactam | NT | S | NT | S | S | S | S |
| | Ampicillin | R | R | R | R | R | R | R |
| Cephalosporins | Cefalotin | R | R | NT | R | R | R | R |
| | Cefuroxime | R | R | NT | R | R | R | R |
| | Cefuroxime Axetil | R | R | NT | R | R | R | R |
| | Cefpodoxime | R | R | NT | R | R | R | R |
| | Cefotaxime | R | R | R | R | R | R | R |
| | Cefazolin | NT | R | R | R | R | R | R |
| | Cefoxitin | R | R | R | R | R | R | R |
| | Ceftazidime | S | S | S | S | S | I/R | S |
| | Ceftriaxone | NT | R | NT | R | R | R | R |
| Carbapenems | Ertapenem | NT | NT | NT | NT | NT | NT | NT |
| | Imipenem | R | S | S | S | S | S | S |
| Quinolones | Ciprofloxacin | S | S | S | S | S | S | R |
| Aminoglycosides | Amikacin | S | S | S | S | S | S | S |
| | Gentamicin | I | S | I | S | S | S | S |
| | Tobramycin | NT | S | S | S | S | S | S |

TABLE 6-continued

Exemplary antibiotics and corresponding *P. aeruginosa* strains used

|   |   | BAA-2108 | BAA-2109 | BAA-2110 | BAA-2111 | BAA-2112 | BAA-2113 | BAA-2114 |
|---|---|---|---|---|---|---|---|---|
| Other | Tetracycline | R | R | R | R | R | R | R |
|   | Tigecycline | R | R | R | R | R | R | R |
|   | Nitrofurantoin | R | R | R | R | R | R | R |
|   | Trimethoprim/ Sulfamethoxazole | R | R | R | R | R | R | R |

R = Resistant;
S = Suspectible;
I = Intermediate;
NT = Note Tested

Synthesis of Glycans Used in the Epitope Analysis are Enumerated in the Section of General Synthetic Methods.

General Synthetic Methods. All reagents, solvents (ACS grade or anhydrous) were used as purchased from Sigma-Aldrich, Alfa-Aeser and Corden Pharma Company without further purification or drying. TLC plates were purchased from Merck Millipore. Sephadex G-10 was purchased from GE Healthcare Life Sciences. Sulfo-NHS-LC-LC-Biotin (cat #: 21338) was purchased from Thermo Fisher Scientific Company. Solvents used for extraction and flash chromatography were ACS grade. Air free reactions were carried out by simplified Schlenk operation: vacuum-N2 gas balloon technique. Flash column chromatography was performed on Teledyne ISCO CombiFlash system equipped with Redisep Gold or regular silica gel columns. 1H-NMR and 13C-NMR spectra were obtained on 300, 400 or 500 MHz Varian® FT-NMR spectrometers of the Department of Chemistry Instrumentation Facility (DCIF) at the Massachusetts Institute of Technology (MIT), with special thanks to the National Science Foundation for their generous financial support; without their continuing support, the DCIF would not be able to supply the MIT and surrounding scientific communities with the level of support needed to maintain this state-of-the-art facility. Mass spectra were obtained using electrospray ionization using an Agilent 1100 Single Quadrupole LC-MS instrument.

Expression of USX. Recombinant expression of antibody was carried out in Expi293F™ cells (Invitrogen, Carlsbad, CA) cultured in Expi293 Expression Medium (Invitrogen, Carlsbad, CA) maintained at 37° C., in humidified incubator with 8% $CO_2$. Expi293F™ cells (with >95% viability) were transfected with ExpiFectamine™ 293 with equivalent amounts of HC and LC containing plasmids. Twenty-four hours later, the transfected cells were supplemented with ExpiFectamine™ 293 Transfection Enhancer 1 and ExpiFectamine™ 293 Transfection Enhancer 2. Seven days post-infection, the cells were harvested by spinning the cells at 4000 rpm for 15 min at 4° C. and filtered through a 0.45 µm filter system (Nalgene, Rochester, NY). The antibody was purified from the supernatant using a MabSelect SuRe resin (GE Healthcare Life Sciences, Marlborough, MA) on an AKTA Purifier FPLC system (GE Healthcare Life Sciences, Marlborough, MA). The antibody was eluted with a 100 mM Glycine-HCl buffer (pH 2.5) buffer and pH neutralized by the addition of 10% 1 M Tris-base with 1 M NaCl (pH 8.5). The purified sample is then buffer exchanged into 1×PBS (pH 7.4) and concentrated by ultrafiltration/diafiltration (UF/DF) using a 30 KDa MWCO spin filter (EMD Millipore, Billerica, MA). Purified antibody is quantified using NanoDrop spectrophotometer.

Mono- and Bidimensional NMR. 1H Monodimensional and bidimensional NMR spectra of four synthetic glycans (Man-2P,4P, Hep-2P,4P, Hep-4P, Hep) were measured at 500 and/or 600 MHz on a Bruker Avance 500/600 spectrometers equipped with a 5 mm TCI cryoprobe at 298K. 0.25 mg of each glycan were exchanged with D2O (99.9%) by freeze-drying to remove residual water, and then dissolved in 0.5 ml of 10 mM phosphate buffer pH 7.2 with 0.15 M NaCl, 0.3 mM EDTA-d16 in $D_2O$. 1H NMR spectra were recorded with suppression of residual water signal, recycle delay of 12 s, 32K fid size and 16 scans. 2D homonuclear correlation spectra were acquired with 32 scans for each of 256 free induction decays (fid). 2D TOCSY were measured in phase-sensitive mode using TPPI, and Fourier transformed onto a data matrix of 2K×1K with a phase shifted (7E/3) square sine-bell function. The sensitivity enhancement 1H/13C chemical shift correlation (HSQC) spectra were acquired using z-gradients for coherence selection with carbon decoupling during acquisition period in phase sensitivity-enhanced pure absorption mode. The spectra were acquired with a recycle delay of 2 s, 1K data points in F2, 256 increments in F1, 24 scans per increment. The final matrix size was zero-filled to 2K×1K and multiplied with shifted (it/3) sine-bell-square prior Fourier transformation. 31P monodimensional NMR, 1H NMR with 31P decoupling and 1H-31P HMBC spectra were acquired on a 500 MHz Bruker Avance spectrometer. Both monodimensional spectra were acquired with recycle delay of 5 s, 20K fid size and 128 scans, while 2D HMBC spectra were acquired using recycle delay of 1.5 s and 16 scans per series in 2K data points in F2 and 48 increments in F1. The spectra were optimized with a nJCH long range of 8 Hz.

Quantitative 1H NMR analysis. Quantitative 1H NMR analysis of each glycan was performed using the quantitative analysis module present in the Bruker Topspin3.5p16 version. Briefly, the spectrum of the test sample and that of the reference solution with a known concentration, were acquired under the same experimental conditions. A synthetic pentasaccharide ($GlcN_{NS6S}$-G-$GlcN_{NS3,6S}$-$I_{2S}GlcN_{NS6S}O^{OMe}$ (34)), at 2.38 mg/ml (1.57 mM) concentration in $D_2O$ was chosen as reference. 5 mm NMR tubes were used for each sample. The spectra were acquired with recycle delay of 12 s that allows complete 1H nuclei relaxation of carbohydrates (Guerrini, M. et al., 2001. Semin Thromb Hemost, 27:473-82.). Under these optimal conditions, integral ratio between a selected H1 of the reference molecule and H1 of a glycan represents their molar ratio and can be used for glycan quantification. The purity of Hep-2P,4P was found to be 92% and this value was used to further calculate ligand concentration for 1H STD and 31P NMR titration experiments.

1H STD NMR. 1H STD NMR spectra were acquired at 600 MHz on a Bruker Avance 600 spectrometer equipped with a 5 mm TCI cryoprobe at 298K. The VSX Fab was exchanged with 10 mM phosphate buffer pH 7.2 in $D_2O$ (containing 0.15 M NaCl and 0.3 mM EDTA-d16) using Vivaspin centrifugal filters with cut-off 10 kDa at 8° C. Each ligand mmol (taking into account the concentrations found by quantitative 1H NMR) was dissolved in 0.5 ml of phosphate buffer pH 7.2 with 0.15 M NaCl, 0.3 mM EDTA, together with $5.5 \cdot 10^{-4}$ mmol Fab reaching a 100:1 ligand-protein molar ratio. Selective irradiation of the protein, during the 1H STD NMR spectra, was achieved by a train of Gaussian shaped pulses with a 1% truncation and each of 50 ms in duration. The protein was irradiated at 0.75 ppm (on-resonance) and at 40 ppm (off-resonance). Spoil sequence to destroy unwanted magnetization and spinlock to suppress protein signals were used.

31P NMR titration experiments. 31P NMR spectra were acquired at 500 MHz on a Bruker Avance 500 at 298K using recycle delay of 3 s and 512 scans. A solution containing $0.26 \cdot 10^{-4}$ mmol Fab was titrated with 20 mg/ml ligand solution in order to reach final 47:1, 42:1, 30:1, 19:1, 10:1 molar ligand-Fab ratios, and a 31P NMR spectra was acquired at each concentration point.

Molecular modeling of the glycans and VSX complexes. The molecular docking of the ligand, 2,4-P-Hep to the VSX antibody was carried out using the SwissDock web server. A unique solution showing ligand bound to five CDR loops was ranked sixth among the top twenty solutions. Inspection of this solution was identified as the possible binding mode and used for further analysis. Then, conformation of the VSX:glycan from molecular docking was then refined by MD simulation (20 ns) in explicit water solvent (TIP3P model), using the AMBER Force Field (parm14.dat set of parameters), and the software NAMD 2.12 molecular dynamic engine (Case, D. A. et al., AMBER 11, University of San Francisco, California; Jorgensen, W. I. et al., 1983. J. Chem. Phys., 79:926-935; Phillips, J. C. et al., 2005. J. Compt. Chem., 26:1781-802). 2,4-P-Hep-VSX ligand-receptor complex geometries were obtained by automatic docking using Autodock 4.2 (Morris, G. M. et al., 2009. J. Compt. Chem., 30:2785-91) after 100 runs, while the parametrization included: a population size of 1000 individuals, with maximum generation number 270,000, and a maximum number of energy evaluation of $2.5 \cdot 10^7$. The ligand/receptor conformational search applied the Lamarckian Genetic Algorithm 4.2 and involved all the 16 dihedral angles of 2,4-P-Hep, while the VSX was left rigid. The ligand/receptor relative initial position and orientation were randomly chosen in all the 100 docking runs, the obtained poses were then clustered using a tolerance RMSD of 2.0 Å. The cluster with the lowest binding energy and highest population (−6.0 Kcal $mol^{-1}$ autodock scoring function) show the C6-C7 aliphatic tail of 2,4-P-Hep matching the VSX binding pocket, in accord to the structure reported in FIG. 5A left. A further refinement of the docking was done starting from a selected geometry of the complex: 2,4-P-Hep-VSX, characterized by the 4-P phosphate group of Hep matching the VSX binding pocket, as previously obtained. In this further 100 runs autodock predict an additional glycan-VSX cluster characterized by the 4-P phosphate group of Hep fitting the VSX binding pocket, in accord to FIG. 5A right, whose estimated binding energy is slightly greater (−3.8 Kcal $mol^{-1}$) compared to the previous solution. At the end of the docking procedure the two docking poses of the complex 2,4-P-Hep-VSX, in which the C6-C7 aliphatic tail, or the 4-P phosphate group fit the VSX binding pocket, were further refined by MD simulation (40 ns approx.) in explicit water solvent (TIP3P). The GLYCAM06 Force-Field was used to model the 2,4-P-Hep glycan (Kirschner, K. N. et al., 2008. J. COmpt. Chem., 29:622-55; Holmberg, N. et al., 1999. Protein Eng., 12:851-6). For the visualization of the MD simulation trajectories, manipulation and dynamic analysis VMD 1.9.3 and wordom 0.22 software was used (Humphrey, W. et al., 1996. J. Mol. Graph, 14:33-8, 27-8; Seeber, M. et al., 2007. Bioinformatics, 23:2625-7). In these MD simulations the relative ligand/receptor distances and orientation were evaluated and analyzed, in particular the Hep dynamic in the two hypothesized bound states were compared trough the Root Mean square Fluctuation (RMSF) functions.

Construction of ADCs. Peptides containing an N-terminal GGG sortase donor sequence were ligated to the C-termini of mAb heavy chains containing the sortase A recognition sequence LPETGG (SEQ ID NO: 244). mAb was buffer exchanged into 150 mM NaCl/50 mM Tris (pH 7.5) prior to ligation. Optimized sortase ligation conditions were performed in 150 mM NaCl/50 mM Tris (pH 7.5) using 20 equivalents of peptide at 1.5 mg/mL mAb (150 kDa), 10 mM $CaCl_2$, 5.8 µg/mL Sortase A (from BPS Bioscience, (21.7 kDa)). After incubation at ambient temperature in the dark for 18 hours, samples were diluted to 10 ml total volume in PBS and purified by FPLC. Conjugation efficiency was determined by Q-TOF mass spectrometry using a reduced antibody prepared by heating 5 µg of sample at 65° C. for 15 min in 10 mM DTT.

Assessment of Serum Stability. Normal Human Serum (NHS) (Sigma S-7023) was thawed, diluted in water, centrifuged at 13000 rpm for 10 minutes and the supernatant was warmed to 37° C. in a water bath. Twenty µl of each test article was placed in a 2.0 ml round bottom microfuge tube. Two ml of diluted NITS was added to each tube and immediately the tubes were vortexed and 200 µl was transferred to a fresh microfuge tube with 40 µl of 15% Trichloroacetic acid (TCA). Assay tubes were placed at 37° C. in a rotating rack between time-points. TCA tubes were placed on ice for 15 minutes and then centrifuged at 13000 rpm for 10 minutes. Supernatant from each tube was collected and frozen at −20° C. for analysis. Samples were harvested and processed at various time-points up to 6 hours.

Assessment of Antimicrobial Activity. MICs were determined according to CLSI guidelines, using 2-fold serial compound dilutions, in 96-well microtiter plates. Briefly, compounds were diluted in water across a mother plate then 2 µl was stamped to assay plates, one plate for each strain to be tested. Bacterial strains were sub-cultured overnight on agar plates at 37° C. Overnight plates were used to prepare 0.5 McFarland cultures in 0.85% saline. These concentrated cultures were diluted 1:200 in growth media to approximately $5 \times 10^5$ cells/ml. All assay plates received 100 µl diluted culture per well. All plates were placed at 37° C. overnight. After 18 hours the plates were read using a mirrored plate reader and reflected incandescent light. The MIC is defined as the lowest concentration of compound that inhibits growth by at least 80%. Wells at and above the MIC should appear void of growth when read by eye.

To assess microbial killing, bacterial cells were grown aerobically overnight on agar plates at 37° C. Overnight plates were used to seed 30 ml cultures of growth media in 250 ml vented flasks. Cultures were grown aerobically at 37° C., shaking at 150 rpm. Growth was monitored at A600 and bacterial cells were harvested at mid-log growth. Ten ml of culture was pelleted at 4000×g for 10 minutes and washed one time with PBS+1% BSA before re-suspending in 2 ml PBS+BSA. The concentrated culture was used to seed 6 ml tubes of PBS+BSA to an OD giving a concentration of $1 \times 10^8$ cells/ml. Cultures were diluted to $1 \times 10^4$ cells/ml in PBS+BSA. Test articles were diluted in PBS+1% BSA and 50 µl per concentration tested was loaded into a 96 well polypropylene microtiter plate. Fifty µl of diluted culture was added to all test wells as well as no compound control wells. Plates were shaken and incubated at 37° C., 90 minutes, static. Ten µl from each assay well was plated onto agar plates and incubated at 37° C. overnight. Percent killing was determined by the CFU for test wells compared to the CFU for no compound control wells.

Mixed Microbial Assay. Bacterial strains were grown aerobically overnight on agar plates at 37° C. Overnight plates were used to establish 0.5 McFarland Cultures in six milliliters PBS (approximately $1 \times 10^8$ cells/ml). Concentrated cultures were diluted to $1 \times 10^4$ cells/ml in PBS. 10 µl of each of the diluted cultures were plated onto blood agar plates (BAPs) to determine initial concentration, check for purity, and establish strain morphology. One ml of each diluted culture was combined (for a total of three) and the volume was brought to 10 milliliters with PBS ($1 \times 10^3$ cells/ml of each strain). 25 µl of the mixed culture was spread on a BAP to establish the CFUs/ml for each strain at t=0. Test articles were serially diluted 4-fold in PBS with a final volume of 200 µl in 2.0 ml round bottom Eppendorf tubes. A no compound control was included. 200 µl of mixed bacterial culture was added to all assay tubes. Tubes were vortexed and immediately 50 µl from each tube was spread on separate BAPs. Assay tubes were incubated at 37° C., rotating between timepoints. The plating procedure was repeated at 1 hour intervals for two hours and all plates were incubated at 37° C. overnight. The following day all plates were counted, noting the CFU for each strain, distinguished by different morphology, and results were plotted as the percent kill compared to a no compound control.

Neutropenic Mouse Model. CD1 Mice were supplied by Charles River (Margate, UK) and were specific pathogen free. Male mice were 11-15 g on receipt and were allowed to acclimatize for at least 7 days. Mice were housed in sterilized individual ventilated cages exposing the mice at all times to HEPA filtered sterile air. Mice were rendered neutropenic by immunosuppression with cyclophosphamide at 200 mg/kg four days before infection and 150 mg/kg one day before infection by intraperitoneal injection. The immunosuppression regime leads to neutropenia starting 24 hours post administration of the first injection which continues throughout the study. *P. aeruginosa* strain ATCC 27853 was used to assess in vivo protection. For infection, animals were first anaesthetized with a Ketamine/Xylazine anesthetic cocktail (90 mg/kg Ketamine/9 mg/kg Xylazine) via IP injection delivered at ~15 mL/kg. Anaesthetized mice were infected with 0.04 mL inoculum by intranasal instillation into mouse nostrils (20λ per nostril, 5 min between nostrils) and were kept in an upright position on a string rack for ~10 minutes post-infection. The inoculum concentration was $2.83 \times 10^5$ CFU/mL (~$1.14 \times 10^4$ CFU/lung). Agents were administered either IN or IP as specified in the Examples. The clinical condition of the animals was monitored and animals that succumbed to the disease were humanely euthanized. The study was terminated ~24.5 h post infection when most of the vehicle mice were displaying significant clinical symptoms. At 24.5 hours post infection, the clinical condition of all remaining animals was assessed, and they were humanely euthanized by pentobarbitone overdose. Animal weights were determined before the lungs were removed and weighed. Lung samples were homogenized in ice cold sterile phosphate buffered saline using a Precellys bead beater; the homogenates were quantitatively cultured onto *Pseudomonas* selective agar and incubated at 37° C. for 16-24 hours before colonies were counted. Data were analyzed using StatsDirect software (version 2.7.8). The non-parametric Kruskal-Wallis test was used to test all pairwise comparisons (Conover-Inman) for tissue burden data.

Acute Lung Infection Model. The acute lung infection model was performed as previously described(3) with some minor modifications. Briefly, after general anesthesia (intraperitoneal injection using ketamine and xylazine) of C3H/H3N female 6-8 week old mice, 10 µL ($1 \times 10^6$ CFU) of the reference strain *P. aeruginosa* PA14 was inoculated in each nostril to induce an acute lung infection. The inoculum was prepared from a dilution of an overnight culture of PA14 grown in LB. Mice were monitored over four days and were humanely euthanized when they showed imminent signs of mortality including ruffled fur, lethargy, shaking, high respiratory rate, inability to move when touched or inability to right itself after being placed on its side. For the protection assays, the ADC or the control compound were injected at 15/mg/kg, IP, three hours after the bacterial challenge.

INCORPORATION BY REFERENCE

All publications, patents, and accession numbers mentioned herein are hereby incorporated by reference in their entirety as if each individual publication or patent was specifically and individually indicated to be incorporated by reference.

EQUIVALENTS

While specific embodiments of the compositions and methods herein have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. An antibody molecule-drug conjugate (ADC) comprising an antibody molecule and a covalently coupled peptide, wherein the antibody molecule is capable of binding to lipopolysaccharide (LPS) on *Pseudomonas aeruginosa* and comprises a heavy chain variable region (VH), wherein the VH comprises three heavy chain complementarity determining regions (HCDR1, HCDR2, and HCDR3), and wherein the VH comprises:

(a) an HCDR1 comprising the amino acid sequence of SEQ ID NO: 105; an HCDR2 comprising the amino acid sequence of SEQ ID NO: 106; and an HCDR3 comprising the amino acid sequence of SEQ ID NO: 107, or (b) an HCDR1 comprising the amino acid sequence of SEQ ID NO: 108; an HCDR2 comprising the amino acid sequence of SEQ ID NO: 146; and an HCDR3 comprising the amino acid sequence of SEQ ID NO: 107; and wherein the antibody molecule comprises a light chain variable region (VL), wherein the VL comprises three light chain complementarity determining regions (LCDR1, LCDR2, and LCDR3), and wherein the VL comprises an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112; and wherein the peptide comprises the amino acid sequence of SEQ ID NO: 257.

2. The ADC of claim 1, wherein the VH comprises the amino acid sequence of SEQ ID NO 117, or an amino acid sequence that differs by no more than 15 amino acid residues from, or has at least 85% homology with, the amino acid sequence of SEQ ID NO 117; and/or wherein the VL comprises the amino acid sequence of SEQ ID NO 135, or an amino acid sequence that differs by no more than 15 amino acid residues from, or has at least 85% homology with, the amino acid sequence of SEQ ID NO 135.

3. The ADC of claim 1, wherein the antibody molecule is a monoclonal antibody molecule, a humanized antibody molecule, an isolated antibody molecule, or a synthetic antibody molecule.

4. The ADC of claim 1, wherein the antibody molecule comprises two VHs and two VLs.

5. The ADC of claim 1, wherein the peptide comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 D-amino acids, or at least 10% of the amino acid residues in the peptide are D-amino acids.

6. The ADC of claim 1, wherein the ADC comprises a linker comprising a (Gly-Ser)n linker sequence, where n=2 to 20 (SEQ ID NO: 262), between the antibody molecule and the peptide.

7. An ADC comprising an antibody molecule comprising two VHs and two VLs, wherein the VH is covalently coupled with a peptide comprising the amino acid sequence of SEQ ID NO: 257; and wherein:

(i) the VH comprises an HCDR1 comprising the amino acid sequence of SEQ ID NO: 105; an HCDR2 comprising the amino acid sequence of SEQ ID NO: 106;

and an HCDR3 comprising the amino acid sequence of SEQ ID NO: 107; and the VL comprises an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112; or (ii) the VH comprises an HCDR1 comprising the amino acid sequence of SEQ ID NO: 108; an HCDR2 comprising the amino acid sequence of SEQ ID NO: 146; and an HCDR3 comprising the amino acid sequence of SEQ ID NO: 107; and the VL comprises an LCDR1 comprising the amino acid sequence of SEQ ID NO: 138; an LCDR2 comprising the amino acid sequence of SEQ ID NO: 142; and an LCDR3 comprising the amino acid sequence of SEQ ID NO: 112 wherein the peptide is coupled to the C-terminus of the VH via a (Gly-Ser)n linker, where n=2 to 20 (SEQ ID NO: 262).

8. A pharmaceutical composition comprising an ADC of claim 1 and a pharmaceutically acceptable carrier.

9. A method of treating or preventing a bacterial infection, the method comprising administering to a subject in need thereof an ADC of claim 1 in an amount effective to treat or prevent the bacterial infection.

10. The method of claim 9, wherein the method further comprises administering to the subject a second antimicrobial agent or therapy.

11. A method of inhibiting or reducing a bacterial infection, the method comprising contacting a cell with an ADC of claim 1 in an amount effective to inhibit or reduce the bacterial infection.

12. A kit comprising: an ADC of claim 1, and instructions for use of the ADC.

13. A container comprising an ADC of claim 1.

14. A nucleic acid molecule encoding a VH and a VL of the antibody molecule of an ADC of claim 1, and the antimicrobial peptide of the ADC.

15. A vector comprising the nucleic acid molecule of claim 14.

16. A cell comprising the vector of claim 15.

17. A method of producing an ADC, the method comprising
culturing the cell of claim 16 under conditions that allow production of an ADC, thereby producing the ADC.

18. The ADC of claim 1, wherein the antibody molecule further comprises a heavy chain constant region of an IgG1, IgG2, IgG3, or IgG4, and/or a light chain constant region of a kappa or lambda chain.

19. The ADC of claim 1, wherein the antibody molecule is a Fab, a F(ab')2, an Fv, a single chain Fv fragment (scFv), or a full-length antibody.

20. The ADC of claim 1, wherein the peptide is coupled to the VH indirectly via a constant region, a linker, or both.

21. The ADC of claim 1, wherein the peptide is coupled to the antibody molecule by an enzymatic ligation via a sortase recognition sequence.

22. The ADC of claim 1, wherein the peptide comprises a sortase donor sequence.

23. The ADC of claim 1, wherein the ADC has a peptide-to-antibody molecule ratio between 2 and 8.

24. The ADC of claim 7, wherein the VH comprises the amino acid sequence of SEQ ID NO: 117, and wherein the VL comprises the amino acid sequence of SEQ ID NO: 135.

25. The method of claim 9, wherein the subject has one or more of: pneumonia, a urinary tract infection (UTI), septicemia, meningitis, diarrhea, a soft tissue infection, a skin infection, bacteremia, a respiratory system infection, endocarditis, an intra-abdominal infection, septic arthritis, osteomyelitis, a CNS infection, an ophthalmic infection, cholecystitis, cholangitis, typhoid fever, food poisoning, gastroenteritis, enteric fever, shigellosis, a blood stream infection, intra-abdominal sepsis, a brain abscess, sepsis, a joint infection, a bone infection, a gastrointestinal infection, or a wound infection.

26. The method of claim 9, wherein the subject has an HIV infection, AIDS, a cancer, a solid organ transplantation, a stem cell transplantation, a sickle cell disease, asplenia, a congenital immune deficiency, a chronic inflammatory condition, a cochlear implant, malnutrition, or a cerebrospinal fluid leak.

27. The method of claim 10, wherein the second antimicrobial agent or therapy comprises an antibiotic or a phage therapy.

* * * * *

SEQUENCE LISTING

```
<160> NUMBER OF SEQ ID NOS: 270

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1
```

```
Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp His
            20                  25                  30

Tyr Ile Asn Trp Val Lys Gln Ser His Gly Lys Ser Leu Glu Trp Ile
        35                  40                  45

Gly Gly Ile Tyr Pro Tyr His Gly Ile Thr Lys Tyr Asn Arg Asn Phe
    50                  55                  60

Lys Asp Lys Ala Thr Leu Thr Val Asp Lys Ser Ser Thr Ala Tyr
65                  70                  75                  80

Met Glu Leu Asn Ser Leu Thr Ser Glu Leu Ser Ala Val Tyr Tyr Cys
                85                  90                  95

Ala Ser Gly Gly Ser Arg Arg Tyr Phe Asp Val Trp Gly Thr Gly Thr
                100                 105                 110

Thr Val Thr Val Ser Ser
            115
```

<210> SEQ ID NO 2
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Gly Leu Ile Arg Asn Lys Arg Asn Gly Asp Thr Ala Glu Tyr Ser Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Gln Gly Arg Gly Tyr Thr Leu Asp Tyr Trp Gly Gln
                100                 105                 110

Gly Thr Leu Val Thr Val Ser Ser
            115                 120
```

<210> SEQ ID NO 3
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Thr Trp Val Arg Gln Ala Pro Gly Lys Gly Leu Glu Trp Val
        35                  40                  45
```

Gly Leu Ile Arg Ala Lys Ala Asn Gly Asp Thr Ala Glu Tyr Ser Ala
            50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                    85                  90                  95

Tyr Cys Ala Arg Gln Gly Arg Gly Tyr Thr Leu Asp Tyr Trp Gly Gln
                100                 105                 110

Gly Thr Leu Val Thr Val Ser Ser
            115                 120

<210> SEQ ID NO 4
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Trp Ile Thr Trp Val Lys Gln Arg Pro Gly Gln Gly Leu Glu Trp Ile
            35                  40                  45

Gly Asp Ile Tyr Pro Gly Ser Gly Ser Thr Asn Tyr Asn Glu Lys Phe
    50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Ser Tyr Ser Leu Asp Tyr Trp Gly Gln Gly Thr Thr Leu
                100                 105                 110

Thr Val Ser Ser
            115

<210> SEQ ID NO 5
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Asn Thr
                20                  25                  30

Tyr Met His Trp Val Lys Gln Arg Pro Glu Gln Gly Leu Glu Trp Ile
            35                  40                  45

Gly Arg Ile Asp Pro Ala Asn Gly Asn Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Ile Tyr Tyr Cys
                85                  90                  95

Ala Pro Ser Asn Tyr His Ala Met Asp Tyr Trp Gly Gln Gly Thr Ser
                100                 105                 110

Val Thr Val Ser Ser
        115

<210> SEQ ID NO 6
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Trp Asn Gly Asn Tyr Phe Asp Tyr Trp Gly Gln Gly Thr Thr
                100                 105                 110

Leu Thr Val Ser Ser
        115

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Thr Arg Gln Leu Gly Leu Arg Trp Phe Ala Tyr Trp Gly Gln
                100                 105                 110

Gly Thr Leu Val Thr Val Ser Ala
        115                 120

<210> SEQ ID NO 8
<211> LENGTH: 112

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8
```

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

```
<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9
```

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asn Ile Asn Ile Trp
            20                  25                  30

Leu Ser Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Gln Ser Tyr Pro Arg
                85                  90                  95

Thr Phe Gly Gly Gly Thr Lys Val Glu Ile Lys
            100                 105

```
<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10
```

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser

```
                35                  40                  45
Pro Gln Arg Leu Ile Tyr Tyr Met Ser Asn Leu Ala Ser Gly Val Pro
            50                  55                  60
Asp Arg Phe Ser Gly Arg Gly Ser Gly Thr Asp Phe Thr Leu Arg Ile
65                  70                  75                  80
Ser Arg Val Glu Ala Glu Asp Val Gly Val Tyr Tyr Cys Met Gln Ser
                85                  90                  95
Leu Glu Tyr Pro Leu Thr Phe Gly Ala Gly Thr Lys Leu Glu Leu Lys
            100                 105                 110

<210> SEQ ID NO 11
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Val Met Thr Gln Ala Ala Pro Ser Val Pro Val Thr Pro Gly
1               5                   10                  15
Glu Ser Val Ser Ile Ser Cys Arg Ser Ser Lys Ser Leu Leu His Ser
            20                  25                  30
Asn Gly Asn Thr Tyr Leu Tyr Trp Phe Leu Gln Arg Pro Gly Gln Ser
                35                  40                  45
Pro Gln Leu Leu Ile Tyr Arg Met Ser Asn Leu Ala Ser Gly Val Pro
            50                  55                  60
Asp Arg Phe Ser Gly Ser Gly Ser Gly Thr Ala Phe Thr Leu Arg Ile
65                  70                  75                  80
Ser Arg Val Glu Ala Glu Asp Val Gly Val Tyr Tyr Cys Met Gln His
                85                  90                  95
Leu Glu Tyr Pro Tyr Thr Phe Gly Gly Gly Thr Lys Leu Glu Ile Lys
            100                 105                 110

<210> SEQ ID NO 12
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Val Met Ser Gln Ser Pro Ser Ser Leu Ala Val Ser Ala Gly
1               5                   10                  15
Glu Lys Val Thr Met Ser Cys Lys Ser Ser Gln Ser Leu Leu Asn Ser
            20                  25                  30
Arg Thr Arg Lys Asn Tyr Leu Ala Trp Tyr Gln Gln Lys Pro Gly Gln
                35                  40                  45
Ser Pro Lys Leu Leu Ile Tyr Trp Ala Ser Thr Arg Glu Ser Gly Val
            50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr Tyr Cys Lys Gln
                85                  90                  95
Ser Tyr Asn Leu Trp Thr Phe Gly Gly Gly Thr Lys Leu Glu Ile Lys
            100                 105                 110
```

```
<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Tyr Ser Thr Pro Trp
                85                  90                  95

Thr Phe Gly Gly Gly Thr Lys Leu Glu Ile Lys
            100                 105

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Tyr Thr Phe Thr Asp His
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Pro Tyr His Gly Ile
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Ser Arg Arg Tyr Phe Asp Val
1               5

<210> SEQ ID NO 17
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 17

Asp His Tyr Ile Asn
1               5

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ile Tyr Pro Tyr His Gly Ile Thr Lys Tyr Asn Arg Asn Phe Lys
1               5                   10                  15

Asp

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Phe Thr Phe Ser Asp Tyr
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Asn Lys Arg Asn Gly Asp Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Gly Arg Gly Tyr Thr Leu Asp Tyr
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Tyr Tyr Met Thr
1               5
```

```
<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Ile Arg Asn Lys Arg Asn Gly Asp Thr Ala Glu Tyr Ser Ala Ser
1               5                   10                  15

Val Lys Gly

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ser Gly Ser Gly Ser Gly Ser Gly Ser Gly Ser Leu Pro Glu Thr
1               5                   10                  15

Gly Gly Gly

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ala Lys Ala Asn Gly Asp Thr
1               5

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Pro Gly Gly Gly Gly Ser Gly Gly Gly Ser Leu Pro Glu Thr Gly
1               5                   10                  15

Gly Ser Gly

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Tyr Trp Met Thr
1               5

<210> SEQ ID NO 28
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Ile Arg Ala Lys Ala Asn Gly Asp Thr Ala Glu Tyr Ser Ala Ser
1               5                   10                  15

Val Lys Gly

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Tyr Thr Phe Thr Ser Tyr
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Pro Gly Ser Gly Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ser Tyr Ser Leu Asp Tyr
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Tyr Trp Ile Thr
1               5

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 33

Asp Ile Tyr Pro Gly Ser Gly Ser Thr Asn Tyr Asn Glu Lys Phe Lys
1               5                   10                  15

Ser

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Phe Asn Ile Lys Asn Thr
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Pro Ala Asn Gly Asn
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Asn Tyr His Ala Met Asp Tyr
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asn Thr Tyr Met His
1               5

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ile Asp Pro Ala Asn Gly Asn Thr Lys Tyr Ala Pro Lys Phe Gln
1               5                   10                  15

Gly
```

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Tyr Ser Ile Thr Ser Gly Tyr
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Tyr Asp Gly Ser
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Trp Asn Gly Asn Tyr Phe Asp Tyr
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Gly Tyr Tyr Trp Asn
1               5

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Ile Ser Tyr Asp Gly Ser Asn Asn Tyr Asn Pro Ser Leu Lys Asn
1               5                   10                  15

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 44

Gly Tyr Thr Phe Thr Asp Tyr
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asn Pro Tyr Asn Gly Gly
1               5

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Arg Gln Leu Gly Leu Arg Trp Phe Ala Tyr
1               5                   10

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Tyr Tyr Met Asn
1               5

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Val Ile Asn Pro Tyr Asn Gly Gly Thr Ser Tyr Asn Gln Lys Phe Lys
1               5                   10                  15

Gly

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Ser Ser Gln Arg Leu Val His Ser Asn Gly Asn Thr Tyr Leu His
1               5                   10                  15

<210> SEQ ID NO 50
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Val Ser Asn Arg Phe Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Gln Ser Thr His Val Pro Tyr Thr
1               5

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ala Ser Gln Asn Ile Asn Ile Trp Leu Ser
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Ala Ser Asn Leu His Thr
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Gln Gly Gln Ser Tyr Pro Arg Thr
1               5

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55
```

Arg Ser Ser Lys Ser Leu Leu His Ser Asn Gly Asn Thr Tyr Leu Tyr
1               5                   10                  15

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Tyr Met Ser Asn Leu Ala Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Met Gln Ser Leu Glu Tyr Pro Leu Thr
1               5

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Ser Ser Lys Ser Leu Leu His Ser Asn Gly Asn Thr Tyr Leu Tyr
1               5                   10                  15

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Met Ser Asn Leu Ala Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Met Gln His Leu Glu Tyr Pro Tyr Thr
1               5

<210> SEQ ID NO 61
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 61

Lys Ser Ser Gln Ser Leu Leu Asn Ser Arg Thr Arg Lys Asn Tyr Leu
1               5                   10                  15

Ala

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Trp Ala Ser Thr Arg Glu Ser
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Gln Ser Tyr Asn Leu Trp Thr
1               5

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Ala Ser Gln Thr Ile Gly Thr Trp Leu Ala
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ala Thr Ser Leu Ala Asp
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Gln Leu Tyr Ser Thr Pro Trp Thr
1               5
```

```
<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Leu Trp Lys Thr Leu Leu Lys Lys Val Leu Lys Ala Ala Ala Lys
1               5                   10                  15

<210> SEQ ID NO 68
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 69
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 70
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Leu Trp Lys Thr Leu Leu Lys Lys Val Leu Lys Ala Ala Ala Lys
1               5                   10                  15

Gly Gly Gly Gly Ser Gly Gly Gly Gly Ser
            20                  25

<210> SEQ ID NO 71
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gly Ile Gly Lys Phe Leu Lys Lys Ala Lys Lys Phe Gly Lys Ala Phe
1               5                   10                  15
```

```
Val Lys Ile Leu Lys Lys Gly Gly Gly Ser Gly Gly Gly Ser
            20                  25              30
```

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

```
Lys Lys Leu Leu Lys Trp Leu Lys Lys Leu Leu
1               5                   10
```

<210> SEQ ID NO 73
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

```
Gly Ile Gly Lys Phe Leu Lys Lys Ala Lys Lys Phe Gly Lys Ala Phe
1               5                   10                  15
Val Lys Ile Leu Lys Lys
            20
```

<210> SEQ ID NO 74
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Arg Leu Gly Asn Phe Phe Arg Lys Ala Lys Lys Ile Gly Arg Gly
1               5                   10                  15
Leu Lys Lys Ile Gly Gln Lys Ile Lys Asp Phe Leu Gly Asn Leu Val
            20                  25                  30
Pro Arg Thr Glu Ser
        35
```

<210> SEQ ID NO 75
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Gly Gly Gly Gly Ser Gly Gly Gly Ser Gly Ile Gly Lys Phe Leu
1               5                   10                  15
Lys Lys Ala Lys Lys Phe Gly Lys Ala Phe Val Lys Ile Leu Lys Lys
            20                  25                  30
```

<210> SEQ ID NO 76
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

Gly Leu Arg Lys Arg Leu Arg Lys Phe Arg Asn Lys Ile Lys Glu Lys
1               5                   10                  15

Leu Lys Lys Ile Gly Gln Lys Ile Gln Gly Leu Leu Pro Lys Leu Ala
            20                  25                  30

<210> SEQ ID NO 77
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Gly Gly Gly Ser Gly Gly Gly Ser Ala Leu Trp Lys Thr Leu
1               5                   10                  15

Leu Lys Lys Val Leu Lys Ala Ala Ala Lys
            20                  25

<210> SEQ ID NO 78
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Trp Lys Lys Trp Phe Asn Arg Ala Lys Lys Val Gly Lys Thr Val
1               5                   10                  15

Gly Gly Leu Ala Val Asp His Tyr Leu Gly
            20                  25

<210> SEQ ID NO 79
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gly Ala Phe Gly Asn Phe Leu Lys Gly Val Ala Lys Lys Ala Gly Leu
1               5                   10                  15

Lys Ile Leu Ser Ile Ala Gln Cys Lys Leu Phe Gly Thr Cys
            20                  25                  30

<210> SEQ ID NO 80
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gly Gly Gly Arg Gly Leu Arg Arg Leu Gly Arg Lys Ile Ala His Gly
1               5                   10                  15

Val Lys Lys Tyr Gly Pro Thr Val Leu Arg Ile Ile Arg Ile Ala Gly
            20                  25                  30

<210> SEQ ID NO 81
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81

```
gaggtccagc tgcagcagtc tggacctgtg ctggtgaagc ctggggcttc agtgaagatg     60
tcctgtaagg cttctggata cacattcact gaccactata aaactgggt gaagcagagc     120 catggaaaga gccttgagtg gattggaggt atttatcctt accacggtat tactaagtac     180
aaccggaatt tcaaggacaa ggccacattg actgttgaca agtcctccag cacagcctac     240
atggagctca acagcctgac atctgaactc tctgcagtct attactgtgc aagcggggga     300
agtcgccggt acttcgatgt ctggggcaca gggaccacgg tcaccgtctc ctca          354
```

<210> SEQ ID NO 82
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82

```
gaagtgcagc tcgtggaatc tggaggagga cttgtgcaac ctggaggttc cctgcgactg     60
tcgtgtgccg catccggttt caccttttcc gactactaca tgacctgggt cagacaggcg    120
ccggggaagg gactggagtg ggtcggcttg atccgcaaca agaggaacgg cgatactgct    180
gaatactcgg ccagcgtgaa ggggcggttc accatctcga gagatgacag caagaactcc    240
ctgtacctcc aaatgaactc cctgaaaacc gaggacactg cggtgtacta ctgcgcccgc    300
cagggtcgcg gctacacgct ggactattgg ggccagggca ccctggtcac tgtgtcaagc    360
```

<210> SEQ ID NO 83
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 83

```
gaagtgcagc tcgtggaatc tggaggagga cttgtgcaac ctggaggttc cctgcgactg     60
tcgtgtgccg catccggttt caccttttcc gactactgga tgacctgggt cagacaggcg    120
ccggggaagg gactggagtg ggtcggcttg atccgcgcca aggcgaacgg cgatactgct    180
gaatactcgg ccagcgtgaa ggggcggttc accatctcga gagatgacag caagaactcc    240
ctgtacctcc aaatgaactc cctgaaaacc gaggacactg cggtgtacta ctgcgcccgc    300
cagggtcgcg gctacacgct ggactattgg ggccagggca ccctggtcac tgtgtcaagc    360
```

<210> SEQ ID NO 84
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84

```
caggtccaac tgcagcagcc tggggctgag cttgtgaagc ctggggcttc agtgaagatg      60
tcctgcaagg cttctggcta caccttcacc agctactgga taacctgggt gaagcagagg     120
cctggacaag gccttgagtg gattggagat atttatcctg gtagtggtag tactaactac     180
aatgagaagt tcaagagcaa ggccacactg actgtagaca catcctccag cacagcctac     240
atgcagctca gcagcctgac atctgaggac tctgcggtct attactgtgc aagaggtagc     300
tactcccttg actactgggg ccaaggcacc actctcacag tctcctca                 348

<210> SEQ ID NO 85
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
gaggttcagc tgcagcagtc tgtggcagag cttgtgaggc caggggcctc agtcaagttg      60
tcctgcacag cttctggctt caacattaaa aacacctata tgcactgggt gaagcagagg     120
cctgaacagg gcctggagtg gattggaagg attgatcctg cgaatggtaa tactaaatat     180
gccccgaagt tccagggcaa ggccactata actgcagaca catcctccaa cacagcctac     240
ctgcagctca gcagcctgac atctgaggac actgccatct attactgtgc tcctagtaac     300
taccatgcta tggactactg gggtcaagga acctcagtca ccgtctcctc a              351

<210> SEQ ID NO 86
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
gatgtacagc ttcaggagtc aggacctggc ctcgtgaaac cttctcagtc tctgtctctc      60
acctgctctg tcactggcta ctccatcacc agtggttatt actggaactg gatccggcag     120
tttccaggaa acaaactgga atggatgggc tacataagct acgatggtag caataactac     180
aacccatctc tcaaaaatcg aatctccatc actcgtgaca catctaagaa ccagttttc     240 ctgaagttga attctgtgac tactgaggac acagccacat attactgtgc aagatggaat     300
ggtaactact ttgactactg gggccaaggc accactctca cagtctcctc a              351

<210> SEQ ID NO 87
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
gaggtccagc tgcaacagtc tggacctgtg ctggtgaagc ctggggcttc agtgaagatg      60
tcctgtaagg cttctggata cacattcact gactactata tgaactgggt gaagcagagc     120
catggaaaga gccttgagtg gattggagtt attaatcctt acaacggtgg tactagctac     180
aaccagaagt tcaagggcaa ggccacattg actgttgaca gtcctccag cacagcctac     240 atggagctca acagcctgac atctgaggac tctgcagtct attactgtgc aagaaccaga     300
```

```
cagctcgggc tacgttggtt tgcttactgg ggccaaggga ctctggtcac tgtctctgca    360
```

<210> SEQ ID NO 88
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

```
gatgttgtga tgacccaaac tccactctcc ctgcctgtca gtcttggaga tcaagcctcc     60
atctcttgca gatctagtca gagacttgta cacagtaatg gaaacaccta tttacattgg    120
tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttccg    300
tacacgttcg gaggggggac caagctggaa ataaaa                              336
```

<210> SEQ ID NO 89
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

```
gacatccaga tgactcagtc cccgtcctca gtctccgcat ccgtgggaga tcgcgtgacg     60
attacttgcc gggcgtcgca gaacatcaac atctggctgt cgtggtacca gcagaagccc    120
gggaaggctc cgaagctgct gatctacaag gcctcaaact tgcacaccgg cgtgccttcc    180
cgcttttctg gttcgggctc cgggactgac ttcaccctga ccatcagcag cctgcaaccc    240
gaggacttcg ccacctatta ctgcctccaa ggacagtcct acccaagaac cttcggcgga    300
ggaaccaagg tcgaaatcaa a                                              321
```

<210> SEQ ID NO 90
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

```
gatattgtga tgactcaggc tgcaccctct gtacctgtca ctcctggaga gtcagtatcc     60
atctcctgca ggtctagtaa gagtcttctg catagtaatg caacactta cttgtattgg    120
ttcctgcaga ggccaggcca gtctcctcag cgcctgatat attatatgtc aaccttgcc    180
tcaggagtcc cagacaggtt cagtggcaga gggtcaggaa ctgatttcac actgagaatc    240
agtagagtgg aggctgagga tgtgggtgtt tattactgta tgcaaagtct agaatatcct    300
ctcacgttcg gtgctgggac caagctggag ctgaaa                              336
```

<210> SEQ ID NO 91
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

```
gatattgtga tgactcaggc tgcaccctct gtacctgtca ctcctggaga gtcagtatcc    60
atctcctgca ggtctagtaa gagtctcctg catagtaatg caacactta cttgtattgg    120
ttcctgcaga ggccaggcca gtctcctcag ctcctgatat atcggatgtc aaccttgcc    180
tcaggagtcc cagacaggtt cagtggcagt gggtcaggaa ctgctttcac actgagaatc    240
agtagagtgg aggctgagga tgtgggtgtt tattactgta tgcaacatct agaatatccg    300
tacacgttcg gagggggac caagctggaa ataaaa                              336
```

<210> SEQ ID NO 92
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

```
gacattgtga tgtcacagtc tccatcctcc ctggctgtgt cagcaggaga gaaggtcact    60
atgagctgca atccagtca gagtctgctc aacagtagaa cccgaaagaa ctacttggct    120
tggtaccagc agaaaccagg gcagtctcct aaactgctga tctactgggc atccactagg    180
gaatctgggg tccctgatcg cttcacaggc agtggatctg gacagattt cactctcacc    240
atcagcagtg tgcaggctga agacctggca gtttattact gcaagcaatc ttataatctg    300
tggacgttcg gtggaggcac caagctggaa atcaaa                             336
```

<210> SEQ ID NO 93
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

```
gacattcaga tgacccagtc tcctgcctcc cagtctgcat ctctgggaga aagtgtcacc    60
atcacatgcc tggcaagtca gaccattggt acatggttag catggtatca gcagaaacca    120
gggaaatctc ctcagctcct gatttatgct gcaaccagct ggcagatgg ggtcccatca    180
aggttcagtg gtagtggatc tggcacaaaa ttttctttca agatcagcag cctacaggct    240
gaagattttg taagttatta ctgtcaacaa ctttacagta ctccgtggac gttcggtgga    300
ggcaccaagc tggaaatcaa a                                              321
```

<210> SEQ ID NO 94
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

```
Gly Ile Gly Lys His Val Gly Lys Ala Leu Lys Gly Leu Lys Gly Leu
1               5                   10                  15

Leu Lys Gly Leu Gly Glu Ser
            20
```

-continued

```
<210> SEQ ID NO 95
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Arg Arg Lys Arg Lys Trp Leu Arg Arg Ile Gly Lys Gly Val Lys
1               5                   10                  15

Ile Ile Gly Gly Ala Ala Leu Asp His Leu
            20                  25

<210> SEQ ID NO 96
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Gly Leu Arg Ser Leu Gly Arg Lys Ile Leu Arg Ala Trp Lys Lys
1               5                   10                  15

Tyr Gly Pro Gln Ala Thr Pro Ala Thr Arg Gln
            20                  25

<210> SEQ ID NO 97
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ile Lys Trp Lys Lys Leu Leu Arg Ala Ala Lys Arg Ile Leu
1               5                   10

<210> SEQ ID NO 98
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ile Gly Lys Lys Trp Lys Arg Ile Val Lys Arg Ile Lys Lys Phe Leu
1               5                   10                  15

Arg Lys Leu

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ile Leu Gly Lys Ile Trp Lys Ile Lys Lys Leu Phe
1               5                   10

<210> SEQ ID NO 100
```

```
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Arg Leu Gly Asp Ile Leu Gln Lys Ala Arg Glu Lys Ile Glu Gly Gly
1               5                   10                  15

Leu Lys Lys Leu Val Gln Lys Ile Lys Asp Phe Phe Gly Lys Phe Ala
            20                  25                  30

Pro Arg Thr Glu Ser
        35

<210> SEQ ID NO 101
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gly Gly Gly Gly Arg Phe Lys Arg Phe Arg Lys Lys Phe Lys Lys Leu
1               5                   10                  15

Phe Lys Lys Leu Ser Pro Val Ile Pro Leu Leu His Leu Gly
            20                  25                  30

<210> SEQ ID NO 102
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Arg Phe Lys Arg Phe Arg Lys Lys Phe Lys Lys Leu Phe Lys Lys
1               5                   10                  15

Leu Ser Pro Val Ile Pro Leu Leu His Leu Gly
            20                  25

<210> SEQ ID NO 103
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Lys Leu Val Glu Ser Gly Gly Asp Leu Val Lys Pro Gly Gly
1               5                   10                  15

Ser Leu Arg Leu Ser Cys Ala Ala Ser Glu Phe Thr Phe Ser Asp Tyr
            20                  25                  30

Ala Met Ser Trp Val Arg Gln Thr Pro Ala Lys Arg Leu Glu Trp Val
        35                  40                  45

Ala Tyr Ile Ser Ser Asp Gly Asp Ser Thr Tyr Tyr Pro Asp Asn Ile
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Met Tyr Phe Cys
```

```
                    85                  90                  95

Ala Arg Glu Ile Arg Leu Arg Gly Tyr Phe Asp Val Trp Gly Ala Gly
            100                 105                 110

Thr Thr Val Thr Val Ser Ser
        115

<210> SEQ ID NO 104
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Phe Gly His
            20                  25                  30

Gly Ile Ser Pro Met His Trp Tyr Gln Gln Lys Pro Gly Gln Pro Pro
        35                  40                  45

Lys Leu Leu Ile Tyr Arg Ala Ser Asn Leu Lys Phe Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Tyr Pro Arg Thr Phe Gly Gly Gly Thr Lys Leu Glu Ile Lys
            100                 105                 110

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Glu Phe Thr Phe Ser Asp Tyr
1               5

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Ser Asp Gly Asp Ser
1               5

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107
```

Glu Ile Arg Leu Arg Gly Tyr Phe Asp Val
1               5                   10

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asp Tyr Ala Met Ser
1               5

<210> SEQ ID NO 109
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Tyr Ile Ser Ser Asp Gly Asp Ser Thr Tyr Tyr Pro Asp Asn Ile Lys
1               5                   10                  15

Gly

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Ala Ser Glu Ser Val Phe Gly His Gly Ile Ser Pro Met His
1               5                   10                  15

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Ala Ser Asn Leu Lys Phe
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Gln Ser Asn Glu Tyr Pro Arg Thr
1               5

<210> SEQ ID NO 113
<211> LENGTH: 357
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 113

```
gaagtgaagt tggtggagtc tgggggagac ttggtgaaac ctggagggtc cctgagactc    60
tcctgtgcag cctctgaatt cactttcagt gattatgcca tgtcttgggt tcgccagact   120
ccggcgaaga ggctggagtg ggtcgcatac attagtagtg atggtgatag tacctactat   180
ccggacaata ttaagggccg attcaccatc tccagagaca atgccaagaa caccctatac   240
ctgcaaatga acagtctgag gtctgaggac acggccatgt attttgtgc aagagaaata   300
cggctaaggg ggtacttcga tgtctggggc gcagggacca cggtcaccgt ctcctca     357
```

<210> SEQ ID NO 114
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 114

```
gacattgtgc tgacccaatc tccagcttct ttggctgtgt ctctagggca gagggccacc    60
atatcctgca gagccagtga aagtgttttt ggtcatggca ttagtcctat gcactggtac   120
cagcagaaac caggacagcc acccaaactc ctcatctatc gtgcatccaa cctaaaattt   180
gggatccctg ccaggttcag tggcagtggg tctaggacag acttcaccct caccattaat   240
cctgtggagg ctgatgatgt tgcaacctat tactgtcagc aaagtaatga atatcctcgg   300
acgttcggtg aggcaccaa gctggagatc aaa                                 333
```

<210> SEQ ID NO 115
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 115

```
Glu Val Lys Leu Val Glu Ser Gly Gly Gly Leu Val Gln Pro Gly Gly
1               5                   10                  15

Ser Leu Arg Leu Ser Cys Ser Ala Ser Glu Phe Thr Phe Ser Asp Tyr
            20                  25                  30

Ala Met Ser Trp Val Arg Gln Ala Pro Gly Lys Gly Leu Glu Trp Val
        35                  40                  45

Ser Tyr Ile Ser Ser Asp Gly Asp Ser Thr Tyr Tyr Pro Asp Asn Ile
    50                  55                  60

Lys Gly Arg Phe Thr Ile Ser Arg Asp Asn Ser Lys Asn Thr Leu Tyr
65                  70                  75                  80

Val Gln Met Ser Ser Leu Arg Ala Glu Asp Thr Ala Val Tyr Phe Cys
                85                  90                  95

Ala Arg Glu Ile Arg Leu Arg Gly Tyr Phe Asp Val Trp Gly Gln Gly
            100                 105                 110

Thr Thr Val Thr Val Ser Ser
        115
```

<210> SEQ ID NO 116

<211> LENGTH: 119
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 116

Glu Val Lys Leu Val Glu Ser Gly Gly Gly Leu Val Lys Pro Gly Gly
1               5                   10                  15

Ser Leu Arg Leu Ser Cys Ala Ala Ser Glu Phe Thr Phe Ser Asp Tyr
            20                  25                  30

Ala Met Ser Trp Val Arg Gln Ala Pro Gly Lys Arg Leu Glu Trp Val
        35                  40                  45

Ala Tyr Ile Ser Ser Asp Gly Asp Ser Ile Tyr Tyr Pro Asp Asn Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Phe Cys
                85                  90                  95

Ala Arg Glu Ile Arg Leu Arg Gly Tyr Phe Asp Val Trp Gly Gln Gly
            100                 105                 110

Thr Thr Val Thr Val Ser Ser
        115

<210> SEQ ID NO 117
<211> LENGTH: 119
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 117

Glu Val Lys Leu Val Glu Ser Gly Gly Gly Leu Val Gln Pro Gly Gly
1               5                   10                  15

Ser Leu Arg Leu Ser Cys Ala Ala Ser Glu Phe Thr Phe Ser Asp Tyr
            20                  25                  30

Ala Met Ser Trp Val Arg Gln Ala Pro Gly Lys Arg Leu Glu Trp Val
        35                  40                  45

Ala Tyr Ile Ser Ser Asp Gly Asp Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Phe Cys
                85                  90                  95

Ala Arg Glu Ile Arg Leu Arg Gly Tyr Phe Asp Val Trp Gly Gln Gly
            100                 105                 110

Thr Thr Val Thr Val Ser Ser
        115

<210> SEQ ID NO 118
<211> LENGTH: 119
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 118

Glu Val Lys Leu Val Glu Ser Gly Glu Gly Leu Val Gln Pro Gly Gly
1               5                   10                  15

Ser Leu Arg Leu Ser Cys Ala Ala Ser Glu Phe Thr Phe Ser Asp Tyr
            20                  25                  30

Ala Met Ser Trp Val Arg Gln Ala Pro Gly Lys Arg Leu Glu Trp Val
        35                  40                  45

Ala Tyr Ile Ser Ser Asp Gly Asp Ser Thr Tyr Tyr Pro Asp Asn Ile
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Met Tyr Phe Cys
                85                  90                  95

Ala Arg Glu Ile Arg Leu Arg Gly Tyr Phe Asp Val Trp Gly Gln Gly
            100                 105                 110

Thr Thr Val Thr Val Ser Ser
            115

<210> SEQ ID NO 119
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Phe Gly His
            20                  25                  30

Gly Ile Ser Pro Leu His Trp Tyr Gln Gln Lys Pro Gly Gln Ala Pro
        35                  40                  45

Lys Leu Leu Ile Tyr Arg Ala Ser Asn Arg Lys Thr Gly Ile Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln Gln Ser Asn
                85                  90                  95

Glu Tyr Pro Arg Thr Phe Gly Gly Gly Thr Lys Val Glu Ile Lys
            100                 105                 110

<210> SEQ ID NO 120
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Ser Val Phe Gly His
            20                  25                  30

Gly Ile Ser Pro Leu His Trp Tyr Gln Gln Lys Pro Gly Lys Ala Pro
        35                  40                  45

Lys Leu Leu Ile Tyr Arg Ala Ser Asn Leu Lys Phe Gly Val Pro Ser
    50                  55                  60

-continued

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln Gln Ser Asn
                85                  90                  95

Glu Tyr Pro Arg Thr Phe Gly Gly Gly Thr Lys Val Glu Ile Lys
            100                 105                 110

<210> SEQ ID NO 121
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Phe Gly His
            20                  25                  30

Gly Ile Ser Pro Leu His Trp Tyr Gln Gln Lys Pro Gly Gln Pro Pro
        35                  40                  45

Arg Leu Leu Ile Tyr Arg Ala Ser Asn Arg Lys Thr Gly Ile Pro Ala
50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln Gln Ser Asn
                85                  90                  95

Glu Tyr Pro Arg Thr Phe Gly Gly Gly Thr Lys Val Glu Ile Lys
            100                 105                 110

<210> SEQ ID NO 122
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Ser Val Phe Gly His
            20                  25                  30

Gly Ile Ser Pro Leu His Trp Tyr Gln Gln Lys Pro Gly Lys Ala Pro
        35                  40                  45

Lys Leu Leu Ile Tyr Arg Ala Ser Asn Leu Lys Phe Gly Val Pro Ser
    50                  55                  60

Arg Phe Ser Gly Ser Gly Ser Arg Thr Asp Phe Thr Leu Thr Ile Ser
65                  70                  75                  80

Ser Leu Gln Pro Asp Asp Phe Ala Thr Tyr Tyr Cys Gln Gln Ser Asn
                85                  90                  95

Glu Tyr Pro Arg Thr Phe Gly Gly Gly Thr Lys Val Glu Ile Lys
            100                 105                 110

<210> SEQ ID NO 123
<211> LENGTH: 111
<212> TYPE: PRT
<213> ORGANISM: Artificial Sequence
<220> FEATURE:

-continued

```
<223> OTHER INFORMATION: Description of Artificial Sequence: Synthetic
      polypeptide

<400> SEQUENCE: 123

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Ser Val Phe Gly His
            20                  25                  30

Gly Ile Ser Pro Leu His Trp Tyr Gln Gln Lys Pro Gly Lys Ala Pro
        35                  40                  45

Lys Leu Leu Ile Tyr Arg Ala Ser Asn Leu Lys Phe Gly Ile Pro Ser
    50                  55                  60

Arg Phe Ser Gly Ser Gly Ser Arg Thr Asp Phe Thr Leu Thr Ile Ser
65                  70                  75                  80

Ser Leu Gln Pro Asp Asp Phe Ala Thr Tyr Tyr Cys Gln Gln Ser Asn
                85                  90                  95

Glu Tyr Pro Arg Thr Phe Gly Gly Gly Thr Lys Val Glu Ile Lys
            100                 105                 110

<210> SEQ ID NO 124
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Ser Val Phe Gly His
            20                  25                  30

Gly Ile Ser Pro Leu His Trp Tyr Gln Gln Lys Pro Gly Gln Pro Pro
        35                  40                  45

Lys Leu Leu Ile Tyr Arg Ala Ser Asn Leu Lys Phe Gly Ile Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln Gln Ser Asn
                85                  90                  95

Glu Tyr Pro Arg Thr Phe Gly Gly Gly Thr Lys Val Glu Ile Lys
            100                 105                 110

<210> SEQ ID NO 125
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Asp Ile Val Leu Thr Gln Ser Pro Ser Thr Leu Ser Ala Ser Val Gly
1               5                   10                  15

Asp Arg Val Thr Ile Thr Cys Arg Ala Ser Glu Ser Val Phe Gly His
            20                  25                  30

Gly Ile Ser Pro Met His Trp Tyr Gln Gln Lys Pro Gly Lys Ala Pro
        35                  40                  45

Lys Leu Leu Ile Tyr Arg Ala Ser Asn Leu Lys Phe Gly Val Pro Ser
```

```
                    50                  55                  60
Arg Phe Ser Gly Ser Gly Ser Gly Thr Glu Phe Thr Leu Thr Ile Ser
 65                  70                  75                  80

Ser Leu Gln Pro Asp Asp Phe Ala Thr Tyr Tyr Cys Gln Gln Ser Asn
                 85                  90                  95

Glu Tyr Pro Arg Thr Phe Gly Gly Gly Thr Lys Val Glu Ile Lys
                100                 105                 110

<210> SEQ ID NO 126
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Asp Ile Gln Met Thr Gln Ser Pro Ser Thr Leu Ser Ala Ser Val Gly
 1               5                  10                  15

Asp Arg Val Thr Ile Thr Cys Arg Ala Ser Glu Ser Val Phe Gly His
                 20                  25                  30

Gly Ile Ser Pro Leu His Trp Tyr Gln Gln Lys Pro Gly Lys Ala Pro
             35                  40                  45

Lys Leu Leu Ile Tyr Arg Ala Ser Asn Leu Lys Phe Gly Ile Pro Ala
 50                  55                  60

Arg Phe Ser Gly Ser Gly Ser Gly Thr Glu Phe Thr Leu Thr Ile Ser
 65                  70                  75                  80

Ser Leu Gln Pro Asp Asp Phe Ala Thr Tyr Tyr Cys Gln Gln Ser Asn
                 85                  90                  95

Glu Tyr Pro Arg Thr Phe Gly Gly Gly Thr Lys Val Glu Ile Lys
                100                 105                 110

<210> SEQ ID NO 127
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Ile Phe Gly His
                 20                  25                  30

Gly Ile Ser Pro Met His Trp Tyr Gln Gln Lys Pro Gly Gln Pro Pro
             35                  40                  45

Lys Leu Leu Ile Tyr Arg Ala Ser Asn Leu Lys Phe Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Tyr Pro Arg Thr Phe Gly Gly Gly Thr Lys Leu Glu Ile Lys
                100                 105                 110

<210> SEQ ID NO 128
<211> LENGTH: 111
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 128

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Phe Gly His
            20                  25                  30

Gly Ile Ser Pro Met His Trp Tyr Gln Gln Lys Pro Gly Gln Pro Pro
        35                  40                  45

Lys Leu Leu Ile Tyr Arg Ala Ser Ser Leu Lys Phe Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Tyr Pro Arg Thr Phe Gly Gly Gly Thr Lys Leu Glu Ile Lys
            100                 105                 110

<210> SEQ ID NO 129
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Phe Gly His
            20                  25                  30

Gly Ile Ser Pro Met His Trp Tyr Gln Gln Lys Pro Gly Gln Pro Pro
        35                  40                  45

Lys Leu Leu Ile Tyr Arg Ala Ser Asn Leu Lys Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Tyr Pro Arg Thr Phe Gly Gly Gly Thr Lys Leu Glu Ile Lys
            100                 105                 110

<210> SEQ ID NO 130
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Asp Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Phe Gly His
            20                  25                  30

Gly Ile Ser Pro Leu His Trp Tyr Gln Gln Lys Pro Gly Gln Ala Pro
        35                  40                  45
```

Lys Leu Leu Ile Tyr Arg Ala Ser Asn Leu Lys Thr Gly Ile Pro Ala
 50                  55                  60

Arg Phe Ser Gly Ser Gly Ser Arg Thr Asp Phe Thr Leu Thr Ile Ser
65                  70                  75                  80

Ser Leu Gln Ser Glu Asp Phe Ala Thr Tyr Tyr Cys Gln Gln Ser Asn
                85                  90                  95

Glu Tyr Pro Arg Thr Phe Gly Gly Gly Thr Lys Val Glu Ile Lys
            100                 105                 110

<210> SEQ ID NO 131
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Glu Ile Val Met Thr Gln Ser Pro Ala Thr Leu Ser Val Ser Pro Gly
1               5                   10                  15

Glu Arg Ala Thr Ile Ser Cys Arg Ala Ser Glu Ser Val Phe Gly His
            20                  25                  30

Gly Ile Ser Pro Leu His Trp Tyr Gln Gln Lys Pro Gly Gln Ala Pro
        35                  40                  45

Lys Leu Leu Ile Tyr Arg Ala Ser Asn Arg Lys Thr Gly Ile Pro Ala
 50                  55                  60

Arg Phe Ser Gly Ser Gly Ser Gly Thr Glu Phe Thr Leu Thr Ile Ser
65                  70                  75                  80

Pro Val Gln Ser Glu Asp Phe Ala Val Tyr Tyr Cys Gln Gln Ser Asn
                85                  90                  95

Glu Tyr Pro Arg Thr Phe Gly Gly Gly Thr Lys Leu Glu Ile Lys
            100                 105                 110

<210> SEQ ID NO 132
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Ser Ile Phe Gly His
            20                  25                  30

Gly Ile Ser Pro Leu His Trp Tyr Gln Gln Lys Pro Gly Lys Ala Pro
        35                  40                  45

Lys Leu Leu Ile Tyr Arg Ala Ser Asn Leu Lys Ser Gly Ile Pro Ser
 50                  55                  60

Arg Phe Ser Gly Ser Gly Ser Arg Thr Glu Phe Thr Leu Thr Ile Ser
65                  70                  75                  80

Ser Leu Gln Pro Asp Asp Phe Ala Thr Tyr Tyr Cys Gln Gln Ser Asn
                85                  90                  95

Glu Tyr Pro Arg Thr Phe Gly Gly Gly Thr Lys Val Glu Ile Lys
            100                 105                 110

<210> SEQ ID NO 133

```
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133
```

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Ser Ile Phe Gly His
            20                  25                  30

Gly Ile Ser Pro Leu His Trp Tyr Gln Gln Lys Pro Gly Lys Ala Pro
        35                  40                  45

Lys Leu Leu Ile Tyr Arg Ala Ser Asn Leu Lys Ser Gly Val Pro Ser
    50                  55                  60

Arg Phe Ser Gly Ser Gly Ser Arg Thr Glu Phe Thr Leu Thr Ile Ser
65                  70                  75                  80

Ser Leu Gln Pro Asp Asp Phe Ala Thr Tyr Tyr Cys Gln Gln Ser Asn
                85                  90                  95

Glu Tyr Pro Arg Thr Phe Gly Gly Gly Thr Lys Val Glu Ile Lys
            100                 105                 110

```
<210> SEQ ID NO 134
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134
```

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Ser Ile Phe Gly His
            20                  25                  30

Gly Ile Ser Pro Leu His Trp Tyr Gln Gln Lys Pro Gly Lys Ala Pro
        35                  40                  45

Lys Leu Leu Ile Tyr Arg Ala Ser Asn Leu Lys Ser Gly Val Pro Ala
    50                  55                  60

Arg Phe Ser Gly Ser Gly Ser Arg Thr Glu Phe Thr Leu Thr Ile Ser
65                  70                  75                  80

Ser Leu Gln Pro Asp Asp Phe Ala Thr Tyr Tyr Cys Gln Gln Ser Asn
                85                  90                  95

Glu Tyr Pro Arg Thr Phe Gly Gly Gly Thr Lys Val Glu Ile Lys
            100                 105                 110

```
<210> SEQ ID NO 135
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135
```

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Ser Val Phe Gly His
            20                  25                  30

Gly Ile Ser Pro Leu His Trp Tyr Gln Gln Lys Pro Gly Lys Ala Pro
            35                  40                  45

Lys Leu Leu Ile Tyr Arg Ala Ser Asn Leu Lys Ser Gly Val Pro Ser
 50                  55                  60

Arg Phe Ser Gly Ser Gly Ser Arg Thr Glu Phe Thr Leu Thr Ile Ser
 65                  70                  75                  80

Ser Leu Gln Pro Asp Asp Phe Ala Thr Tyr Tyr Cys Gln Gln Ser Asn
                85                  90                  95

Glu Tyr Pro Arg Thr Phe Gly Gly Gly Thr Lys Val Glu Ile Lys
                100                 105                 110

<210> SEQ ID NO 136
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Asp Ile Gln Met Thr Gln Ser Pro Ser Thr Leu Ser Ala Ser Val Gly
 1               5                  10                  15

Asp Arg Val Thr Ile Thr Cys Arg Ala Ser Glu Ser Ile Phe Gly His
                20                  25                  30

Gly Ile Ser Pro Leu His Trp Tyr Gln Gln Lys Pro Gly Lys Ala Pro
            35                  40                  45

Lys Leu Leu Ile Tyr Arg Ala Ser Asn Leu Lys Ser Gly Val Pro Ser
 50                  55                  60

Arg Phe Ser Gly Ser Gly Ser Arg Thr Asp Phe Thr Leu Thr Ile Ser
 65                  70                  75                  80

Ser Leu Gln Pro Asp Asp Phe Ala Thr Tyr Tyr Cys Gln Gln Ser Asn
                85                  90                  95

Glu Tyr Pro Arg Thr Phe Gly Gly Gly Thr Lys Val Glu Ile Lys
                100                 105                 110

<210> SEQ ID NO 137
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Asp Ile Gln Met Thr Gln Ser Pro Ser Thr Leu Ser Ala Ser Val Gly
 1               5                  10                  15

Asp Arg Val Thr Ile Thr Cys Arg Ala Ser Glu Ser Ile Phe Gly His
                20                  25                  30

Gly Ile Ser Pro Leu His Trp Tyr Gln Gln Lys Pro Gly Lys Ala Pro
            35                  40                  45

Lys Leu Leu Ile Tyr Arg Ala Ser Asn Leu Lys Ser Gly Ile Pro Ser
 50                  55                  60

Arg Phe Ser Gly Ser Gly Ser Arg Thr Asp Phe Thr Leu Thr Ile Ser
 65                  70                  75                  80

Ser Leu Gln Pro Asp Asp Phe Ala Thr Tyr Tyr Cys Gln Gln Ser Asn
                85                  90                  95

Glu Tyr Pro Arg Thr Phe Gly Gly Gly Thr Lys Val Glu Ile Lys
                100                 105                 110

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Arg Ala Ser Glu Ser Val Phe Gly His Gly Ile Ser Pro Leu His
1               5                   10                  15

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Arg Ala Ser Asn Arg Lys Thr
1               5

<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Arg Ala Ser Glu Ser Ile Phe Gly His Gly Ile Ser Pro Met His
1               5                   10                  15

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Arg Ala Ser Ser Leu Lys Phe
1               5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Arg Ala Ser Asn Leu Lys Ser
1               5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 143

Arg Ala Ser Asn Leu Lys Thr
1               5

<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Arg Ala Ser Glu Ser Ile Phe Gly His Gly Ile Ser Pro Leu His
1               5                   10                  15

<210> SEQ ID NO 145
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Tyr Ile Ser Ser Asp Gly Asp Ser Ile Tyr Tyr Pro Asp Asn Ile Lys
1               5                   10                  15

Gly

<210> SEQ ID NO 146
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Tyr Ile Ser Ser Asp Gly Asp Ser Thr Tyr Tyr Pro Asp Ser Val Lys
1               5                   10                  15

Gly

<210> SEQ ID NO 147
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Gly Gly Gly Leu Leu Gly Asp Phe Phe Arg Lys Ser Lys Glu Lys Ile
1               5                   10                  15

Gly Lys Glu Phe Lys Arg Ile Val Gln Arg Ile Lys Asp Phe Leu Arg
            20                  25                  30

Asn Leu Val Pro Arg Thr Glu Ser
        35                  40

<210> SEQ ID NO 148
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 148

Gly Gly Gly Lys Trp Lys Ser Phe Ile Lys Lys Leu Thr Lys Ala Ala
1               5                   10                  15
Lys Lys Val Val Thr Thr Ala Lys Lys Pro Leu Ile Val
            20                  25

<210> SEQ ID NO 149
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Gly Gly Val Asn Trp Lys Lys Ile Leu Gly Lys Ile Ile Lys Val
1               5                   10                  15
Val Lys

<210> SEQ ID NO 150
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gly Gly Gly Thr Leu Ile Ser Trp Ile Lys Asn Lys Arg Lys Gln Arg
1               5                   10                  15
Pro Arg Val Ser Arg Arg Arg Arg Arg Gly Gly Arg Arg Arg Arg
            20                  25                  30

<210> SEQ ID NO 151
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Gly Gly Gly Ile Gly Ala Ile Leu Lys Val Leu Ala Thr Gly Leu
1               5                   10                  15
Pro Thr Leu Ile Ser Trp Ile Lys Asn Lys Arg Lys Gln
            20                  25

<210> SEQ ID NO 152
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gly Gly Gly Gly Leu Arg Lys Arg Leu Arg Lys Phe Arg Asn Lys Ile
1               5                   10                  15
Lys Glu Lys Leu Lys Lys Ile Gly Gln Lys Ile Gln Gly Leu Leu Pro
            20                  25                  30
Lys Leu Ala
        35

<210> SEQ ID NO 153
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gly Gly Gly Gly Leu Arg Arg Leu Gly Arg Lys Ile Ala His Gly Ile
1               5                   10                  15

Lys Lys Tyr Gly Pro Thr Ile Leu Arg Ile Ile Arg Ile Ala Gly
            20                  25                  30

<210> SEQ ID NO 154
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gly Gly Gly Arg Gly Leu Arg Arg Leu Gly Arg Lys Ile Ala His Gly
1               5                   10                  15

Val Lys Lys Tyr Gly Pro Thr Val Leu Arg Ile Ile Lys Lys Tyr Gly
            20                  25                  30

<210> SEQ ID NO 155
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Gly Gly Gly Lys Arg Phe Lys Lys Phe Phe Lys Lys Leu Lys Asn Ser
1               5                   10                  15

Val Lys Lys Arg Ala Lys Lys Phe Phe Lys Lys Pro Arg Val Ile Gly
            20                  25                  30

Val Ser Ile Pro Phe
        35

<210> SEQ ID NO 156
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Gly Gly Gly Lys Phe Phe Arg Lys Leu Lys Lys Ser Val Lys Lys Arg
1               5                   10                  15

Ala Lys Glu Phe Phe Lys Lys Pro Arg Val Ile Gly Val Ser Ile Pro
            20                  25                  30

Phe

<210> SEQ ID NO 157
<211> LENGTH: 30
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 157

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser
            20                  25                  30

<210> SEQ ID NO 158
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Ile Gly Lys Phe Leu Lys Lys Ala Lys Lys Cys Gly Lys Ala Cys
1               5                   10                  15

Val Lys Ile Leu Lys Lys
            20

<210> SEQ ID NO 159
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Gly Gly Gly Gly Arg Cys Lys Arg Phe Arg Lys Lys Cys Lys Lys Leu
1               5                   10                  15

Phe Lys Lys Leu Ser Pro Val Ile Pro Leu Leu His Leu Gly
            20                  25                  30

<210> SEQ ID NO 160
<211> LENGTH: 5
<212> TYPE: PRT
<213> ORGANISM: Staphylococcus aureus
<220> FEATURE:
<221> NAME/KEY: MOD_RES
<222> LOCATION: (3)..(3)
<223> OTHER INFORMATION: Any amino acid

<400> SEQUENCE: 160

Leu Pro Xaa Thr Gly
1               5

<210> SEQ ID NO 161
<211> LENGTH: 5
<212> TYPE: PRT
<213> ORGANISM: Staphylococcus pyogenes
<220> FEATURE:
<221> NAME/KEY: MOD_RES
<222> LOCATION: (3)..(3)
<223> OTHER INFORMATION: Any amino acid

<400> SEQUENCE: 161

Leu Pro Xaa Thr Ala
1               5

<210> SEQ ID NO 162
<211> LENGTH: 5
<212> TYPE: PRT
```

```
<213> ORGANISM: Staphylococcus sp.

<400> SEQUENCE: 162

Leu Pro Glu Thr Gly
1               5

<210> SEQ ID NO 163
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Gly Gly Gly Ile Gly Lys Phe Leu Lys Lys Ala Lys Lys Phe Gly
1               5                   10                  15

Lys Ala Phe Val Lys Ile Leu Lys Lys
            20                  25

<210> SEQ ID NO 164
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Dab
<220> FEATURE:
<221> NAME/KEY: MOD_RES
<222> LOCATION: (5)..(6)
<223> OTHER INFORMATION: Dab
<220> FEATURE:
<221> NAME/KEY: SITE
<222> LOCATION: (5)..(11)
<223> OTHER INFORMATION: Cyclic
<220> FEATURE:
<221> NAME/KEY: MOD_RES
<222> LOCATION: (7)..(7)
<223> OTHER INFORMATION: D-Leu
<220> FEATURE:
<221> NAME/KEY: MOD_RES
<222> LOCATION: (9)..(10)
<223> OTHER INFORMATION: Dab

<400> SEQUENCE: 164

Gly Gly Gly Xaa Xaa Xaa Leu Phe Xaa Xaa Leu
1               5                   10

<210> SEQ ID NO 165
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ile or Thr
<220> FEATURE:
<221> NAME/KEY: MOD_RES
<222> LOCATION: (14)..(14)
<223> OTHER INFORMATION: Asn or Ser
<220> FEATURE:
<221> NAME/KEY: MOD_RES
<222> LOCATION: (15)..(15)
<223> OTHER INFORMATION: Ile or Val
```

```
<400> SEQUENCE: 165

Tyr Ile Ser Ser Asp Gly Asp Ser Xaa Tyr Tyr Pro Asp Xaa Xaa Lys
1               5                   10                  15

Gly

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Val or Ile
<220> FEATURE:
<221> NAME/KEY: MOD_RES
<222> LOCATION: (14)..(14)
<223> OTHER INFORMATION: Met or Leu

<400> SEQUENCE: 166

Arg Ala Ser Glu Ser Xaa Phe Gly His Gly Ile Ser Pro Xaa His
1               5                   10                  15

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asn or Ser
<220> FEATURE:
<221> NAME/KEY: MOD_RES
<222> LOCATION: (5)..(5)
<223> OTHER INFORMATION: Leu or Arg
<220> FEATURE:
<221> NAME/KEY: MOD_RES
<222> LOCATION: (7)..(7)
<223> OTHER INFORMATION: Phe, Thr or Ser

<400> SEQUENCE: 167

Arg Ala Ser Xaa Xaa Lys Xaa
1               5

<210> SEQ ID NO 168
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 168

Leu Xaa Thr Pro Ser Arg
1               5

<210> SEQ ID NO 169
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 169

Leu Cys Thr Pro Ser Arg
1               5

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ala Ala Leu Leu Thr Gly Arg
1               5

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ser Gln Leu Leu Thr Gly Arg
1               5

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ala Ala Phe Met Thr Gly Arg
1               5

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ala Ala Phe Leu Thr Gly Arg
1               5

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ser Ala Phe Leu Thr Gly Arg
1               5
```

```
<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ala Ser Ile Leu Thr Gly Lys
1               5

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Val Ser Phe Leu Thr Gly Arg
1               5

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Ser Leu Leu Thr Gly Leu
1               5

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ala Ser Ile Leu Ile Thr Gly
1               5

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ser Ala Ile Met Thr Gly Arg
1               5

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180
```

```
Ser Ala Ile Val Thr Gly Arg
1               5

<210> SEQ ID NO 181
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Thr Asn Leu Trp Arg Gly
1               5

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Thr Asn Leu Trp Arg Gly Gln
1               5

<210> SEQ ID NO 183
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Thr Asn Leu Cys Ala Ala Ser
1               5

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Val Ser Leu Trp Thr Gly Lys
1               5

<210> SEQ ID NO 185
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ser Met Leu Leu Thr Gly
1               5

<210> SEQ ID NO 186
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 186

Ser Met Leu Leu Thr Gly Asn
1               5

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ser Met Leu Leu Thr Gly Thr
1               5

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ala Ser Phe Met Ala Gly Gln
1               5

<210> SEQ ID NO 189
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gly Ser Leu Phe Thr Gly Arg
1               5

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Met or Ala

<400> SEQUENCE: 190

Cys Gly Pro Ser Arg Xaa Ser
1               5

<210> SEQ ID NO 191
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (6)..(6)
<223> OTHER INFORMATION: Met or Ala

<400> SEQUENCE: 191

Cys Gly Pro Ser Arg Xaa
1               5

<210> SEQ ID NO 192
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Met Cys Thr Pro Ser Arg
1               5

<210> SEQ ID NO 193
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Val Cys Thr Pro Ser Arg
1               5

<210> SEQ ID NO 194
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Leu Cys Ser Pro Ser Arg
1               5

<210> SEQ ID NO 195
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Leu Cys Ala Pro Ser Arg
1               5

<210> SEQ ID NO 196
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Leu Cys Val Pro Ser Arg
1               5
```

-continued

```
<210> SEQ ID NO 197
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Leu Cys Gly Pro Ser Arg
1               5

<210> SEQ ID NO 198
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ile Cys Thr Pro Ala Arg
1               5

<210> SEQ ID NO 199
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Leu Cys Thr Pro Ser Lys
1               5

<210> SEQ ID NO 200
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Met Cys Thr Pro Ser Lys
1               5

<210> SEQ ID NO 201
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Val Cys Thr Pro Ser Lys
1               5

<210> SEQ ID NO 202
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202
```

```
Leu Cys Ser Pro Ser Lys
1               5

<210> SEQ ID NO 203
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Leu Cys Ala Pro Ser Lys
1               5

<210> SEQ ID NO 204
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Leu Cys Val Pro Ser Lys
1               5

<210> SEQ ID NO 205
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Leu Cys Gly Pro Ser Lys
1               5

<210> SEQ ID NO 206
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Leu Cys Thr Pro Ser Ala
1               5

<210> SEQ ID NO 207
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ile Cys Thr Pro Ala Ala
1               5

<210> SEQ ID NO 208
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 208

Met Cys Thr Pro Ser Ala
1               5

<210> SEQ ID NO 209
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Val Cys Thr Pro Ser Ala
1               5

<210> SEQ ID NO 210
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Leu Cys Ser Pro Ser Ala
1               5

<210> SEQ ID NO 211
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Leu Cys Ala Pro Ser Ala
1               5

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Leu Cys Val Pro Ser Ala
1               5

<210> SEQ ID NO 213
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Leu Cys Gly Pro Ser Ala
1               5
```

```
<210> SEQ ID NO 214
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 214

Leu Xaa Thr Pro Ser Arg
1               5

<210> SEQ ID NO 215
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 215

Met Xaa Thr Pro Ser Arg
1               5

<210> SEQ ID NO 216
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 216

Val Xaa Thr Pro Ser Arg
1               5

<210> SEQ ID NO 217
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 217

Leu Xaa Ser Pro Ser Arg
1               5

<210> SEQ ID NO 218
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
              peptide
<220> FEATURE:
<221> NAME/KEY: MOD_RES
<222> LOCATION: (2)..(2)
<223> OTHER INFORMATION: Formylglycine

<400> SEQUENCE: 218

Leu Xaa Ala Pro Ser Arg
1               5

<210> SEQ ID NO 219
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 219

Leu Xaa Val Pro Ser Arg
1               5

<210> SEQ ID NO 220
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 220

Leu Xaa Gly Pro Ser Arg
1               5

<210> SEQ ID NO 221
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 221

Ile Xaa Thr Pro Ala Arg
1               5

<210> SEQ ID NO 222
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 222
```

```
Leu Xaa Thr Pro Ser Lys
1               5

<210> SEQ ID NO 223
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 223

Met Xaa Thr Pro Ser Lys
1               5

<210> SEQ ID NO 224
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 224

Val Xaa Thr Pro Ser Lys
1               5

<210> SEQ ID NO 225
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 225

Leu Xaa Ser Pro Ser Lys
1               5

<210> SEQ ID NO 226
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 226

Leu Xaa Ala Pro Ser Lys
1               5

<210> SEQ ID NO 227
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 227

Leu Xaa Val Pro Ser Lys
1               5

<210> SEQ ID NO 228
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 228

Leu Xaa Gly Pro Ser Lys
1               5

<210> SEQ ID NO 229
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 229

Leu Xaa Thr Pro Ser Ala
1               5

<210> SEQ ID NO 230
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 230

Met Xaa Thr Pro Ser Ala
1               5

<210> SEQ ID NO 231
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: Formylglycine

<400> SEQUENCE: 231

Val Xaa Thr Pro Ser Ala
1               5

<210> SEQ ID NO 232
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 232

Leu Xaa Ser Pro Ser Ala
1               5

<210> SEQ ID NO 233
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 233

Leu Xaa Ala Pro Ser Ala
1               5

<210> SEQ ID NO 234
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 234

Leu Xaa Val Pro Ser Ala
1               5

<210> SEQ ID NO 235
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Formylglycine

<400> SEQUENCE: 235

Leu Xaa Gly Pro Ser Ala
1               5
```

```
<210> SEQ ID NO 236
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 236

Gly Ser Gly Gly Ser
1               5

<210> SEQ ID NO 237
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 237

Gly Gly Gly Ser
1

<210> SEQ ID NO 238
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gly Gly Ser Gly Gly
1               5

<210> SEQ ID NO 239
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Ser Gly Ser Gly
1               5

<210> SEQ ID NO 240
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Ser Gly Gly Gly
1               5

<210> SEQ ID NO 241
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gly Gly Gly Ser Gly
1               5

<210> SEQ ID NO 242
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Ser Ser Ser Gly
1               5

<210> SEQ ID NO 243
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Leu Cys Thr Pro Ser Arg Gly Gly Gly Gly Leu Cys Thr Pro Ser Arg
1               5                   10                  15

<210> SEQ ID NO 244
<211> LENGTH: 7
<212> TYPE: PRT
<213> ORGANISM: Unknown
<220> FEATURE:
<223> OTHER INFORMATION: Description of Unknown:
      Sortase A recognition sequence

<400> SEQUENCE: 244

Leu Pro Glu Thr Gly Gly Gly
1               5

<210> SEQ ID NO 245
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 246
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 246

Gly Gly Gly Lys Phe Phe Arg Ala Leu Lys Lys Ser Val Ala Lys Arg
1               5                   10                  15

Ala Lys Glu Phe Phe Lys Ala Pro Arg Val Ile Gly Val Ser Ile Pro
            20                  25                  30

Phe

<210> SEQ ID NO 247
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Gly Gly Gly Lys Phe Phe Arg Thr Leu Lys Lys Ser Val Thr Lys Arg
1               5                   10                  15

Ala Lys Glu Phe Phe Lys Thr Pro Arg Val Ile Gly Val Ser Ile Pro
            20                  25                  30

Phe

<210> SEQ ID NO 248
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Gly Gly Gly Lys Phe Phe Arg Thr Leu Lys Lys Ser Val Lys Thr Arg
1               5                   10                  15

Ala Lys Glu Phe Phe Lys Thr Pro Arg Val Ile Gly Val Ser Ile Pro
            20                  25                  30

Phe

<210> SEQ ID NO 249
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Gly Gly Gly Lys Phe Phe Ala Lys Leu Lys Lys Ser Val Lys Lys Arg
1               5                   10                  15

Ala Lys Glu Phe Phe Lys Lys Pro Ala Val Ile Gly Val Ser Ile Pro
            20                  25                  30

Phe

<210> SEQ ID NO 250
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Gly Gly Gly Lys Phe Phe Ala Lys Leu Lys Lys Ser Val Lys Arg
1               5                   10                  15

Ala Lys Glu Phe Phe Ala Lys Pro Arg Val Ile Gly Val Ser Ile Pro
            20                  25                  30

Phe

<210> SEQ ID NO 251
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Gly Gly Gly Lys Phe Phe Ser Lys Leu Lys Lys Ser Val Lys Arg
1               5                   10                  15

Ala Lys Glu Phe Phe Ser Lys Pro Arg Val Ile Gly Val Ser Ile Pro
            20                  25                  30

Phe

<210> SEQ ID NO 252
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Gly Gly Gly Ala Phe Phe Ala Lys Leu Lys Lys Ser Val Lys Arg
1               5                   10                  15

Ala Lys Glu Phe Phe Lys Lys Pro Arg Val Ile Gly Val Ser Ile Pro
            20                  25                  30

Phe

<210> SEQ ID NO 253
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Gly Gly Gly Lys Phe Phe Arg Lys Leu Lys Lys Ser Val Lys Arg
1               5                   10                  15

Ala Lys Glu Phe Phe Ala Lys Pro Ala Val Ile Gly Val Ser Ile Pro
            20                  25                  30

Phe

<210> SEQ ID NO 254
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Gly Gly Gly Glu Glu Glu Glu Ala Ala Ala Gly Lys Phe Phe Arg Lys
1               5                   10                  15

Leu Lys Lys Ser Val Lys Lys Arg Ala Lys Glu Phe Phe Lys Pro
            20                  25                  30

Arg Val Ile Gly Val Ser Ile Pro Phe
        35                  40

<210> SEQ ID NO 255
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Gly Gly Gly Lys Phe Phe Arg Lys Leu Lys Lys Ser Val Lys Lys Arg
1               5                   10                  15

Ala Lys Glu Phe Phe Lys Lys Pro Arg Val Ile Gly Val Ser Ile Pro
            20                  25                  30

Phe Ala Ala Ala Gly Glu Glu Glu Glu
        35                  40

<210> SEQ ID NO 256
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Gly Gly Gly Lys Phe Phe Arg Lys Leu Lys Lys Ser Val Lys Lys Arg
1               5                   10                  15

Ala Lys Glu Phe Phe Lys Lys Pro Arg Val Ile Gly Val Ser Ile Pro
            20                  25                  30

Phe Ala Ala Ala Gly Ala Val Glu Asp Leu Glu Asp
        35                  40

<210> SEQ ID NO 257
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Gly Gly Gly Lys Leu Leu Arg Lys Leu Lys Lys Ser Val Lys Lys Arg
1               5                   10                  15

Ala Lys Glu Leu Leu Lys Lys Pro Arg Val Ile Gly Val Ser Ile Pro
            20                  25                  30

Leu

<210> SEQ ID NO 258
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gly Gly Gly His Thr Ala Ser Asp Ala Ala Ala Ala Ala Leu Thr
1               5                   10                  15

```
Ala Ala Asn Ala Ala Ala Ala Ala Ala Ser Met Ala
            20                  25
```

<210> SEQ ID NO 259
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 259

```
His His His His His His
1               5
```

<210> SEQ ID NO 260
<211> LENGTH: 5
<212> TYPE: PRT
<213> ORGANISM: Unknown
<220> FEATURE:
<223> OTHER INFORMATION: Description of Unknown:
      Sortase A recognition sequence
<220> FEATURE:
<221> NAME/KEY: MOD_RES
<222> LOCATION: (3)..(3)
<223> OTHER INFORMATION: Any amino acid

<400> SEQUENCE: 260

```
Leu Pro Xaa Thr Gly
1               5
```

<210> SEQ ID NO 261
<211> LENGTH: 7
<212> TYPE: PRT
<213> ORGANISM: Unknown
<220> FEATURE:
<223> OTHER INFORMATION: Description of Unknown:
      Sortase A recognition sequence
<220> FEATURE:
<221> NAME/KEY: MOD_RES
<222> LOCATION: (3)..(3)
<223> OTHER INFORMATION: Any amino acid

<400> SEQUENCE: 261

```
Leu Pro Xaa Thr Gly Gly Gly
1               5
```

<210> SEQ ID NO 262
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 2-20 "Gly Ser"
      repeating units

<400> SEQUENCE: 262

```
Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser Gly Ser
            20                  25                  30

Gly Ser Gly Ser Gly Ser Gly Ser
        35                  40
```

```
<210> SEQ ID NO 263
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ser Ser Asp Gly Asp
1               5

<210> SEQ ID NO 264
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Glu Val Lys Leu Val Glu Ser Gly Gly Gly Leu Val Gln Pro Gly Gly
1               5                   10                  15

Ser Leu Arg Leu Ser Cys Ala Ala Ser Glu Phe Thr Phe Ser Asp Tyr
            20                  25                  30

Ala Met Ser Trp Val Arg Gln Ala Pro Gly Lys Arg Leu Glu Trp Val
        35                  40                  45

Ala Tyr Ile Ser Ser Asp Gly Asp Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Phe Cys
                85                  90                  95

Ala Arg Glu Ile Arg Leu Arg Gly Tyr Phe Asp Val Trp Gly Gln Gly
            100                 105                 110

Thr Thr Val Thr Val Ser Ser
        115

<210> SEQ ID NO 265
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Glu Val Lys Leu Val Glu Ser Gly Gly Gly Leu Val Gln Pro Gly Gly
1               5                   10                  15

Ser Leu Arg Leu Ser Cys Ala Ala Ser Glu Phe Thr Phe Ser Asp Tyr
            20                  25                  30

Ala Met Ser Trp Val Arg Gln Ala Pro Gly Lys Arg Leu Glu Trp Val
        35                  40                  45

Ala Tyr Ile Ser Ser Asp Gly Asp Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Phe Cys
                85                  90                  95

Ala Arg Glu Ile Arg Leu Arg Gly Tyr Phe Asp Val Trp Gly Gln Gly
            100                 105                 110
```

Thr Thr Val Thr Val Ser Ser
        115

<210> SEQ ID NO 266
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Ser Val Phe Gly His
            20                  25                  30

Gly Ile Ser Pro Leu His Trp Tyr Gln Gln Lys Pro Gly Lys Ala Pro
        35                  40                  45

Lys Leu Leu Ile Tyr Arg Ala Ser Asn Leu Lys Ser Gly Val Pro Ser
    50                  55                  60

Arg Phe Ser Gly Ser Gly Ser Arg Thr Glu Phe Thr Leu Thr Ile Ser
65                  70                  75                  80

Ser Leu Gln Pro Asp Asp Phe Ala Thr Tyr Tyr Cys Gln Gln Ser Asn
                85                  90                  95

Glu Tyr Pro Arg Thr Phe Gly Gly Gly Thr Lys Val Glu Ile Lys
            100                 105                 110

<210> SEQ ID NO 267
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser Leu Pro
            20                  25                  30

Glu Thr Gly Gly Ser Gly
        35

<210> SEQ ID NO 268
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Leu Pro
            20                  25                  30

Glu Thr Gly Gly Gly
        35

<210> SEQ ID NO 269
<211> LENGTH: 49

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Asn Arg Gly Glu Cys Pro Gly Gly Gly Ser Gly Ser Gly Ser Gly
1               5                   10                  15

Ser Gly Ser Gly Ser Gly Ser Gly Ser Gly Ser Gly Ser Gly
            20                  25                  30

Ser Gly Ser Gly Ser Gly Ser Ala Ser Leu Pro Glu Thr Gly Gly Ser
        35                  40                  45

Gly

<210> SEQ ID NO 270
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Pro Gly Lys Gly Ser Gly Ser Gly Ser Gly Ser Gly Ser Gly Ser Gly
1               5                   10                  15

Ser Gly Ser Gly Ser Gly Ser Gly Ser Gly Ser Gly Ser Gly
            20                  25                  30

Ser Ala Ser Leu Pro Glu Thr Gly Gly Ser Gly
        35                  40
```

UNITED STATES PATENT AND TRADEMARK OFFICE
CERTIFICATE OF CORRECTION

PATENT NO. : 11,969,476 B2
APPLICATION NO. : 17/221421
DATED : April 30, 2024
INVENTOR(S) : Viswanathan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 12 days.

Signed and Sealed this
Twelfth Day of November, 2024

Katherine Kelly Vidal
*Director of the United States Patent and Trademark Office*